US012778882B2

(12) United States Patent
Du et al.

(10) Patent No.: US 12,778,882 B2
(45) Date of Patent: Nov. 3, 2026

(54) COMPOSITIONS AND METHODS FOR TREATING OCULAR DISORDERS

(71) Applicant: UNIVERSITY OF PITTSBURGH—OF THE COMMONWEALTH SYSTEM OF HIGHER EDUCATION, Pittsburgh, PA (US)

(72) Inventors: Yiqin Du, Pittsburgh, PA (US); Ajay Kumar, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 719 days.

(21) Appl. No.: 17/902,050

(22) Filed: Sep. 2, 2022

(65) Prior Publication Data

US 2023/0000760 A1 Jan. 5, 2023

Related U.S. Application Data

(63) Continuation of application No. PCT/US2021/021416, filed on Mar. 8, 2021.

(60) Provisional application No. 62/986,409, filed on Mar. 6, 2020.

(51) Int. Cl.

| | |
|---|---|
| ***A61K 9/00*** | (2006.01) |
| ***A61K 35/28*** | (2015.01) |
| ***A61K 35/30*** | (2015.01) |
| ***C12N 5/079*** | (2010.01) |

(52) U.S. Cl.

CPC ............ *A61K 9/0019* (2013.01); *A61K 35/28* (2013.01); *A61K 35/30* (2013.01); *C12N 5/0621* (2013.01); *A61K 2121/00* (2013.01); *C12N 2533/90* (2013.01)

(58) Field of Classification Search

None

See application file for complete search history.

(56) References Cited

U.S. PATENT DOCUMENTS

| | | | | |
|---|---|---|---|---|
| 2006/0083774 | A1 | 4/2006 | Pang et al. | |
| 2015/0231180 | A1* | 8/2015 | Du | C12N 5/0621 424/93.7 |
| 2017/0253854 | A1 | 9/2017 | Du et al. | |
| 2019/0046576 | A1* | 2/2019 | Gangaraju | A61K 47/183 |

OTHER PUBLICATIONS

Alvarado et al., "Age-related changes in trabecular meshwork cellularity," Invest Ophthalmol Vis Sci 21:714-727 (1981).

Bosco et al., "Neurodegeneration severity can be predicted from early microglia alterations monitored in vivo in a mouse model of chronic glaucoma," Dis Model Mech 8:443-455 (2015).

Chen et al., "Commensal microflora-induced T cell responses mediate progressive neurodegeneration in glaucoma," Nat Commun 9:3209 (2018) 13 pgs.

Comes et al., "Evidence for a role of angiopoietin-like 7 (ANGPTL7) in extracellular matrix formation of the human trabecular meshwork: implications for glaucoma," Genes to Cells 16:243-259 (2011).

Crofford, "COX-1 and COX-2 tissue expression: implications and predictions," J Rheumatol Suppl 49:15-19 (1997) [Abstract].

Deng et al., "Prostacyclin-producing human mesenchymal cells target H19 lncRNA to augment endogenous progenitor function in hindlimb ischaemia," Nature Communications 7(11276):1-12 (2015).

Du et al., "Multipotent Stem Cells from Trabecular Meshwork Become Phagocytic TM Cells," Invest Ophthalmol Vis Sci 53:1566-1575 (2012).

Du et al., "Stem Cell Therapy Restores Transparency to Defective Murine Corneas," Stem Cells 27:1635-1642 (2009).

Du et al., "Stem Cells from Trabecular Meshwork Home to TM Tissue In Vivo," Invest Ophthalmol Vis Sci 54:1450-1459 (2013).

Eibl et al., "PGE(2) is generated by specific COX-2 activity and increases VEGF production in COX-2-expressing human pancreatic cancer cells," Biochem Biophys Res Commun 306:887-897 (2003).

Epstein, "Framing Glaucoma Questions: What are the Opportunities for Glaucoma Treatment? A Personal Perspective," Invest Ophthalmol Vis Sci 53(5):2462-2463 (2012).

Faralli et al., "Role of Fibronectin in Primary Open Angle Glaucoma," Cells 8:1518 (2019) 20 pgs.

Fu et al., "Baclofen Protects Primary Rat Retinal Ganglion Cells from Chemical Hypoxia-Induced Apoptosis Through the Akt and PERK Pathways," Front Cell Neurosci 10:255 (2016) 14 pgs.

Gao et al., "Exosomes secreted by hiPSC-derived cardiac cells improve recovery from myocardial infarction in swine," Sci Transl Med 12:1-11 (2020).

Garbe et al., "Risk of ocular hypertension or open-angle glaucoma in elderly patients on oral glucocorticoids," Lancet 350:979-982 (1997).

Guo et al., "Retinal Ganglion Cell Apoptosis in Glaucoma is Related to Intraocular Pressure and IOP-Induced Effects on Extracellular Matrix," Invest Ophthalmol Vis Sci 46:175-182 (2005).

International Search Report mailed Jun. 11, 2021 in International Application No. PCT/US2021/021416.

Jablonska-Trypuc et al., "Matrix metalloproteinases (MMPs), the main extracellular matrix (ECM) enzymes in collagen degradation, as a target for anticancer drugs," J Enzyme Inhib Med Chem 31(S1):177-183 (2016).

Kaplan-Messas et al., "Ocular hypotensive effects of cholinergic and adrenergic drugs may be influenced by prostaglandins E2 in the human and rabbit eye," Eur J Ophthalmol 13:18-23 (2003).

(Continued)

*Primary Examiner* — Michael V Meller

(74) *Attorney, Agent, or Firm* — Baker Botts L.L.P.

(57) ABSTRACT

Compositions for treating an ocular disorder are provided. The composition includes an effective amount of a human trabecular meshwork stem cell (TMSC) secretome, wherein the effective amount is present in an amount to reduce impairment of retinal ganglion cells (RGC). Methods for treating ocular disorders using the disclosed compositions are also provided. The compositions reduce and prevent cell apoptosis, axon loss, vision loss, increased intraocular pressure, and dysregulated aqueous humor outflow of a subject when used in accordance with the methods disclosed herein.

6 Claims, 118 Drawing Sheets

Figure 1A:
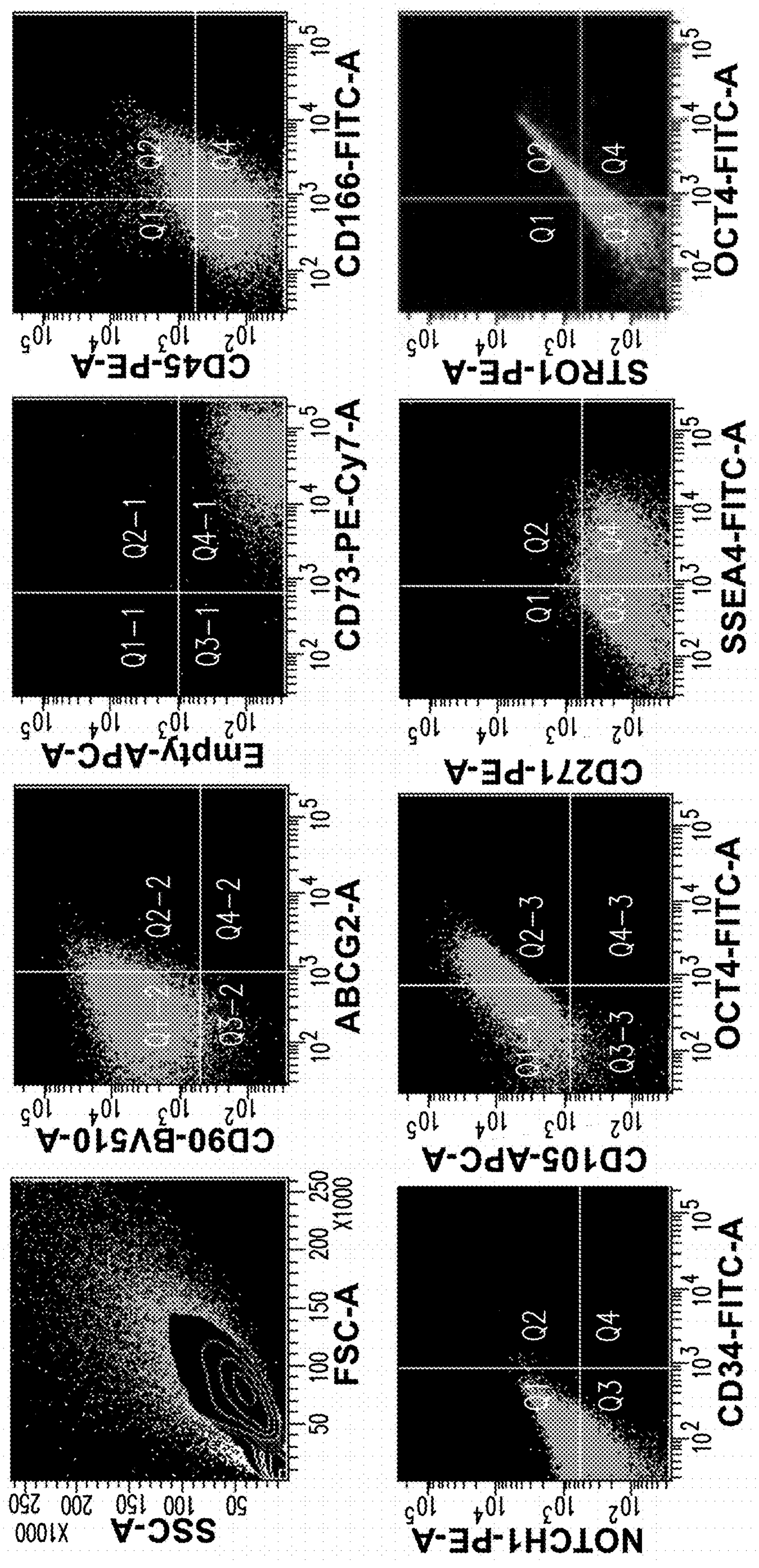

Specification includes a Sequence Listing.

(56) References Cited

OTHER PUBLICATIONS

Keller et al., "Consensus recommendations for trabecular meshwork cell isolation, characterization and culture," Exp Eye Res 171:164-173 (2018).
Kumar et al., "Stem Cells from Human Trabecular Meshwork Hold the Potential to Develop into Ocular and Non-Ocular Lineages after Long-Term Storage," Stem Cells and Development 29(1):49-61 (2020).
Kumar et al., "Stemness and Regenerative Potential of Corneal Stromal Stem Cells and Their Secretome After Long-Term Storage: Implications for Ocular Regeneration," Invest Ophthalmol Vis Sci 59:3728-3738 (2018).
Laha et al., "Regenerating optic pathways from the eye to the brain," Science 356:1031-1034 (2017).
Lee et al., "PGE2 maintains self-renewal of human adult stem cells via EP2-mediated autocrine signaling and its production is regulated by cell-to-cell contact," Sci Rep 6:26298 (2016) 12 pgs.
Li et al., "In vivo measurement of trabecular meshwork stiffness in a corticosteroid-induced ocular hypertensive mouse model," Proc Natl Acad Sci USA 116(5):1714-1722 (2019).
Lorenzi et al., "The mitochondnal TMEM177 associates with COX20 during COX2 biogenesis," Biochim Biophys Acta Mol Cell Res 1865:323-333 (2018).
Maihofner et al., "Expression of cyclooxygenase-1 and -2 in normal and glaucomatous human eyes," Invest Ophthalmol Vis Sci 42:2616-2624 (2001).
Manuguerra-Gagne et al., "Transplantation of Mesenchymal Stem Cells Promotes Tissue Regeneration in a Glaucoma Model Through Laser-Induced Paracrine Factor Secretion and Progenitor Cell Recruitment," Stem Cells 31:1136-1148 (2013).
Miller et al., Mobilizing Endogenous Stem Cells for Repair and Regeneration: Are We There Yet? Cell Stem Cell 10:650-652 (2012).
Mohan et al., "Combination of N-(4-hydroxyphenyl) retinamide and apigenin suppressed starvation-induced autophagy and promoted apoptosis in malignant neuroblastoma cells," Neurosci Lett 502:24-29 (2011).
Oyadomari et al., "Roles of CHOP/GADD153 in endoplasmic reticulum stress," Cell Death Differ 11:381-389 (2004).
Patel et al., "Dexamethasone-Induced Ocular Hypertension in Mice: Effects of Myocilin and Route of Administration," Am J Pathol 187:713-723 (2017).
Porciatti, "Electrophysiological assessment of retinal ganglion cell function," Exp Eye Res 141:164-170 (2015).
Rodriguez et al., "The RNA binding protein RBPMS is a selective marker of ganglion cells in the mammalian retina," J Comp Neurol 522:1411-1443 (2014).
Rodriguez-Muela et al., "Autophagy promotes survival of retinal ganglion cells after optic nerve axotomy in mice," Cell Death Differ 19:162-169 (2012).
Roubeix et al., "Intraocular pressure reduction and neuroprotection conferred by bone marrow-derived mesenchymal stem cells in an animal model of glaucoma," Stem Cell Res Ther 6:177 (2015) 13 pgs.
Sano et al., "In vivo cyclooxygenase expression in synovial tissues of patients with rheumatoid arthritis and osteoarthritis and rats with adjuvant and streptococcal cell wall arthritis," J Clin Invest 89:97-108 (1992).
Scott et al., "Public Attitudes About Eye and Vision Health," JAMA Ophthalmol 134(10):1111-1118 (2016).
Siddiqui et al., "Downregulation of BM88 after optic nerve injury," Invest Ophthalmol Vis Sci 55:1919-1929 (2014).
Stahnke et al., "Different fibroblast subpopulations of the eye: a therapeutic target to prevent postoperative fibrosis in glaucoma therapy," Exp Eye Res 100:88-97 (2012).
Stamer et al., "Cultured human trabecular meshwork cells express aquaporin-1 water channels," Curr Eye Res 14:1095-1100 (1995).
Tamm, "Myocilin and glaucoma: facts and ideas," Prog Retin Eye Res 21:395-428 (2002).
Tham et al., "Global Prevalence of Glaucoma and Projections of Glaucoma Burden through 2040: A Systematic Review and Meta-Analysis," Ophthalmology 121:2081-2090 (2014).
Wang et al., "Endoplasmic Reticulum Stress Response of Trabecular Meshwork Stem Cells and Trabecular Meshwork Cells and Protective Effects of Activated PERK Pathway," Invest Ophthalmol Vis Sci 60:265-273 (2019).
Weinreb et al., "Prostaglandin Production by Human Trabecular Cells: In Vitro Inhibition by Dexamethasone," Invest Ophthalmol Vis Sci 24:1541-1545 (1983).
Wiklander et al., "Advances in therapeutic applications of extracellular vesicles," Sci Transl Med 11(492):1-34 (2019).
Witwer et al., "Standardization of sample collection, isolation and analysis methods in extracellular vesicle research," J Extracell Vesicles 2:20360 (2013) 26 pgs.
Xia et al., "Mesenchymal stem cells promote healing of nonsteroidal anti-inflammatory drug-related peptic ulcer through paracrine actions in pigs," Sci Transl Med 11:eaat7455 (2019) 15 pgs.
Xiong et al., "α5β1 Integrin Promotes Anchoring and Integration of Transplanted Stem Cells to the Trabecular Meshwork in the Eye for Regeneration," Stem Cells Dev, 29(5):290-300 (2020).
Yun et al., "Human stem cells home to and repair laser-damaged trabecular meshwork in a mouse model," Commun Biol 1:216 (2018) 14 pgs.
Zhou et al., "Adipose-Derived Stem Cells Integrate into Trabecular Meshwork with Glaucoma Treatment Potential," FASEB J 34:7160-7177 (2020).
Zhu et al., "Transplantation of iPSC-derived TM cells rescues glaucoma phenotypes in vivo," Proc Natl Acad Sci USA 113:E3492-E3500 (2016).
Zode et al., "Ocular-specific ER stress reduction rescues glaucoma in murine glucocorticoid-induced glaucoma," J Clin Invest 124(5):1956-1965 (2014).
Zode et al., "Reduction of ER stress via a chemical chaperone prevents disease phenotypes in a mouse model of primary open angle glaucoma," J Clin Invest 121(9):3542-3553 (2011).

* cited by examiner

Protein folding

Cell adhesion

Collagen Catabolic Process

Axon guidance-ROBO4, RYK, UNC5B, ARTN, VASP

Axon-guidance-Plexin A1, Ephrin-A receptor 7, Neuromodulin, BMP7, ROBO1

Axon guidance-Plexin B1, SOS1, Smoothened, NRCAM, Neogenin

Axon-guidance-PI3K reg class IA, OTX2, Rac1, WNT5A, FEZF2

Axon guidance-PTPR-alpha, Tubulin (in microtubules), NGFR(TNFRSF16), PLC-gamma, Ephrin-B2

Platelet Degranulation

SEQUENCE LISTING

```
Sequence total quantity: 6
SEQ ID NO: 1            moltype = DNA  length = 20
FEATURE                 Location/Qualifiers
misc_feature            1..20
                        note = Synthetic sequence
source                  1..20
                        mol_type = other DNA
                        organism = synthetic construct
SEQUENCE: 1
aagcccacct acccctacac                                              20

SEQ ID NO: 2            moltype = DNA  length = 20
FEATURE                 Location/Qualifiers
misc_feature            1..20
                        note = Synthetic sequence
source                  1..20
                        mol_type = other DNA
                        organism = synthetic construct
SEQUENCE: 2
tccagtggcc taggcagtat                                              20

SEQ ID NO: 3            moltype = DNA  length = 20
FEATURE                 Location/Qualifiers
misc_feature            1..20
                        note = Synthetic sequence
source                  1..20
                        mol_type = other DNA
                        organism = synthetic construct
```

-continued

```
SEQUENCE: 3
gcaccaagga caaggacaat                                           20

SEQ ID NO: 4            moltype = DNA  length = 20
FEATURE                 Location/Qualifiers
misc_feature            1..20
                        note = Synthetic sequence
source                  1..20
                        mol_type = other DNA
                        organism = synthetic construct
SEQUENCE: 4
gatgccatcc aggtgcttat                                           20

SEQ ID NO: 5            moltype = DNA  length = 23
FEATURE                 Location/Qualifiers
misc_feature            1..23
                        note = Synthetic sequence
source                  1..23
                        mol_type = other DNA
                        organism = synthetic construct
SEQUENCE: 5
ccctgtaatt ggaatgagtc cac                                       23

SEQ ID NO: 6            moltype = DNA  length = 18
FEATURE                 Location/Qualifiers
misc_feature            1..18
                        note = Synthetic sequence
source                  1..18
                        mol_type = other DNA
                        organism = synthetic construct
SEQUENCE: 6
gctggaatta ccgcggct                                             18
```

COMPOSITIONS AND METHODS FOR TREATING OCULAR DISORDERS

2. CROSS-REFERENCE TO RELATED APPLICATIONS

This application is a continuation of International Application No. PCT/US2021/021416, filed on Mar. 8, 2021, which claims priority to U.S. Provisional Application Ser. No. 62/986,409, filed Mar. 6, 2020, the contents of which are hereby incorporated by reference in their entireties.

1. GRANT INFORMATION

This invention was made with government support under Grant No. EY025643 awarded by the National Institutes of Health. The government has certain rights in the invention.

3. SEQUENCE LISTING

This application contains a Sequence Listing, which has been submitted in XML format via EFS-Web, and is hereby incorporated by reference in its entirety. Said XML copy, created on Aug. 30, 2022, is named 072396_0936 SLST26.xml and is 8,661 bytes in size.

4. FIELD

The present disclosure relates to methods of treating ocular disorders using a composition including a human trabecular meshwork stem cell (TMSC) secretome, wherein the composition can reduce or treat the impairment of ocular cells.

5. BACKGROUND

Glaucoma can be a cause of blindness, as there is irreversible damage to the optic nerve, which connects the eye to the brain, due to increased intraocular pressure (IOP) in the eye. This damage can result in permanent vision loss.

Increased IOP in glaucoma is due to the dysregulation of the major outflow pathway in the eye comprised of the trabecular meshwork (TM), causing accumulation of aqueous humor (AH) inside the eye. This accumulation causes an increased IOP, which can lead to damage of the optic nerve head and death of retinal ganglion cells (RGCs). IOP is mainly regulated by the TM and the Schlemm's canal endothelium by providing resistance to the aqueous humor outflow. Primary open-angle glaucoma (POAG), which accounts for up to 90% of all forms of glaucoma, is characterized by an elevation of IOP without pain. A certain range of IOP and anterior chamber angle can appear normal and remain asymptomatic until patients realize that there is a significant permanent loss of eyesight. There is a reduction of TM cells with age at the rate of 0.58% per year. There is a reduction in TM cellularity in glaucoma, and this loss can be aggravated by pathological conditions involving TM thickness, hyperplasia, abnormal ECM deposition, leading to increased outflow resistance.

Hypoxia is implicated in the death of RGCs in glaucoma through increased VEGF production, causing retinal edema, elevated reactive oxygen species (ROS), and increased accumulation of glutamate extracellularly, which causes excessive $Ca^{+}$ influx and RGC death by ionotropic and metabotropic receptor activation and enhanced production of inflammatory cytokines.

Existing treatment options for glaucoma include eye drops (beta-blockers, alpha agonists, carbonic anhydrase inhibitors, rho kinase inhibitors, and prostaglandin analogs), laser procedures, and surgery. However, all such treatments have various limitations and side effects. Therefore, there is a need in the art for improved techniques to treat ocular disorders without significant adverse side effects.

6. SUMMARY

The disclosed subject matter relates to compositions and methods for treating an ocular disorder. It is based, at least in part, on the discovery that the administration of the disclosed composition can treat and/or prevent glaucoma by reducing impairment of retinal ganglion cells (RGCs). For example, the impairment of RGCs in glaucoma can include cell apoptosis, axon loss, vision loss, along with abnormalities of trabecular meshwork which can cause increased intraocular pressure, dysregulation of aqueous humor outflow, and/or combinations thereof.

The disclosed subject matter provides a composition comprising an effective amount of a human trabecular meshwork stem cell (TMSC) secretome, wherein the effective amount can be present in an amount to reduce impairment of retinal ganglion cells (RGC).

In certain embodiments, the TMSC secretome can include proteins involved in neuroprotection. The neuroprotection is selected from the group consisting of axon guidance, neurogenesis, negative regulation of neuron death, clearance of neuron apoptotic bodies, and combinations thereof. In non-limiting embodiments, the TMSC secretome can be a cell-free secretome. In certain embodiments, the TMSC secretome can be harvested from TMSCs by incubating the TMSCs with serum-free media. In non-limiting embodiments, the TMSC secretome can be a concentrated formulation from TMSC. The TMSC secretome can be concentrated by a factor of about 25 after harvesting.

In certain embodiments, the disclosed composition can be formulated in a form. The form can be selected from the group consisting of a solution, a suspension, a semi-solid, gel, a gel, an emulsion, semi-liquid, an ointment, a cream, foam gel, a controlled-release/sustain-release vehicle, and combinations thereof. In non-limiting embodiments, the disclosed composition can be formulated as an eye drop. In non-limiting embodiments, the disclosed composition can be formulated in the form of a solution for injection into the subject. The injection can be selected from the group consisting of a systemic injection, an intravenous injection, an intramuscular injection, and combinations thereof.

The disclosed subject matter also provides a method for treating an ocular disorder of a subject. In certain embodiments, the method can include administering an effective amount of a TMSC secretome to reduce impairment of RGCs to a target tissue of the subject.

In non-limiting embodiments, the method can further include harvesting the TMSC secretome by incubating the TMSCs with serum-free media. In certain embodiments, the method can further include concentrating the TMSC secretome by a factor of about 25.

In certain embodiments, the effective amount of the TMSC secretome can be periocularly administered to the target tissue. The target tissue can be an eye tissue of the subject. In non-limiting embodiments, the effective amount of the TMSC secretome is administered in appropriate amounts divided into multiple portions.

In certain embodiments, the TMSC secretome can include proteins involved in neuroprotection. The neuroprotection is selected from the group consisting of axon guidance, neurogenesis, negative regulation of neuron death, clearance of neuron apoptotic bodies, and combinations thereof.

In certain embodiments, the target tissue can be an eye of the subject. In non-limiting embodiments, the impairment can be selected from the group consisting of cell apoptosis, axon loss, vision loss, increased intraocular pressure, dysregulation of aqueous humor outflow, and combinations thereof. In non-limiting embodiments, the ocular disorder can be glaucoma.

In certain embodiments, the composition can be formulated in a form. The form can be selected from the group consisting of a solution, a suspension, a semi-solid gel, a gel, an emulsion, semi-liquid, an ointment, a cream, foam gel, a controlled-release/sustain-release vehicle, and combinations thereof. In non-limiting embodiments, the effective amount of the TMSC secretome can be administered to the target tissue via an injection. The injection can be selected from the group consisting of a systemic injection, an intravenous injection, an intramuscular injection, and combinations thereof.

In certain embodiments, the effective amount of the TMSC secretome can be present in an amount to decrease the intraocular pressure of the subject by increasing an expression level of a neuroprotective factor. The neuroprotective factor can be selected from the group consisting of an axon guidance factor, a neurogenesis factor, a negative regulation of neuron death factor, a clearance of neuron apoptotic bodies factor, and combinations thereof. In non-limiting embodiments, the axon guidance factor can be selected from the group consisting of Tubulin beta-2A (TUBB2A), ACTR3, ARPC4, Semaphorin 5A (SEMA5A), and combinations thereof. In non-limiting embodiments, the neurogenesis factor can be selected from the group consisting of NEO1, SPTBN1, GAS6, SDC2, and combinations thereof. In non-limiting embodiments, the negative regulation of neuron death factor can be selected from the group consisting of PARK7, HYOU1, NONO, PIN1, and combinations thereof. In non-limiting embodiments, the clearance of neuron apoptotic bodies factor can be selected from the group consisting of NQO1, HSP90AB1, G6PD, UBE2V2, and combinations thereof.

In certain embodiments, the effective amount of the TMSC secretome can be present in an amount to reduce gliosis by promoting the regeneration of the RGC. In non-limiting embodiments, the effective amount of the TMSC secretome can be present in an amount to increase autophagy in the RGC and regenerate the RGC.

7. BRIEF DESCRIPTION OF THE FIGURES

Figure 1C:
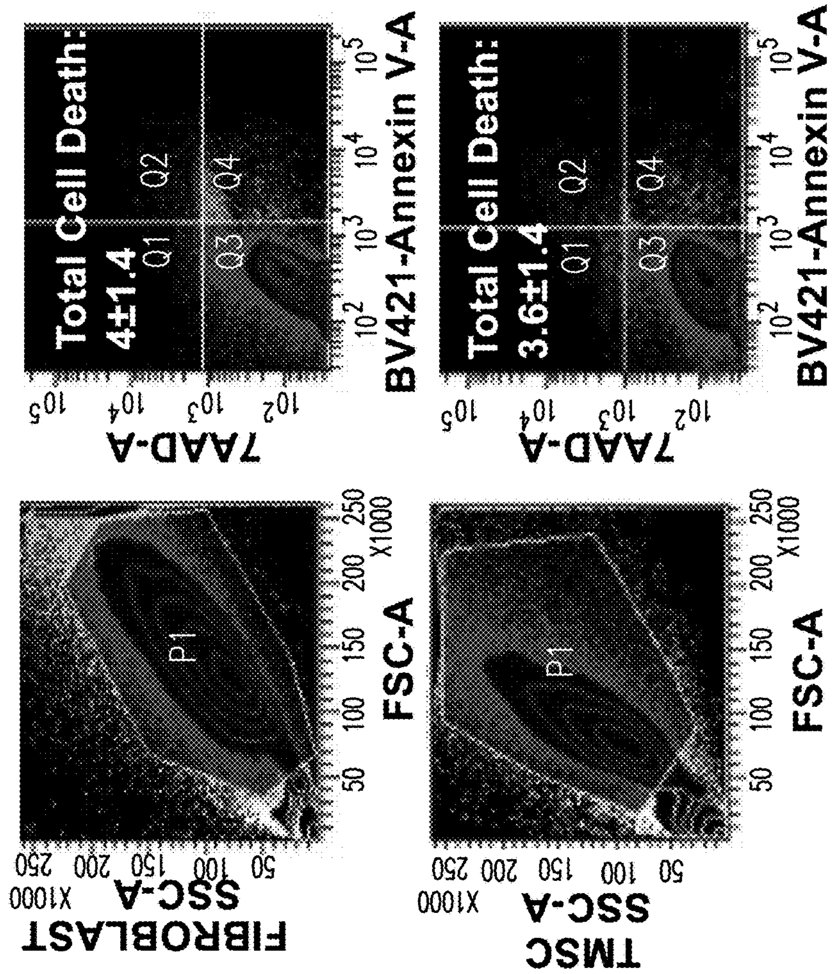
Figure 1B:
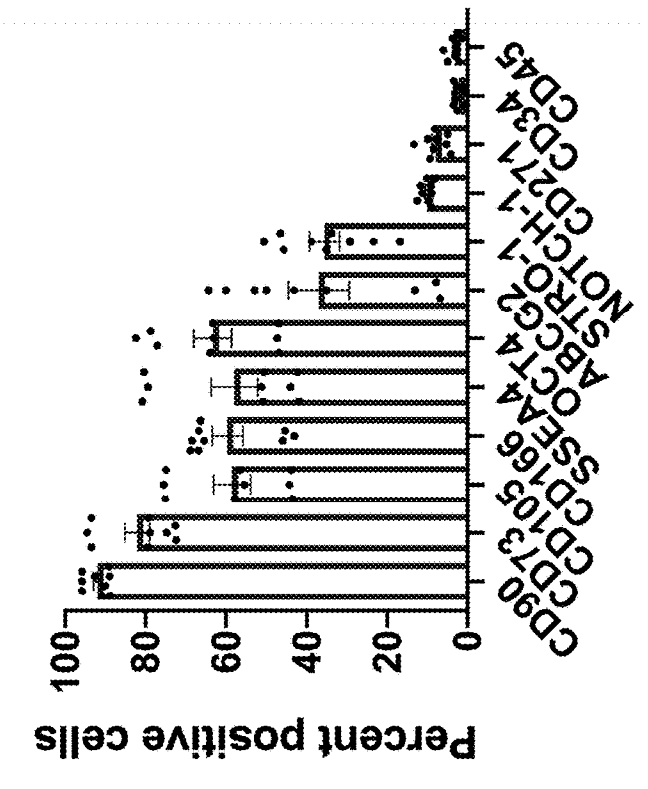
Figure 1D:
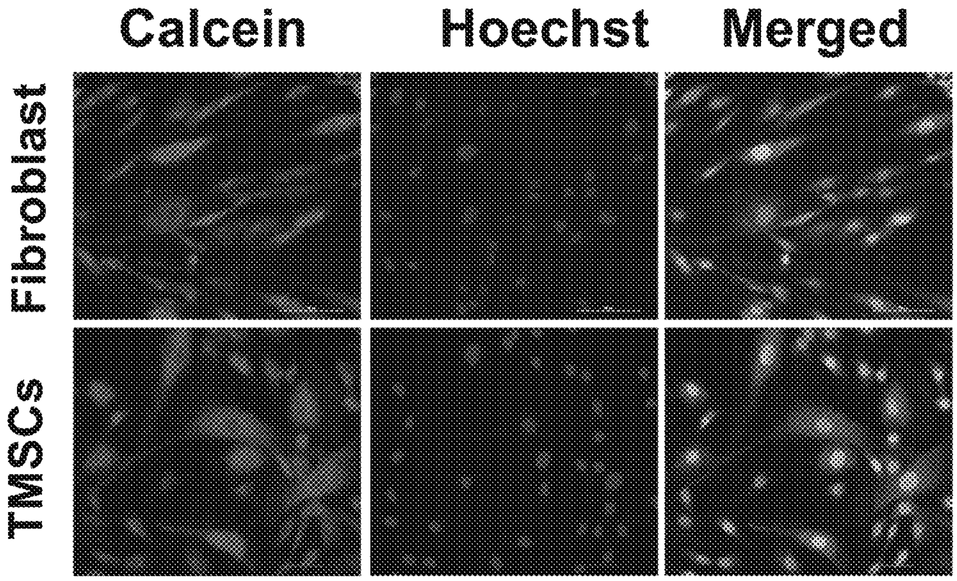
Figure 1E:
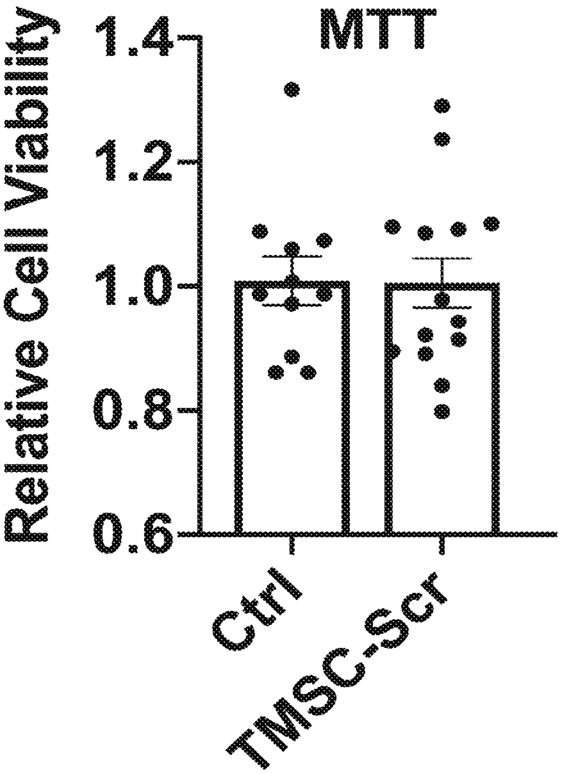
Figure 1F:
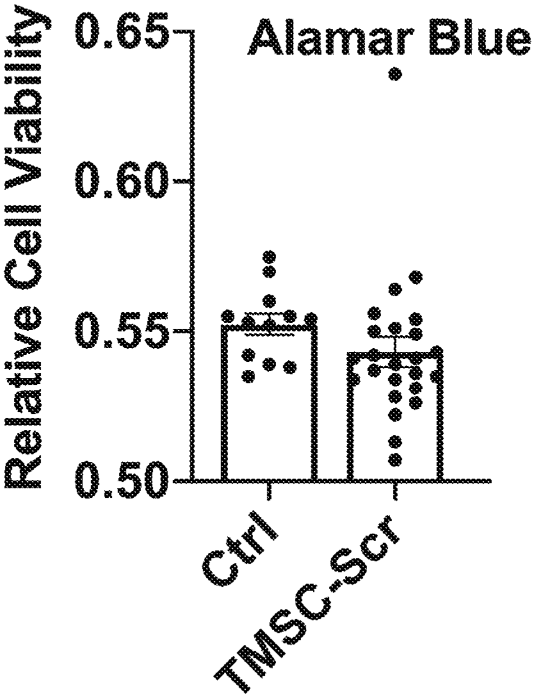

FIGS. 1A-1F provide the trabecular meshwork stem cell (TMSC) characterization and evaluation of cell viability in corneal fibroblasts and TMSC post secretome harvesting. FIGS. 1A-1B provide dot plots and bar diagrams showing percent positivity for different stem cell markers of TMSC. FIG. 1C provides an annexin V/7-AAD flow cytometry analysis for cell viability assessment in corneal fibroblasts and TMSC post secretome harvesting after incubation in serum-free media. Gate was set on Unstained control cells for normalizing the background fluorescence. Results are representative of average±SD of three independent experiments (n=3). FIG. 1D provides live-cell fluorescent microscopy images for cell viability in corneal fibroblasts and TMSC post secretome harvesting. Calcein AM and Hoechst 33342 were used to stain viable cells. FIG. 1E provides a graph showing the MTT assay results. FIG. 1F provides an alamar blue assay results showing maintenance of cell viability after secretome incubation for 48 hours in TM cells, an indication of non-toxicity of secretome in the TM cells (n=4). Multiple dots in bar graphs represent combined results of biological and technical replicates. The scale bar is 100 μm.

Figure 2B:
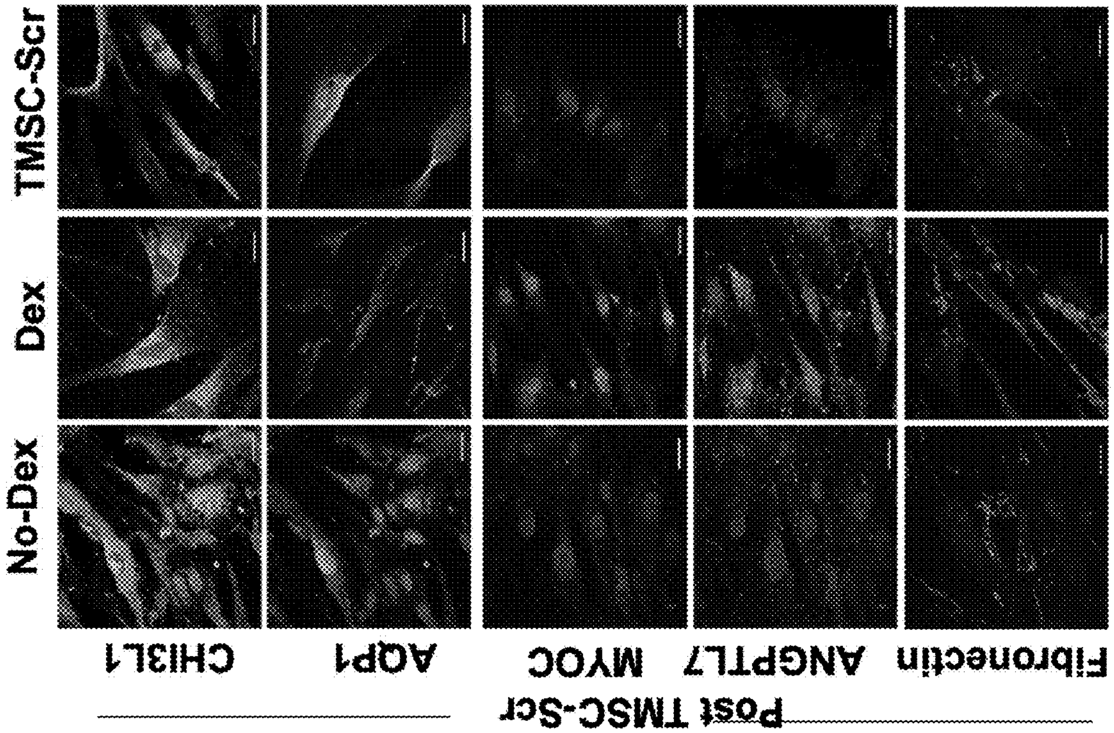
Figure 2A:
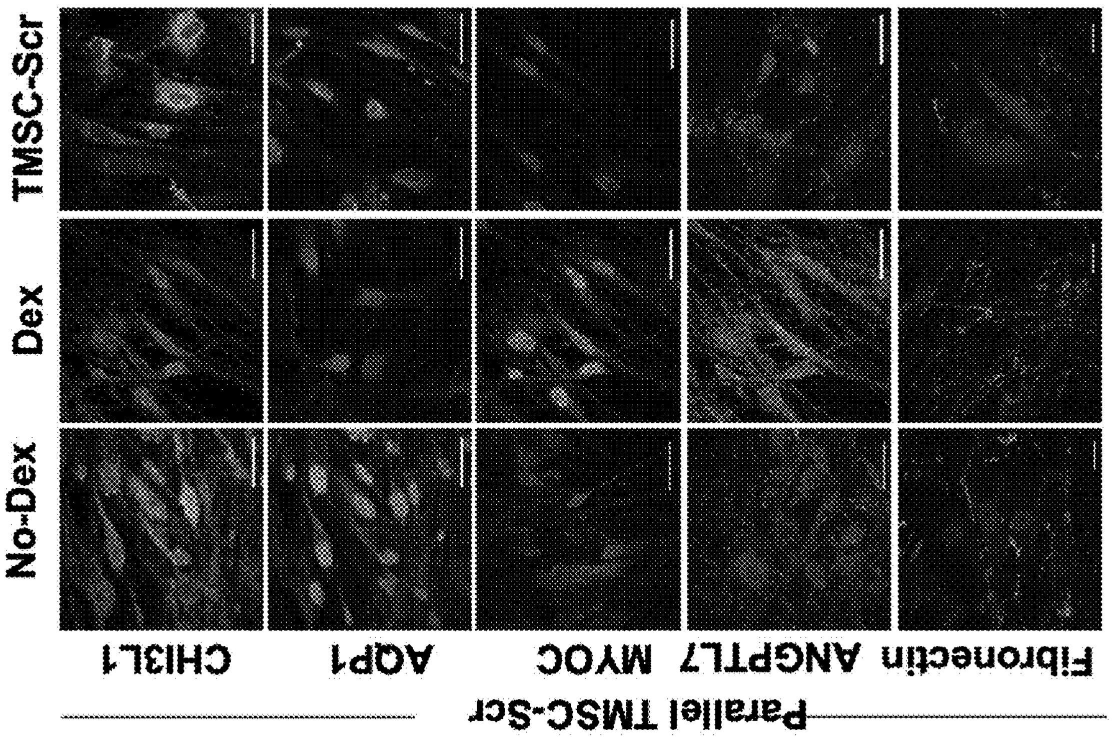
Figure 2C:
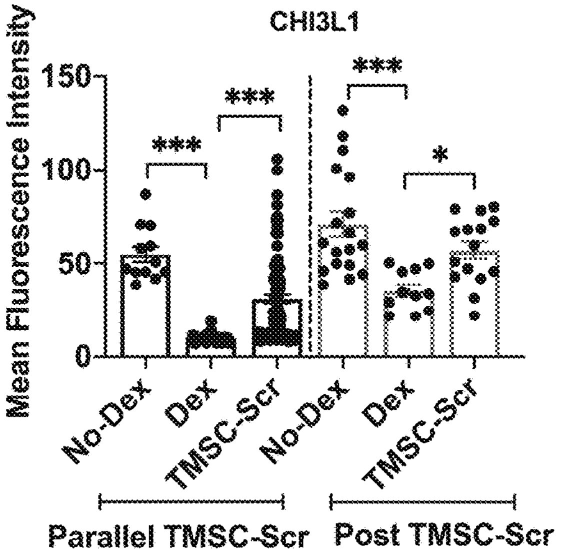
Figure 2D:
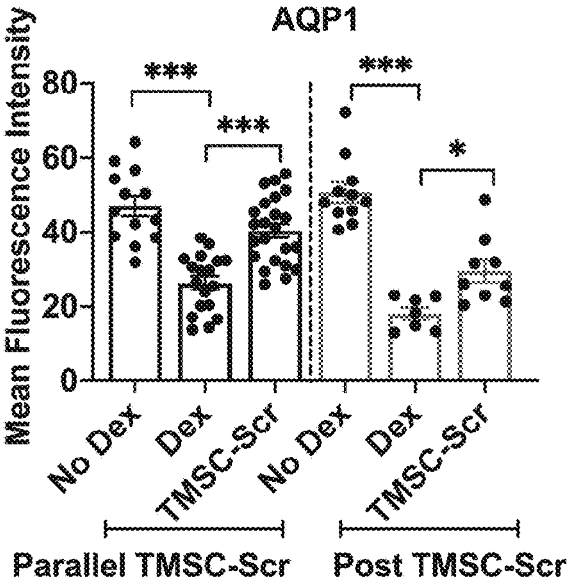
Figure 2E:
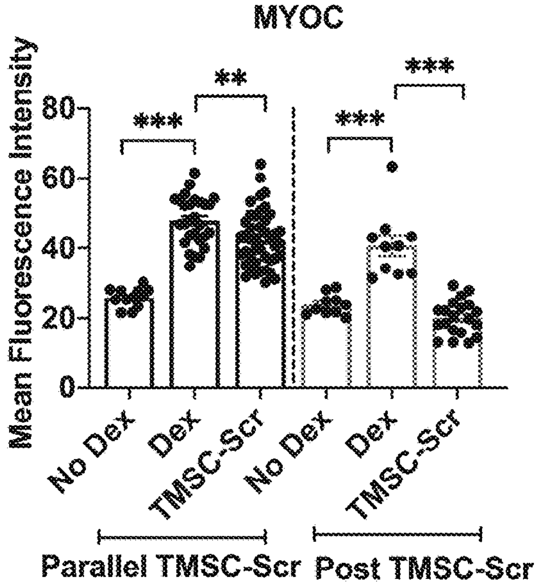
Figure 2F:
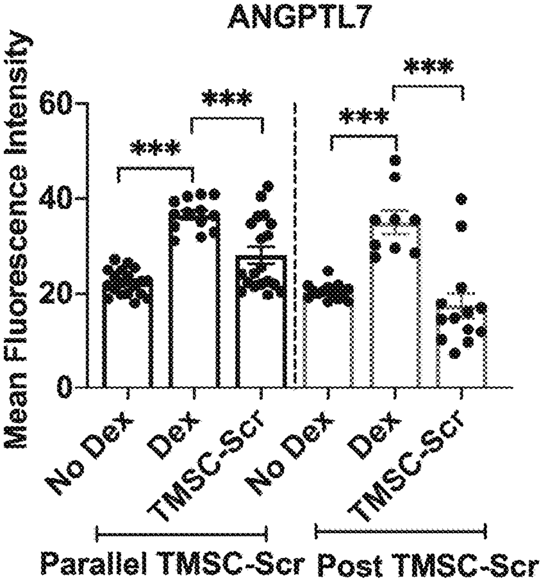
Figure 2G:
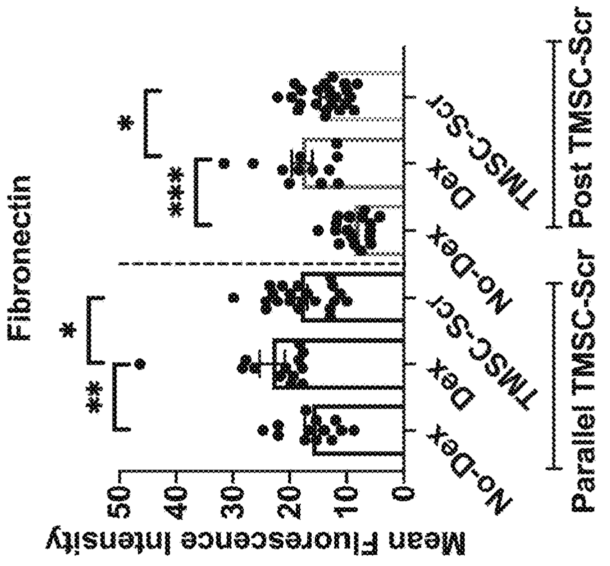
Figure 2H:
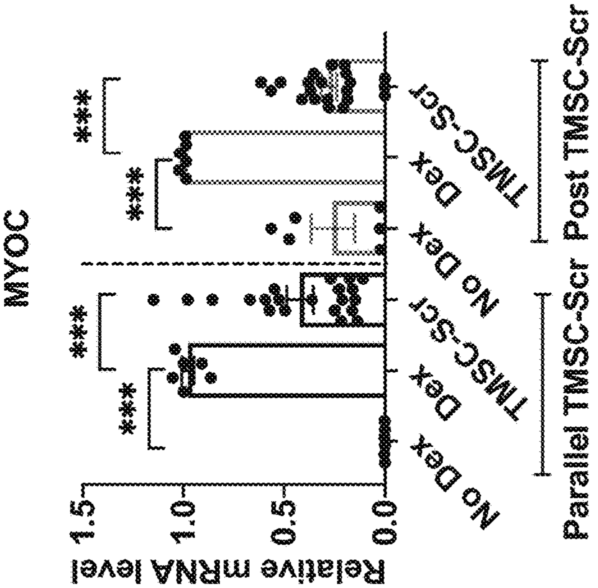
Figure 2I:
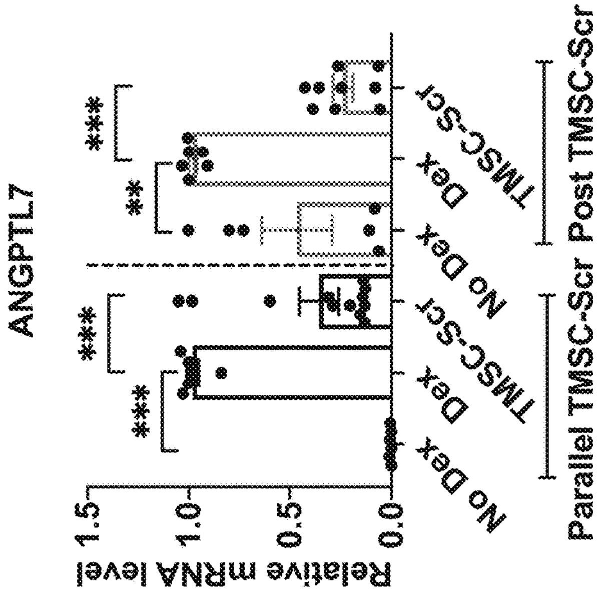

FIGS. 2A-2I provide images and graphs showing that the TMSC secretome induces regeneration in Dex-induced TM cells. FIGS. 2A-2B provides immunofluorescent pictures showing protein expression of CHI3L1, AQP1, Myoc, ANGPTL7, and fibronectin in the secretome derived from human TMSC (TMSC-Scr) treated cells in parallel and post to Dex induction. FIGS. 2C-2G provide bar diagrams showing quantification of mean fluorescent intensity of the staining in FIGS. 2A-2B. FIGS. 2H-2I provide bar diagrams showing relative mRNA expression of glaucoma-associated genes MYOC and ANGPTL7 comparing TMSC-Scr treated and untreated cells. Experiments were repeated with at least three primary TM cell strains with secretome used from four different TMSC strains. Multiple dots in bar graphs represent combined results of biological and technical replicates. The scale bar is 50 um for FIG. 2A), and the scale bar is 30 um for FIG. 2A-fibronectin and FIG. 2B), * represents that the p-value is less than 0.05.  represents that the p-value is less than 0.001. * represents that the p-value is less than 0.0001.

Figure 3A:
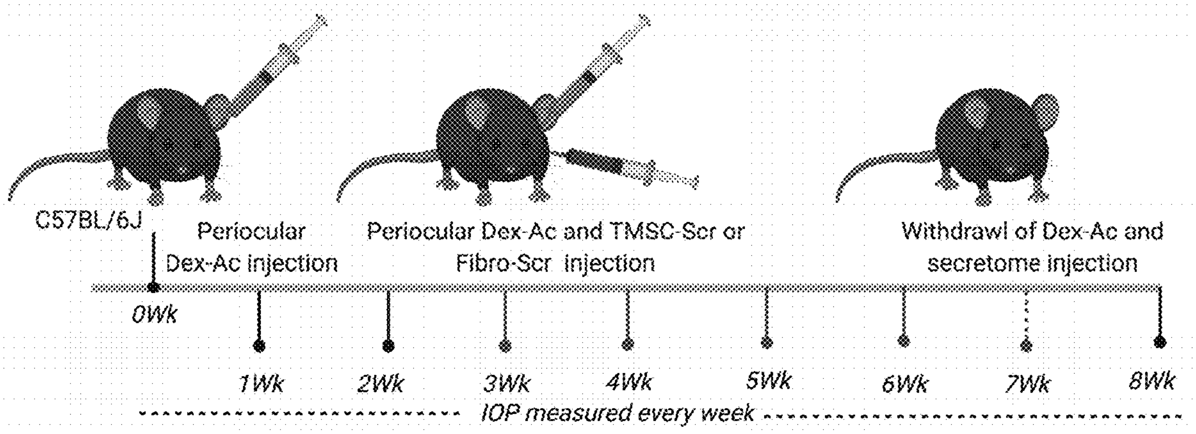
Figure 3B:
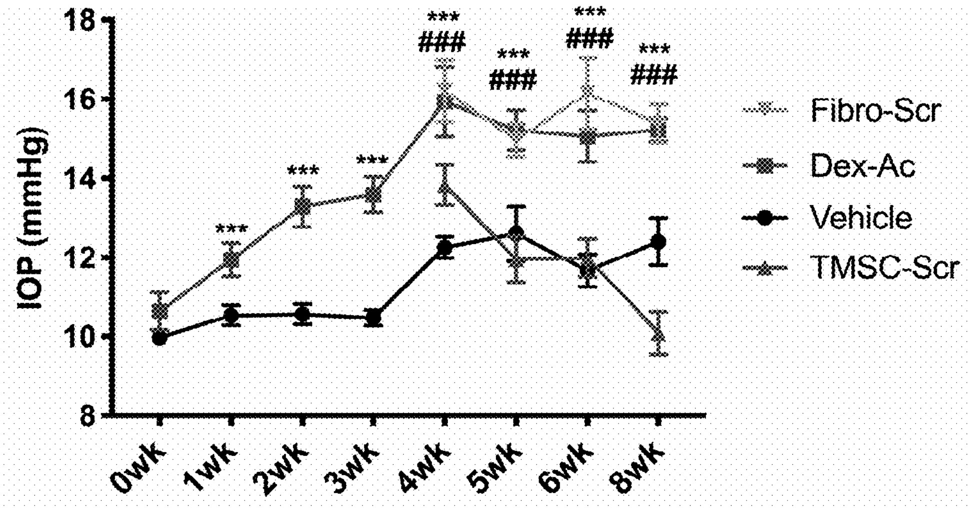
Figure 3C:
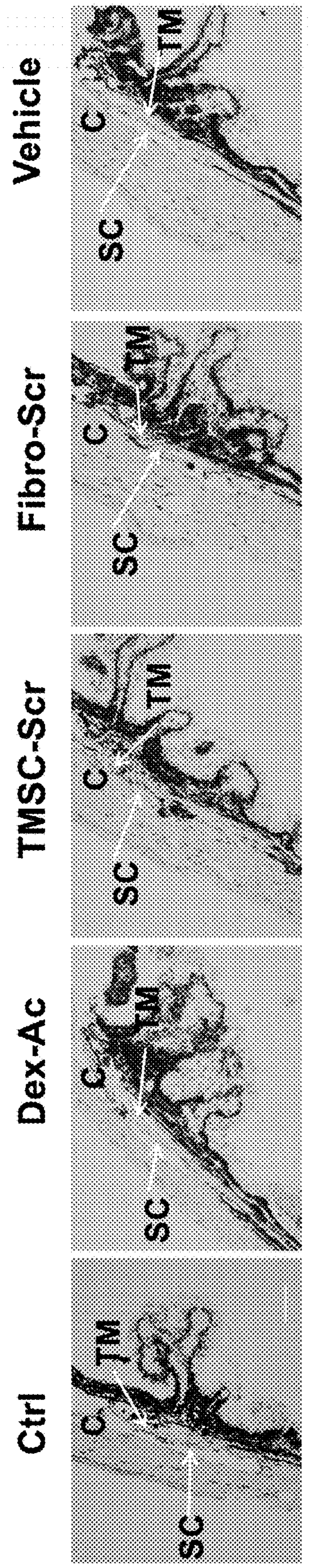
Figure 3D:
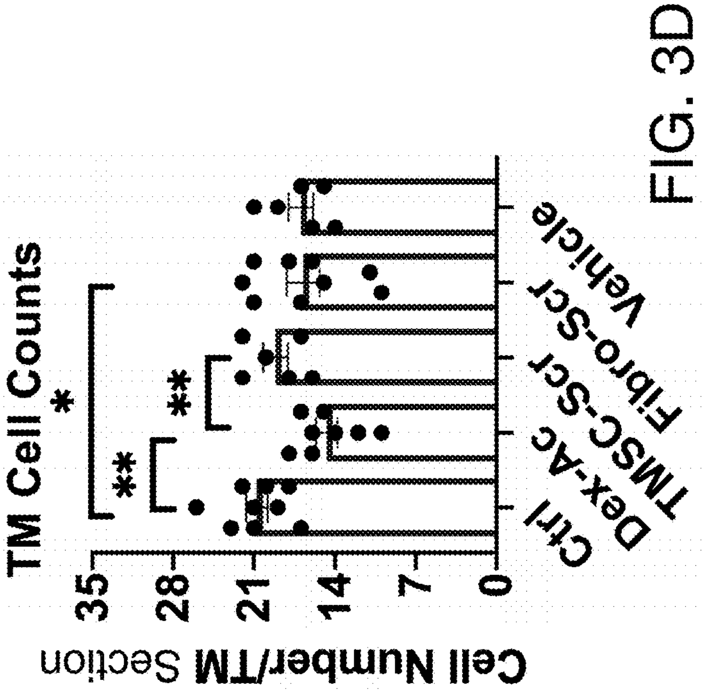
Figure 3E:
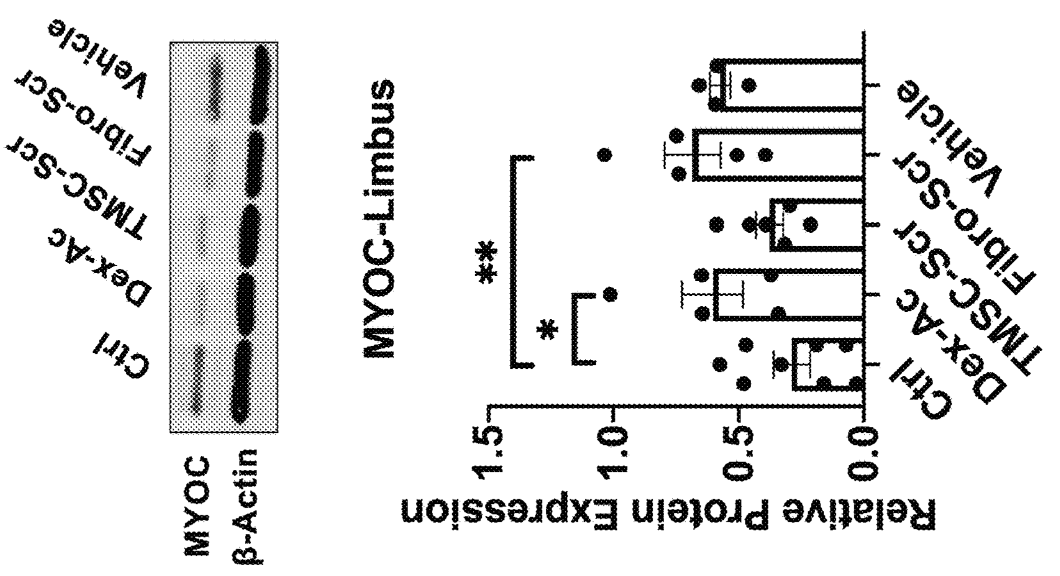
Figure 3F:
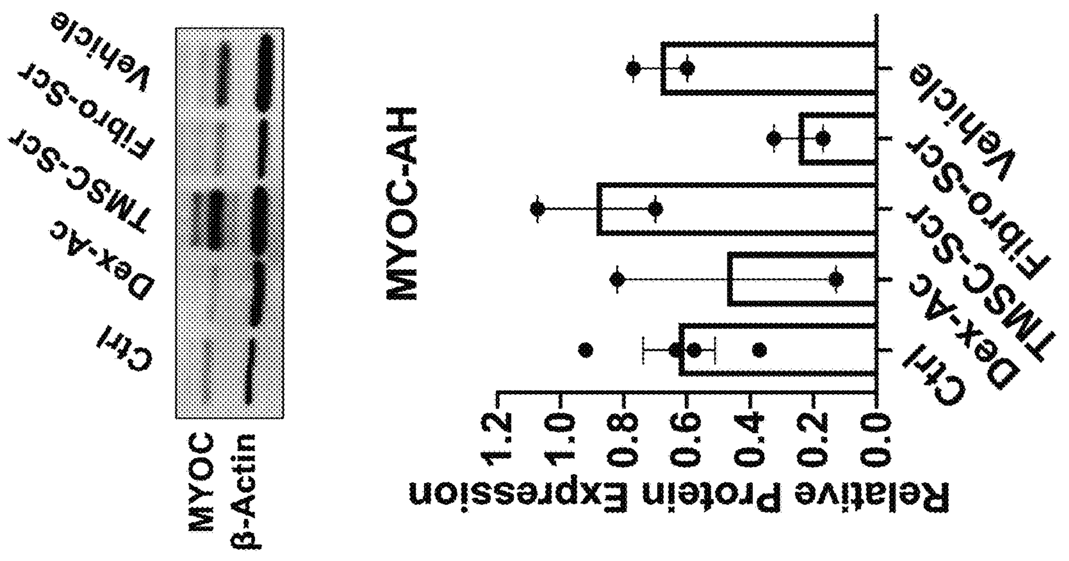
Figure 3G:
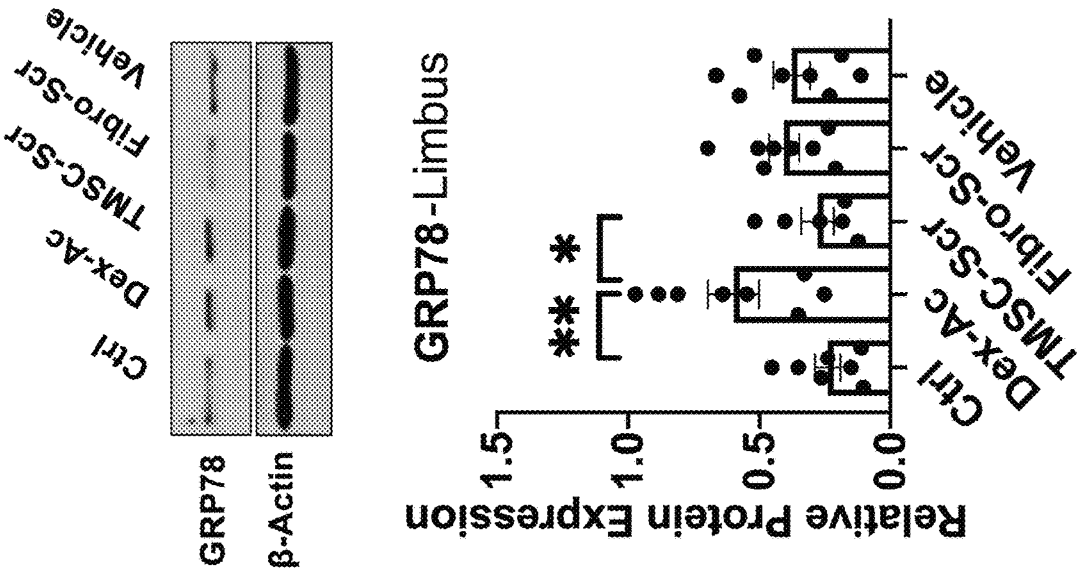
Figure 3H:
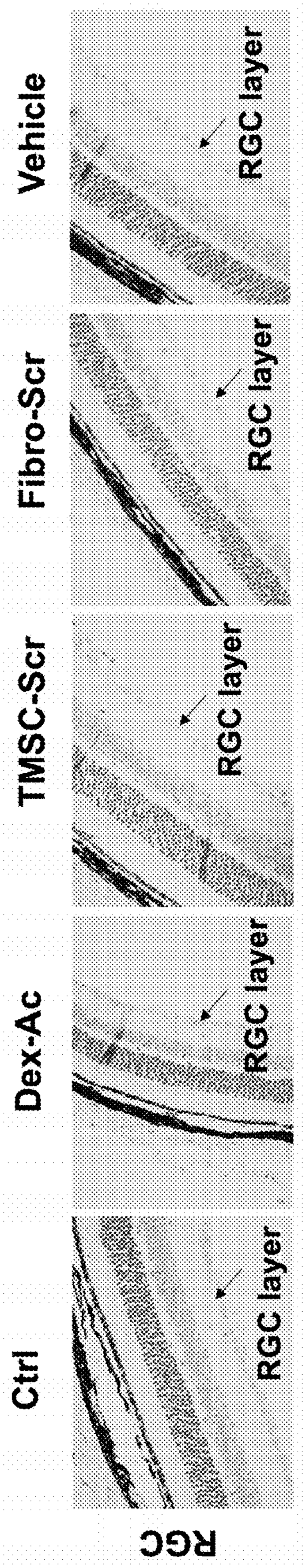
Figure 3I:
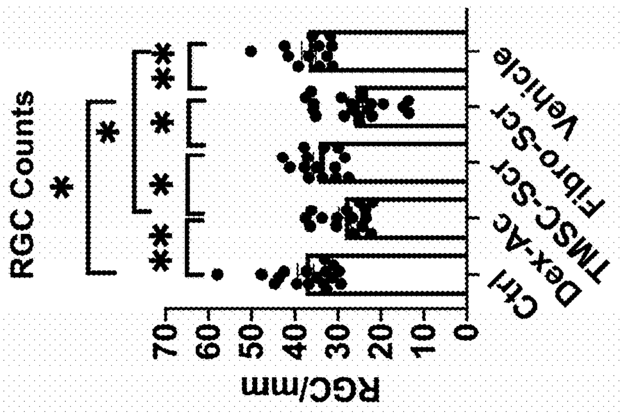

FIGS. 3A-3I provide graphs and images showing that the TMSC secretome reduces IOP, restores TM cellularity, and modulates myocilin in Dex-Ac mice. FIG. 3A provides schematic showing procedures for Dex-Ac and secretome treatment in Dex-Ac induced mouse model. FIG. 3B provides a graph showing IOP dynamics in Dex-Ac induced model showing higher IOP in Dex-Ac and fibro-Scr treated animals while treatment with TMSC-Scr reduced the IOP to the normal level. * represents the comparison between vehicle and Dex-Ac mice. # represents the comparison between Dex-Ac and TMSC-Scr treated mice (n=10-21). ***/### represents that the p-value is less than 0.001. FIG. 3C provides DIC monocolor images showing anterior angle structure in Dex-Ac mice. FIG. 3D provides bar diagrams showing quantification of TM cell number in Dex-Ac mice (n=3-4). FIGS. 3E-3F provide immunoblotting bands and bar diagram showing protein expression and quantification for Myoc in the limbus tissue and aqueous humor, respectively. FIG. 3G provides images and graphs showing immunoblotting expression and quantification of GRP78 in limbus tissue, limbus (n=4), AH (n=2). FIG. 3H provides DIC monocolor images showing the retinal ganglion cells (RGC) layer in Dex-Ac mice. FIG. 3I provides bar diagrams showing quantification of RGC number (n=3-4). Multiple dots in bar graphs represent combined results of biological and technical replicates. The scale bar is 100 um. * represents that the p-value is less than 0.05. ** represents that the p-value is less than 0.01.

Figure 4A:
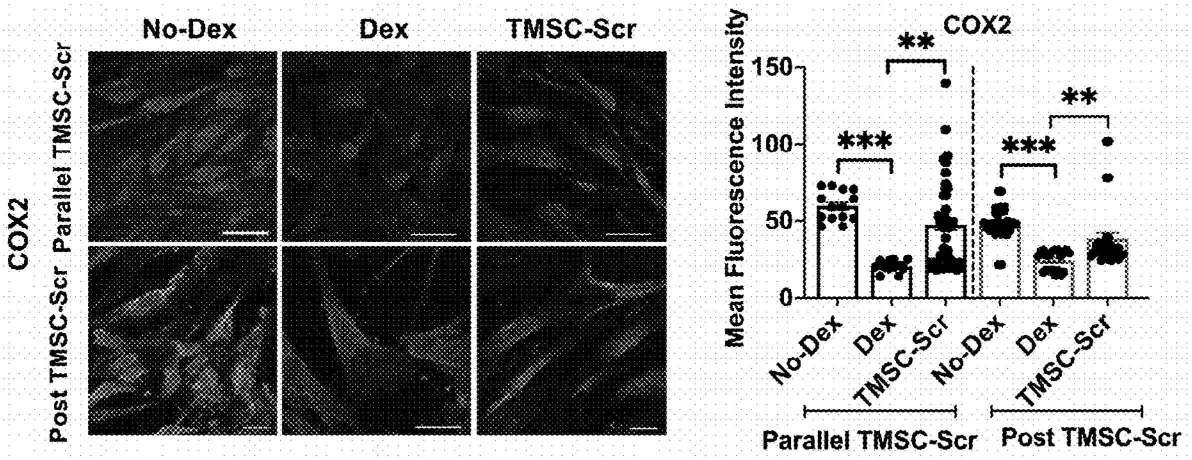
Figure 4B:
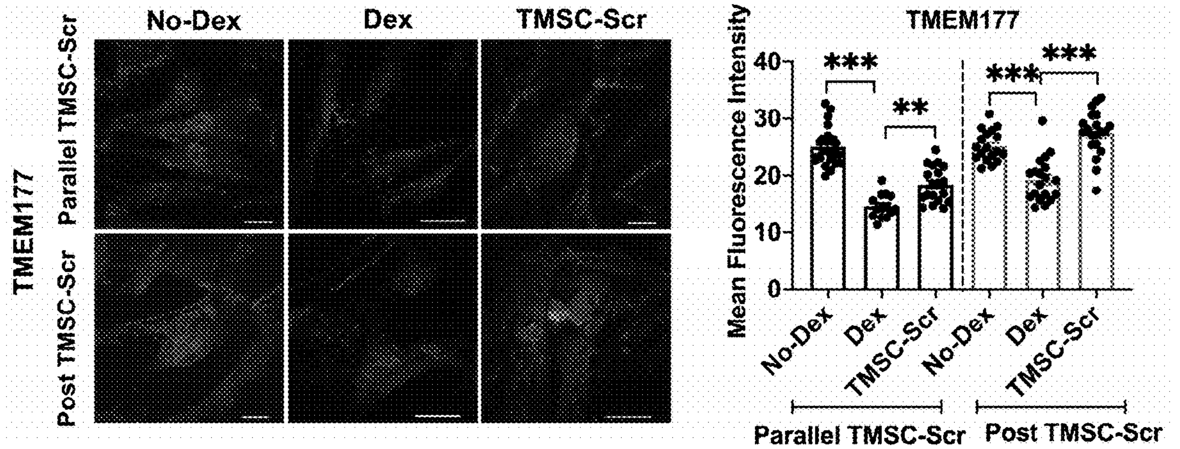
Figure 4C:
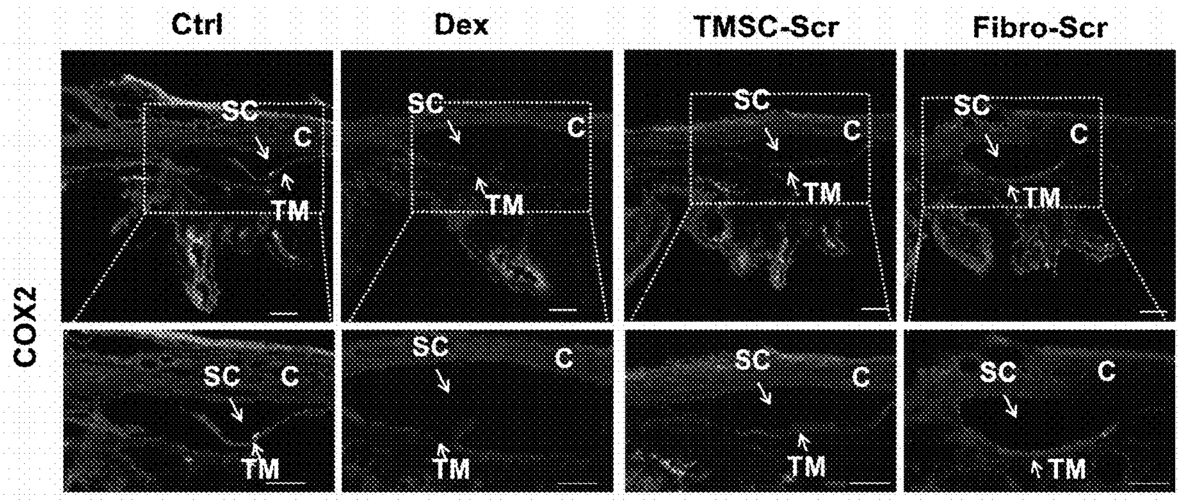
Figure 4E:
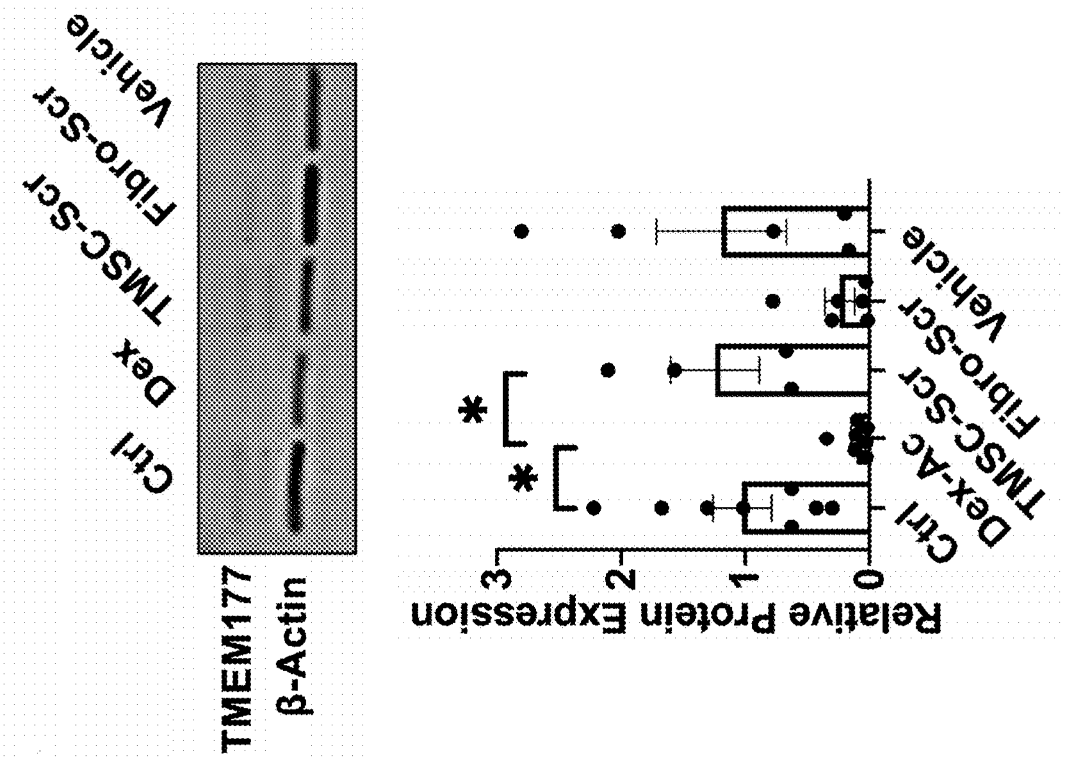
Figure 4D:
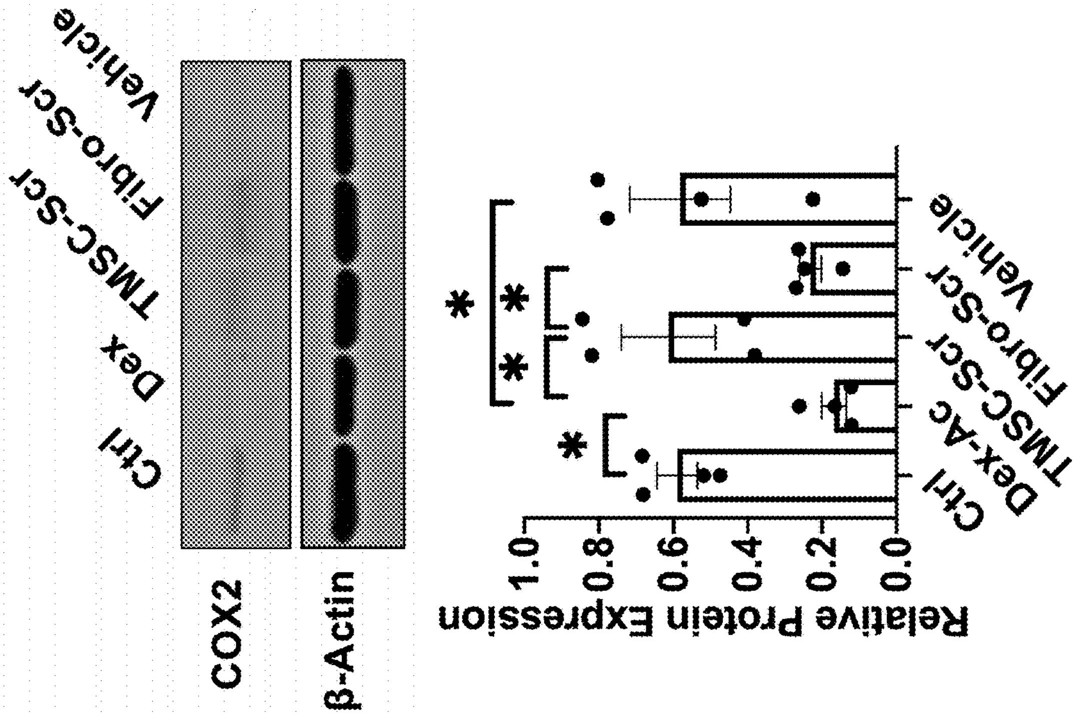
Figure 4F:
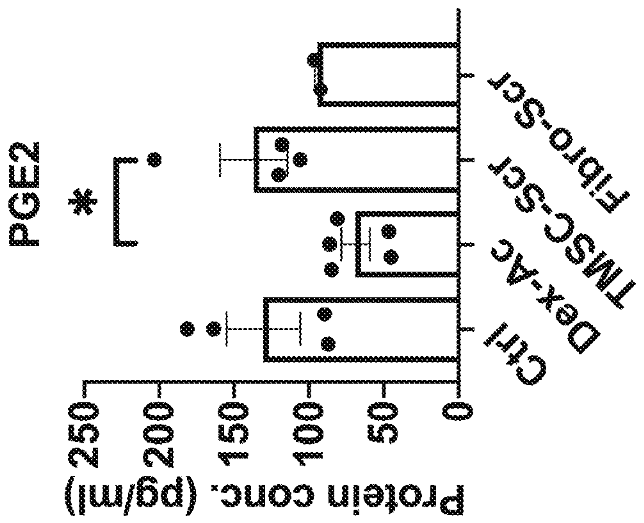
Figure 4G:
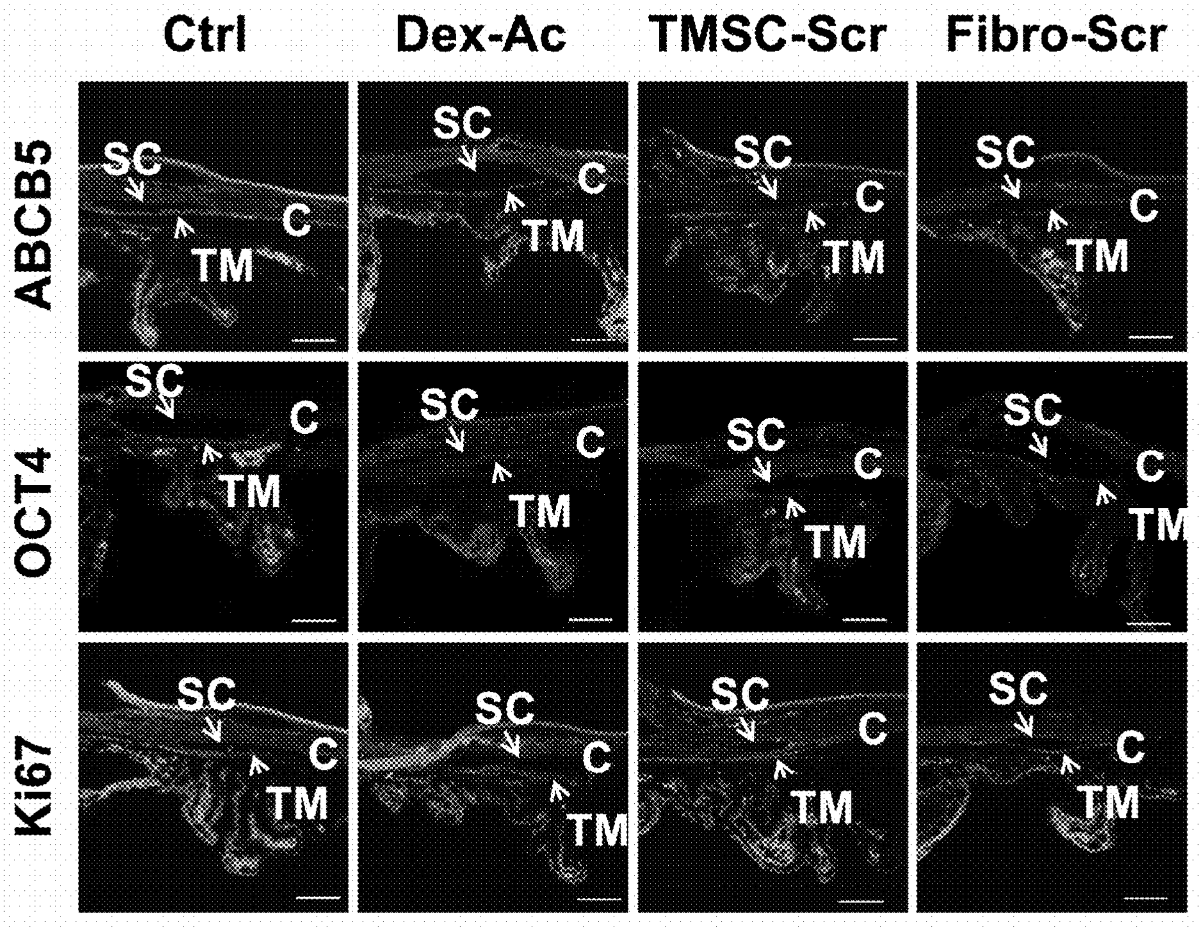
Figure 4H:
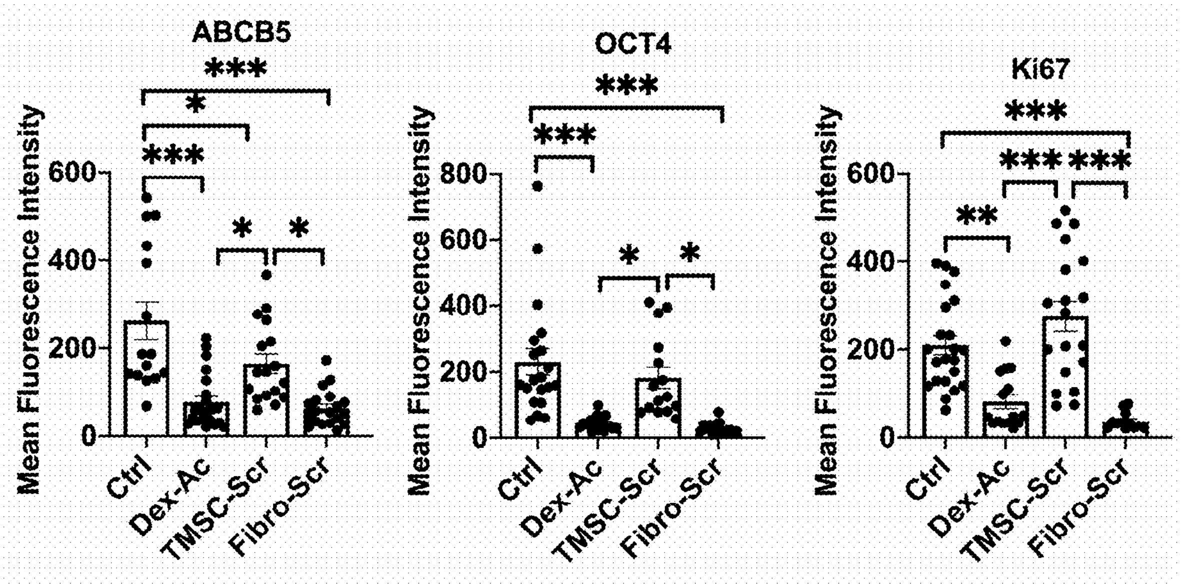

FIGS. 4A-4H provide images and graphs showing that TMSC secretome modulates COX2-PGE2 signaling in Dex-Ac mice. FIG. 4A provides images and graphs showing immunofluorescent staining and quantification of COX2 in TMSC-Scr (four different TMSC-Scr) treated cells (three different TM cell strains) in parallel and post-Dex induction. Multiple dots in bar graphs represent combined results of biological and technical replicates. FIG. 4B provides images and graphs showing protein expression profile that illustrates immunofluorescent staining and quantification of TMEM177 in secretome treated cells in parallel and post Dex induction. FIG. 4C provides immunofluorescent images showing protein expression of COX2 in limbus tissue of Dex-Ac mice. FIGS. 4D-4E provide immunoblotting images and graphs showing protein expression profile and quantification of COX2 and TMEM177 in limbus tissue (n=4). Multiple dots in bar graphs represent combined results of biological and technical replicates. FIG. 4F provides bar diagrams showing levels of PGE2 in aqueous humor secreted in different treatment groups of Dex-Ac mice (n=4-6). FIGS. 4G-4H provide immunofluorescent images and bar graphs showing protein expression and quantification of ABCB5, OCT4, and Ki67 in Dex-Ac mice (n=3). Multiple dots on the bar graph indicates fluorescence intensity values measured from at least 3-16 different limbus sections of the eye. The scale bar is 50 um. * represent that the p-value is less than 0.05.  represents that the p-value is less than 0.001. * represents that the p-value is less than 0.0001.

Figure 5A:
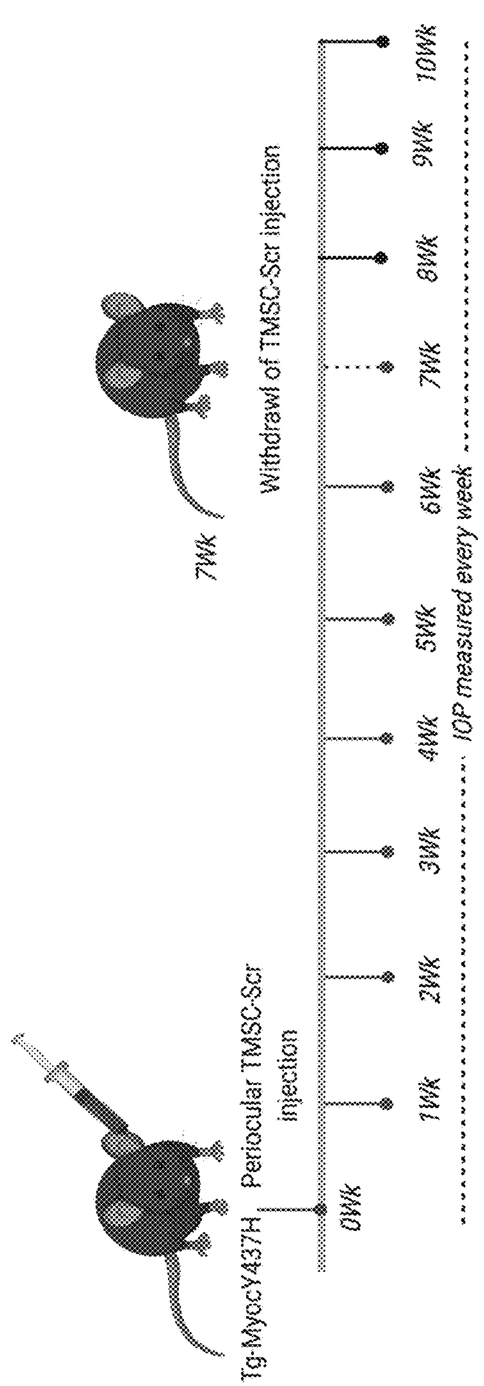
Figure 5B:
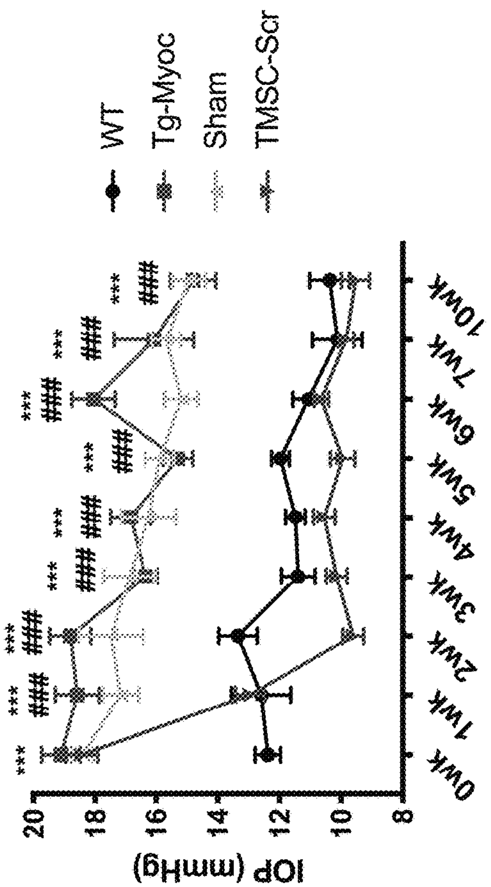
Figure 5C:
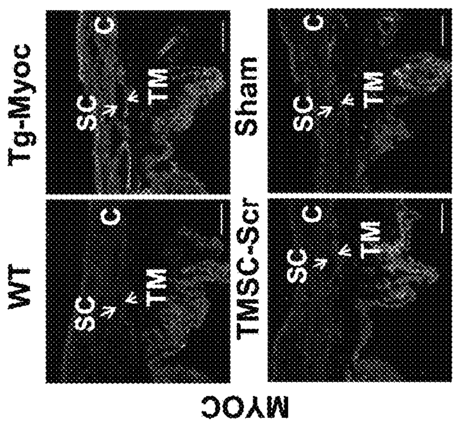
Figure 5F:
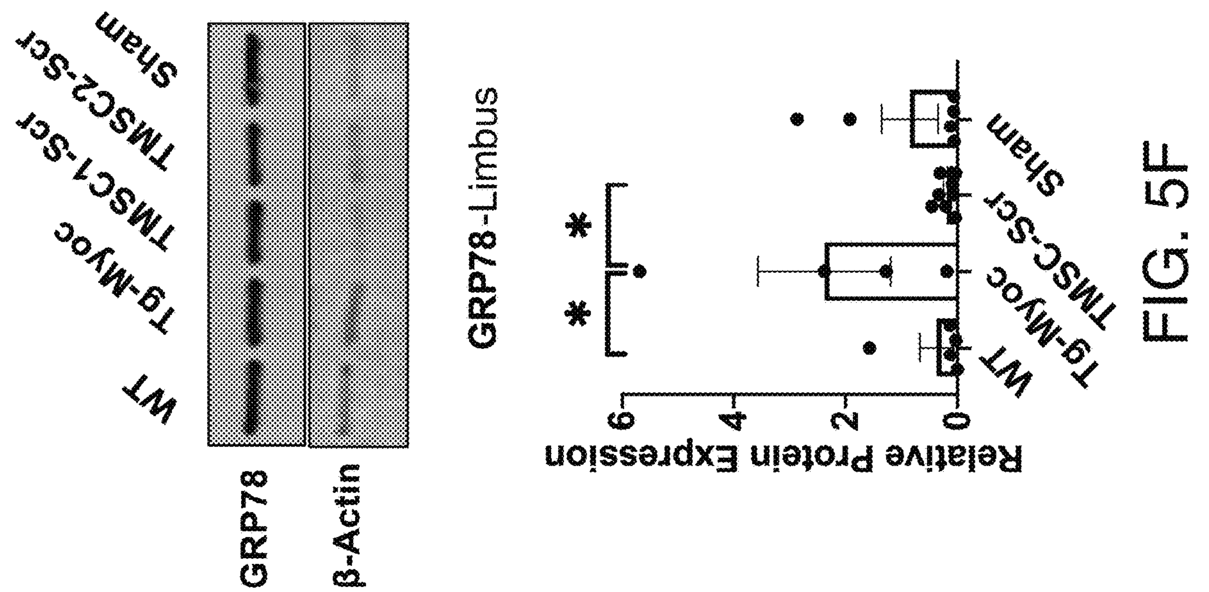
Figure 5E:
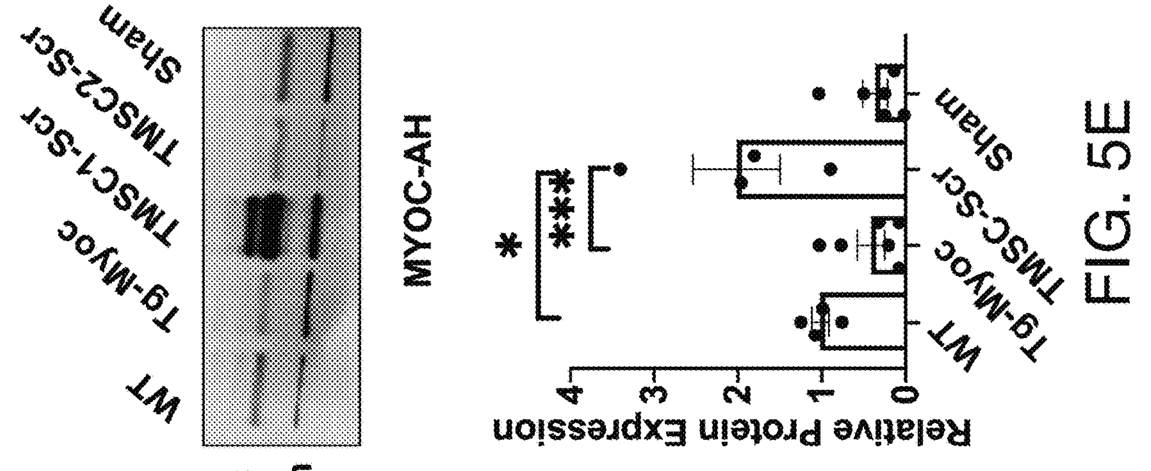
Figure 5D:
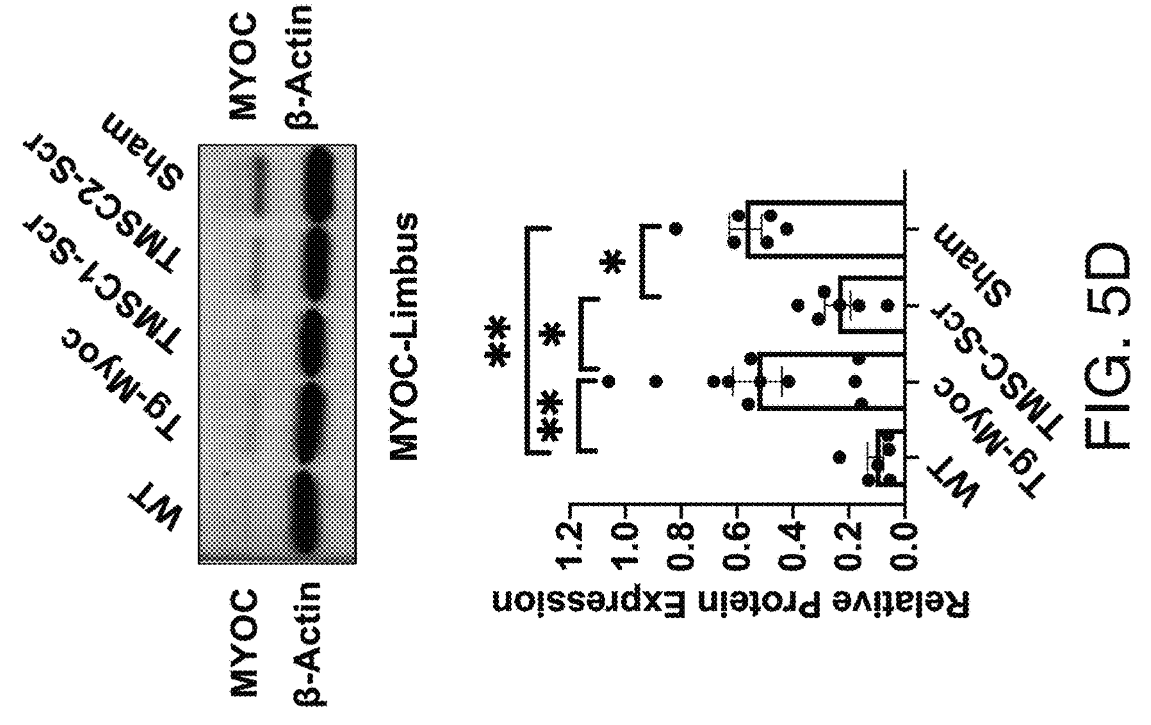
Figure 5G:
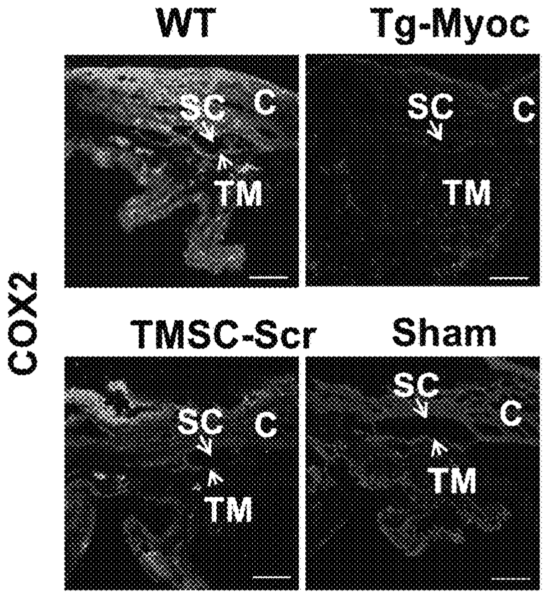
Figure 5H:
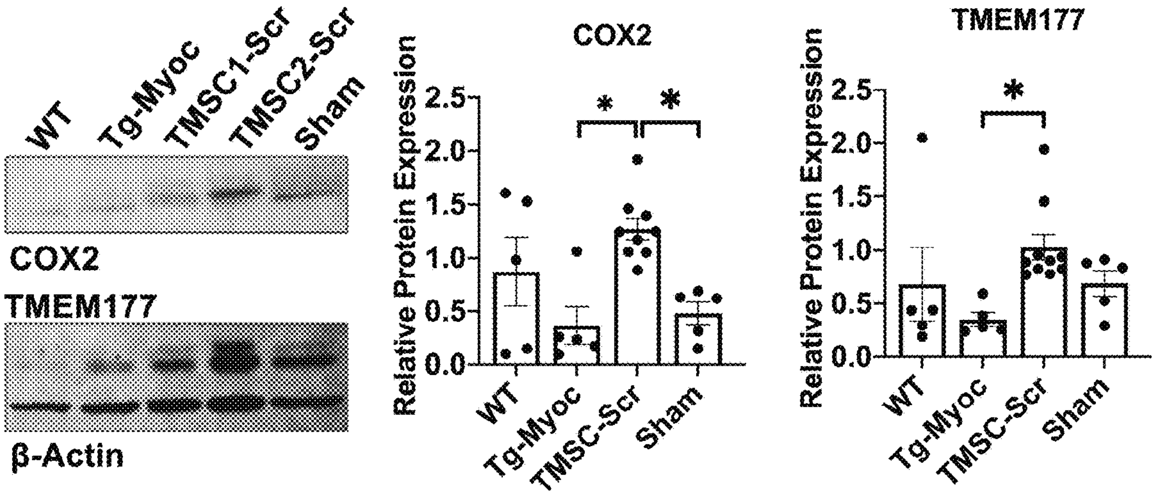
Figure 5I:
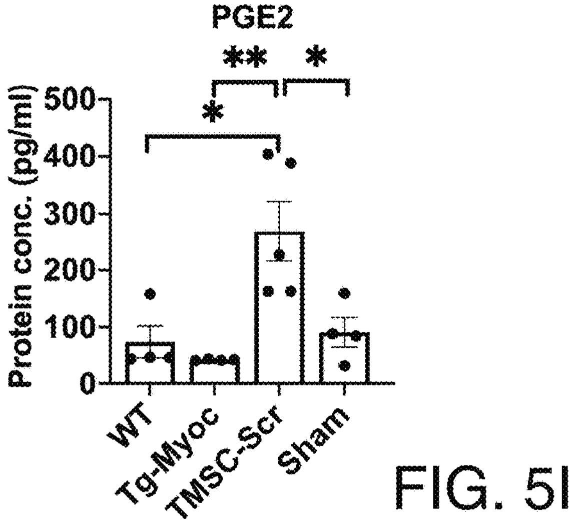
Figure 5J:
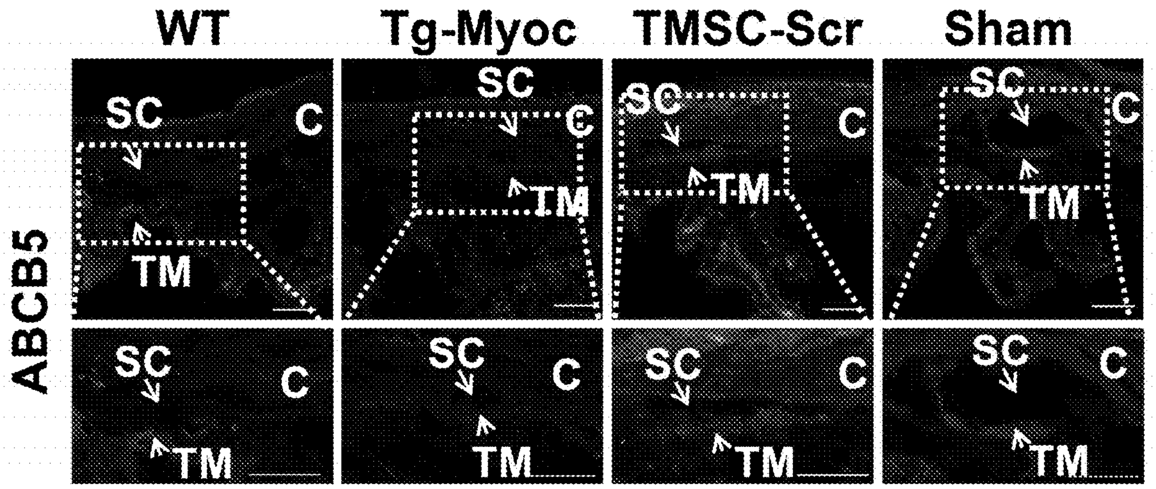
Figure 5K:
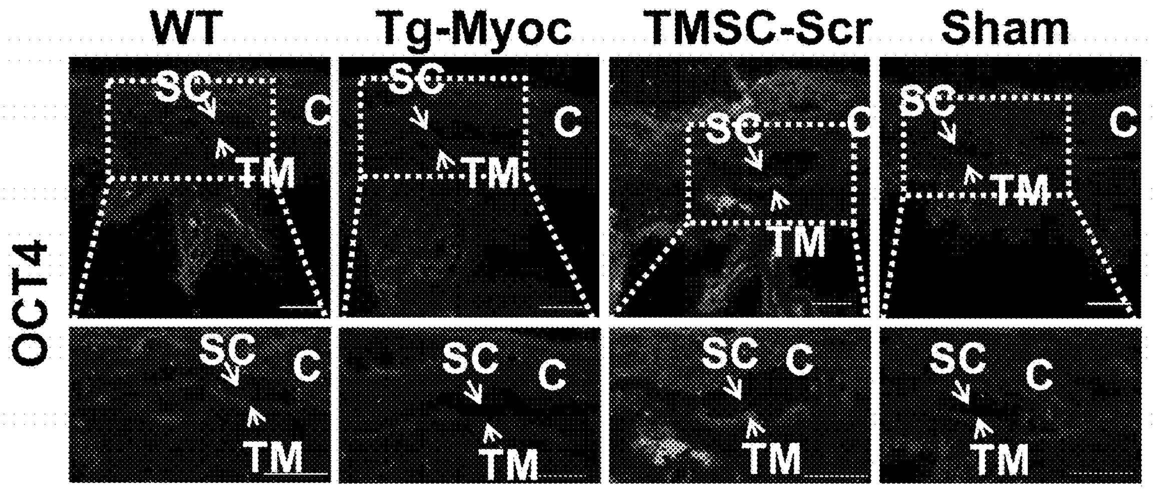
Figure 5L:
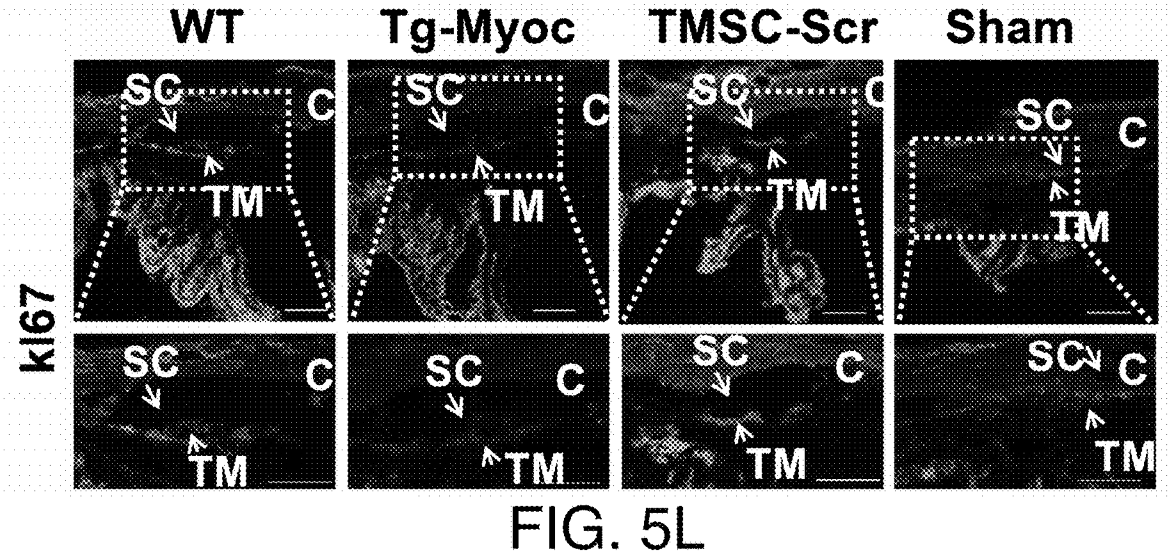
Figure 5M:
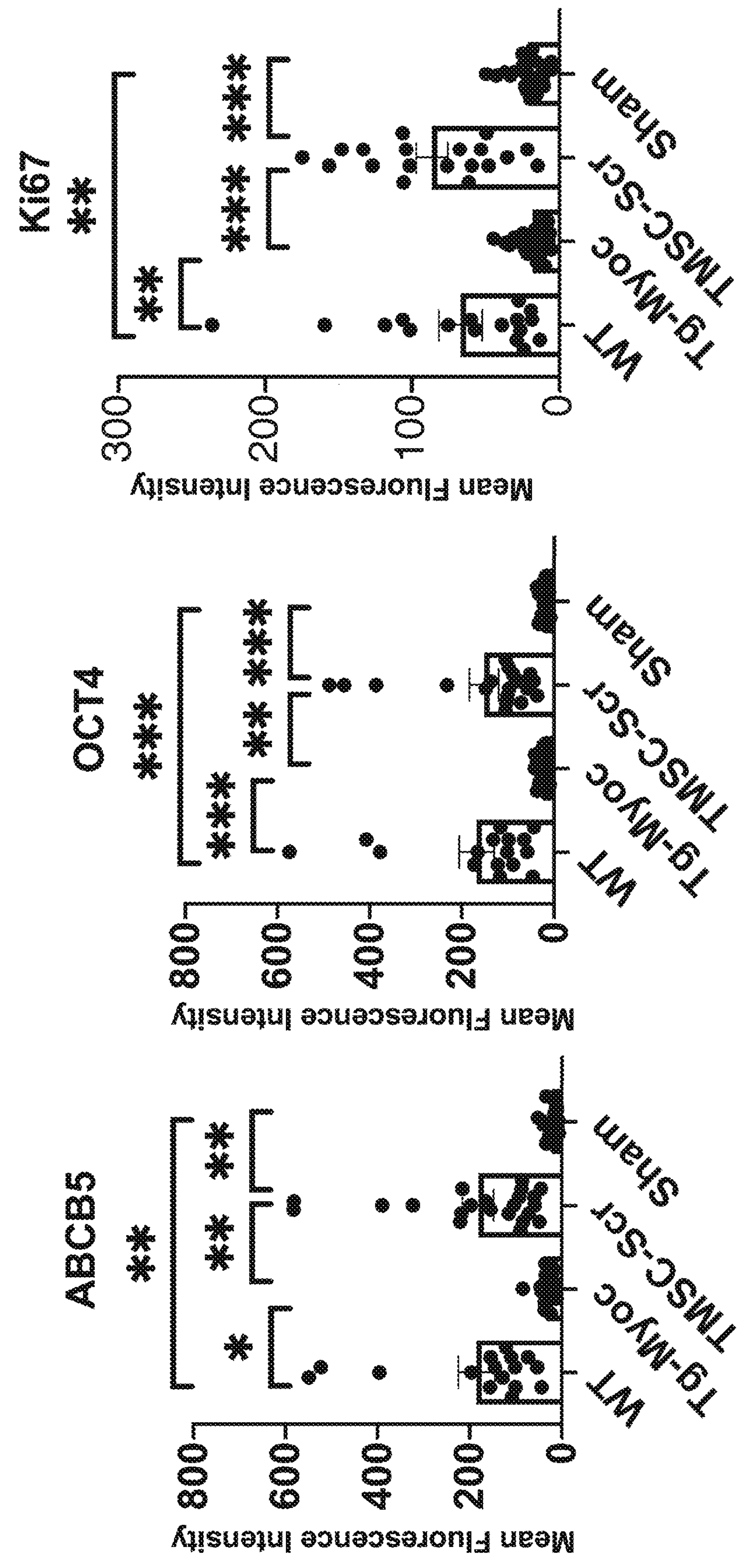

FIGS. 5A-5M provide images and graphs showing that the TMSC secretome reduces the intraocular pressure (IOP), restores TM homeostasis, and modulates COX2-PGE2 signaling in Tg-MyocY437H mice. FIG. 5A provides schematics showing the procedure followed for TMSC-Scr treatment in Tg-Myocy437H mice. FIG. 5B provides IOP level graphs in Tg-MyocY437H mice showing IOP reduction by TMSC-Scr while no effect on sham-treated Tg-MyocY437H mice. * represents the comparison between WT and Tg-MyocY437H mice. # represents the comparison between Tg-MyocY437H and TMSC-Scr treated mice (n=10-32). ***/### represent that the p-value is less than 0.001. FIG. 5C provides immunofluorescent images showing protein expression of MYOC in limbus tissue of Tg-MyocY437H mice. FIG. 5D provides immunoblotting bands showing protein expression for Myoc in limbus tissue and aqueous humor and that of GRP78 in limbus tissue of different treatment groups in Tg-MyocY437H mice. FIGS. 5D-5F provide immunoblotting images and graphs showing protein expression and quantification of Myoc in limbus tissue and aqueous humor, respectively, and that of GRP78 in limbus of different treatment groups in Tg-MyocY437H mice, respectively, limbus (n=4). Multiple dots in bar graphs represent combined results of biological and technical replicates (n=4-6). FIG. 5G provides immunofluorescent images showing protein expression of COX2 in limbus tissue of Tg-MyocY437H mice. SC represents the Schlemm's canal. FIG. 5H provides immunoblotting images showing protein expression and quantification profile of COX2 and TMEM177 in limbus tissue (n=4). Multiple dots in bar graphs represent combined results of biological and technical replicates. FIG. 5I provides bar diagrams showing levels of PGE2 in aqueous humor secreted in different treatment groups of Tg-MyocY437H mice (n=4-6). FIGS. 5J-5M provide immunofluorescent images and bar graphs showing protein expression and quantification of ABCB5, OCT4, and Ki67. The scale bar is 50 um. Dots represent MFI quantified in multiple sections (4-16 limbus sections) per eye. * represents that the p-value is less than 0.05,  represents that the p-value is less than 0.001. * represents that the p-value is less than 0.0001.

Figure 6A:
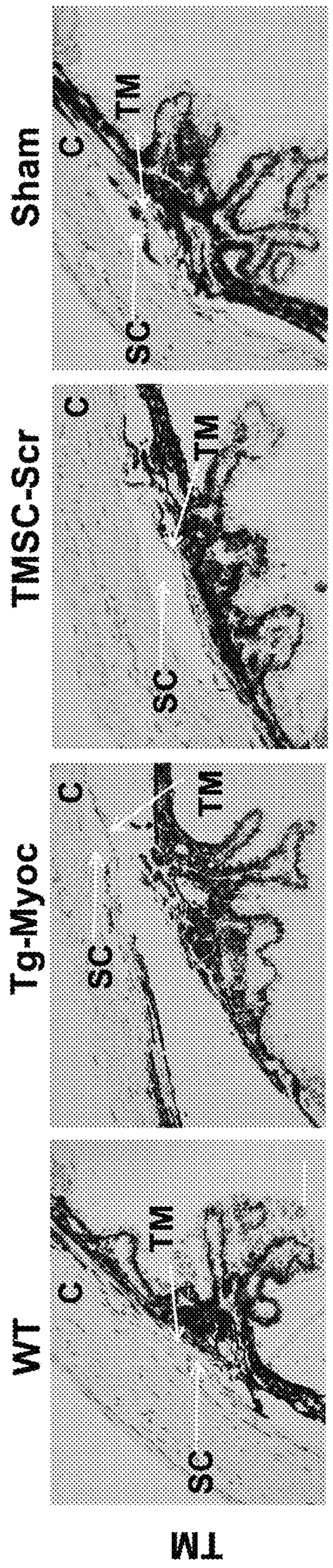
Figure 6B:
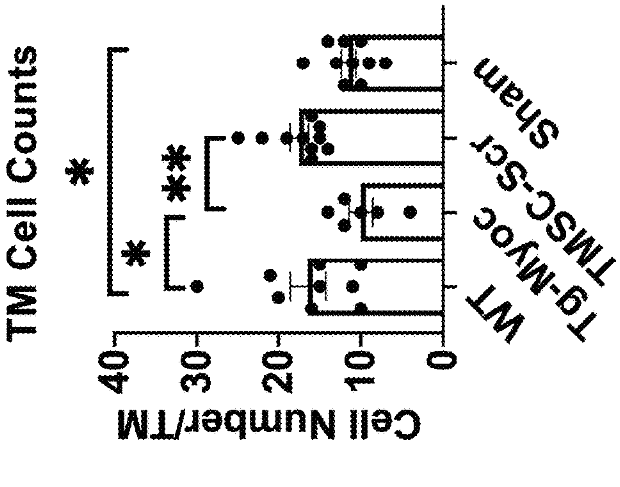
Figure 6C:
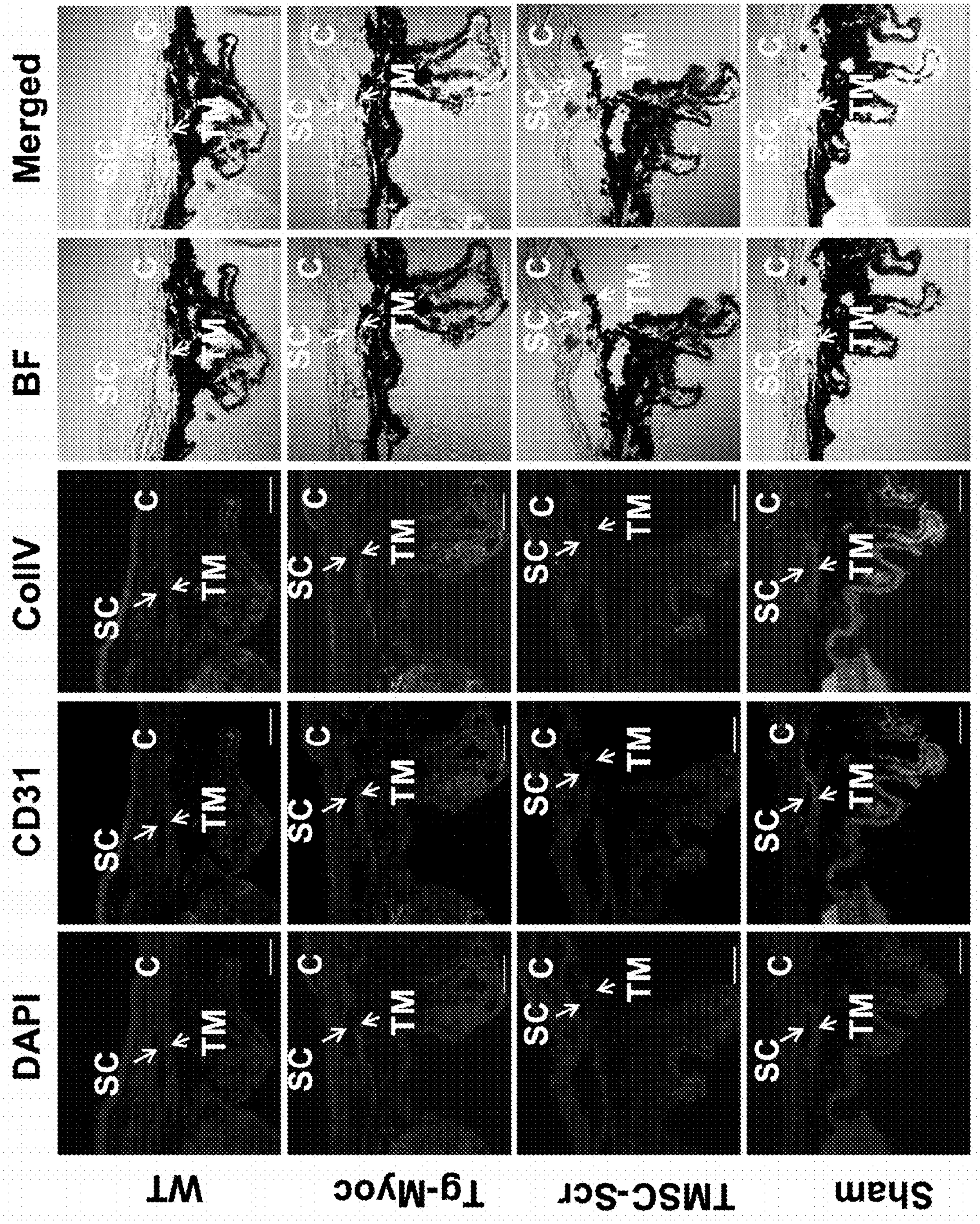
Figure 6D:
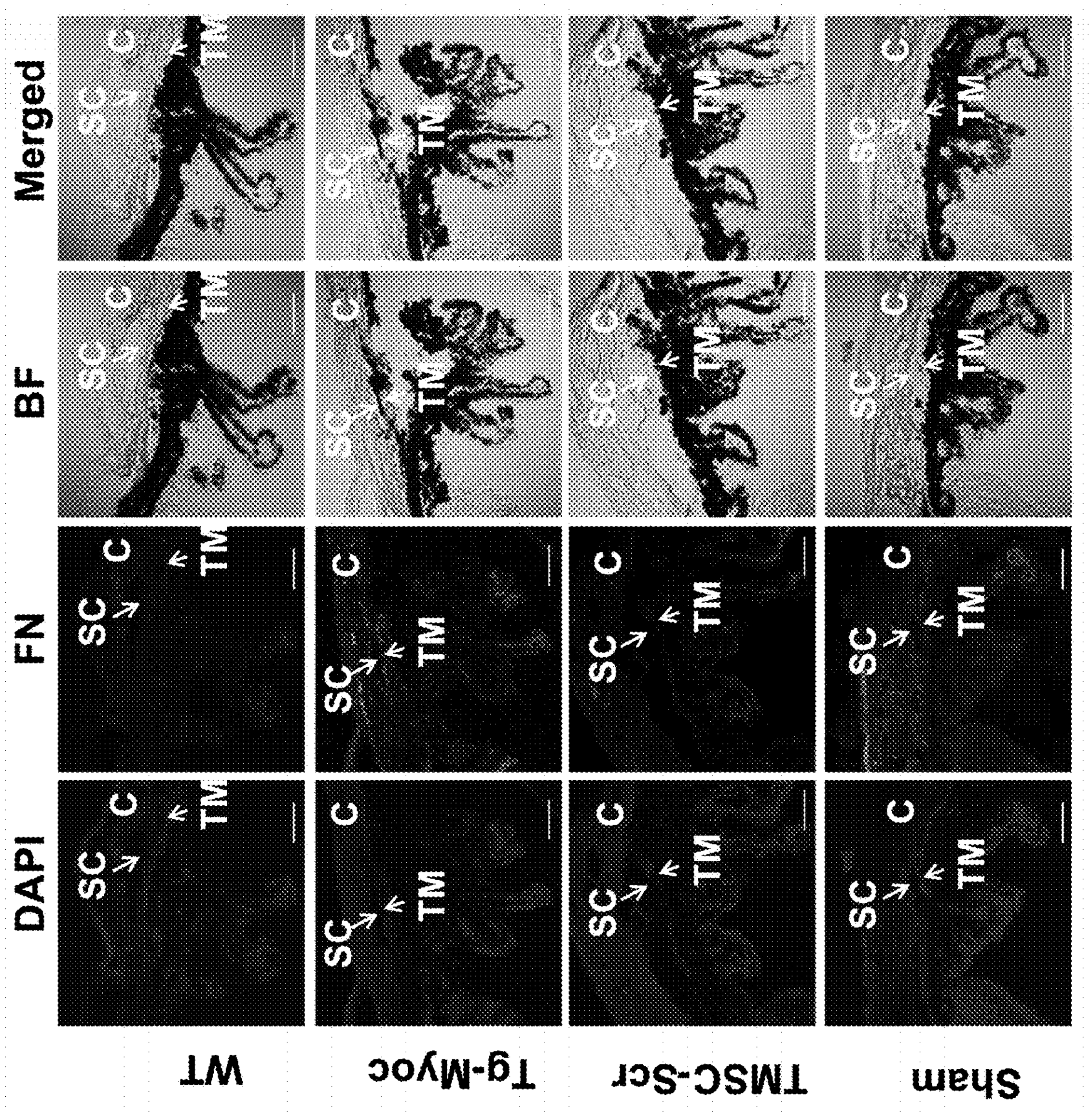

FIGS. 6A-6D provide images and graphs showing that the TMSC secretome modulates myocilin and ECM in Tg-MyocY437H. FIG. 6A provides DIC monocolor images showing TM cells in trabecular meshwork in Tg-MyocY437H mice. The scale bar is 100 um. FIG. 6B provides bar diagrams showing quantification of TM cell number in Tg-MyocY437H mice (n=3-4). FIG. 6C provides immunofluorescent images showing protein expression of CD31 and ColV in Tg-MyocY437H mice. FIG. 6D provides immunofluorescent images showing expression patterns of FN in Tg-MyocY437H mice. Scale bar is 30 um. * represents that the p-value is less than 0.05.  represents that the p-value is less than 0.01. * represents that the p-value is less than 0.0001.

Figure 7A:
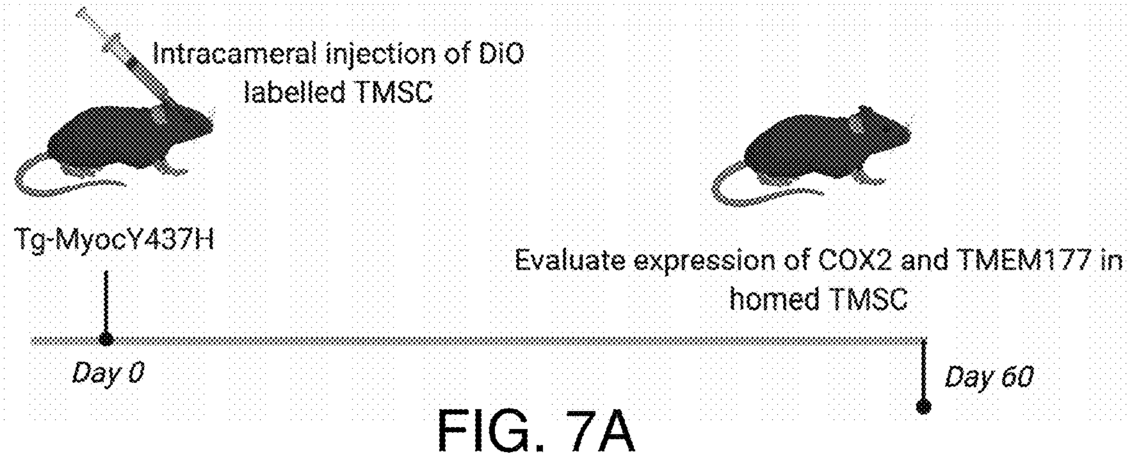
Figure 7B:
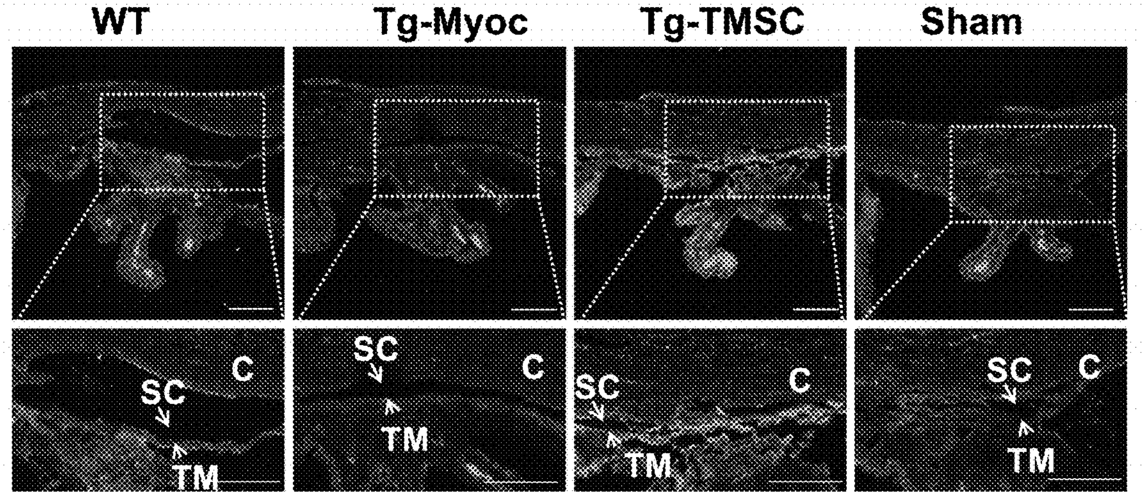
Figure 7C:
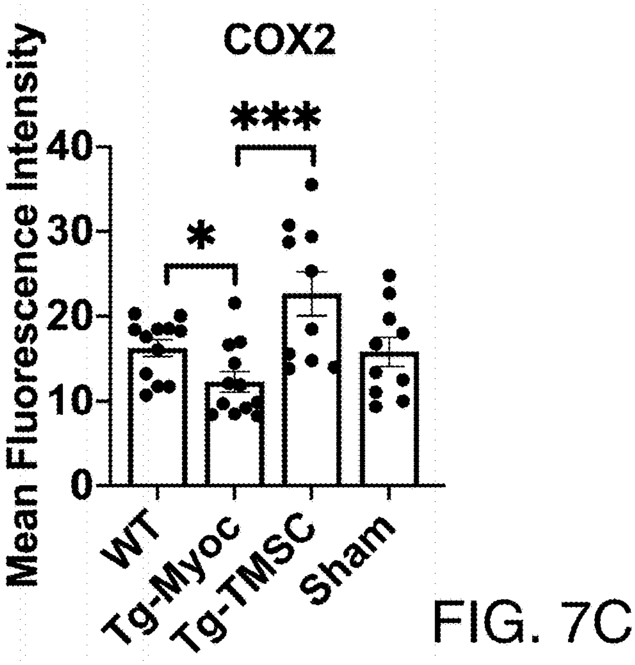
Figure 7D:
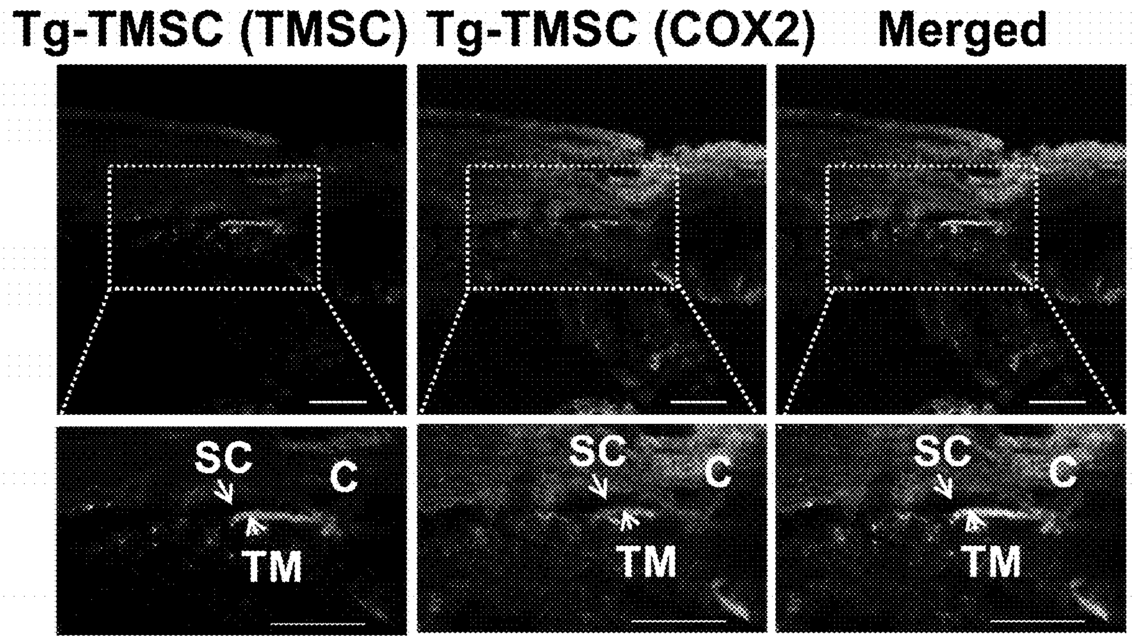
Figure 7E:
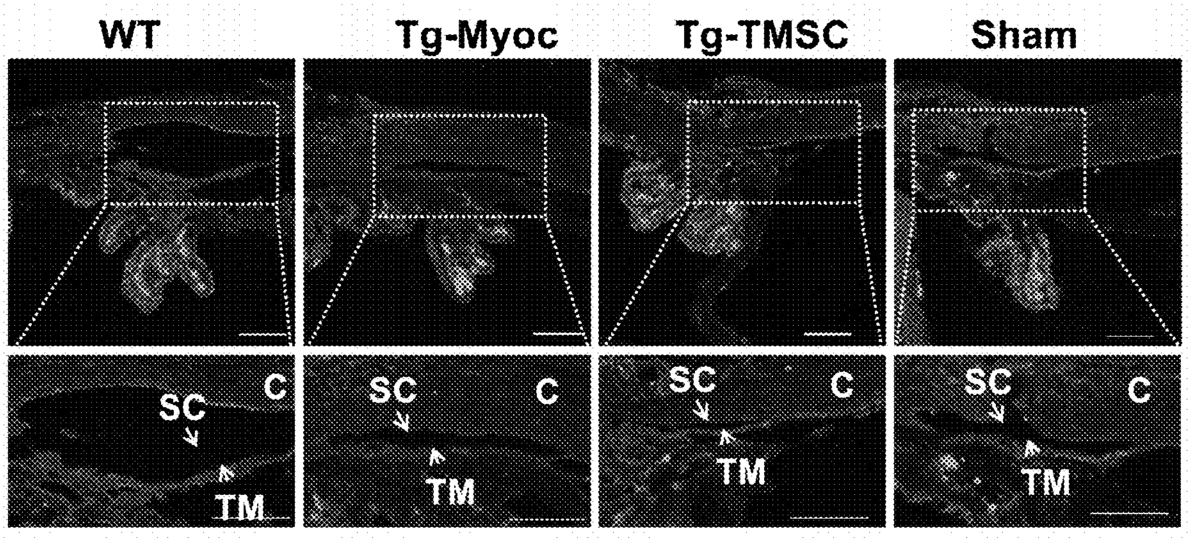
Figure 7G:
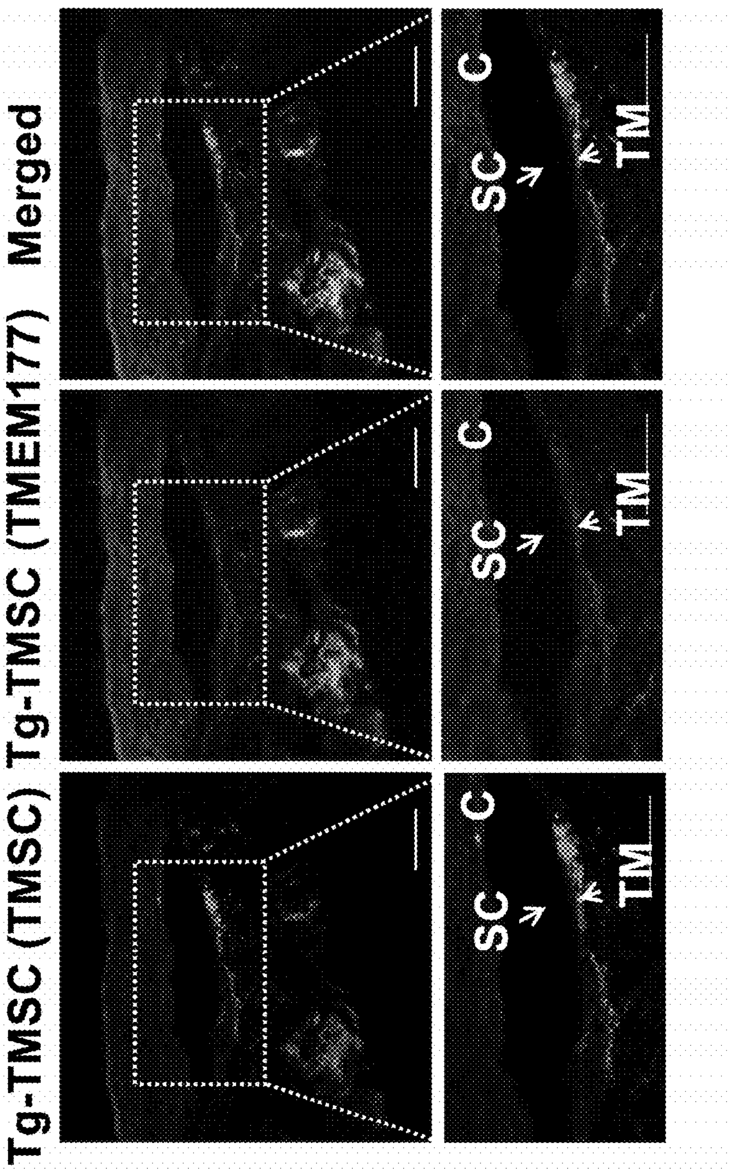
Figure 7F:
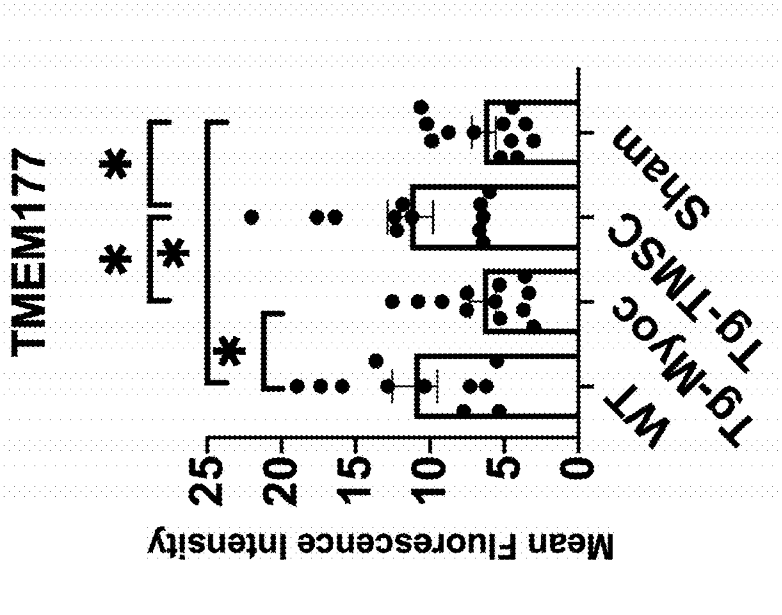

FIGS. 7A-7G provide images and graphs showing that TMSC transplantation actuates COX2 and TMEM177 expression. FIG. 7A provides schematics for the protocol followed for evaluating the effect of TMSC transplantation on Tg-MyocY437H mice. $5\times10^4$ TMSC were transplanted per eye intracamerally in Tg-MyocY437H mice and evaluated after two months for their homing in potential in damaged TM and the expression of TMEM177 and COX2. FIGS. 7B-7C provide immunofluorescent staining images and quantification data showing reduced expression of COX2 in Tg-MyocY437H mice as compared to control, which was increased after TMSC transplantation. FIG. 7D provides images showing transplanted TMSC home to TM region and expressed COX2 in Tg-MyocY437H model. FIGS. 7E-7F provide immunofluorescent staining and quantification data showing restored expression of TMEM177 in Tg-MyocY437H mice after TMSC transplantation. FIG. 7G provides images showing that transplanted TMSC homed into the TM region also expressed TMEM177 in Tg-MyocY437H mice. Dots on the bar represent MFI quantification in the cornea/TM region and ciliary body per section. The scale bar is 50 μm.

Figure 8B:
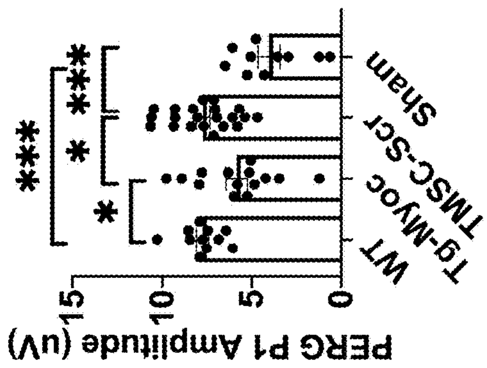
Figure 8A:
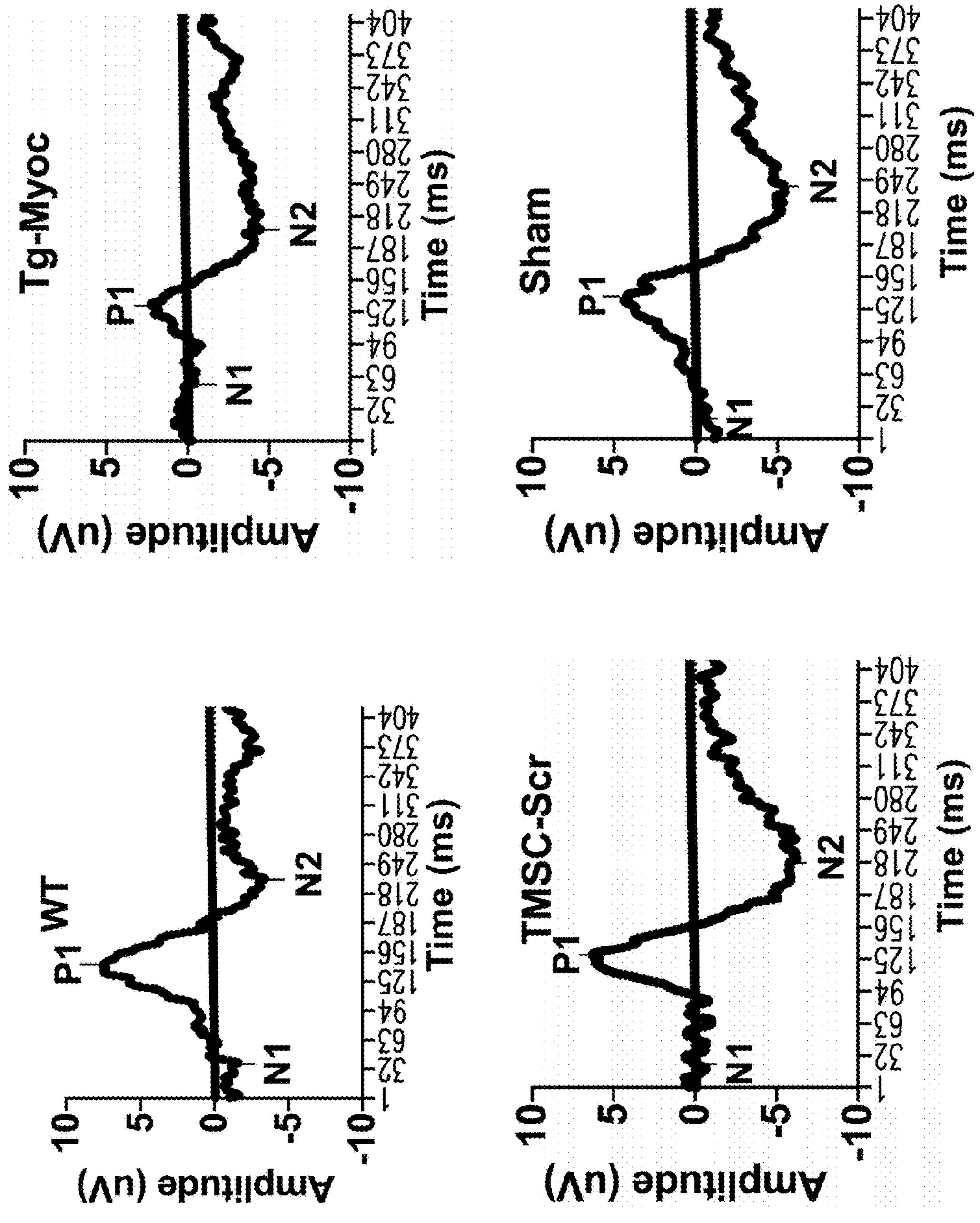
Figure 8C:
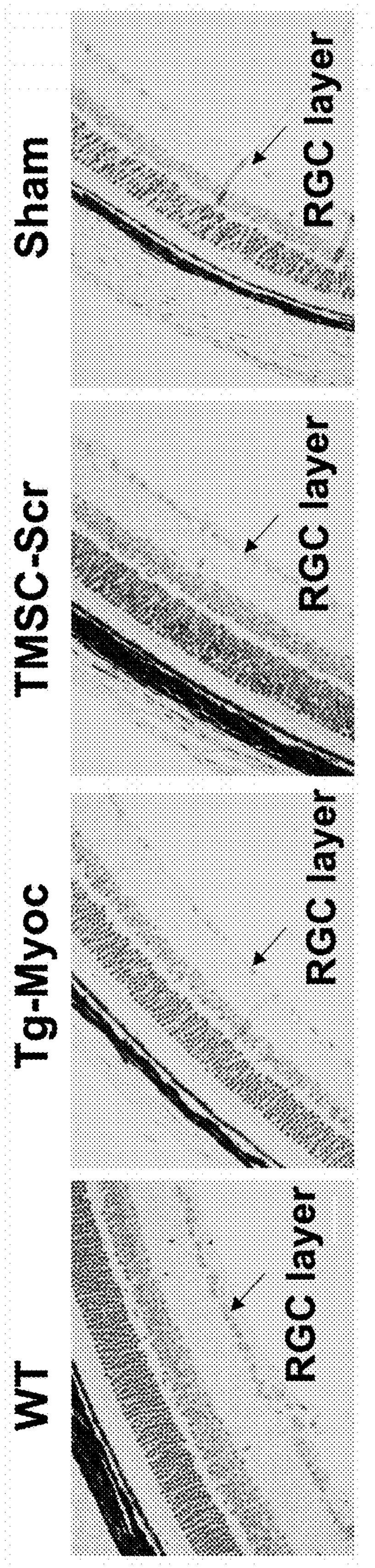
Figure 8D:
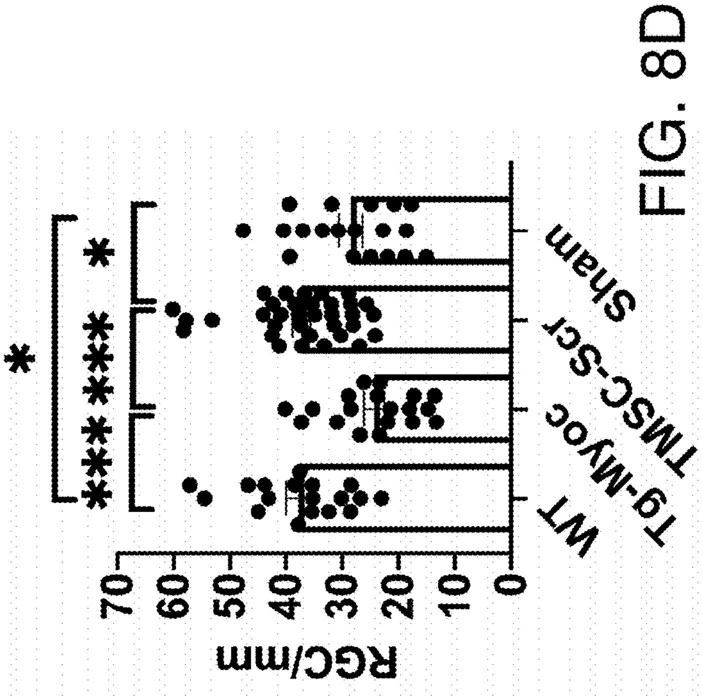
Figure 8E:
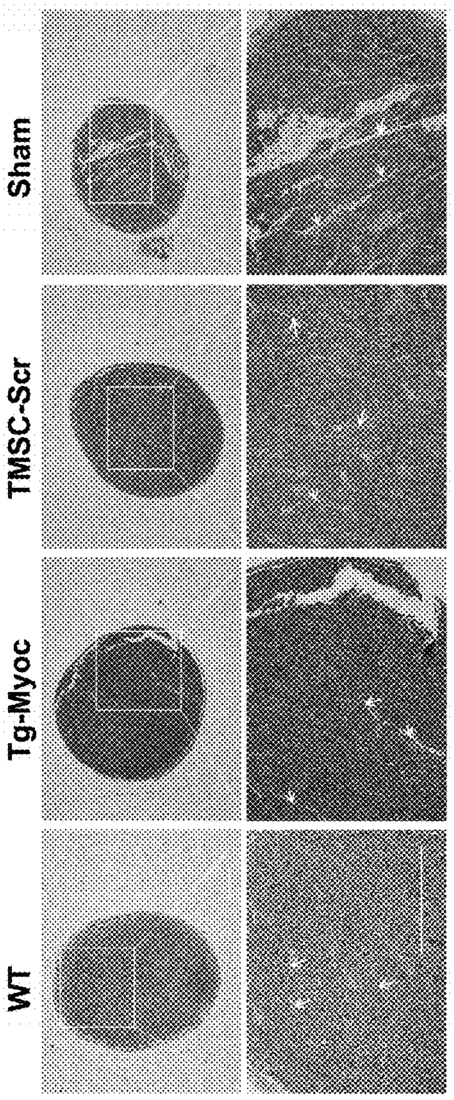
Figure 8F:
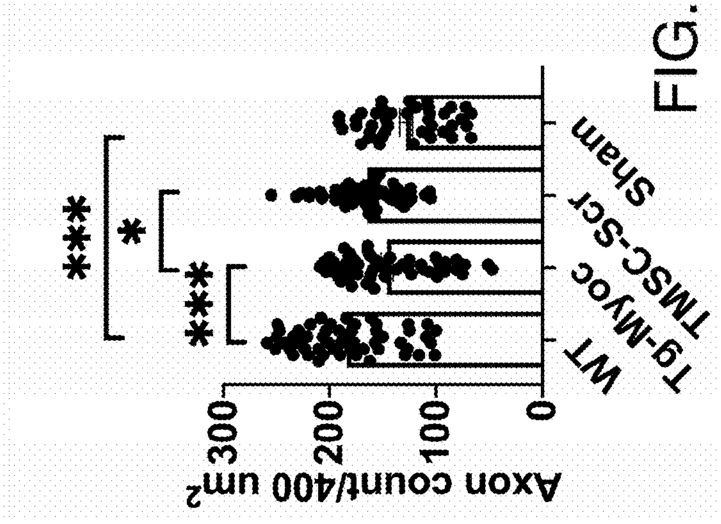
Figure 8G:
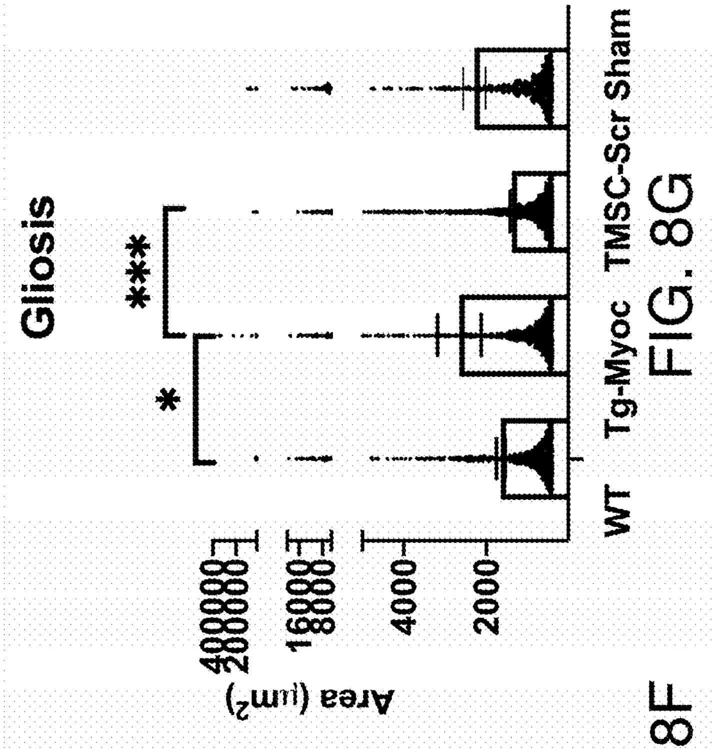

FIGS. 8A-8G provide images and graphs showing that TMSC secretome rescues RGC and retains function in Tg-MyocY437H mice. FIG. 8A provides graphs showing pattern electroretinogram (PERG) peaks illustrating amplitude of waves with P1 amplitude as an indicator of RGC function (n=11-21). FIG. 8B provides bar diagrams showing the average amplitude of PERG P1-wave peaks obtained for each group. FIG. 8C provides DIC monocolor images showing the RGC layer in Tg-MyocY437H mice. FIG. 8D provides bar diagrams showing quantification of RGC number in Tg-MyocY437H mice retina (n=3-4). Multiple dots in bar graphs represent combined results of biological and technical replicates. FIG. 8E provides DIC images showing a cross-section of the optic nerve with low (20×) and high magnification (60×) (arrowheads indicating gliosis). FIG. 8F provides bar diagrams showing quantification of optic nerve axon count in different treatment groups. FIG. 8G provides bar diagrams showing quantification of gliosis among different treatment groups in the optic nerve of Tg-MyocY437H mice. The scale bar is 100 μm. * represents that the p-value is less than 0.05.  represents that the p-value is less than 0.001. * represents that the p-value is less than 0.0001.

Figure 9A:
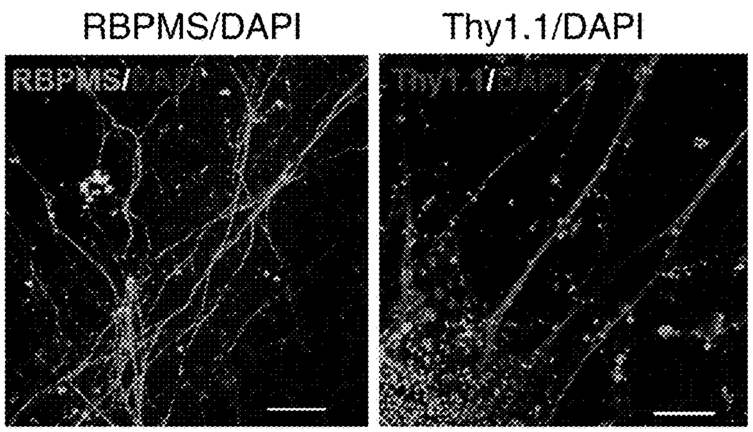
Figure 9B:
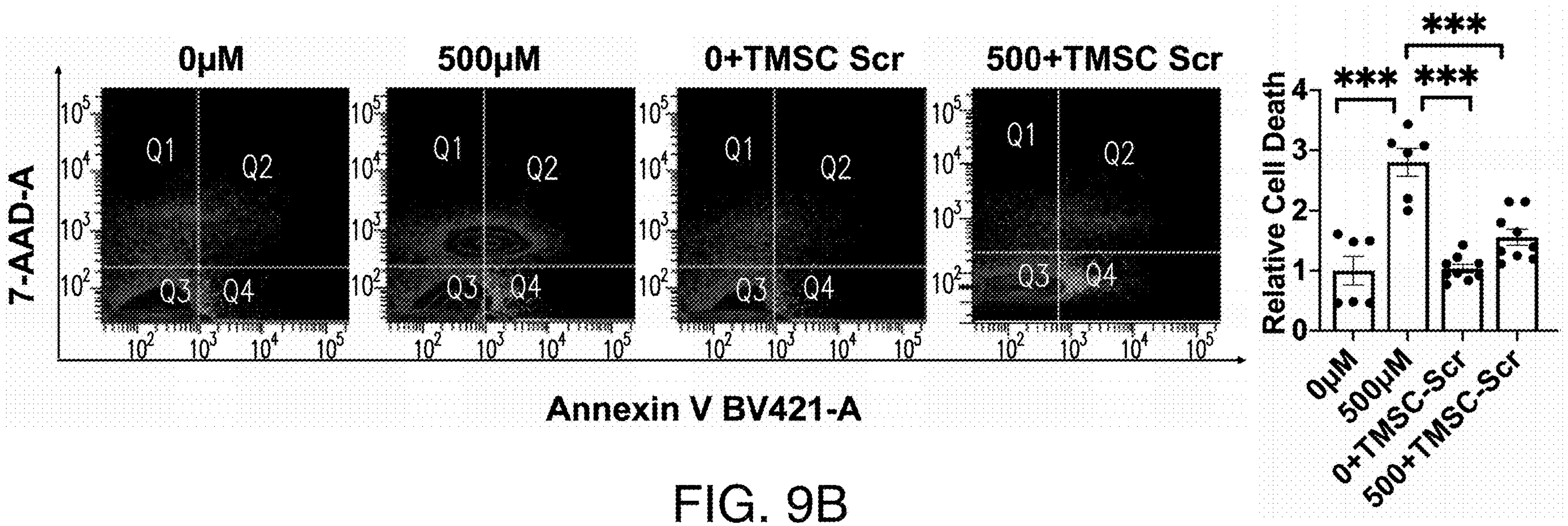
Figure 9C:
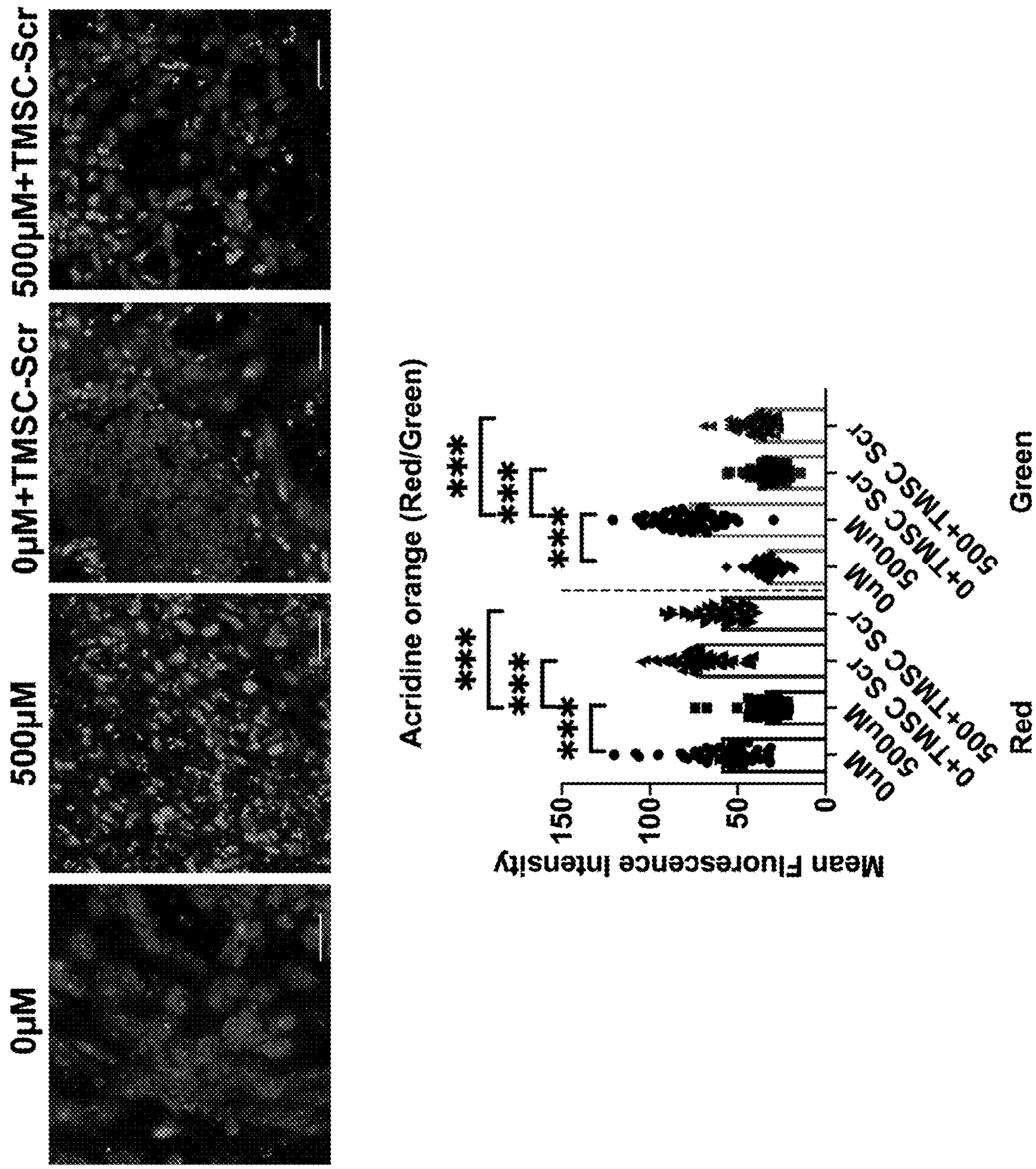
Figure 9D:
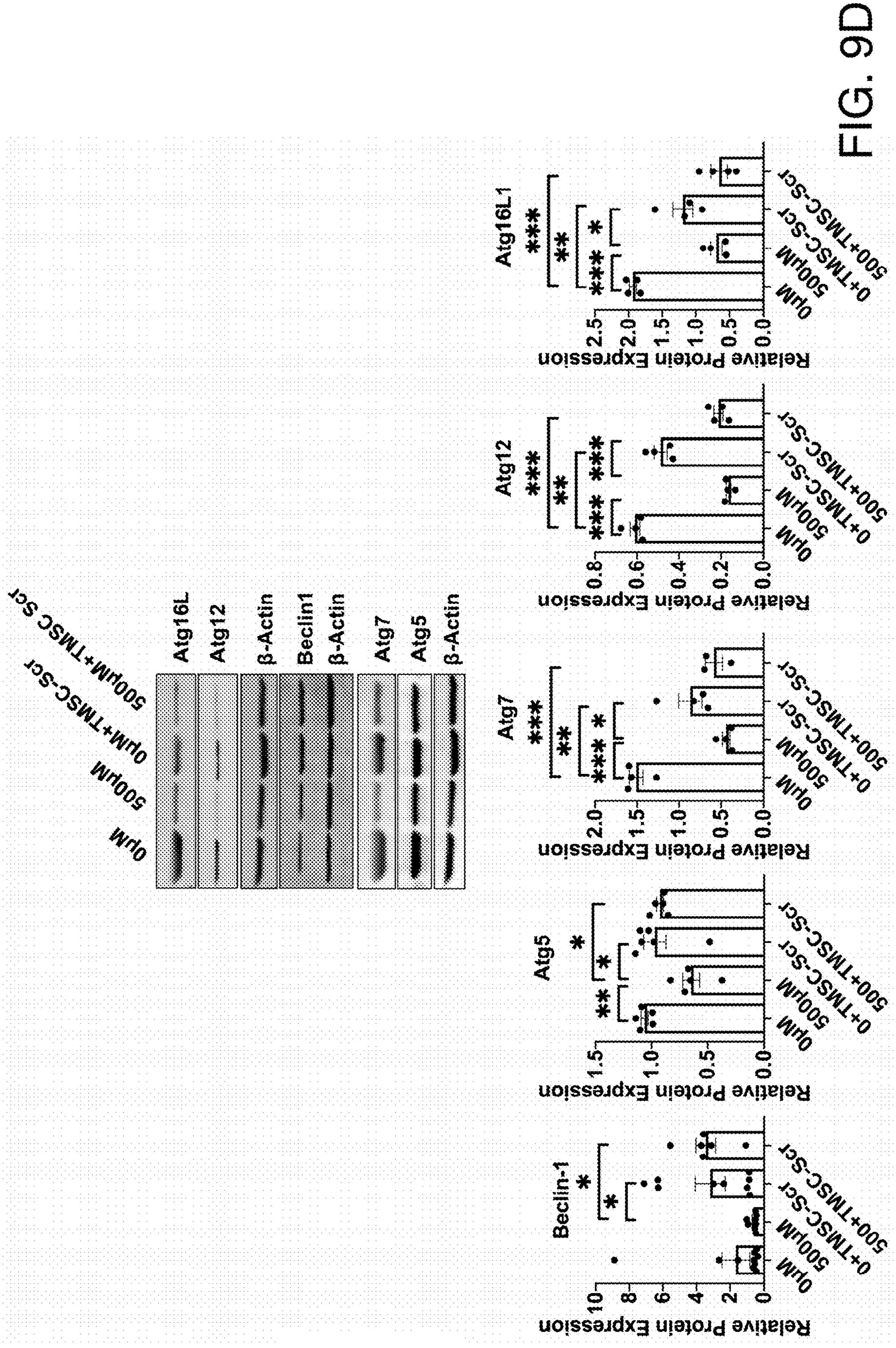

FIGS. 9A-D provide images and graphs showing that TMSC secretome rescues RGC in cell culture via upregulation of autophagy. FIG. 9A provides immunofluorescent staining images showing expression of RBPMS and Thy1.1 in RGC differentiated from iPSC. FIG. 9B provides dot plots and bar diagrams showing the quantitative comparison of apoptotic RGC between control (untreated, 0 uM), 500 μM CoCl2 treated, secretome alone (0+TMSC-Scr), and 500 μM CoCl2+secretome treated cells (500+TMSC-Scr) as evaluated by flow cytometry. FIG. 9C provides immunofluorescent staining images and bar diagrams showing acridine orange (an indicator of autophagy) staining and quantification in differently treated cells (n=3 each). FIG. 9D provides immunoblotting band images and bar diagrams showing relative protein expression of autophagy proteins, beclin-1, Atg5, Atg7, Atg12, and Atg16L1, in various treatment groups in the iPSC-derived RGC (n=4 each). Multiple dots in bar graphs represent combined results of biological and technical replicates. The scale bar is 100 um. * represent that the p-value is less than 0.05.  represents that the p-value is less than 0.001. * represents that the p-value is less than 0.0001.

Figure 10A:
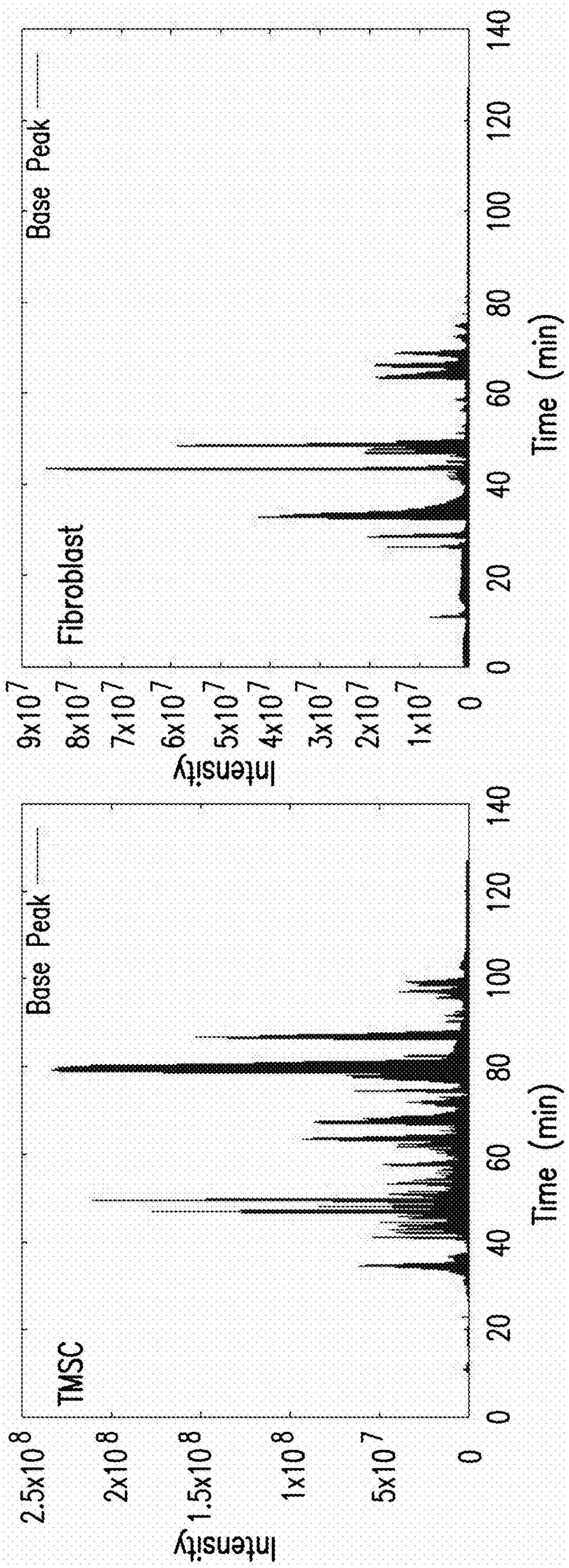
Figure 10B:
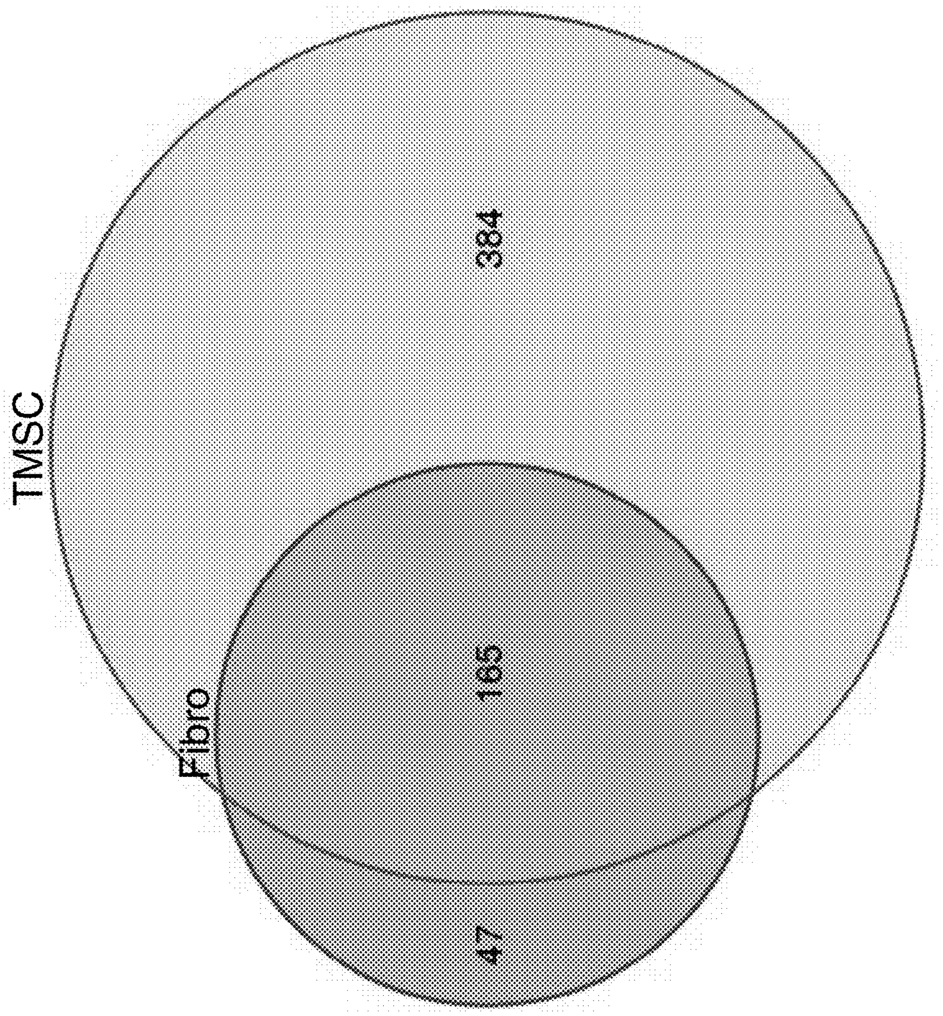
Figure 10C:
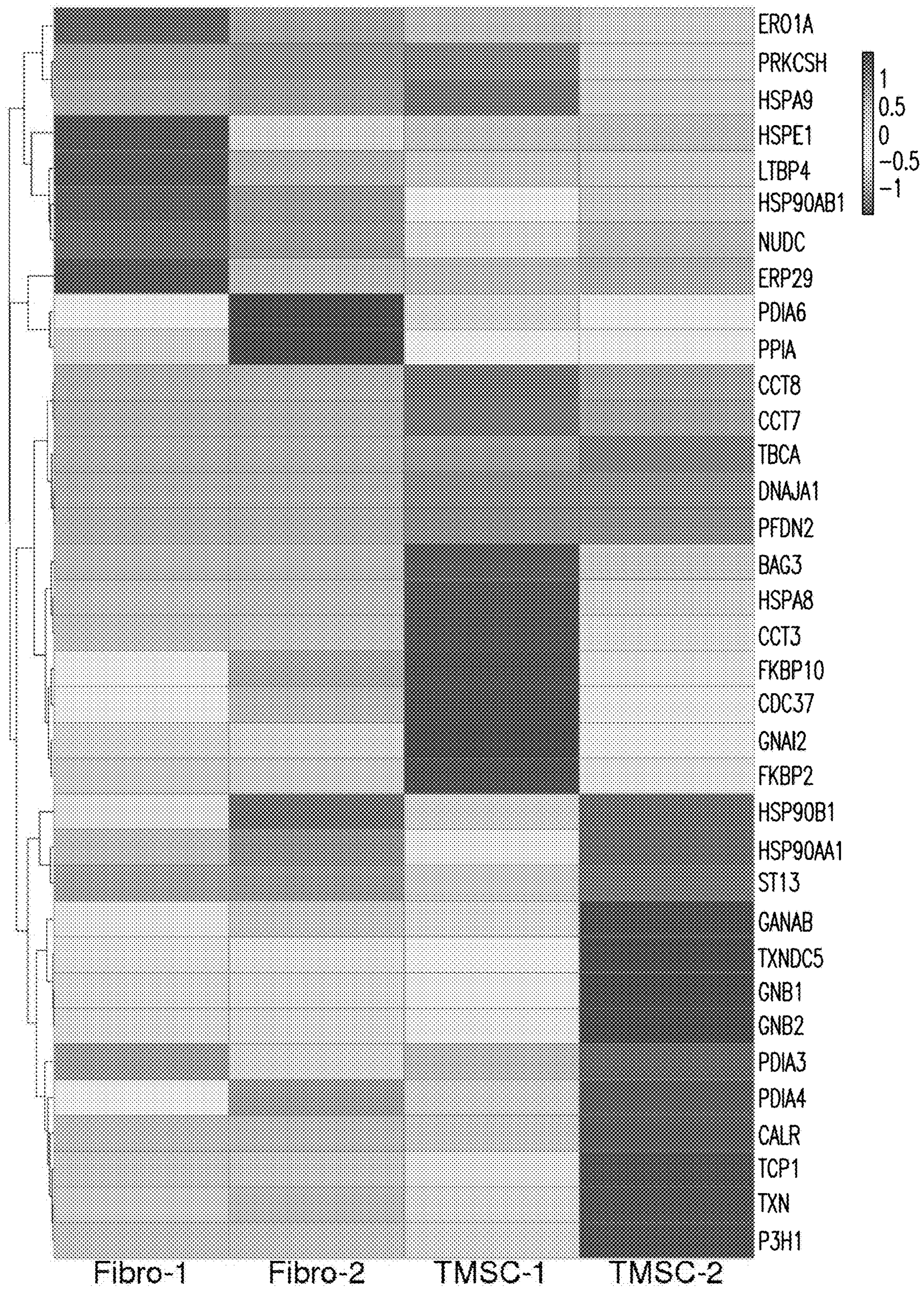
Figure 10D:
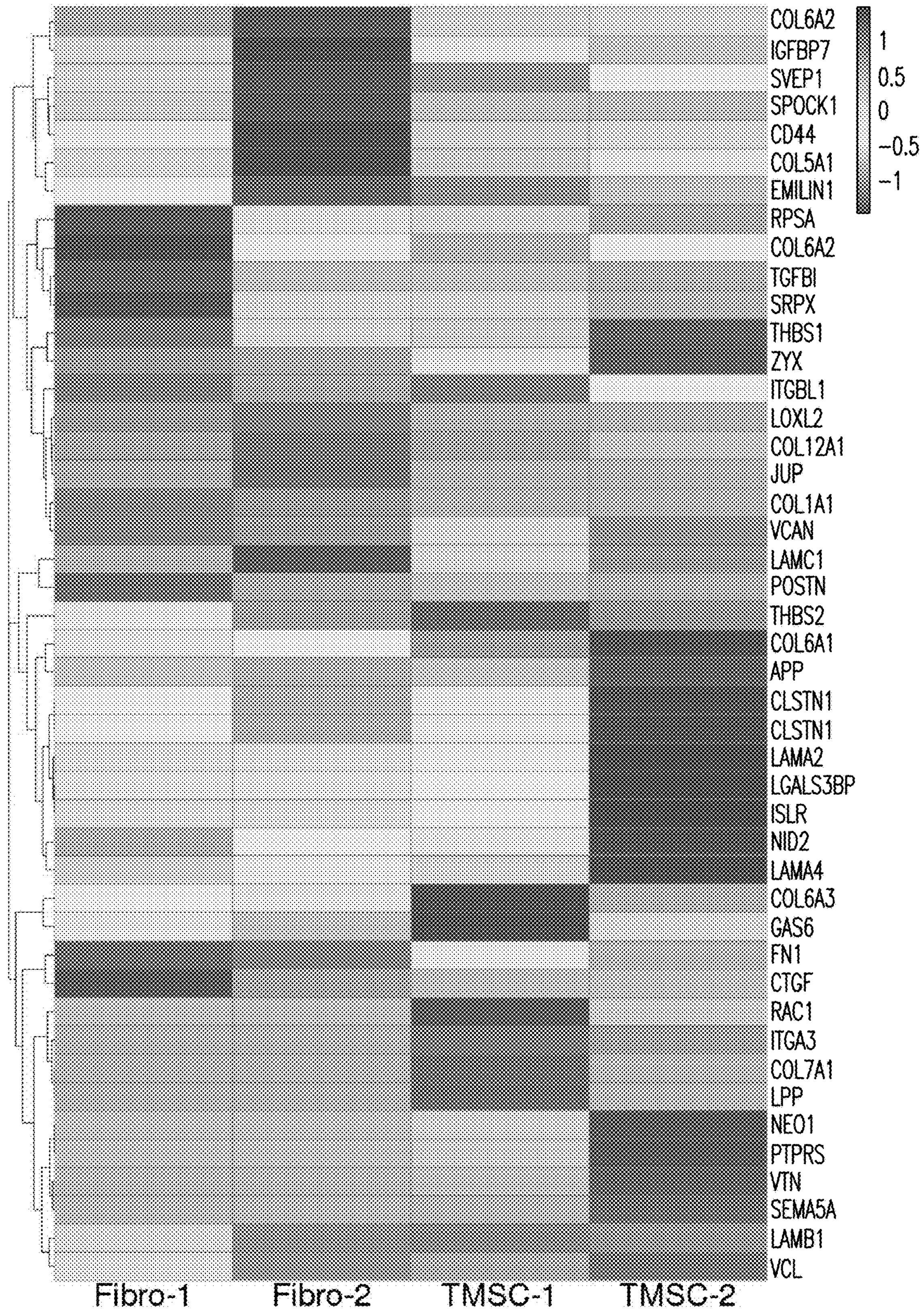
Figures 1, 10E:
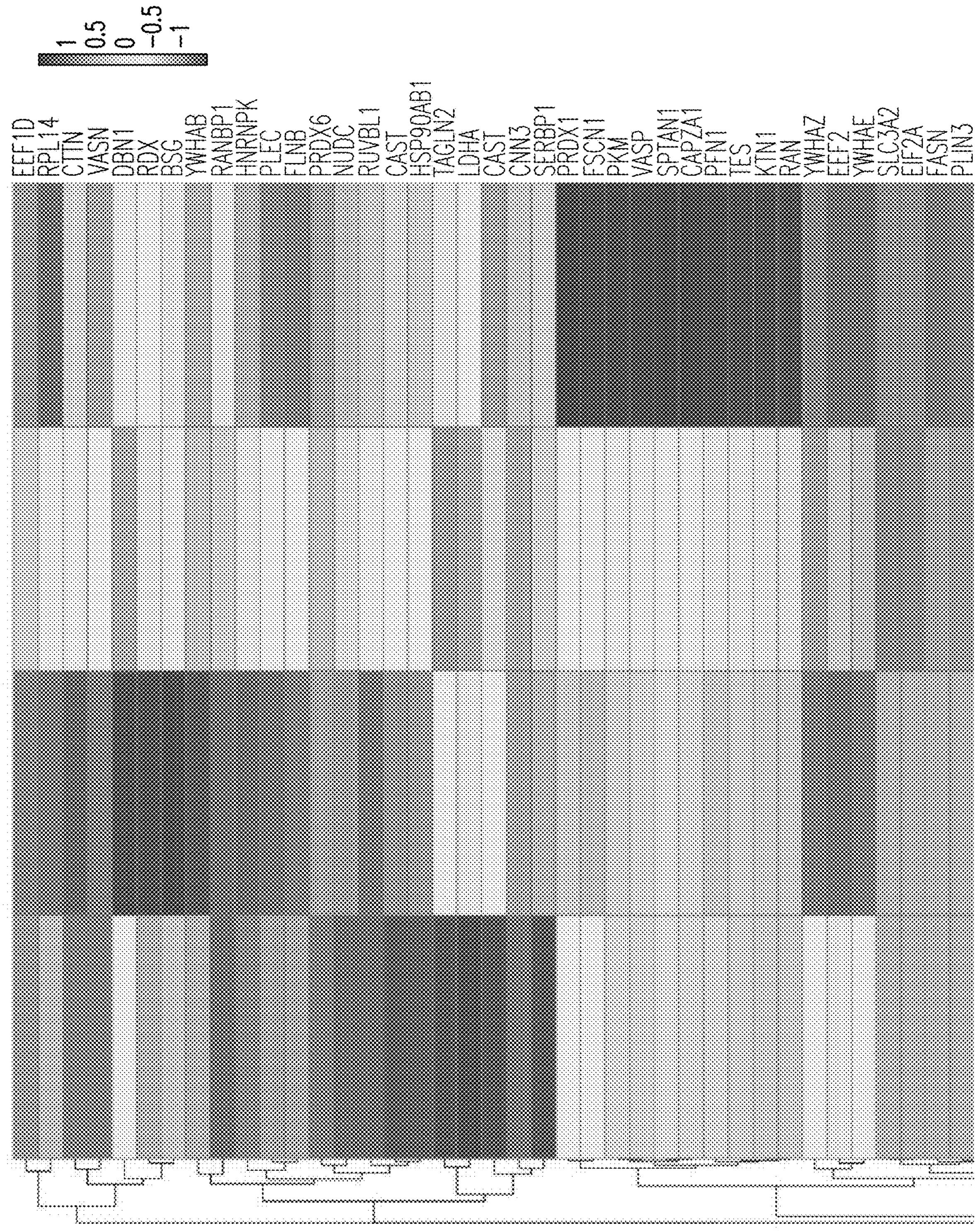
Figures 2, 10E:
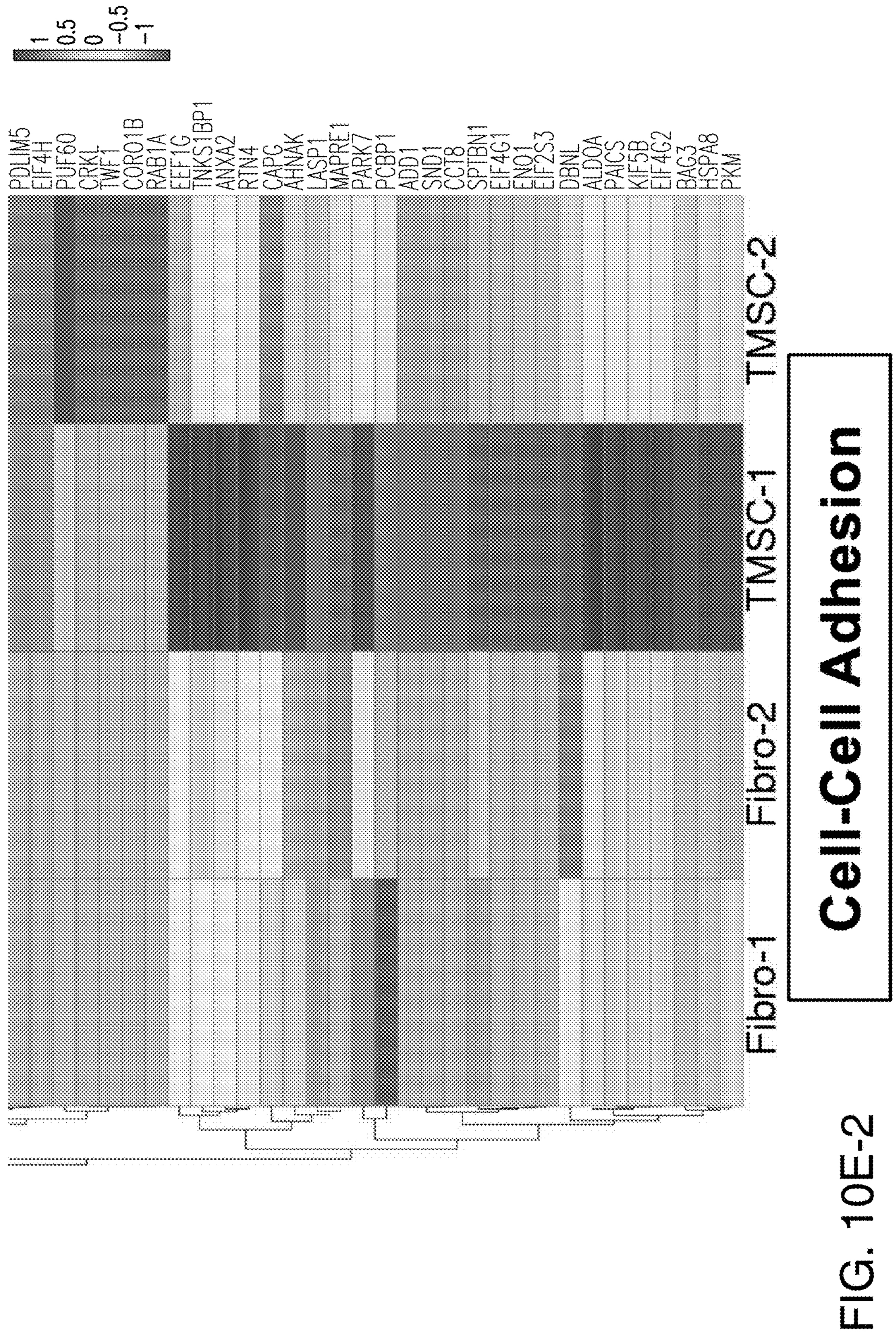
Figure 10F:
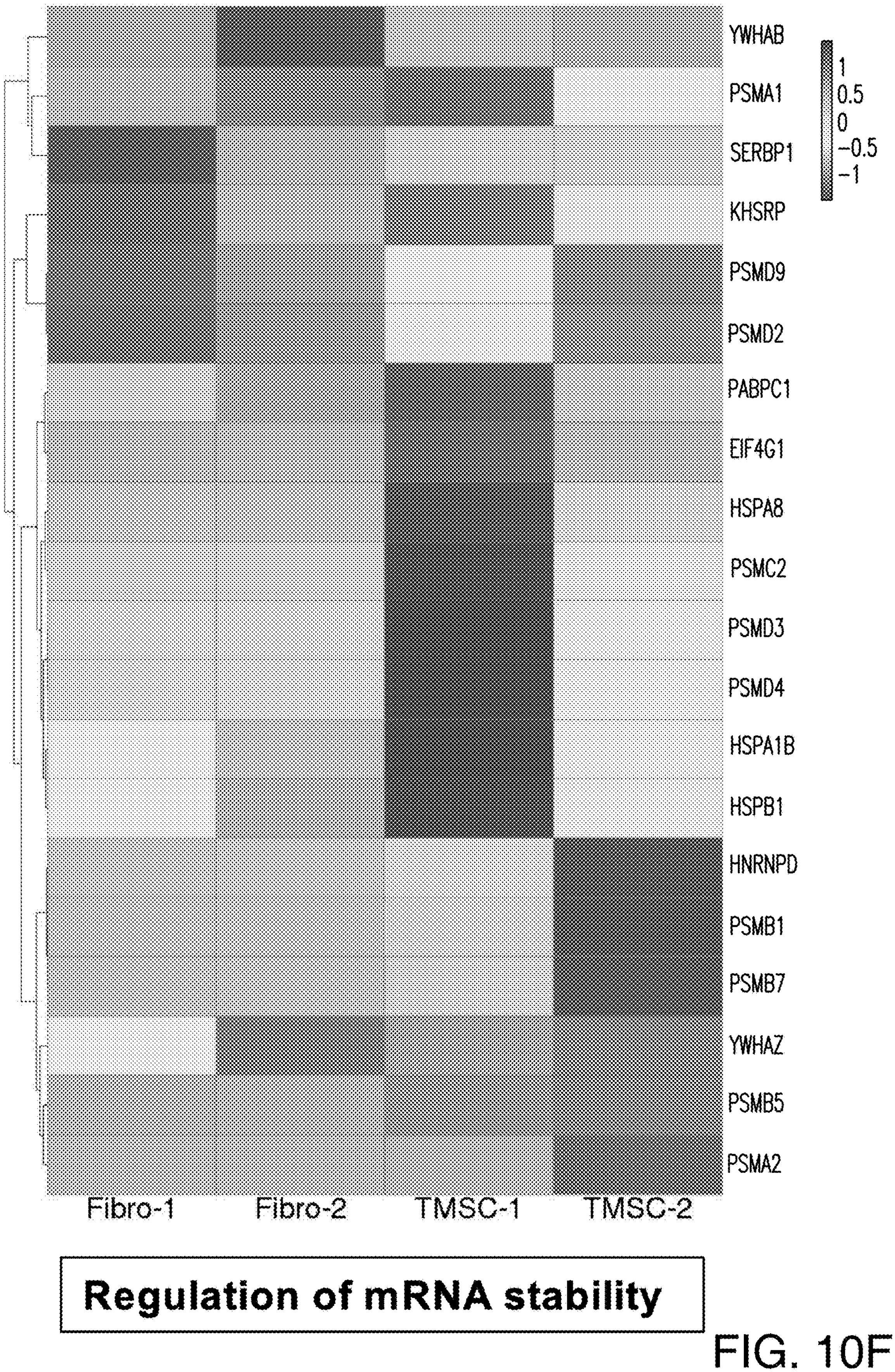

FIGS. 10A-10F provide graphs showing comparative analysis of TMSC and fibroblast secretome proteins. FIG. 10A provides chromatographs showing the integrated intensity of peaks for secretome proteins derived from TMSC and fibroblast. FIG. 10B provides yen diagrams showing exclusive and common secretome proteins expressed in TMSC and fibroblasts. FIGS. 10C-10F provide heatmaps showing differences in secretome proteins between TMSC and fibroblasts, involved in protein folding, cell adhesion, cell-cell adhesion, and regulation of mRNA stability (n=2, for each TMSC and fibroblast).

Figures 1, 11A:
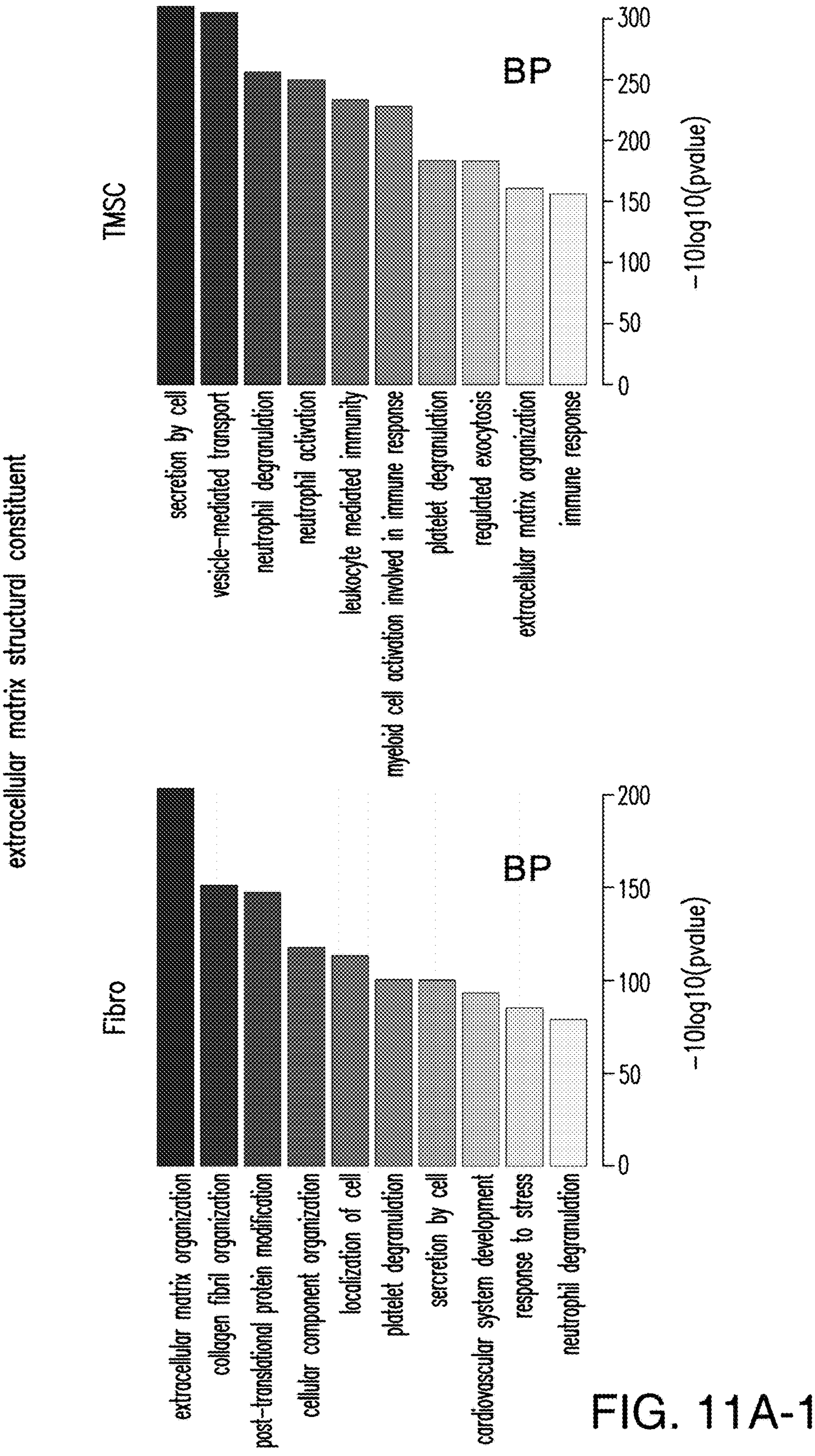
Figures 2, 11A:
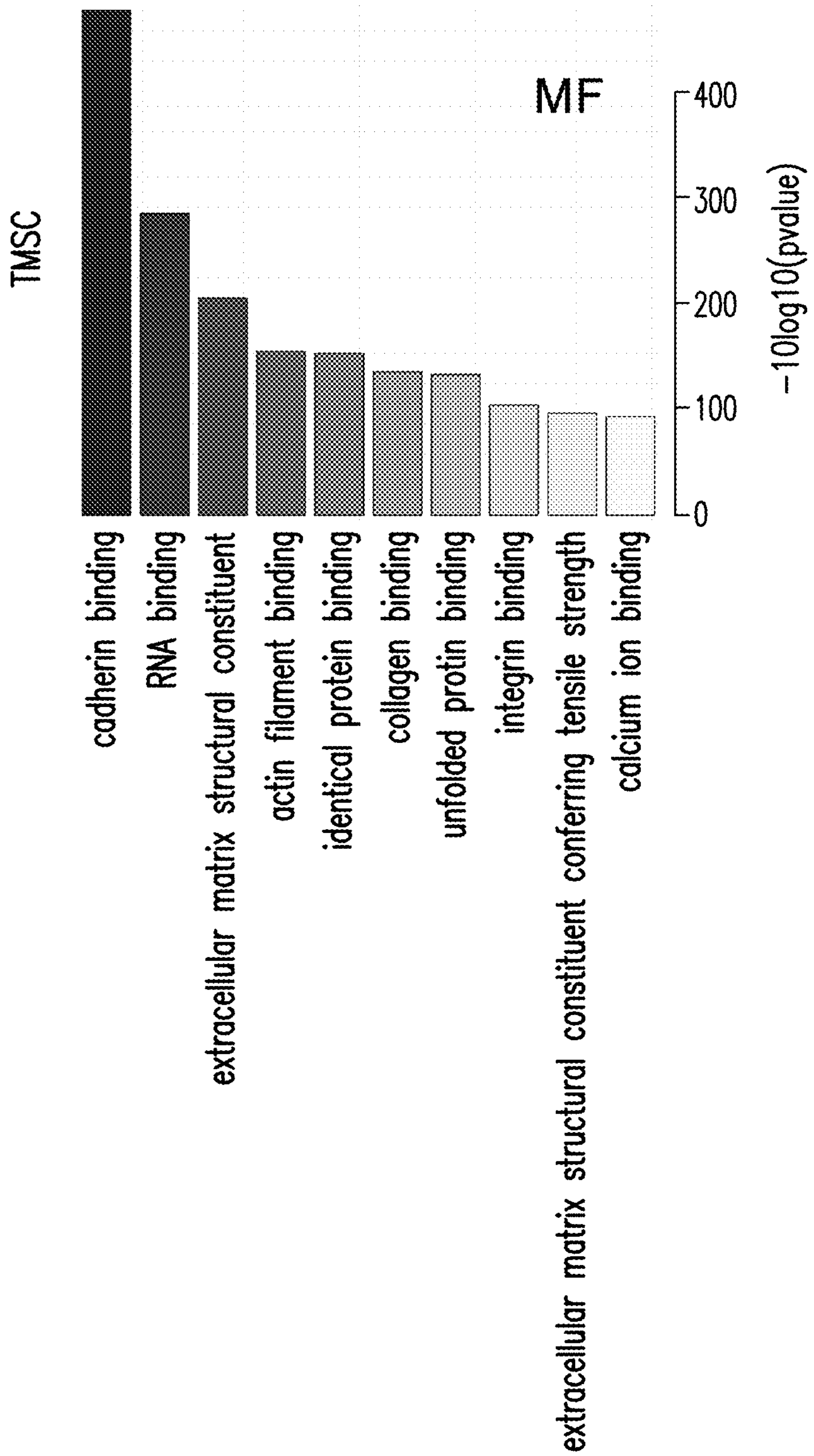
Figures 3, 11A:
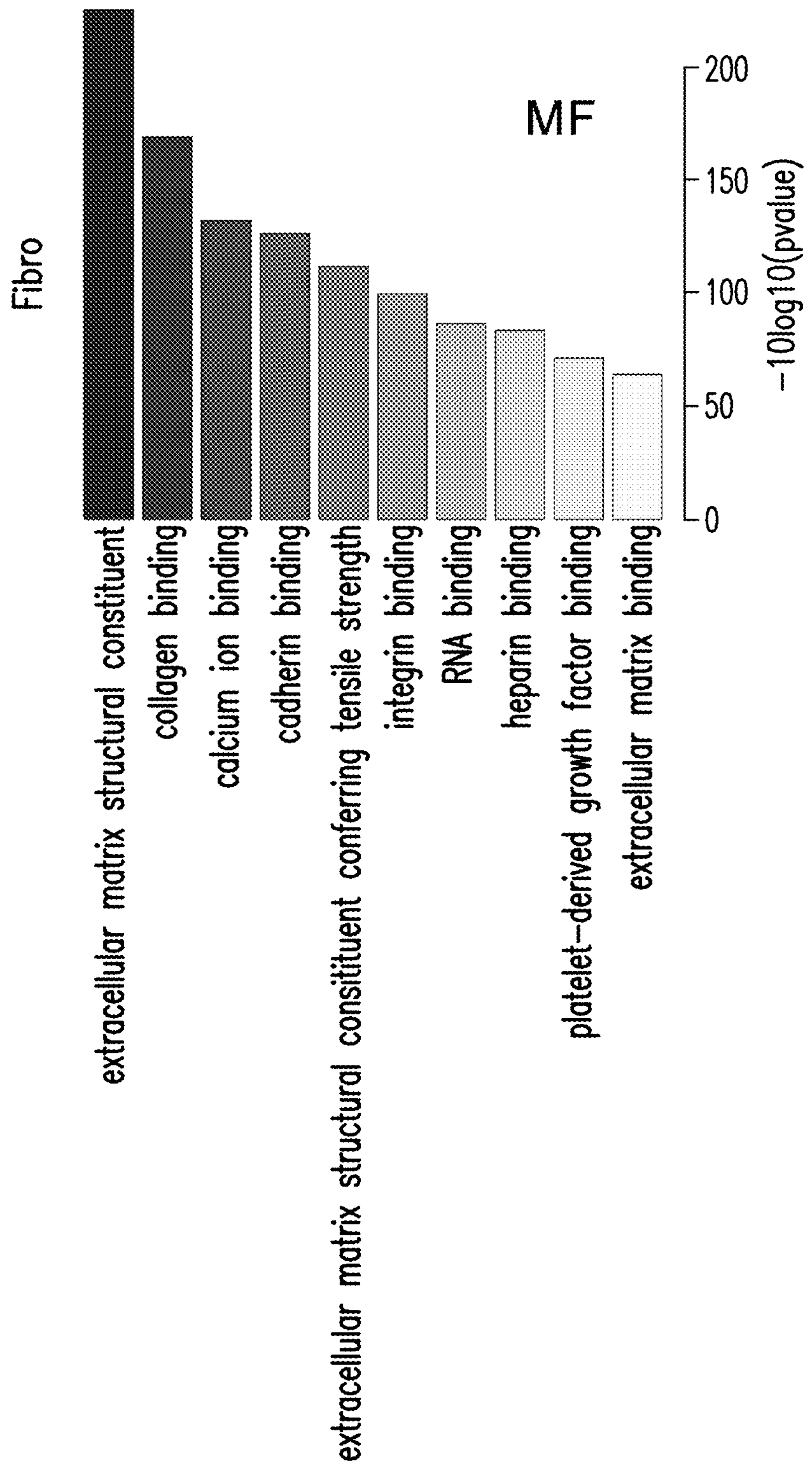
Figures 4, 11A:
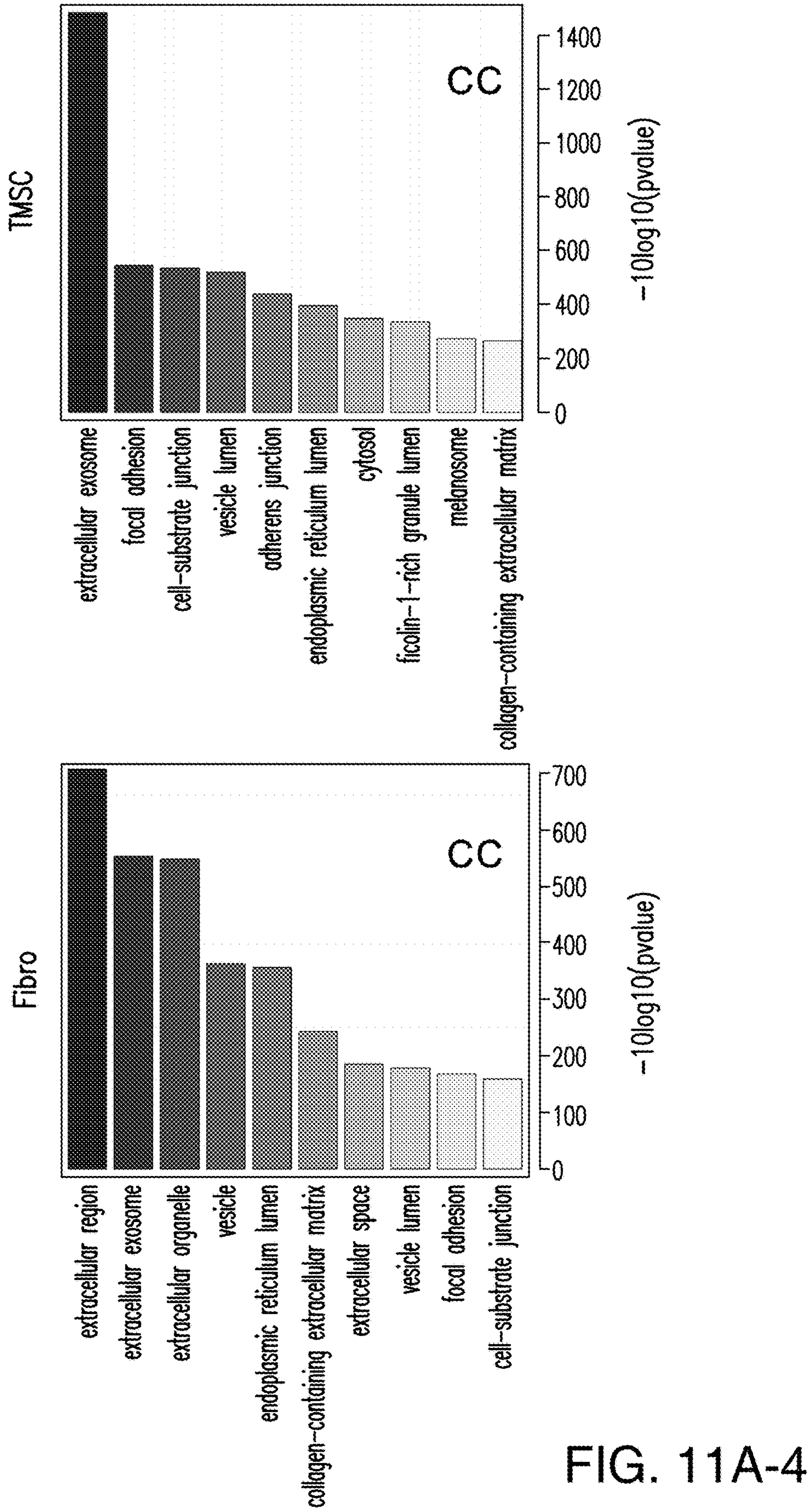
Figure 11B:
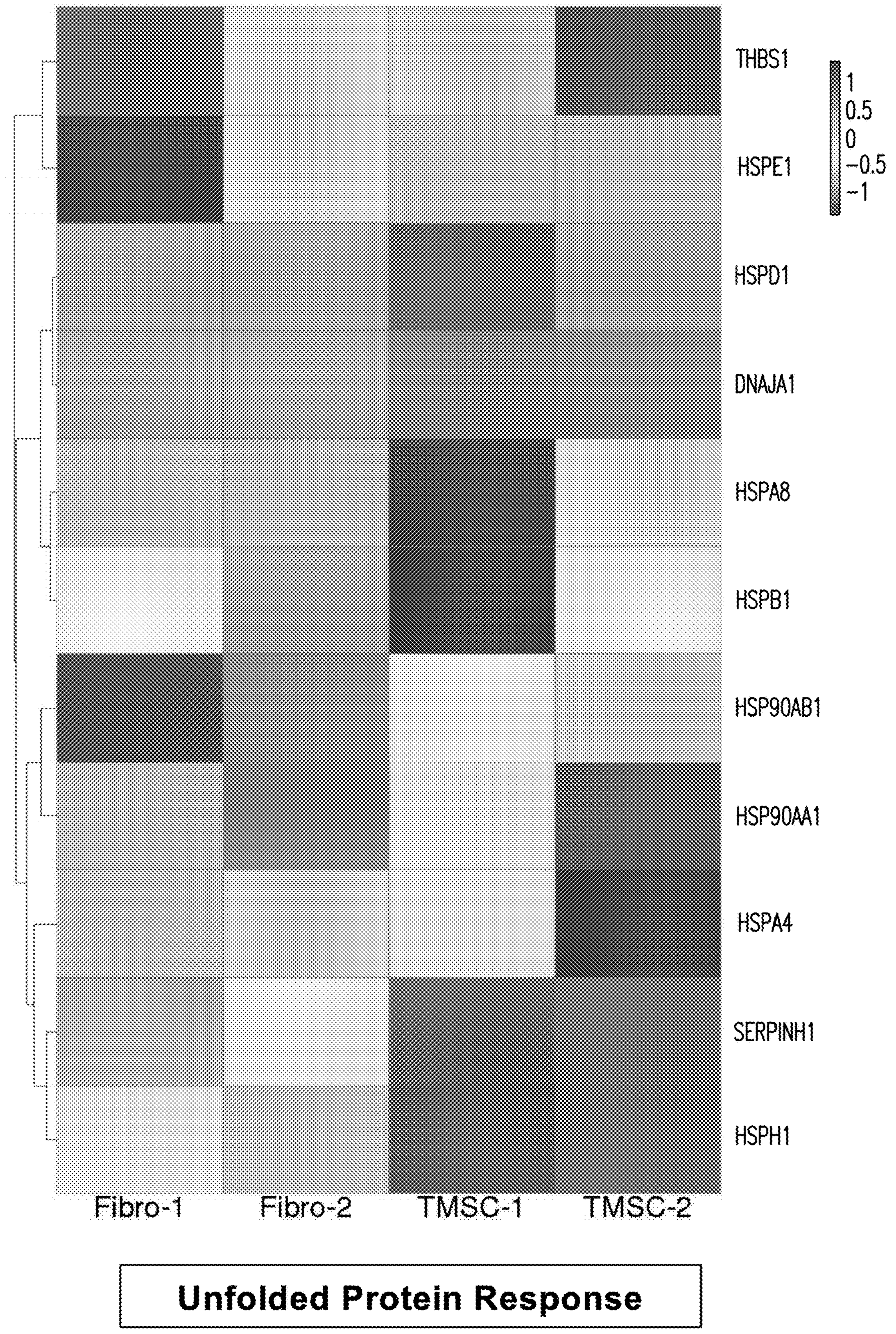
Figures 1, 11C:
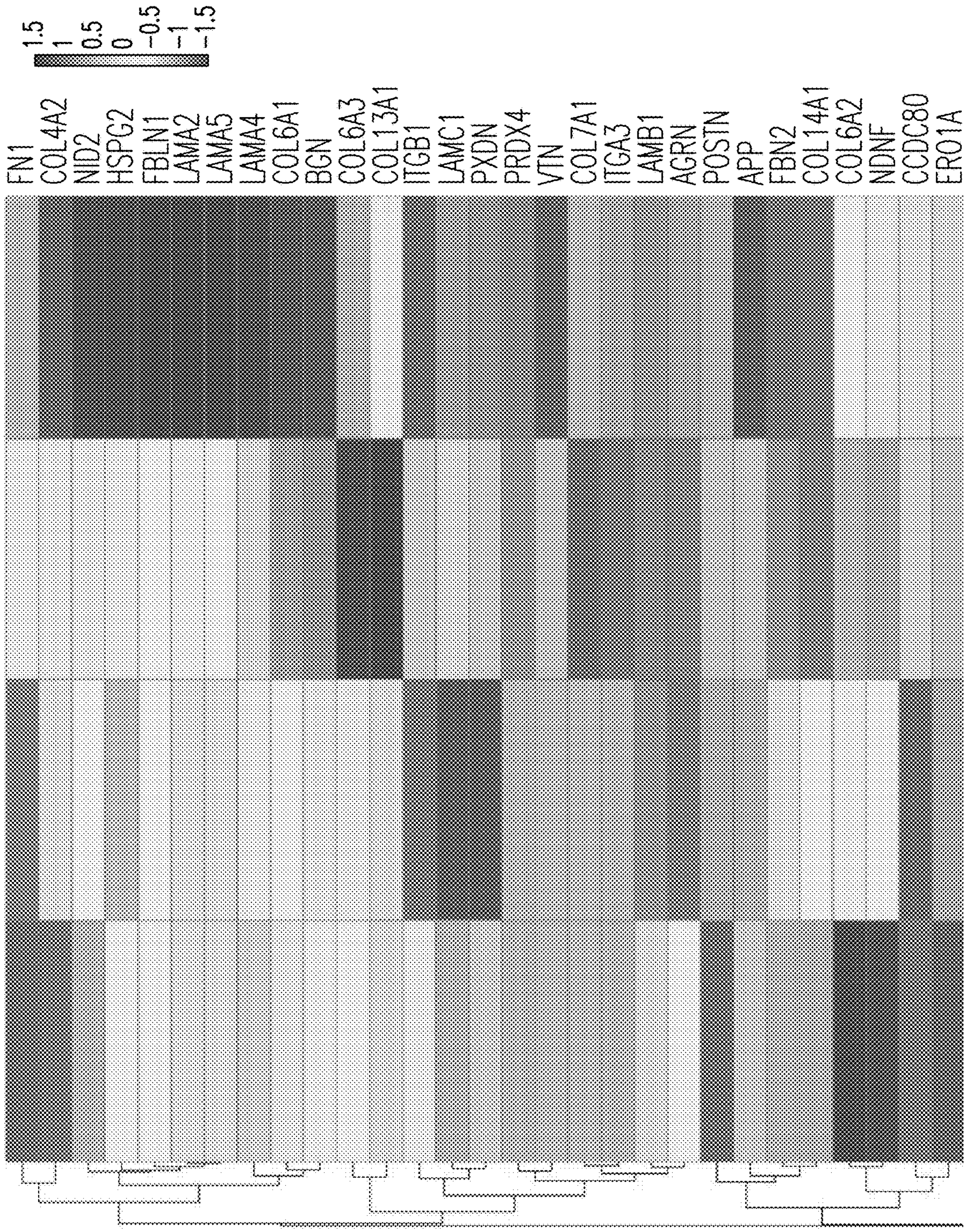
Figures 2, 11C:
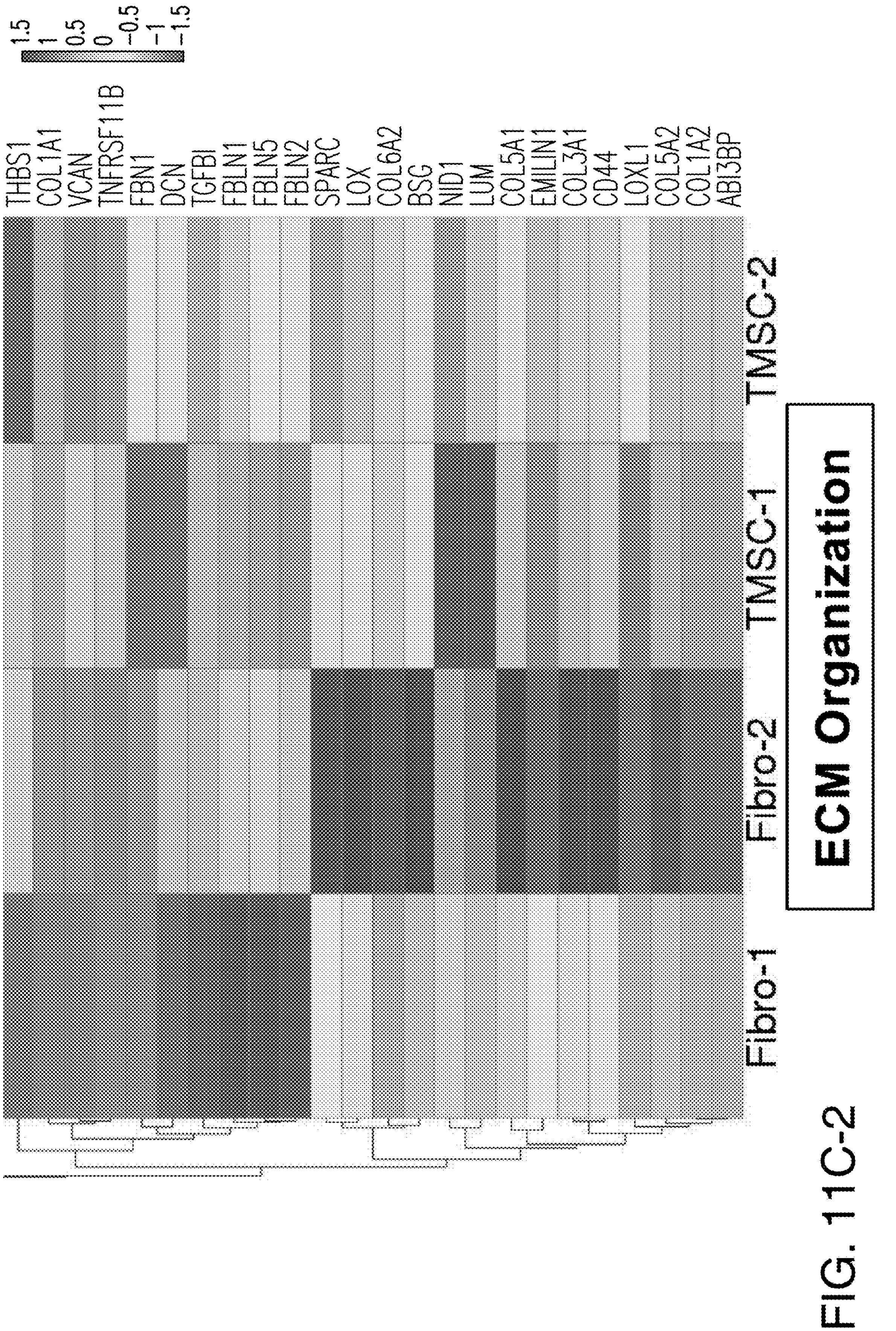
Figure 11D:
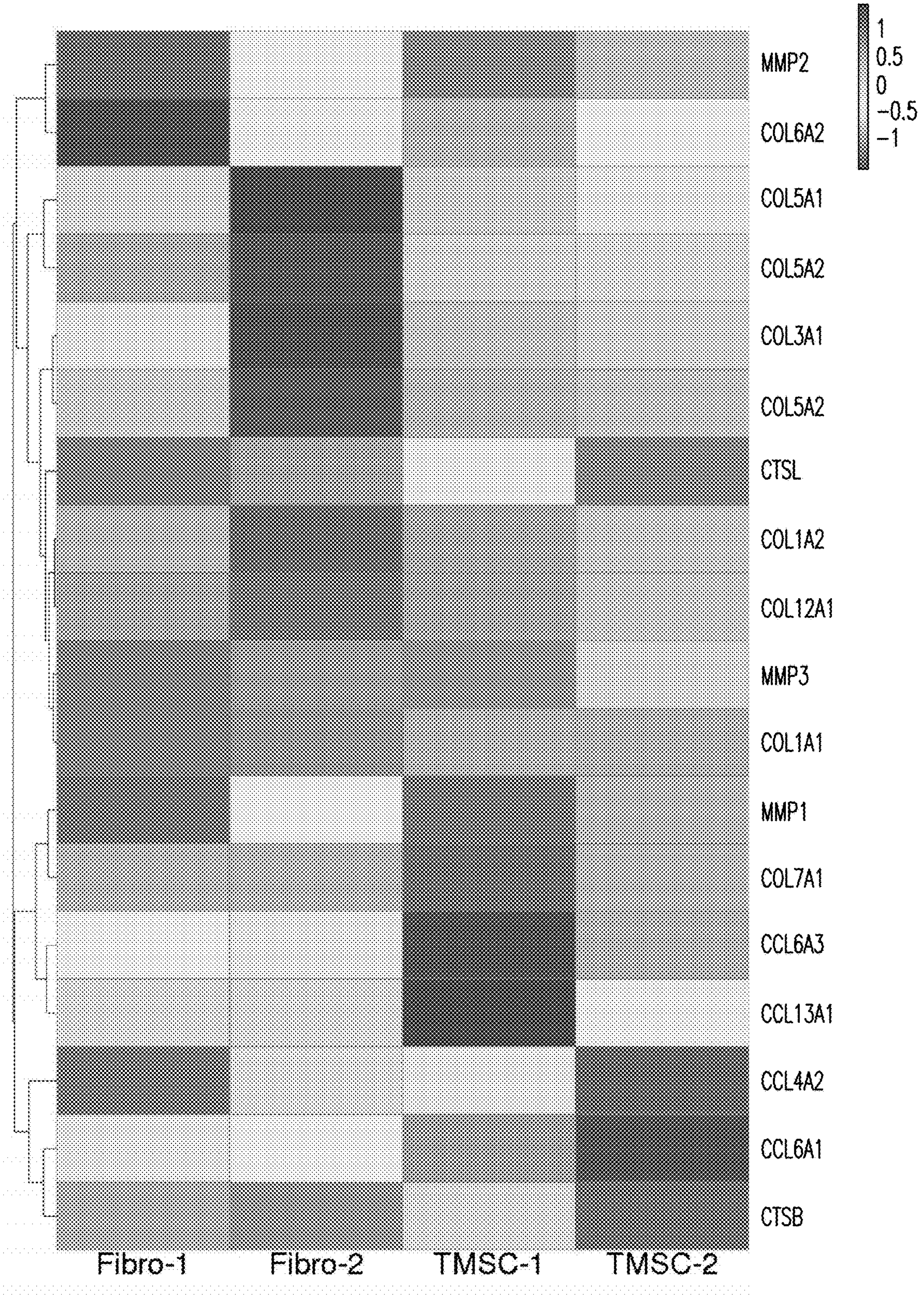
Figure 11E:
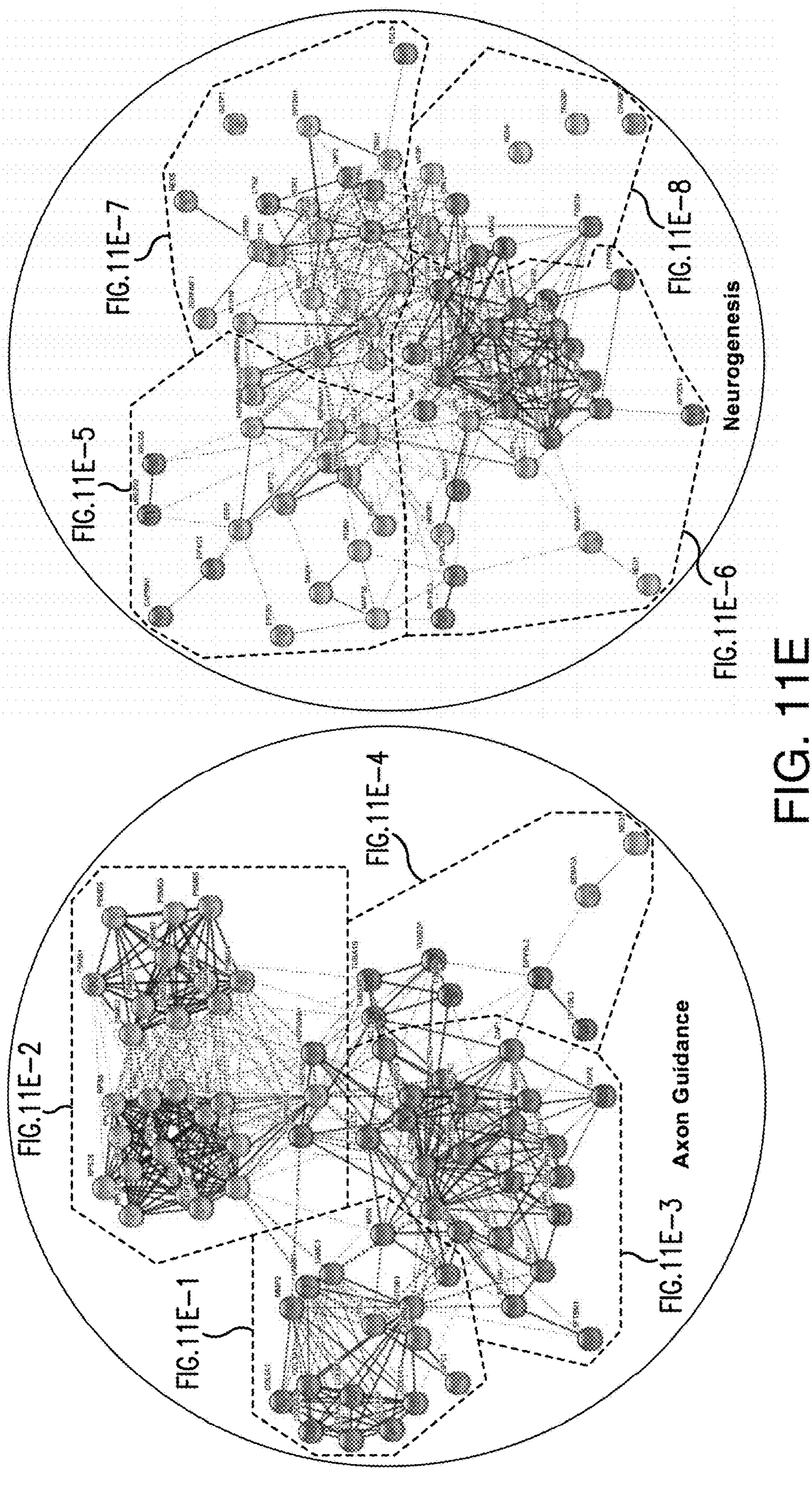
Figures 1, 11E:
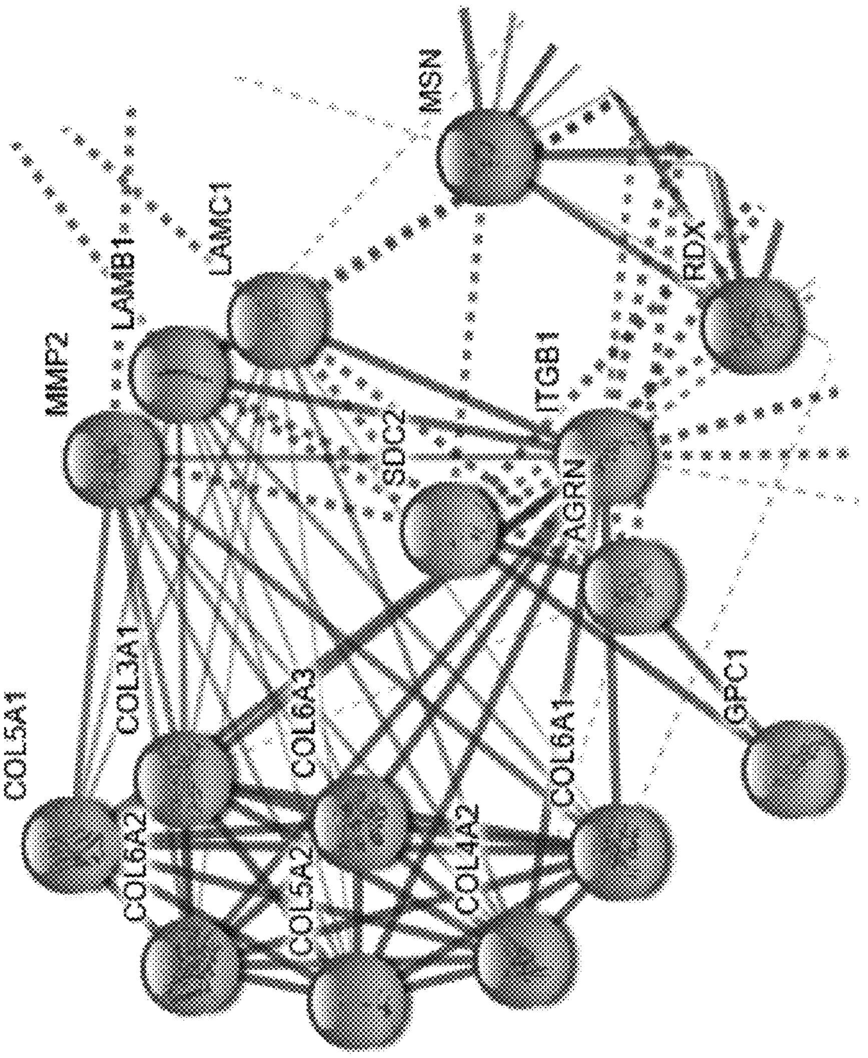
Figures 2, 11E:
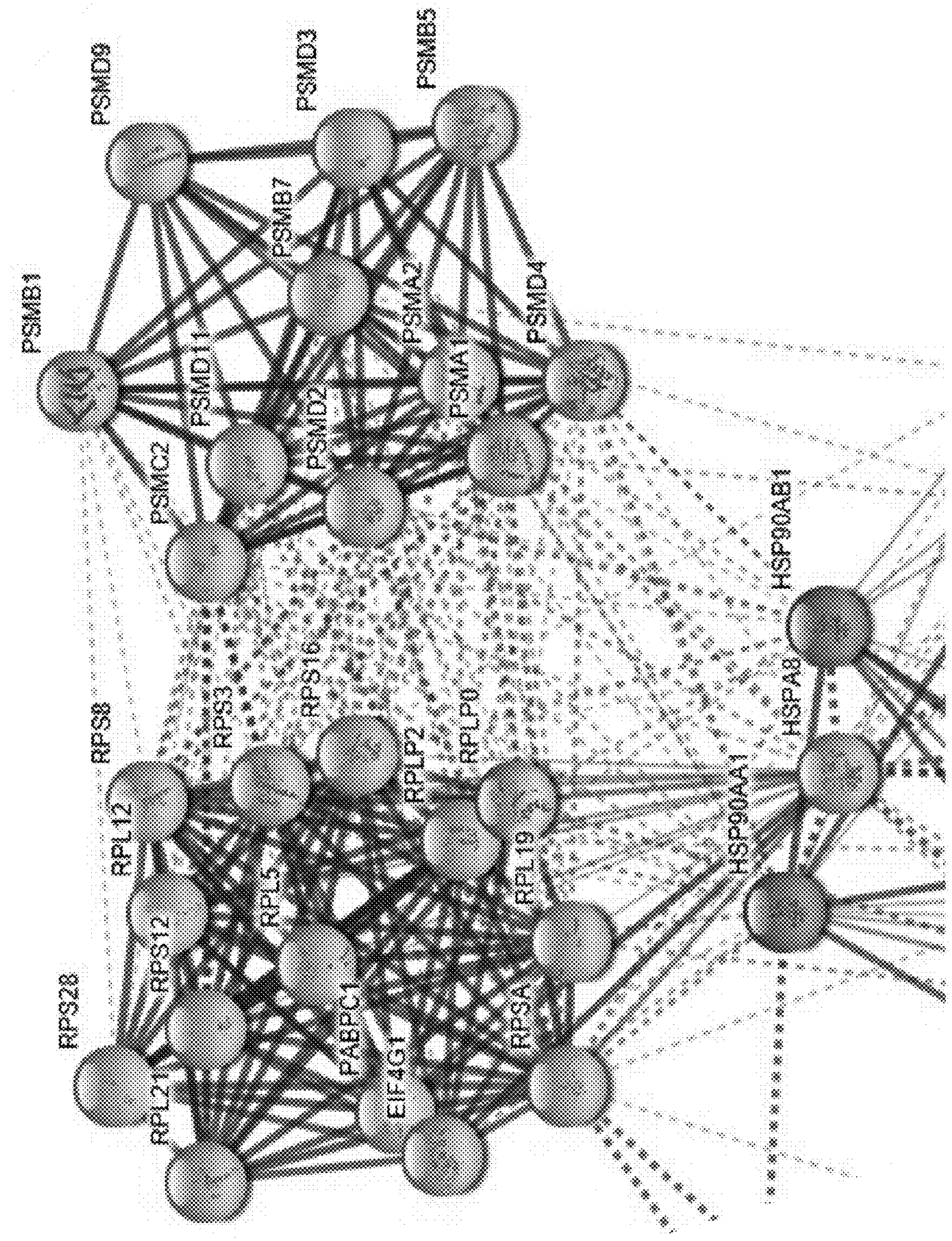
Figures 3, 11E:
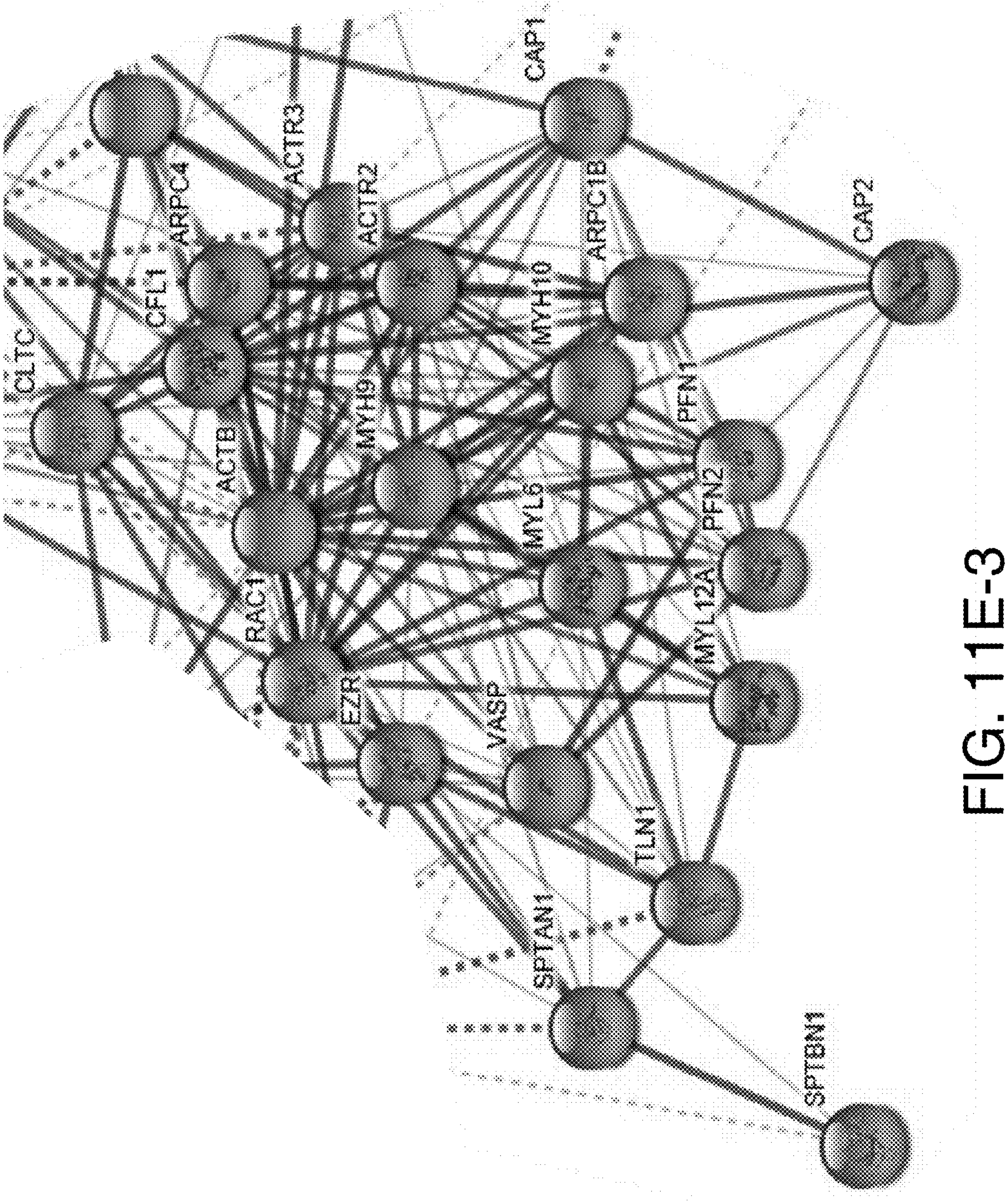
Figures 4, 11E:
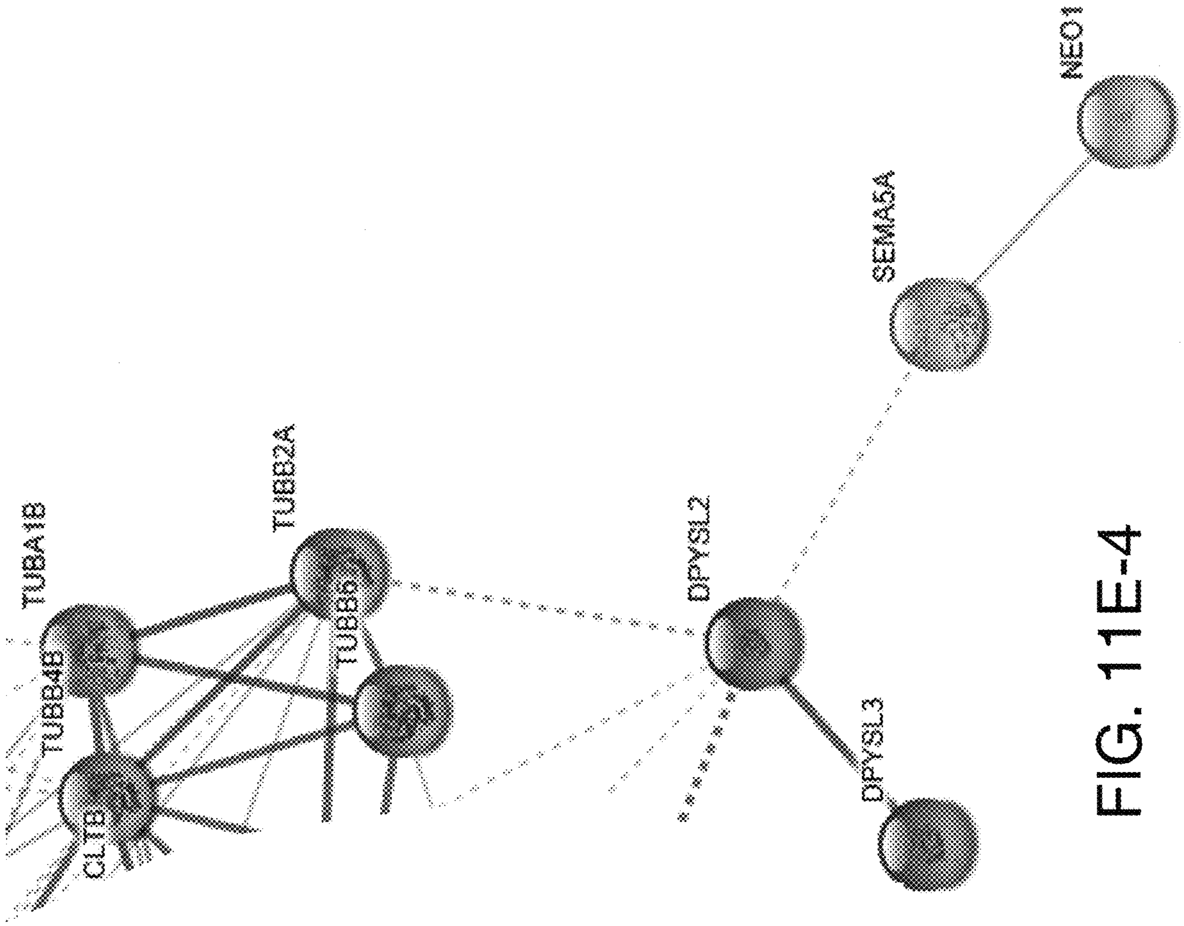
Figures 5, 11E:
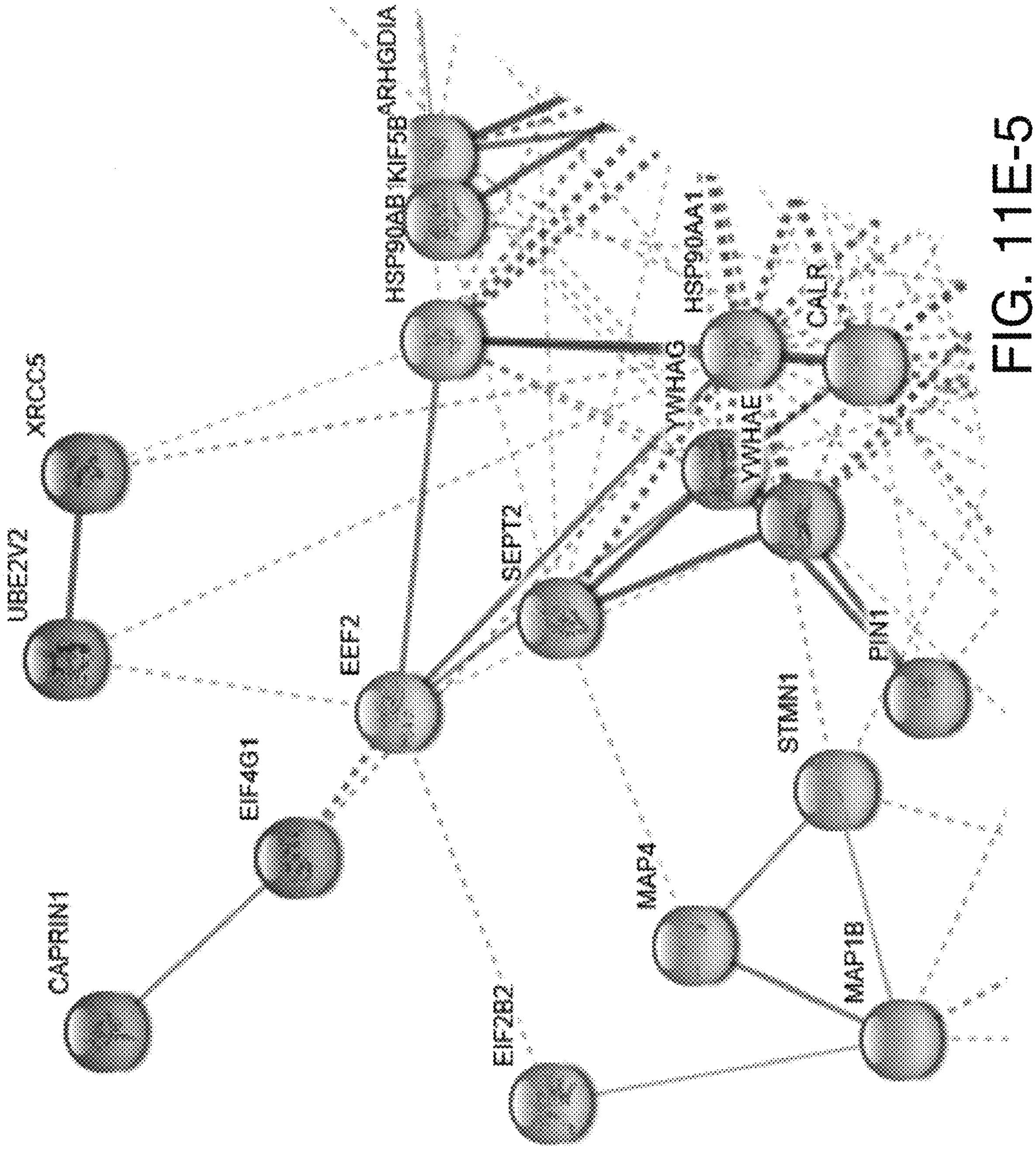
Figures 6, 11E:
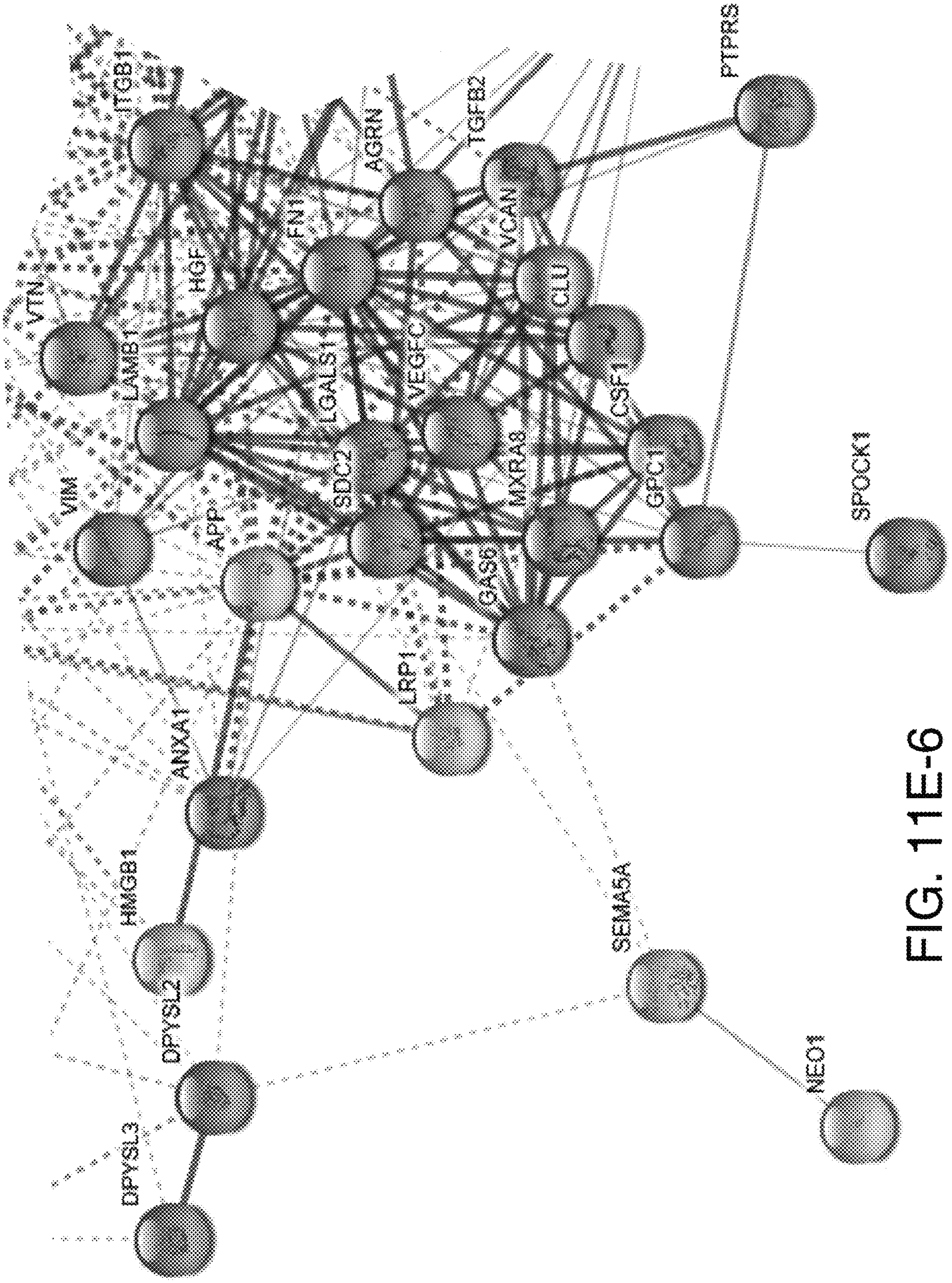
Figures 7, 11E:
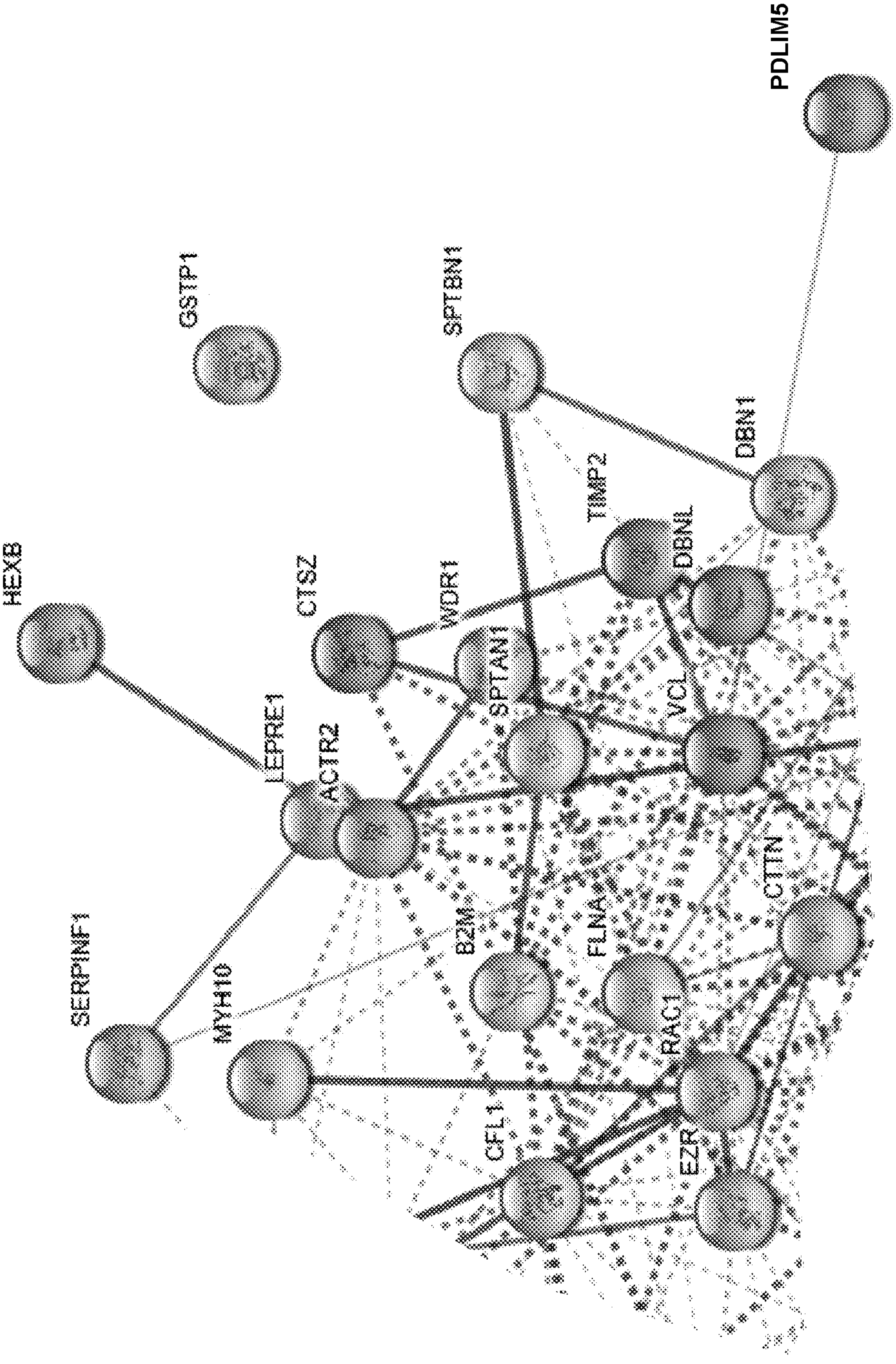
Figures 8, 11E:
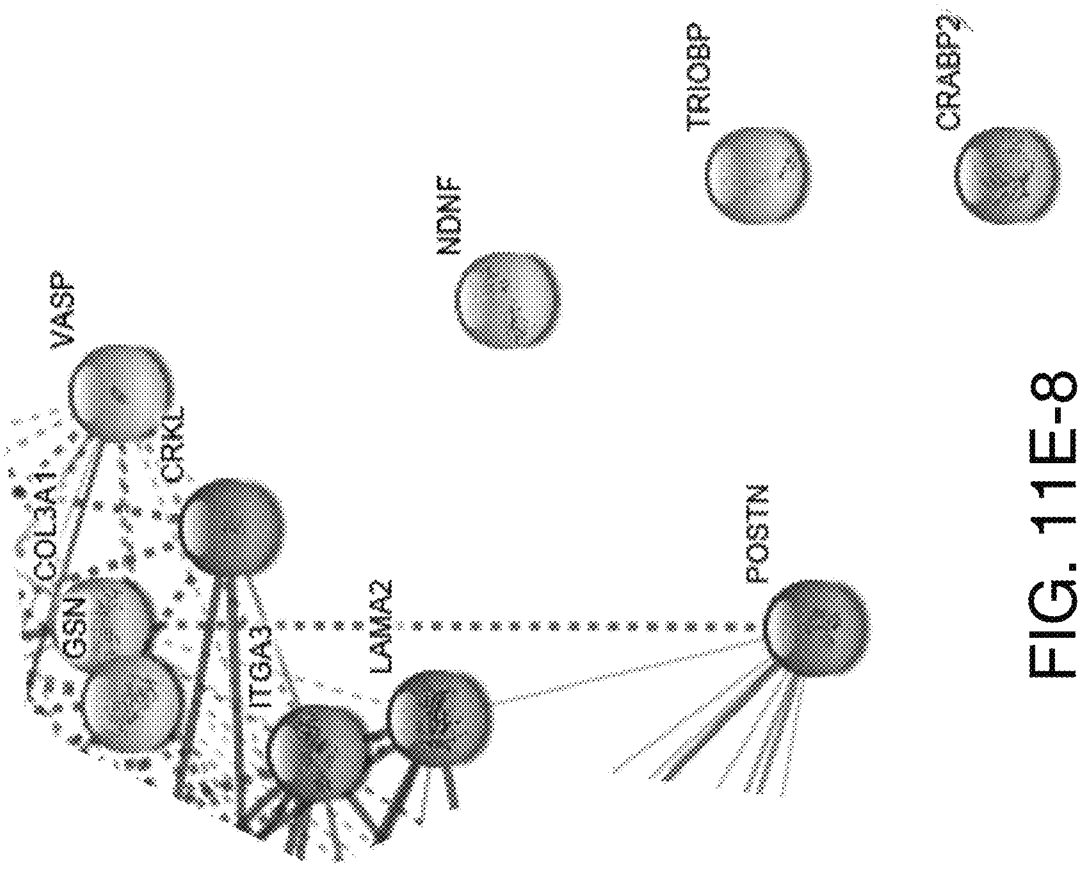
Figures 1, 11F:
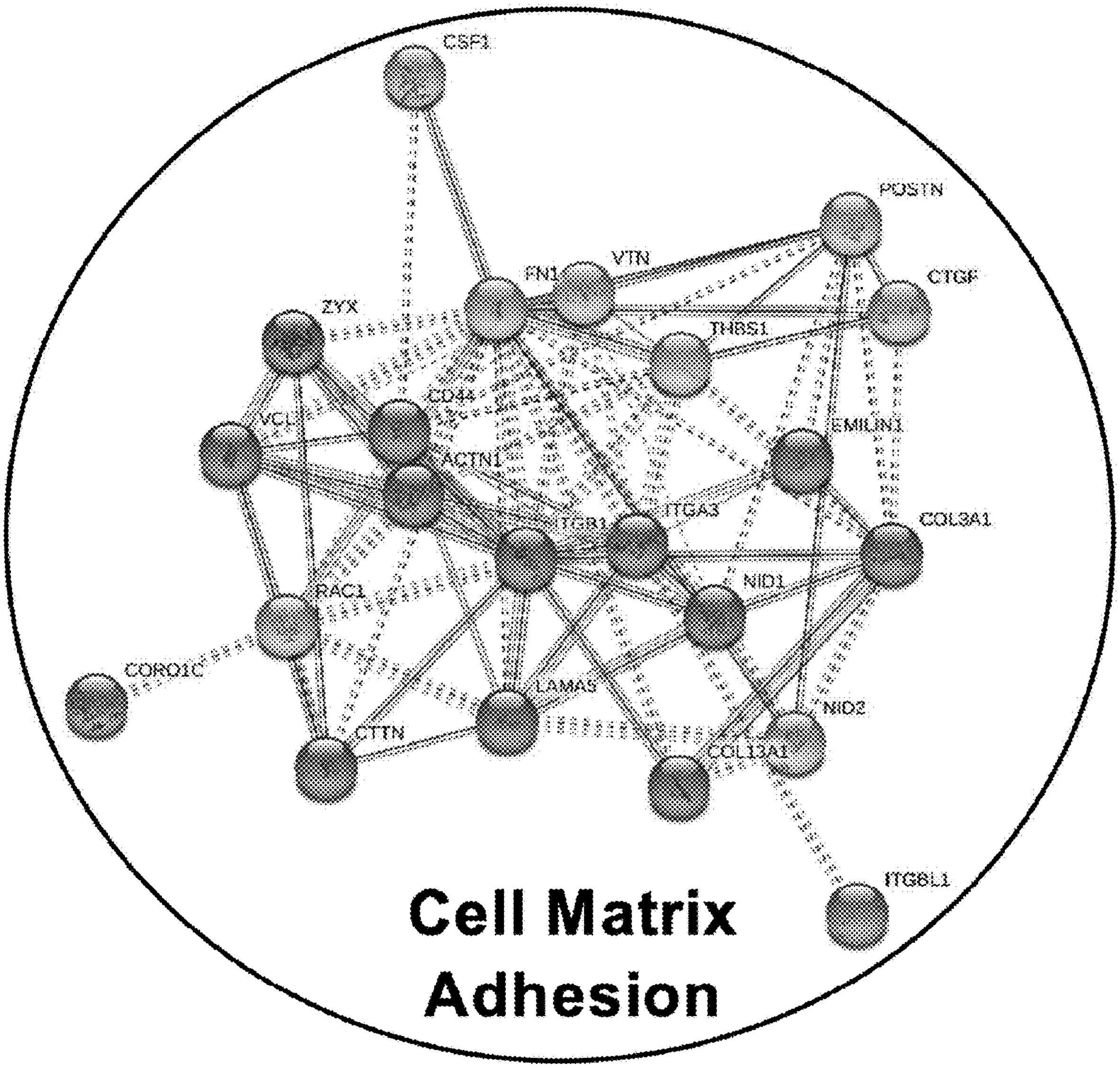
Figures 2, 11F:
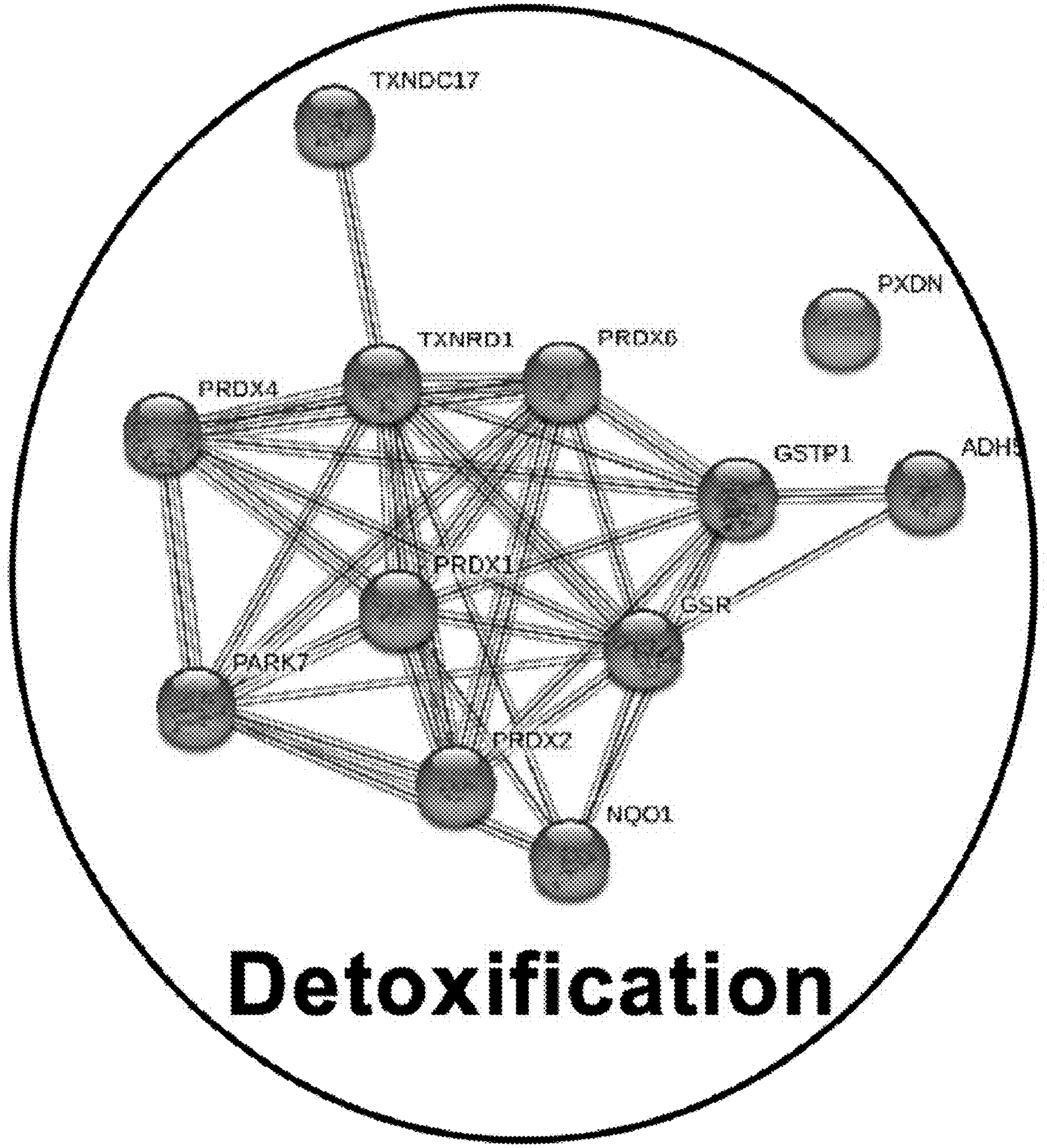
Figures 3, 11F:
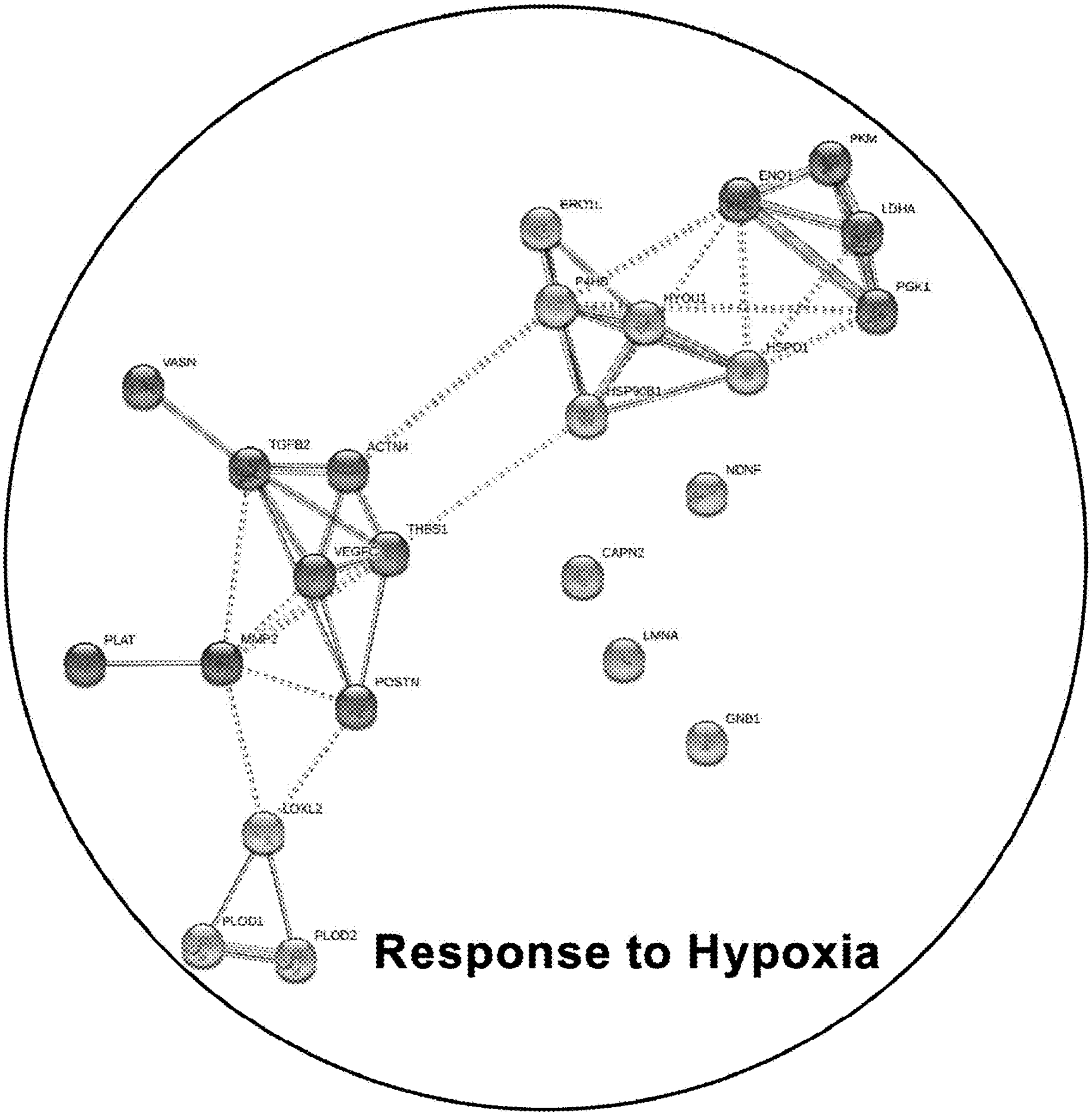
Figures 4, 11F:
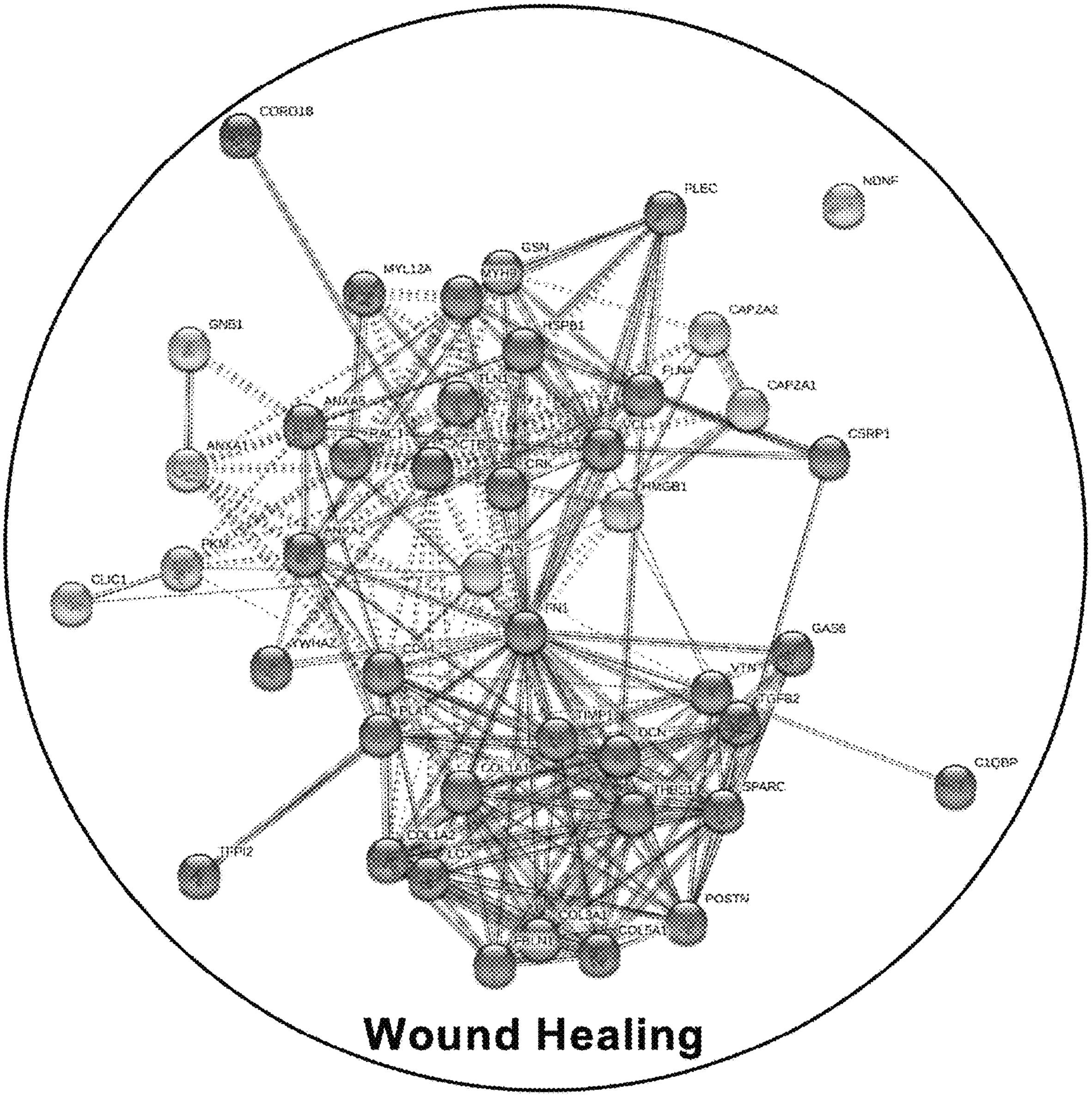
Figure 12A:
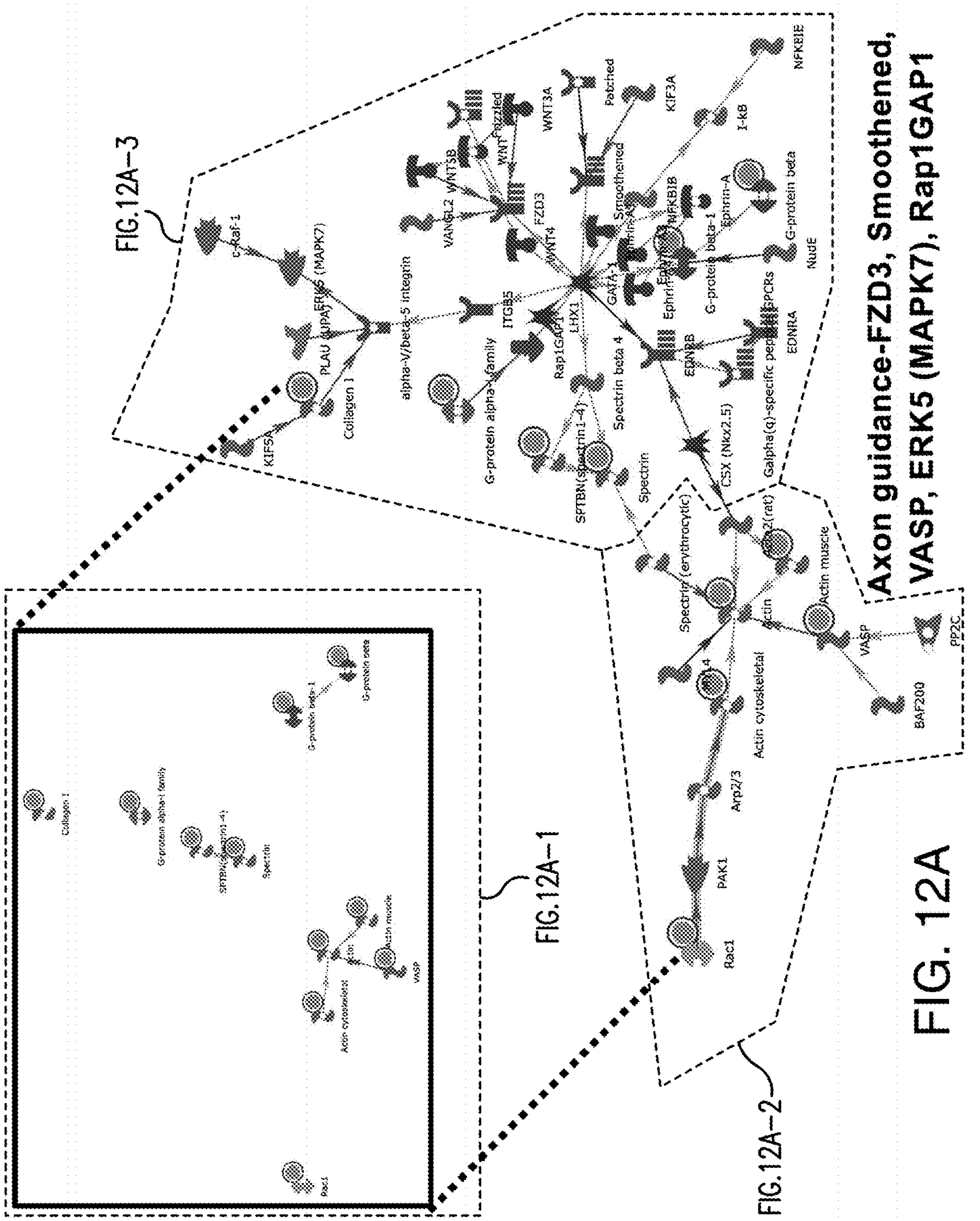
Figures 1, 12A:
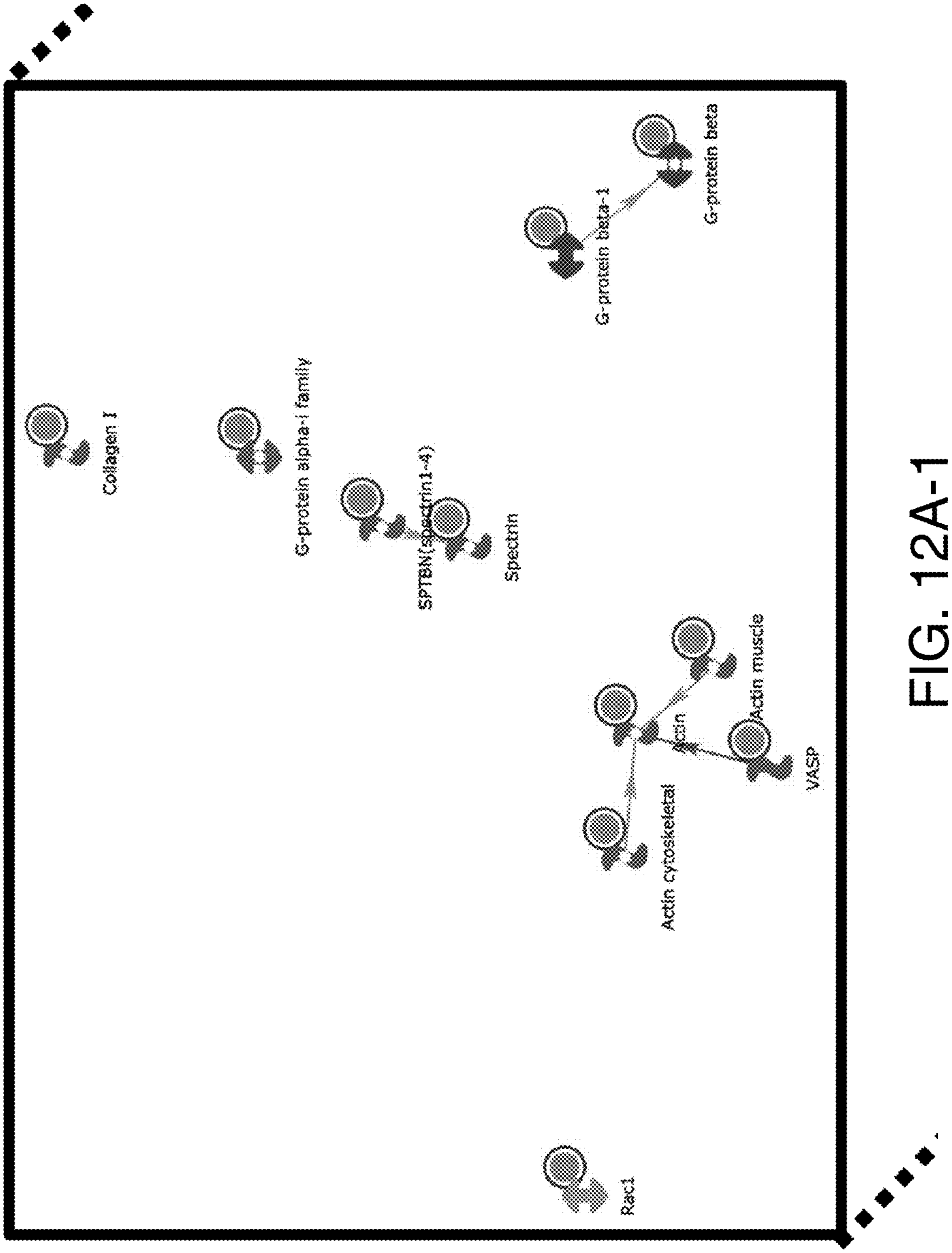
Figures 2, 12A:
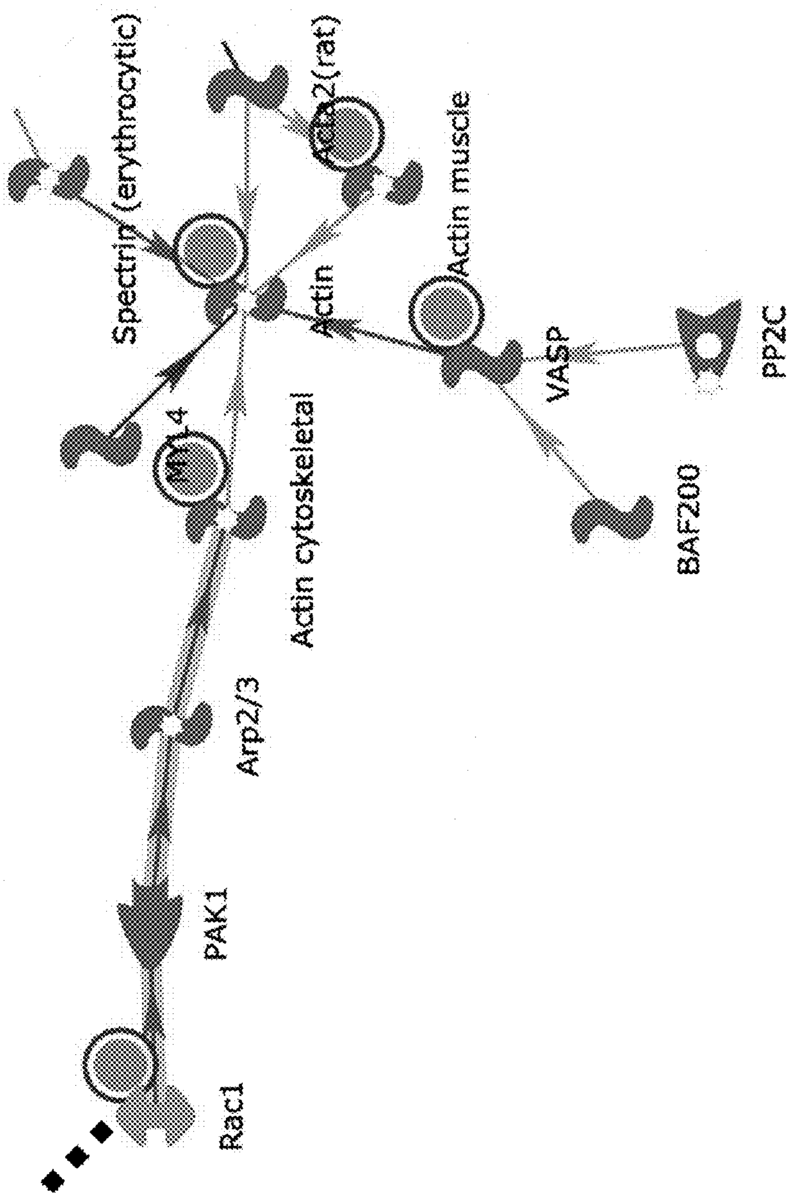
Figures 3, 12A:
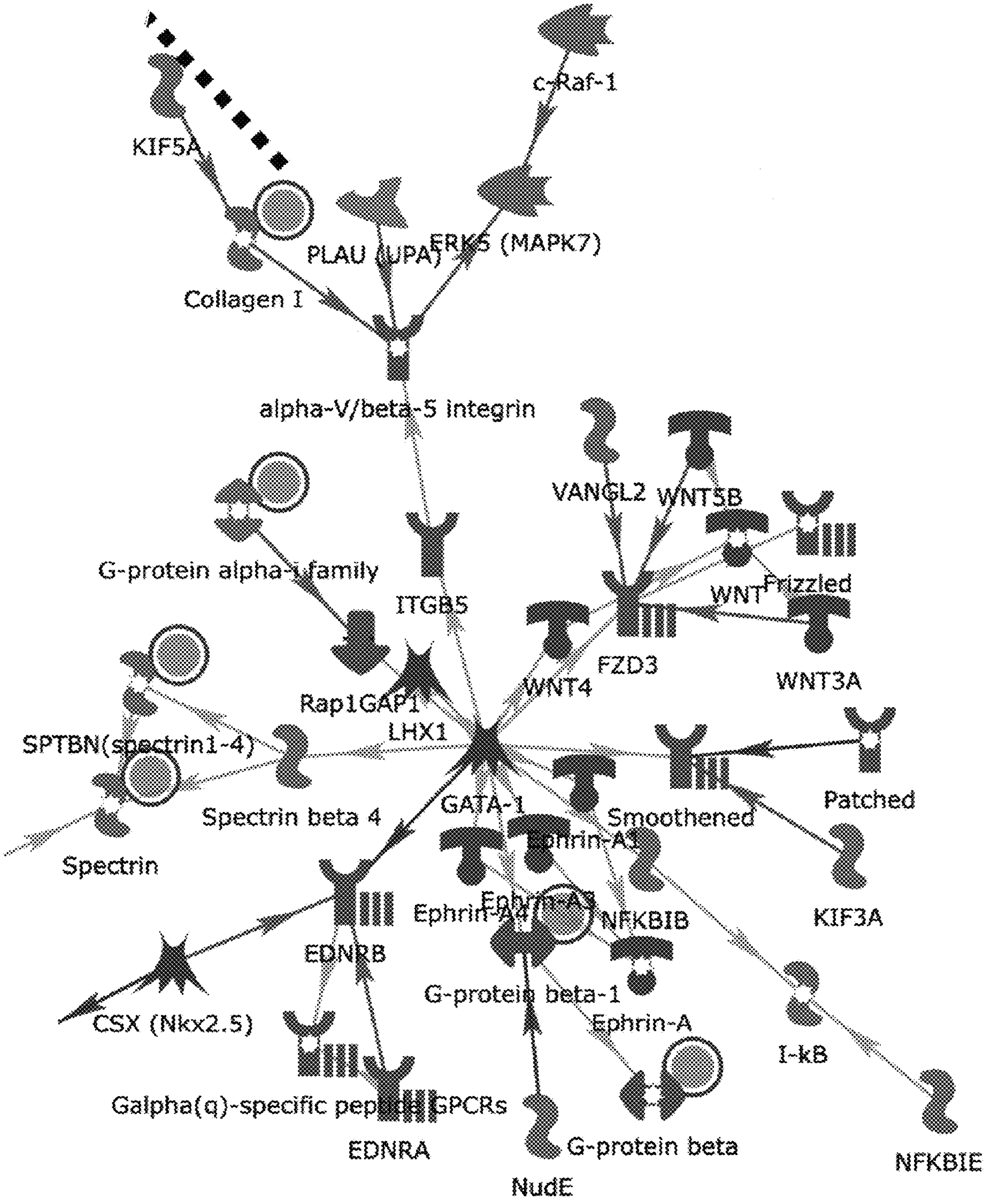
Figure 12B:
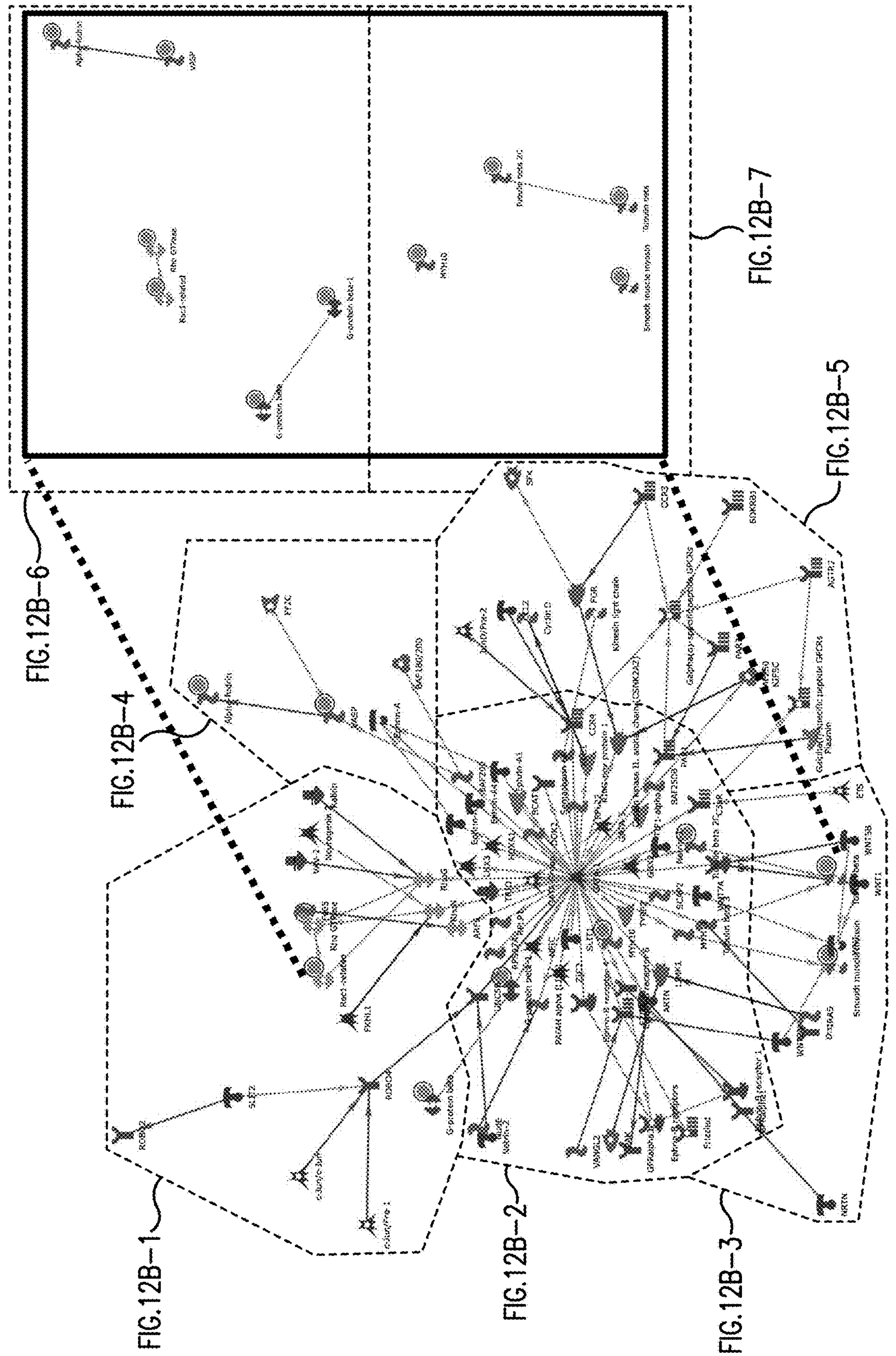
Figures 1, 12B:
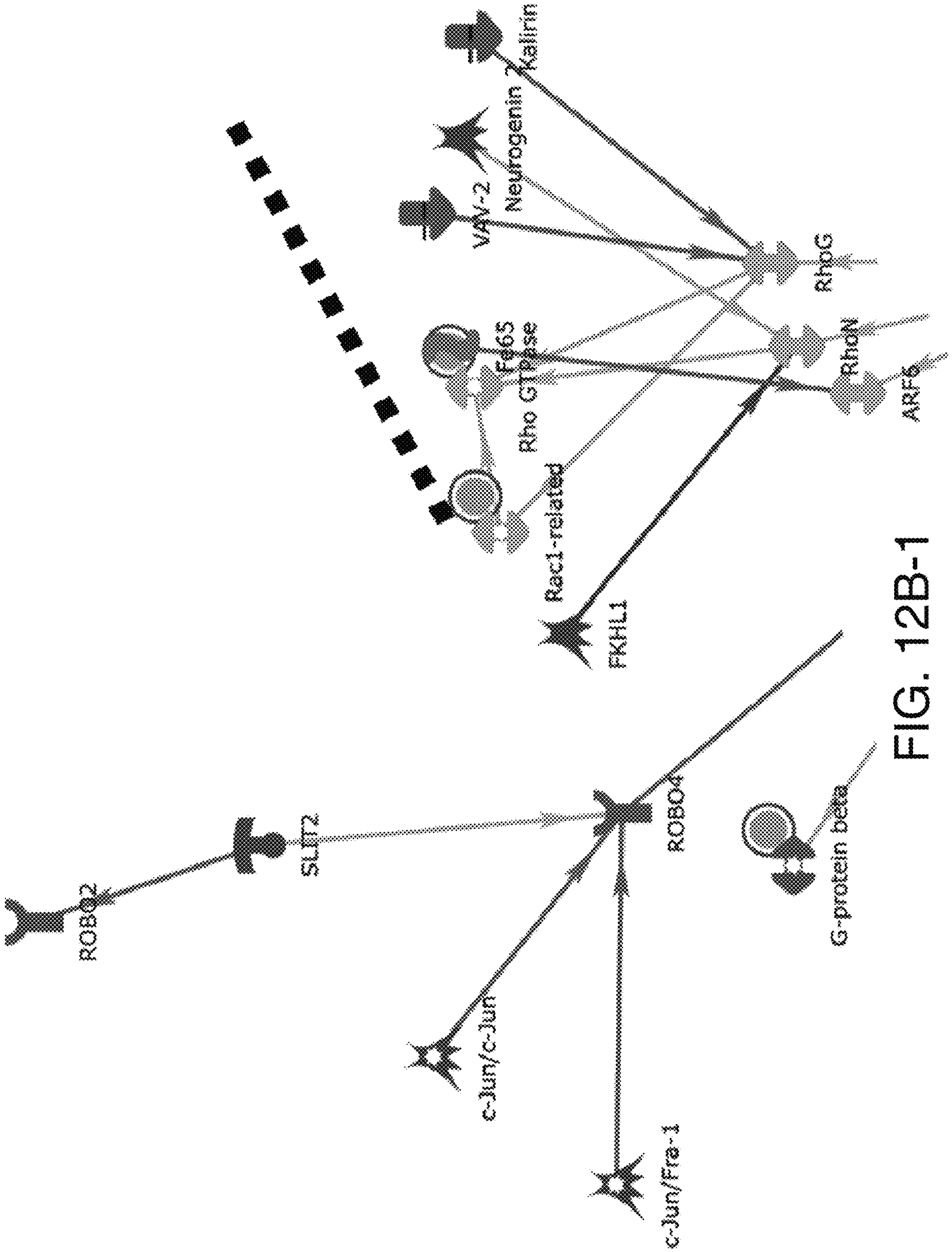
Figures 2, 12B:
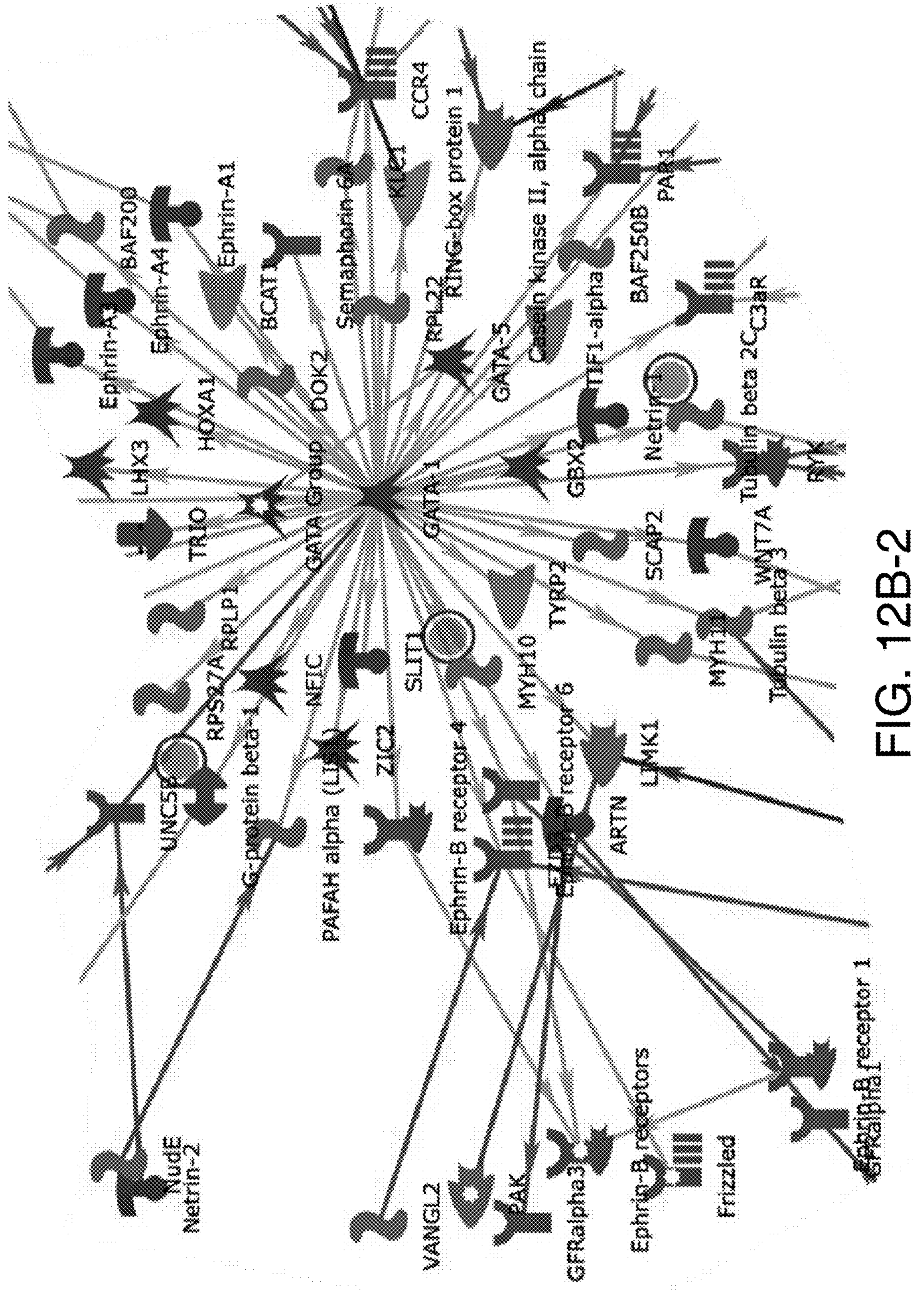
Figures 3, 12B:
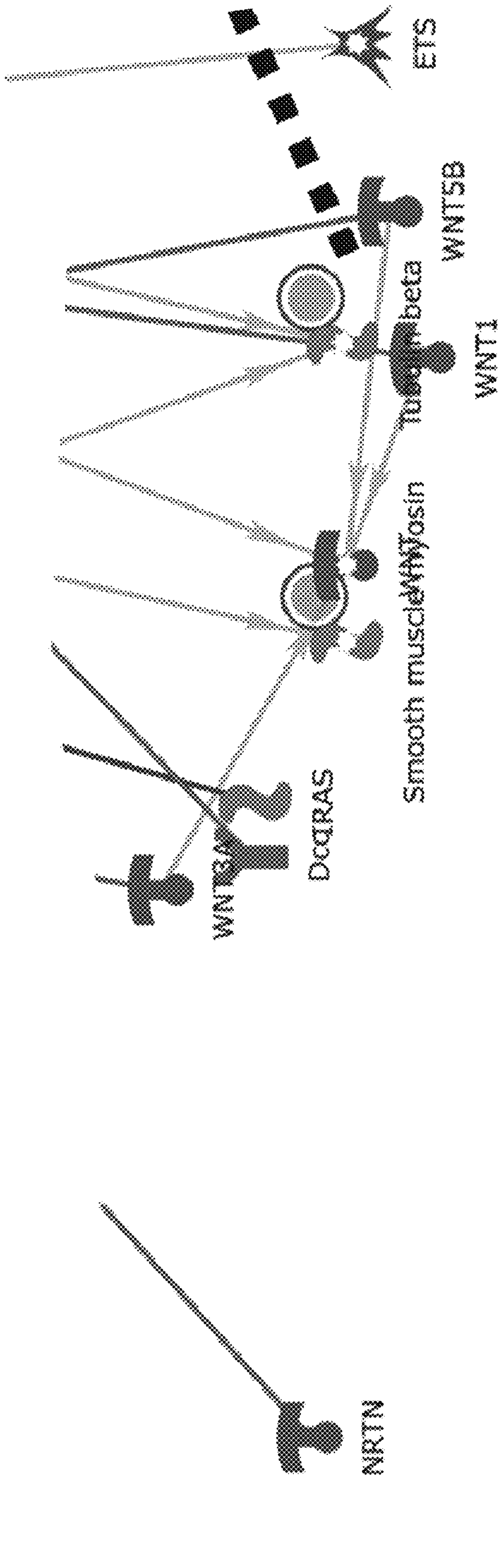
Figures 4, 12B:
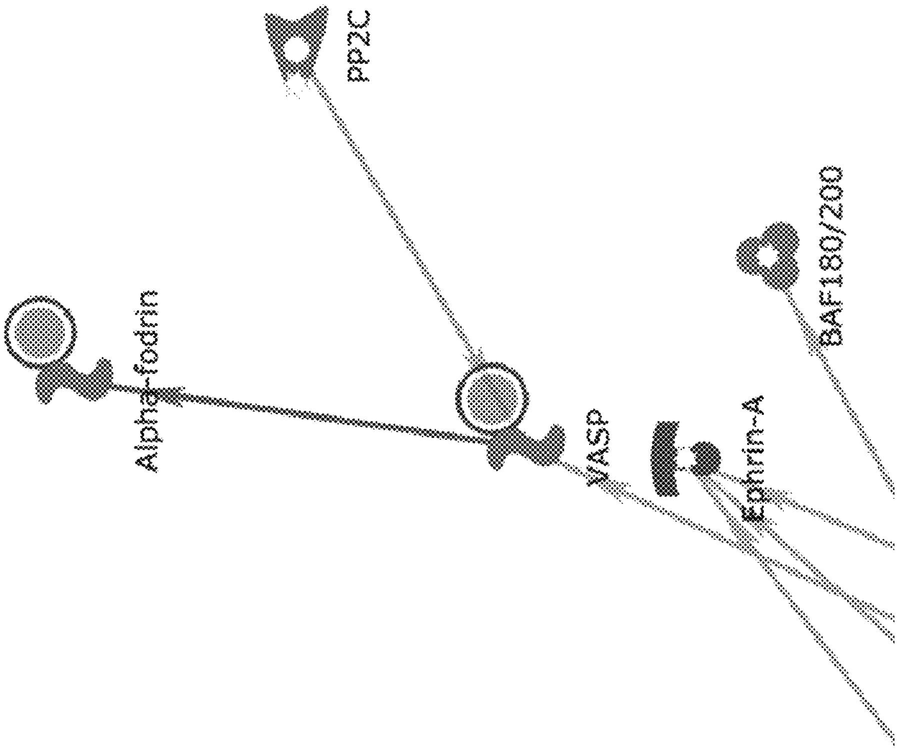
Figures 5, 12B:
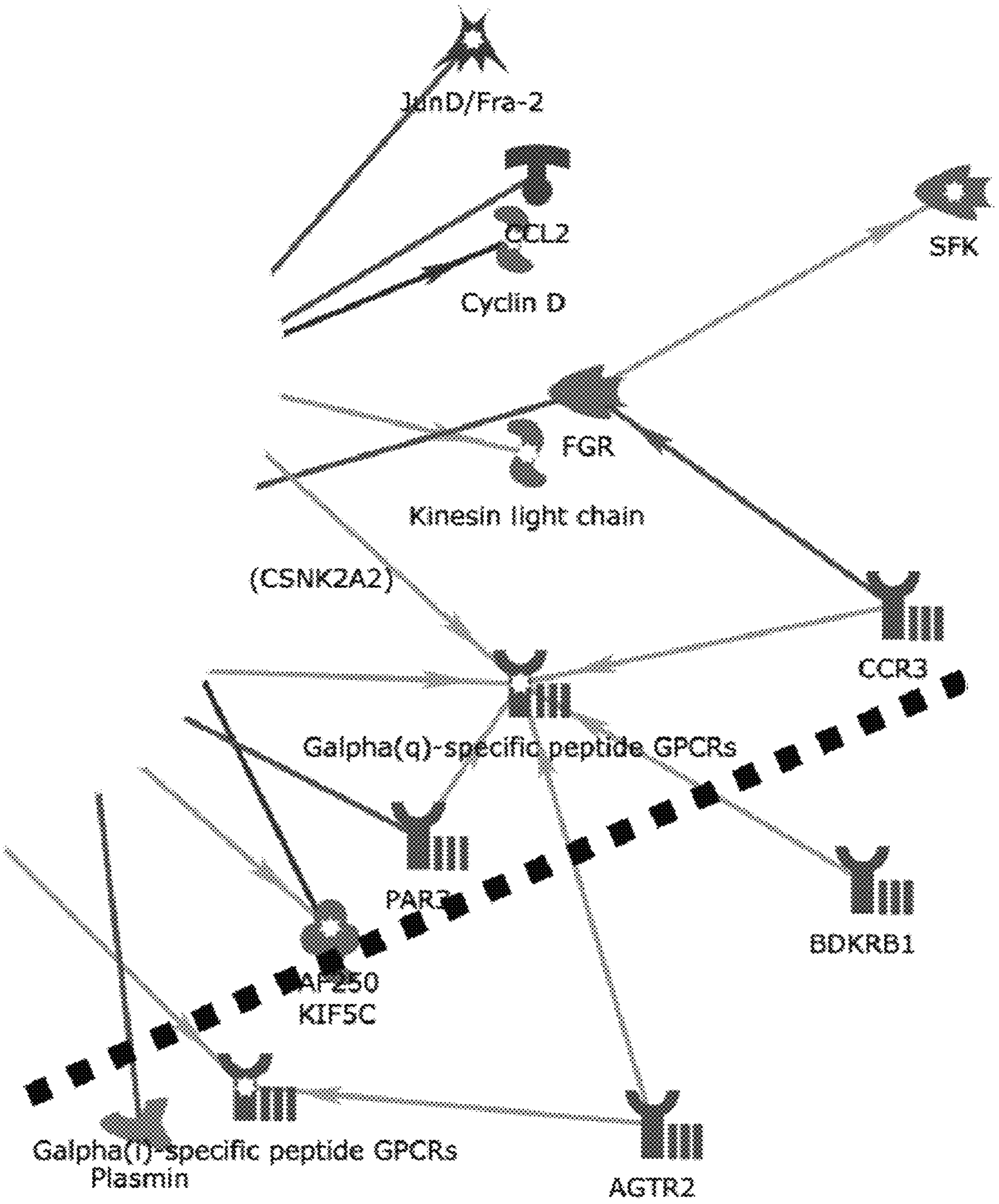
Figures 6, 12B:
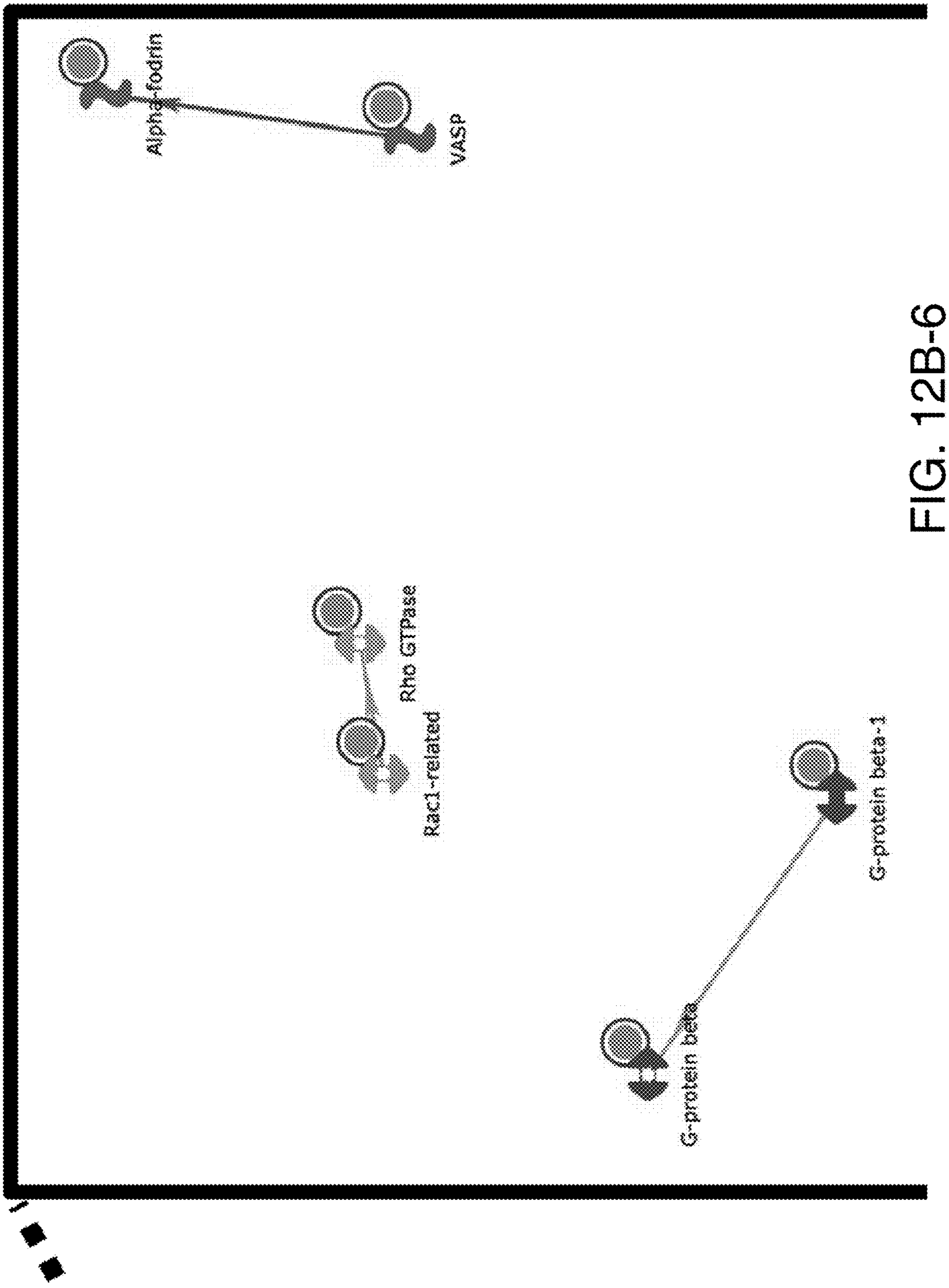
Figures 7, 12B:
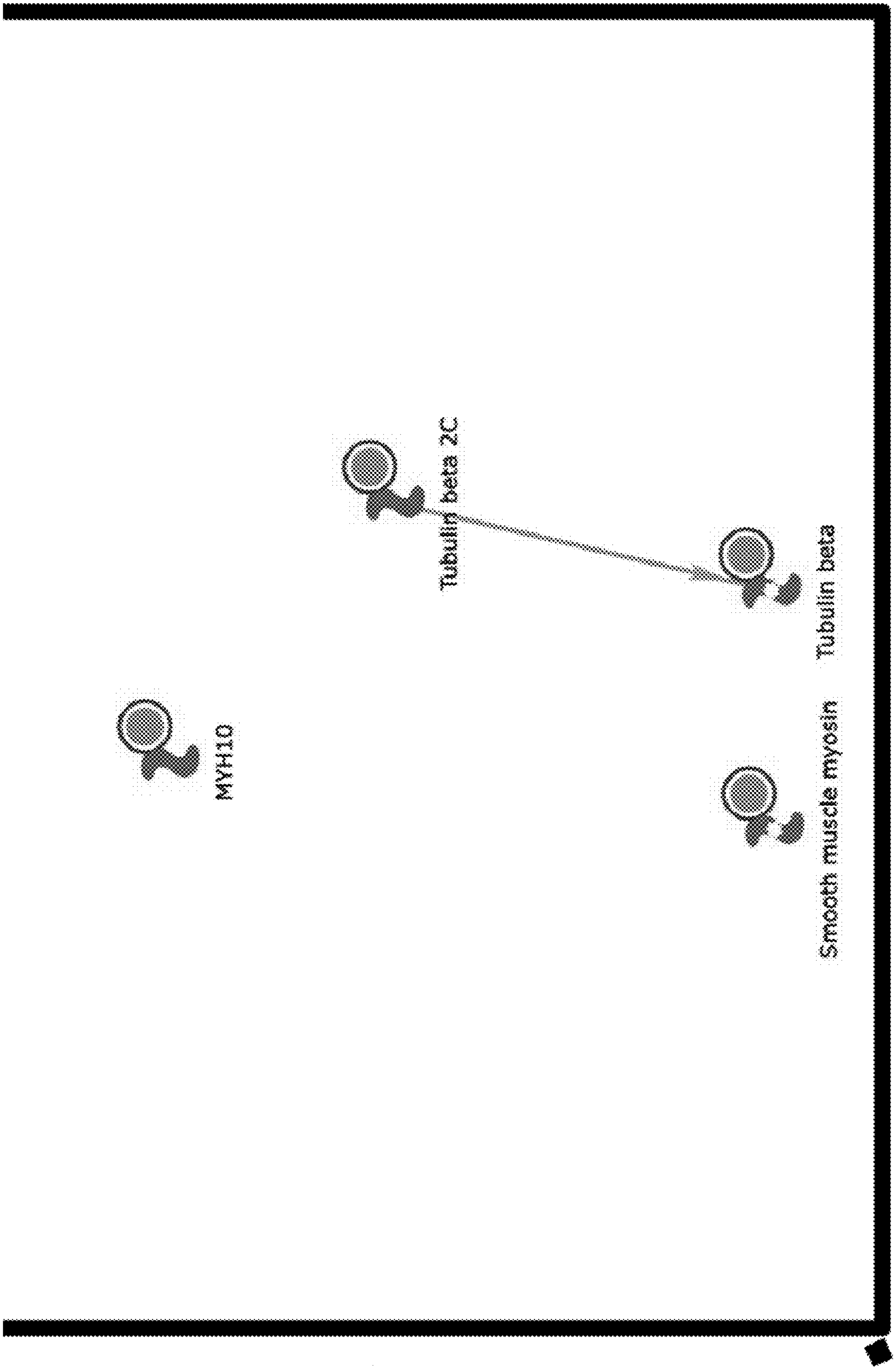
Figure 12C:
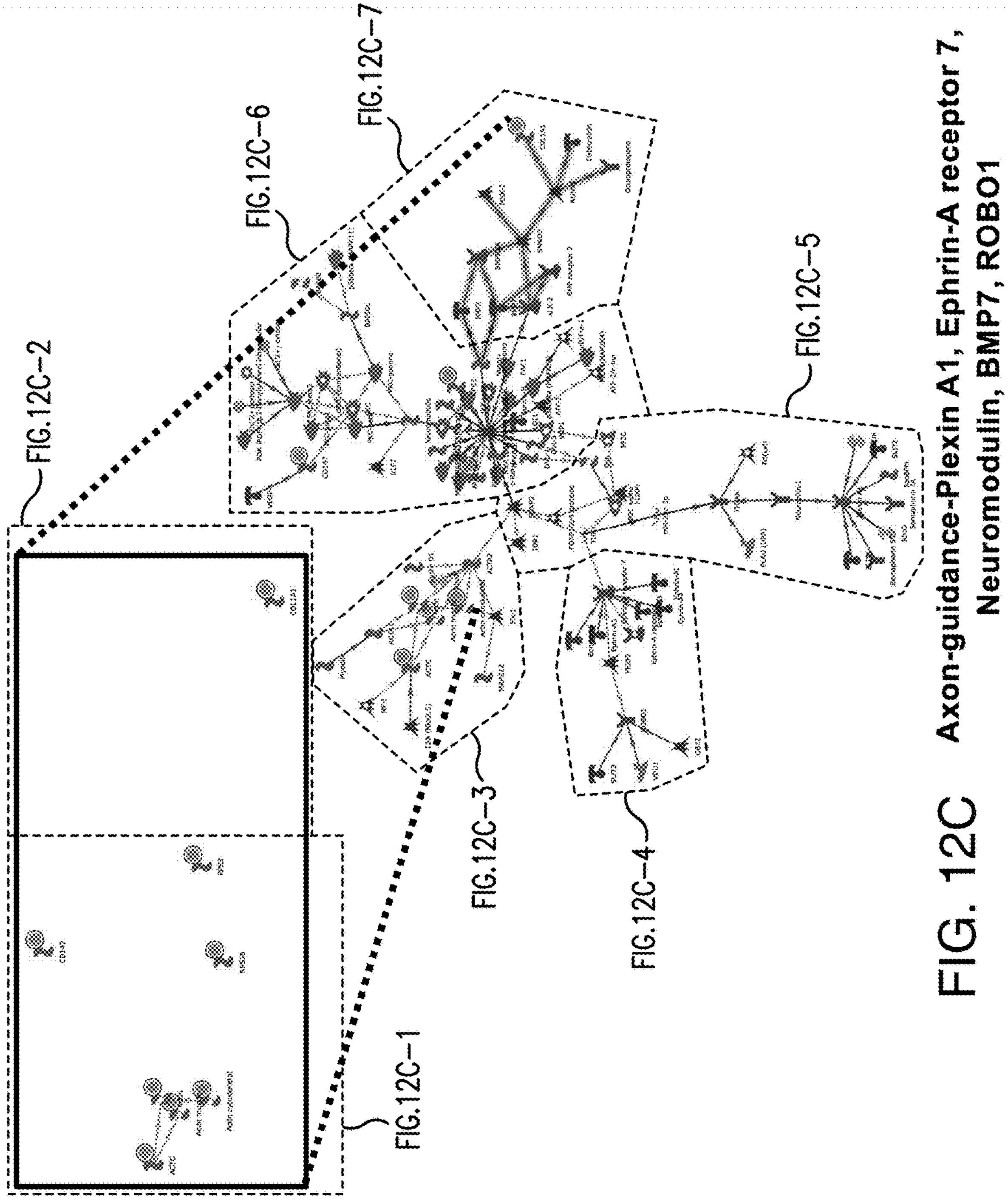
Figures 1, 12C:
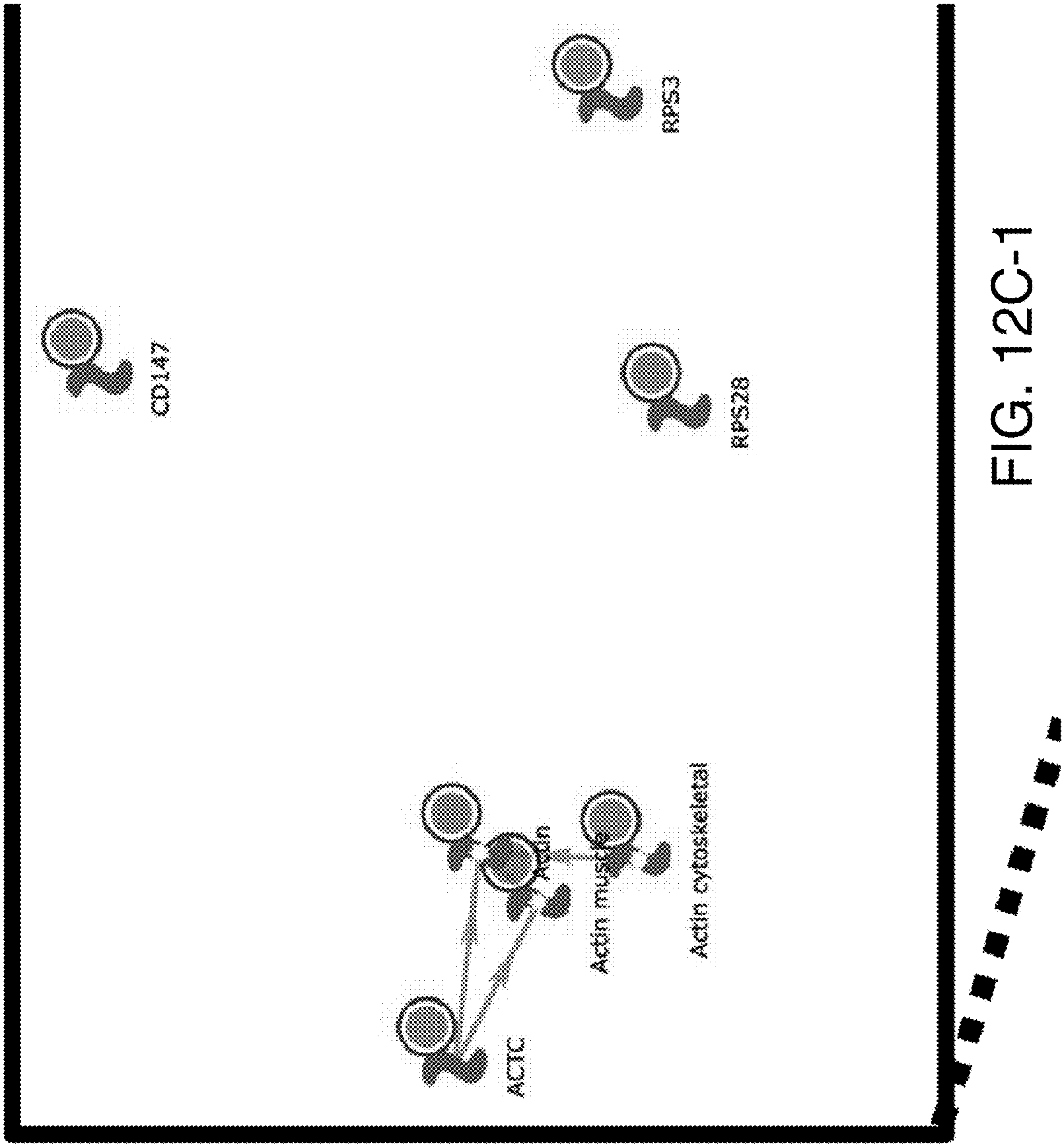
Figures 2, 12C:
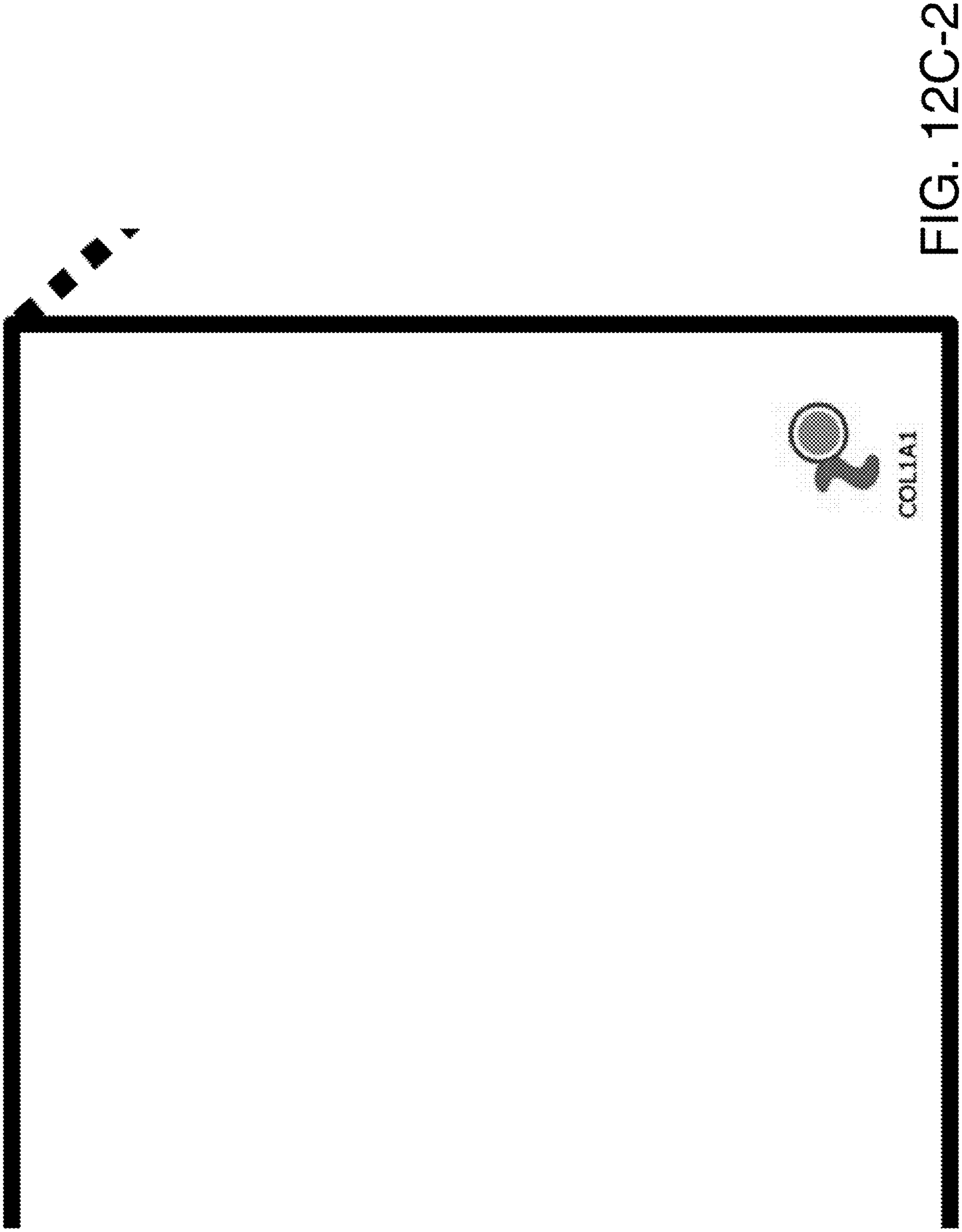
Figures 3, 12C:
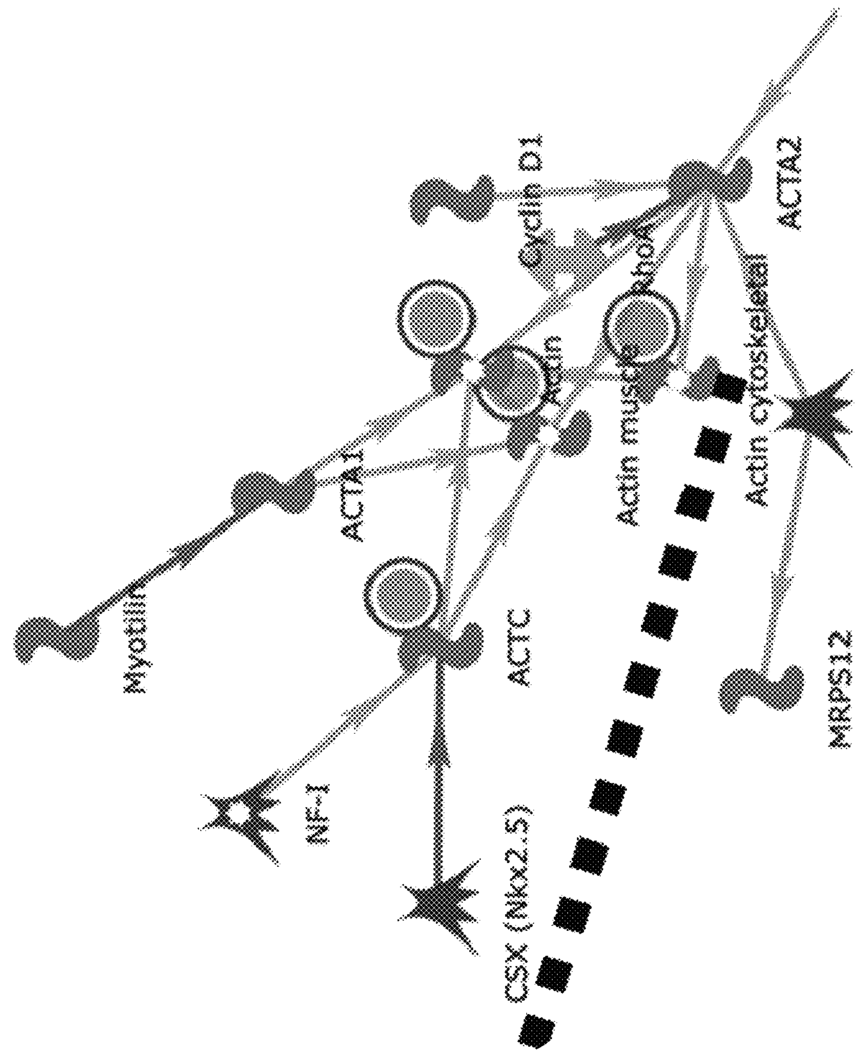
Figures 4, 12C:
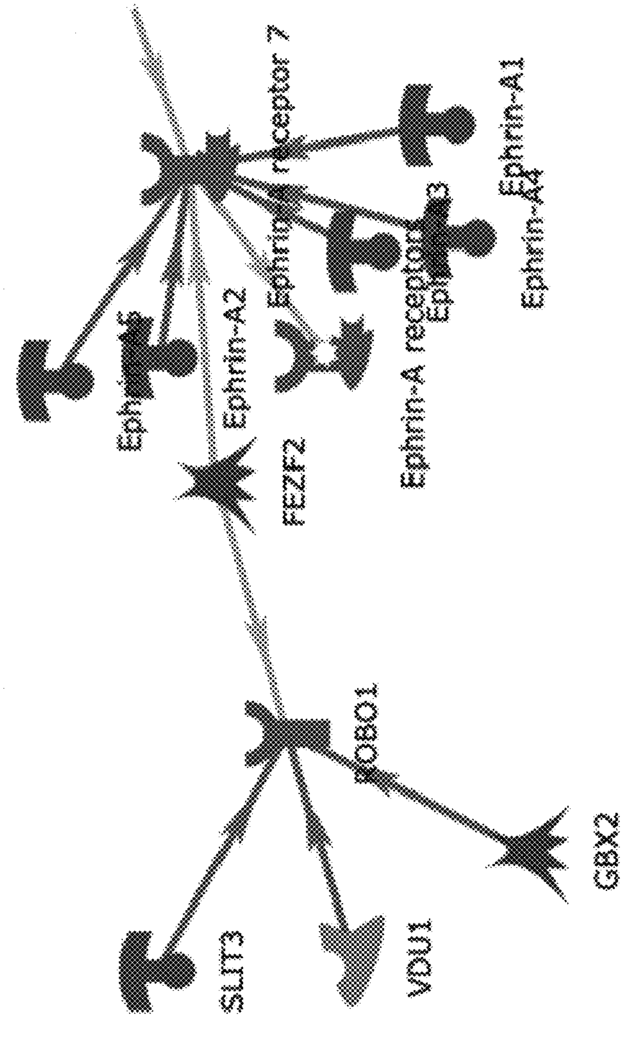
Figures 5, 12C:
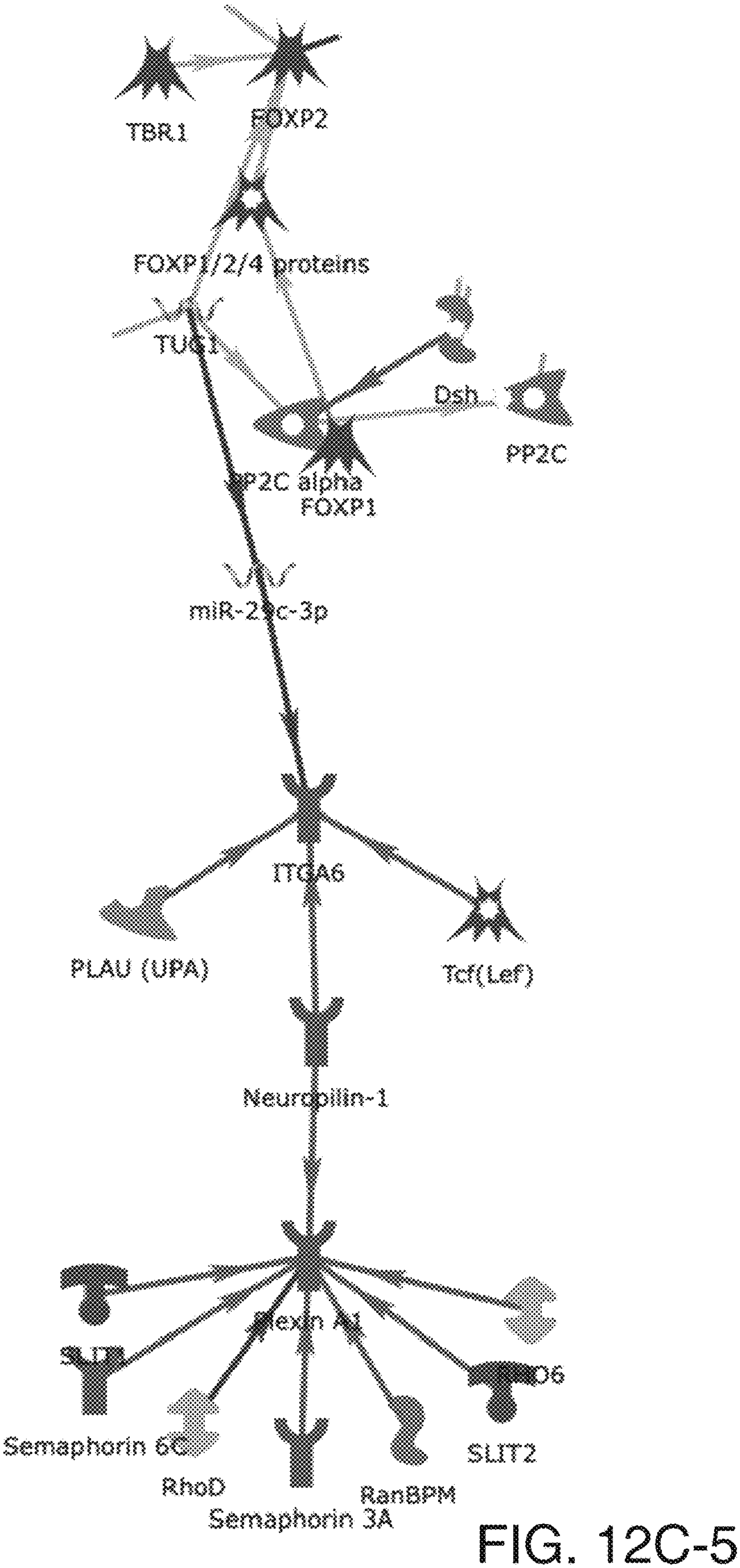
Figures 6, 12C:
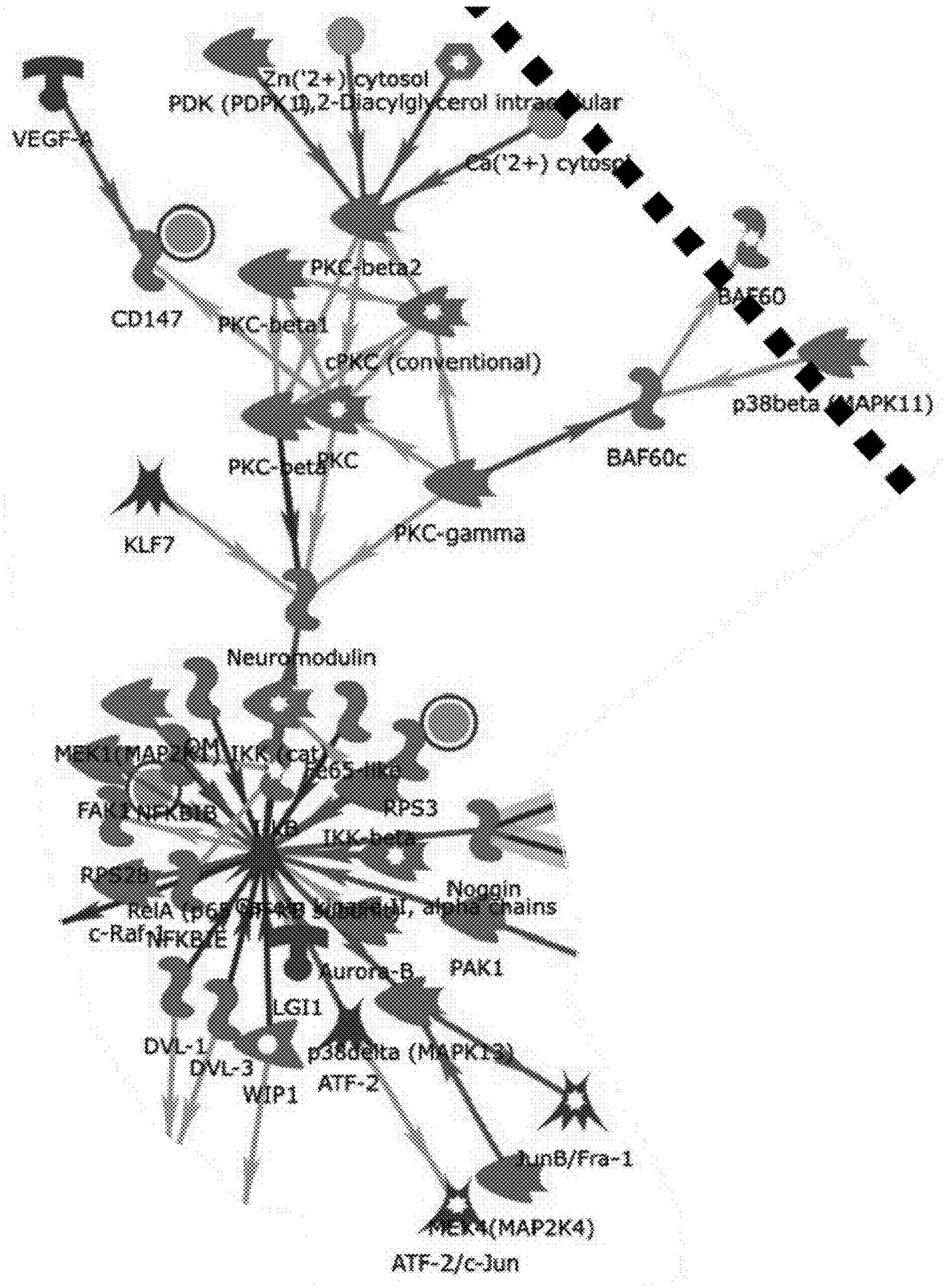
Figures 7, 12C:
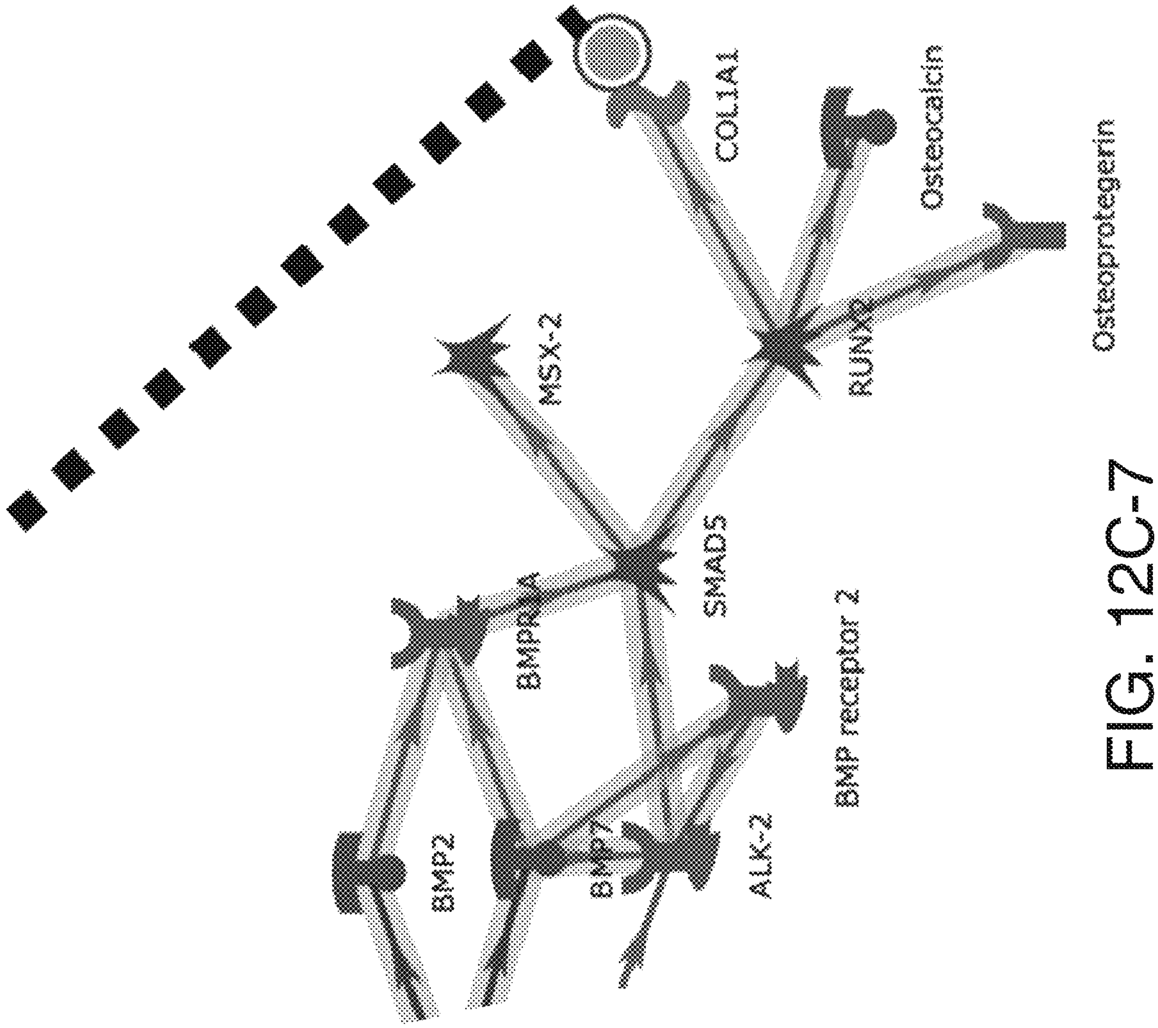
Figure 12D:
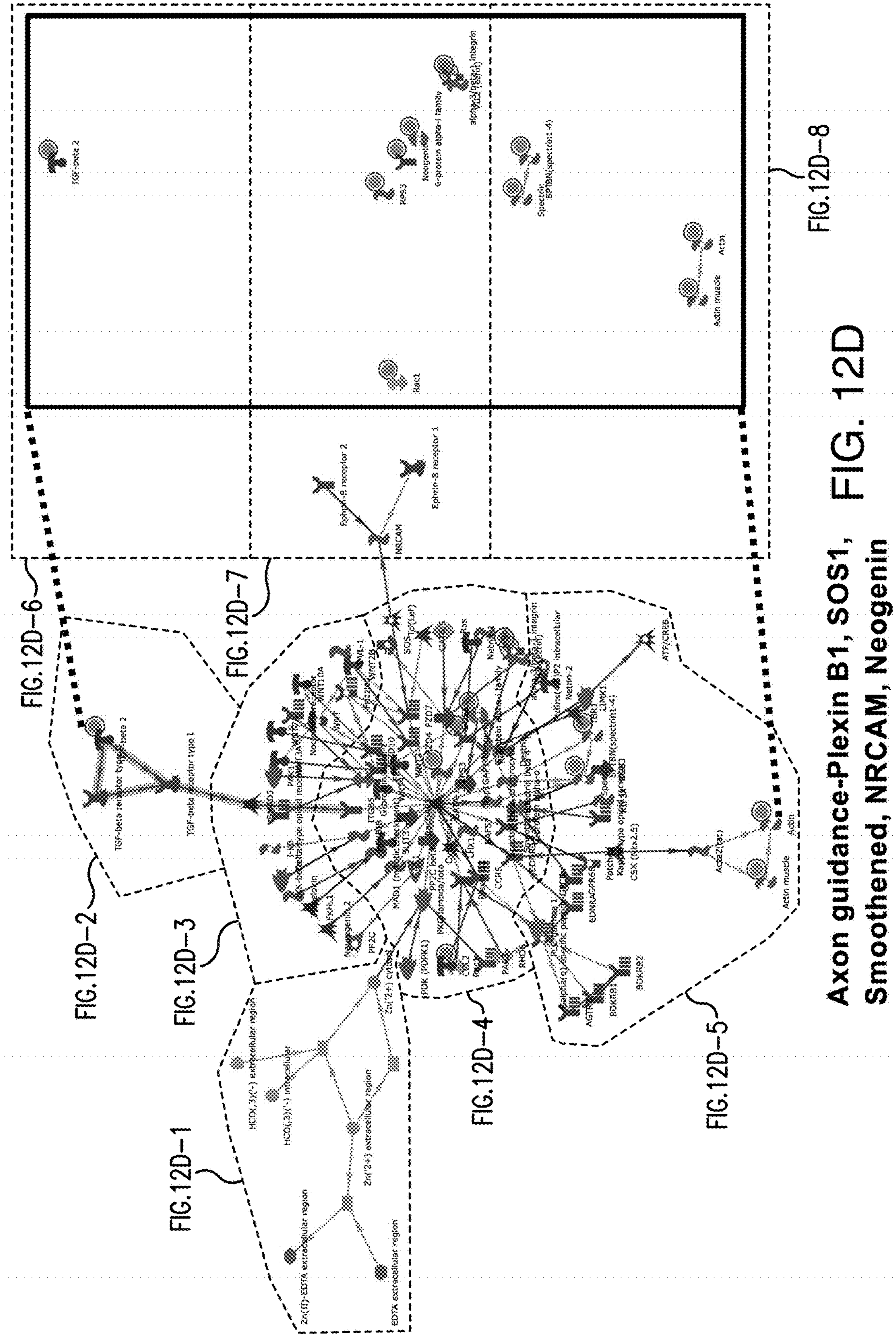
Figures 1, 12D:
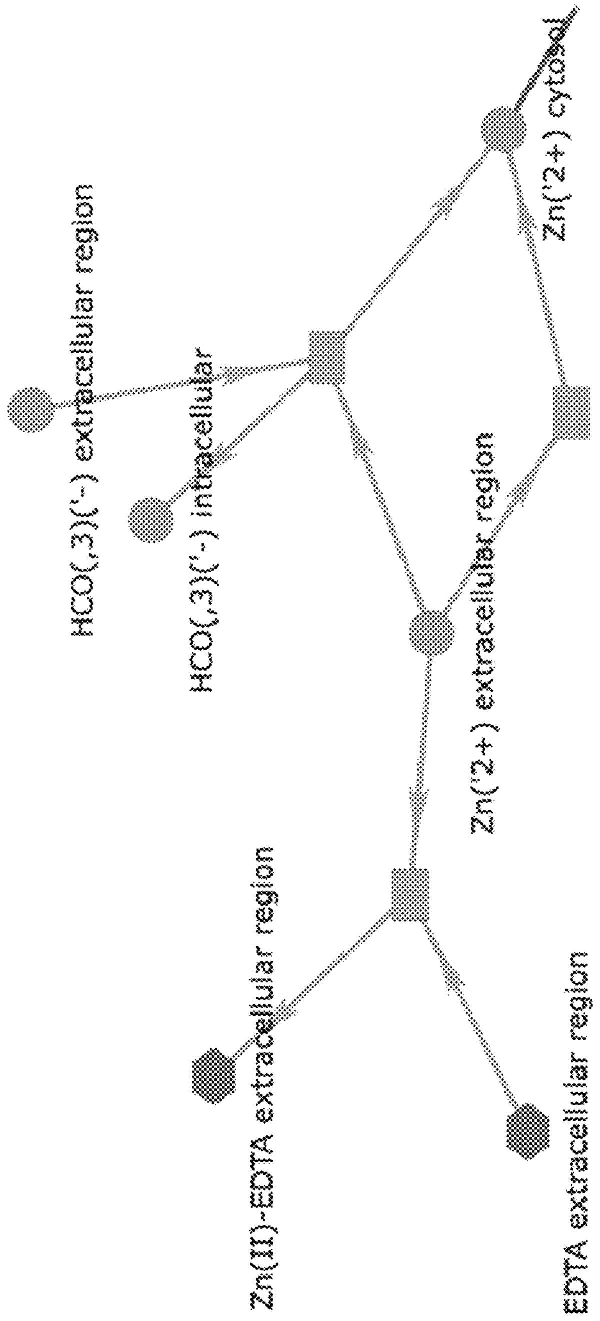
Figures 2, 12D:
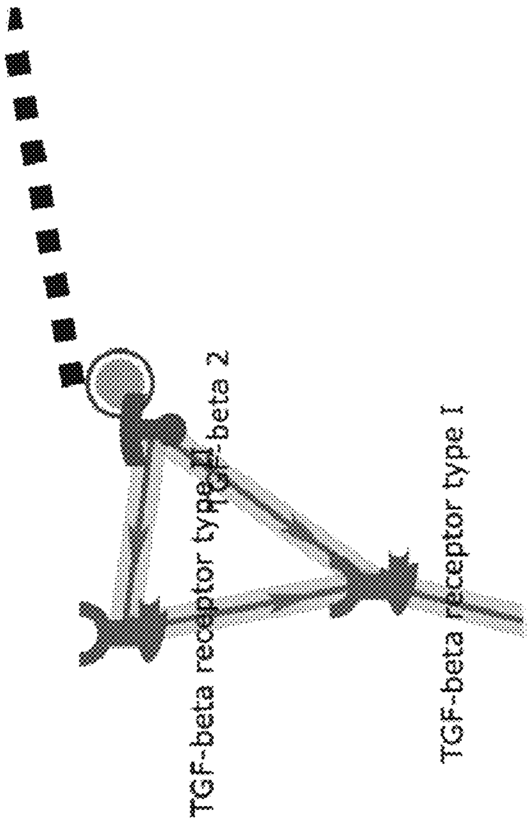
Figures 3, 12D:
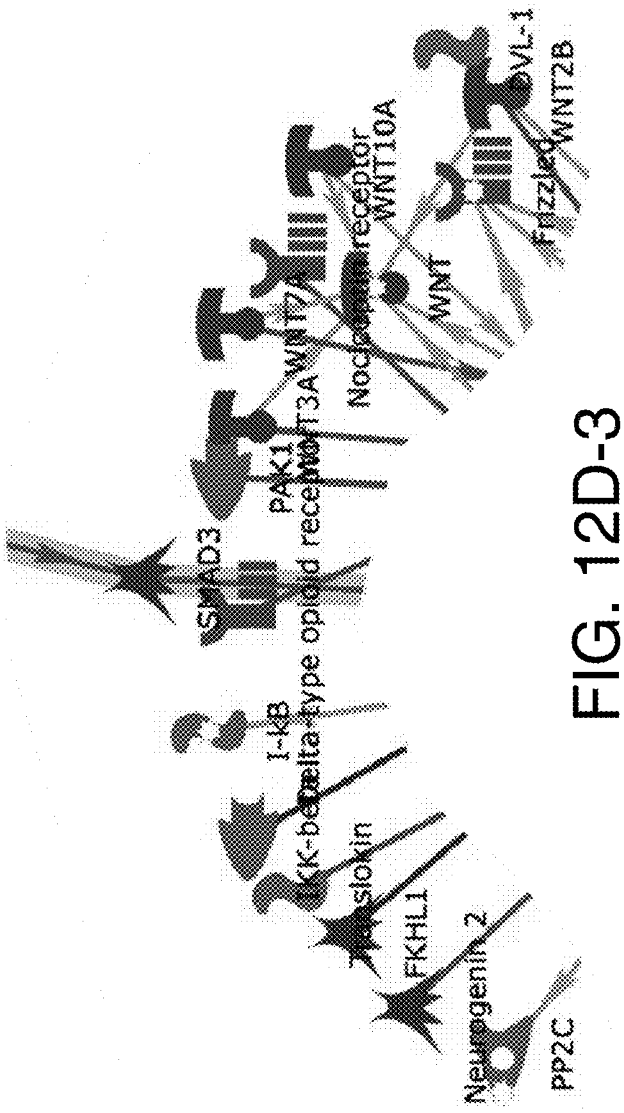
Figures 4, 12D:
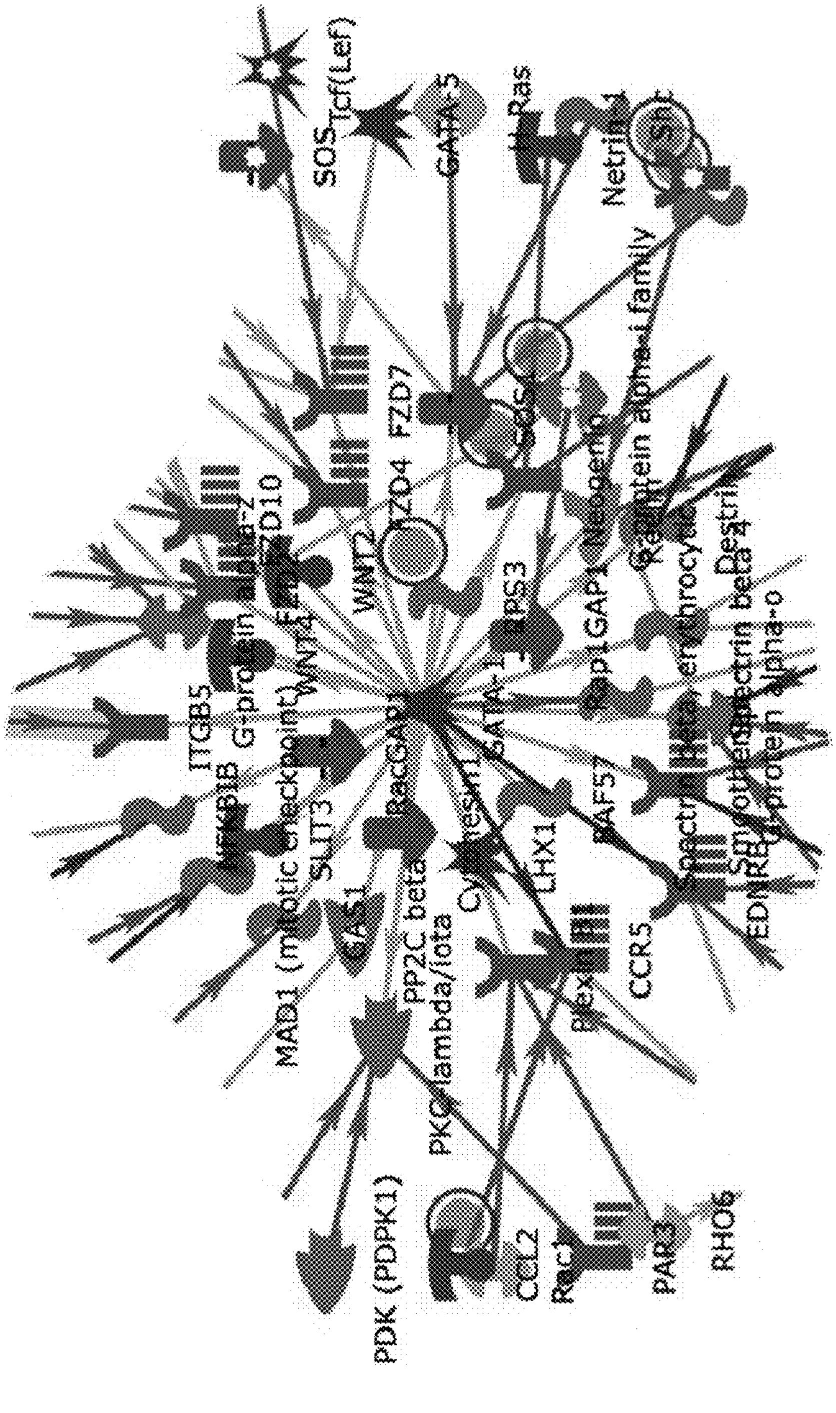
Figures 5, 12D:
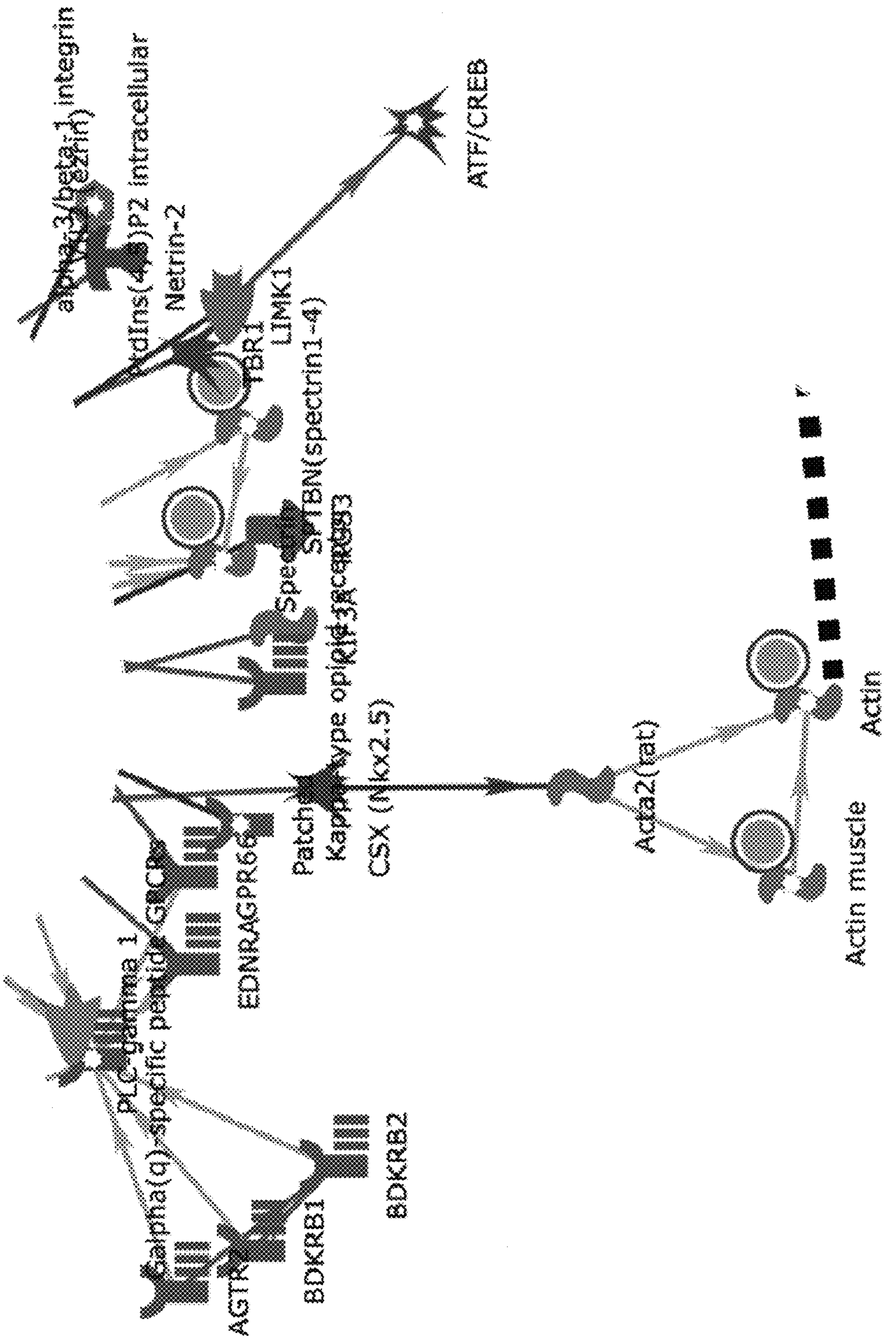
Figures 6, 12D:
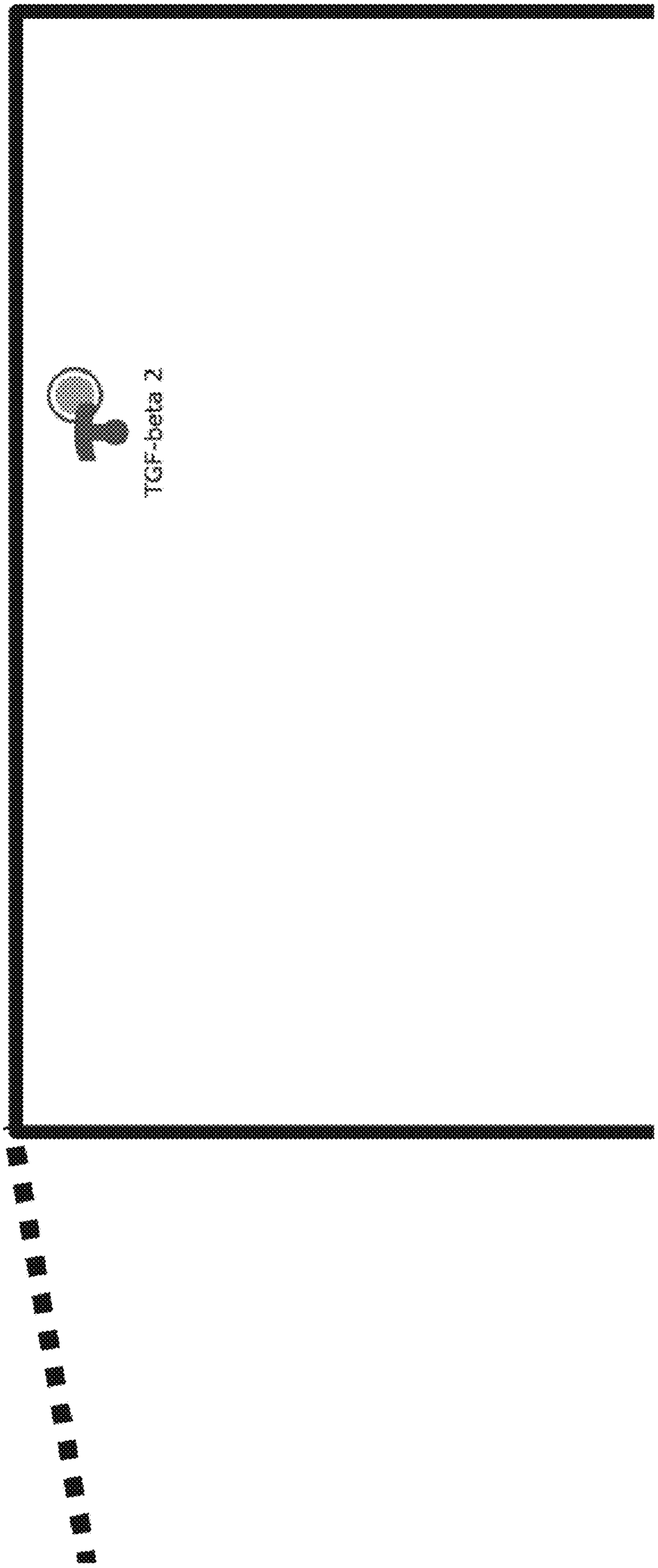
Figures 7, 12D:
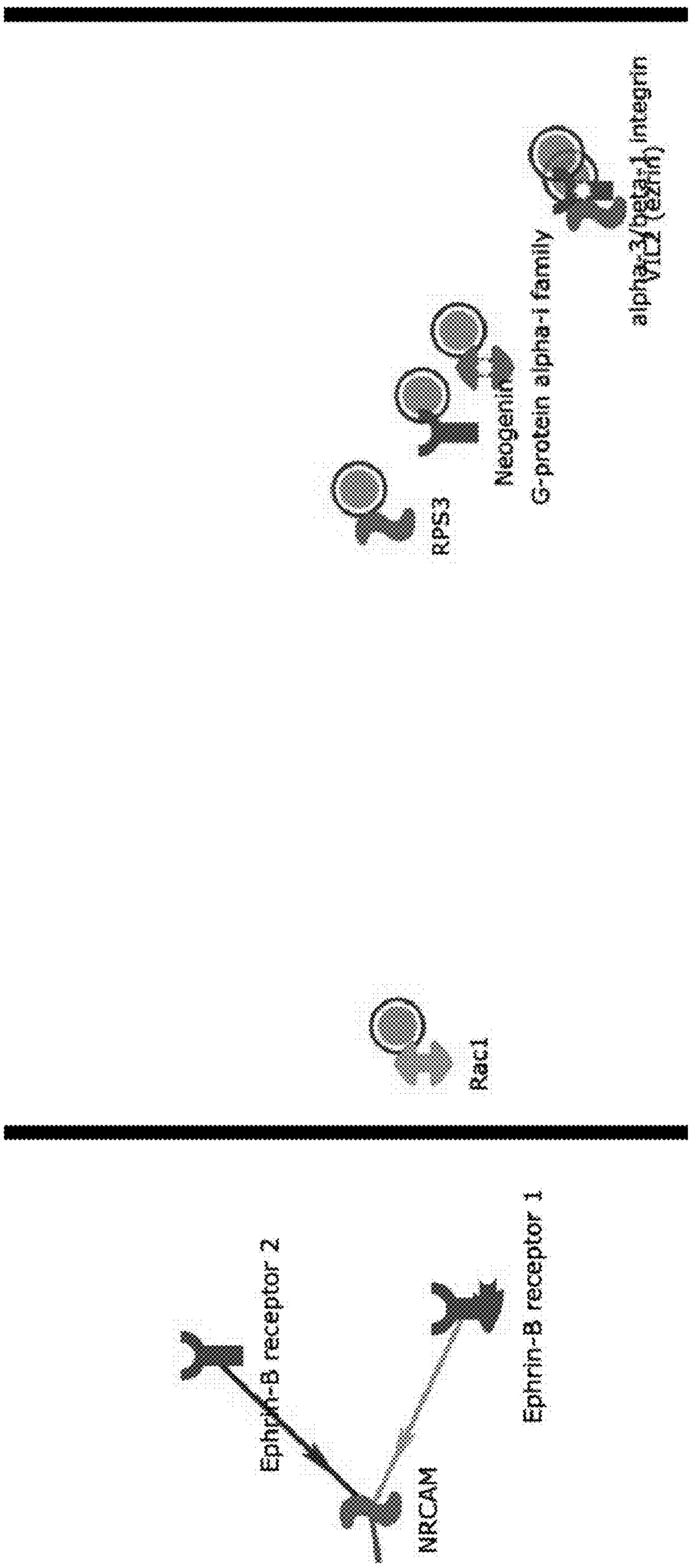
Figures 8, 12D:
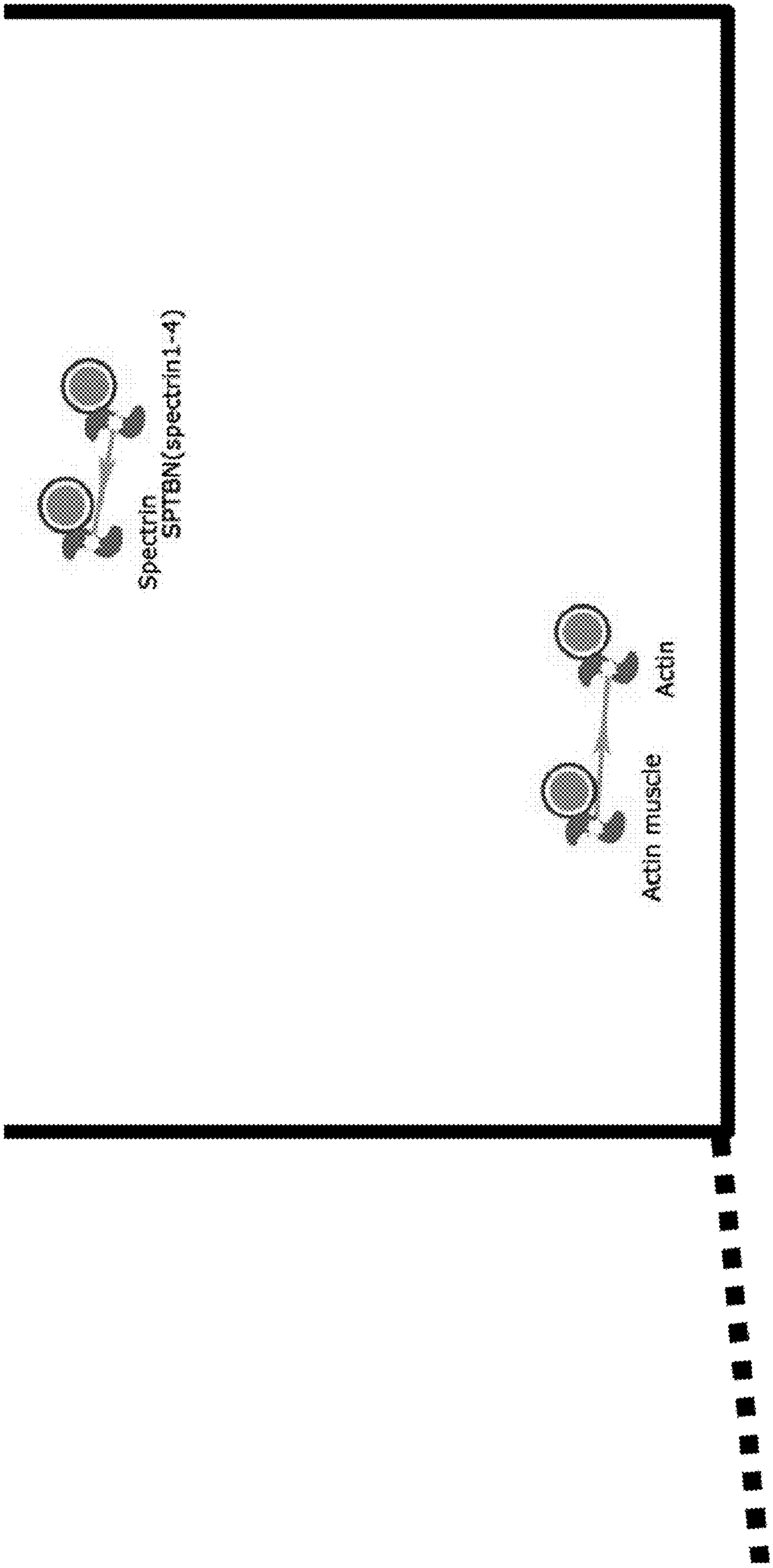
Figure 12E:
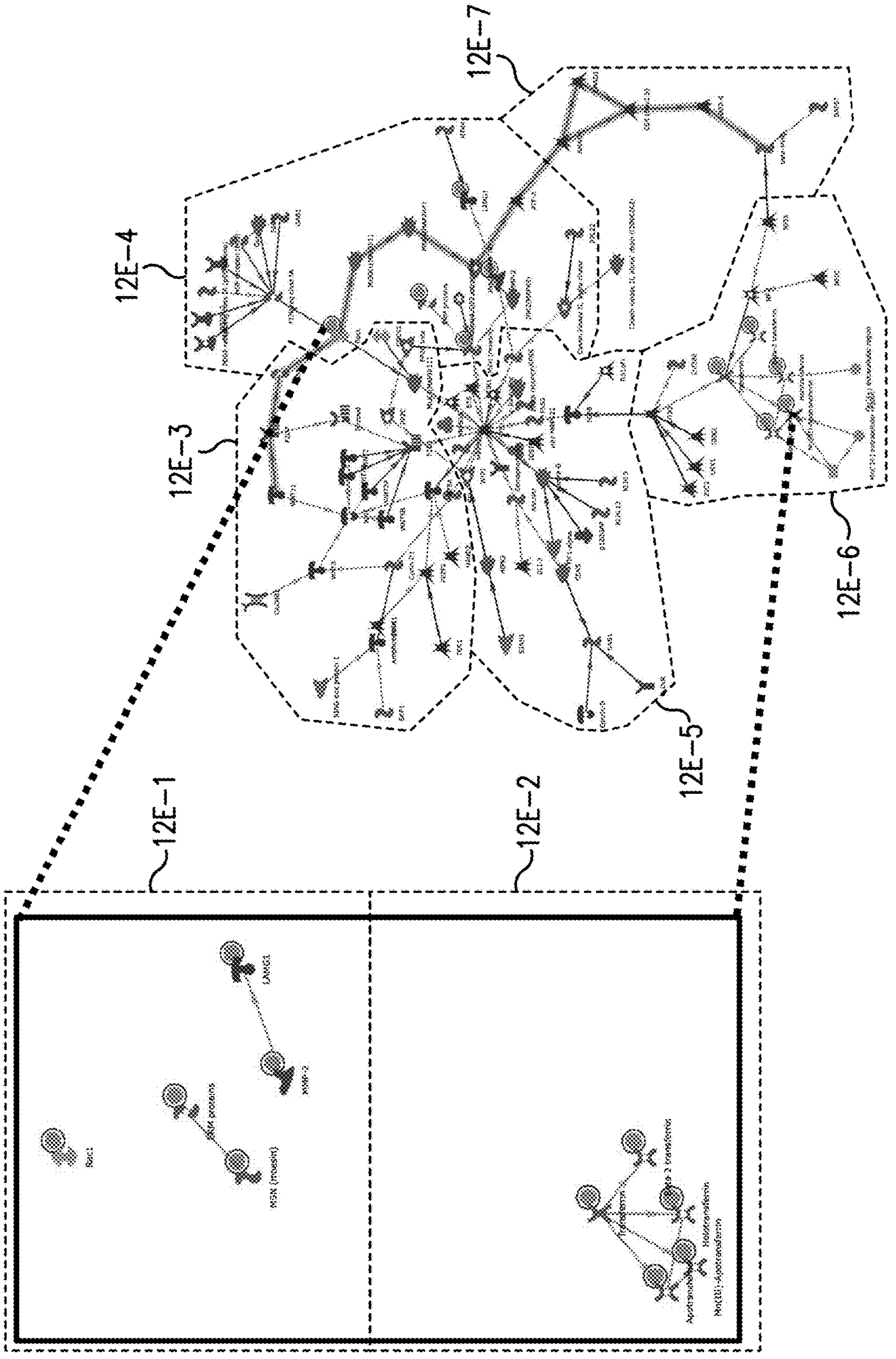
Figures 1, 12E:
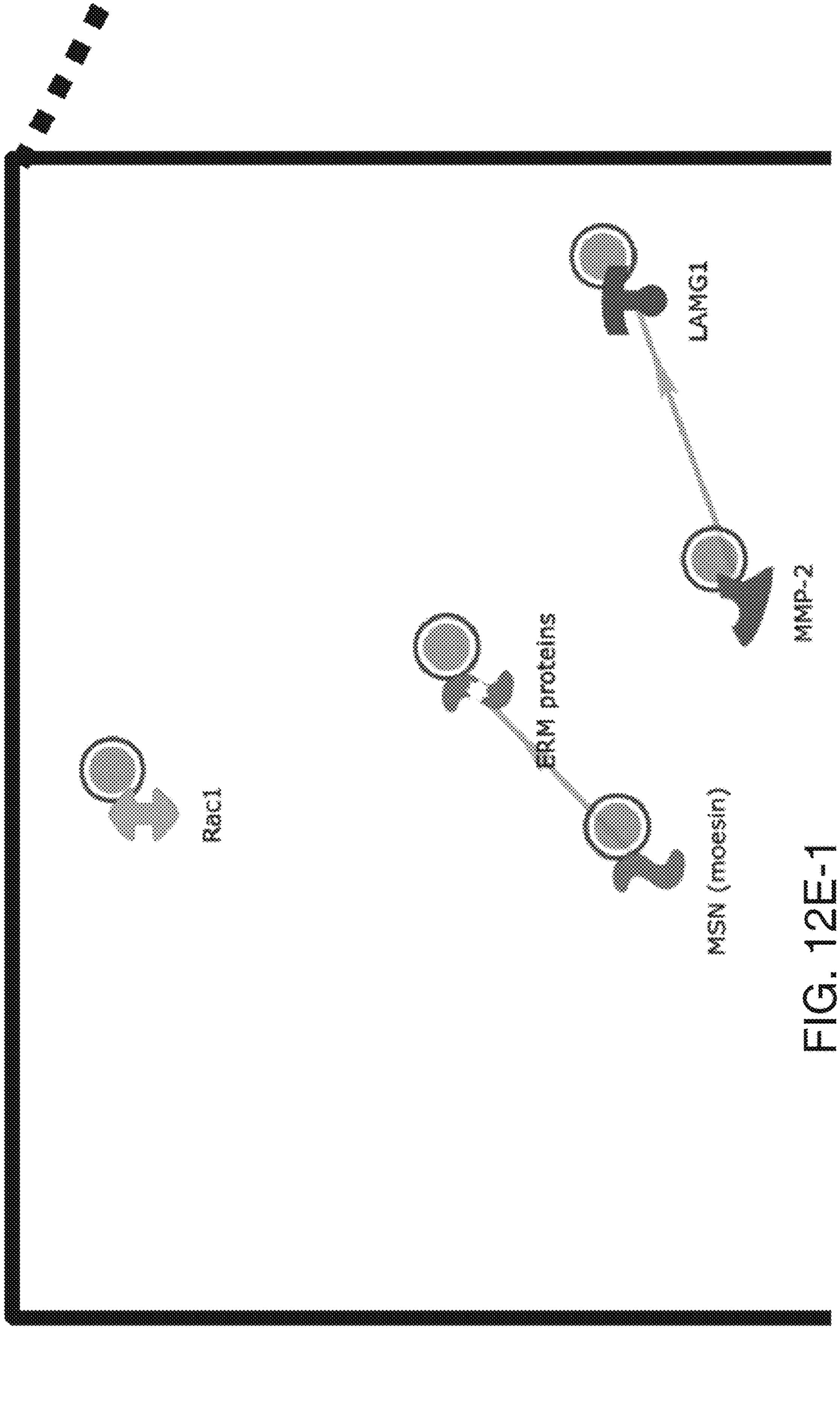
Figures 2, 12E:
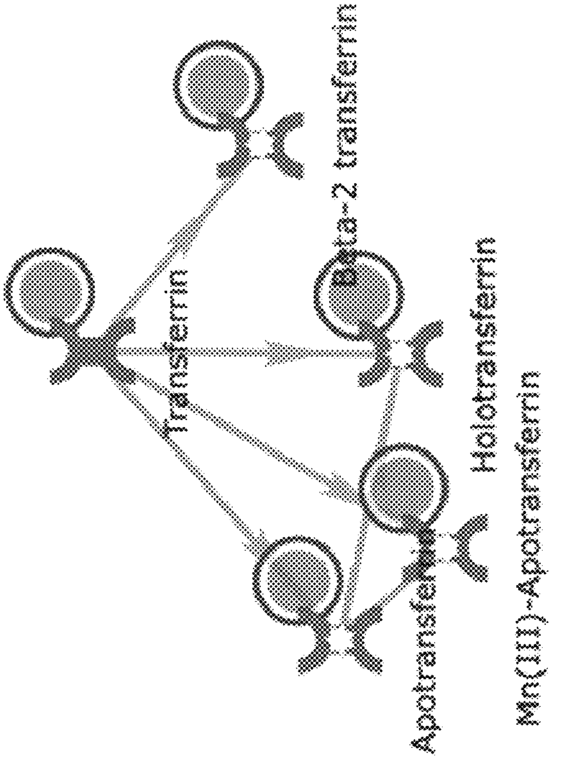
Figures 3, 12E:
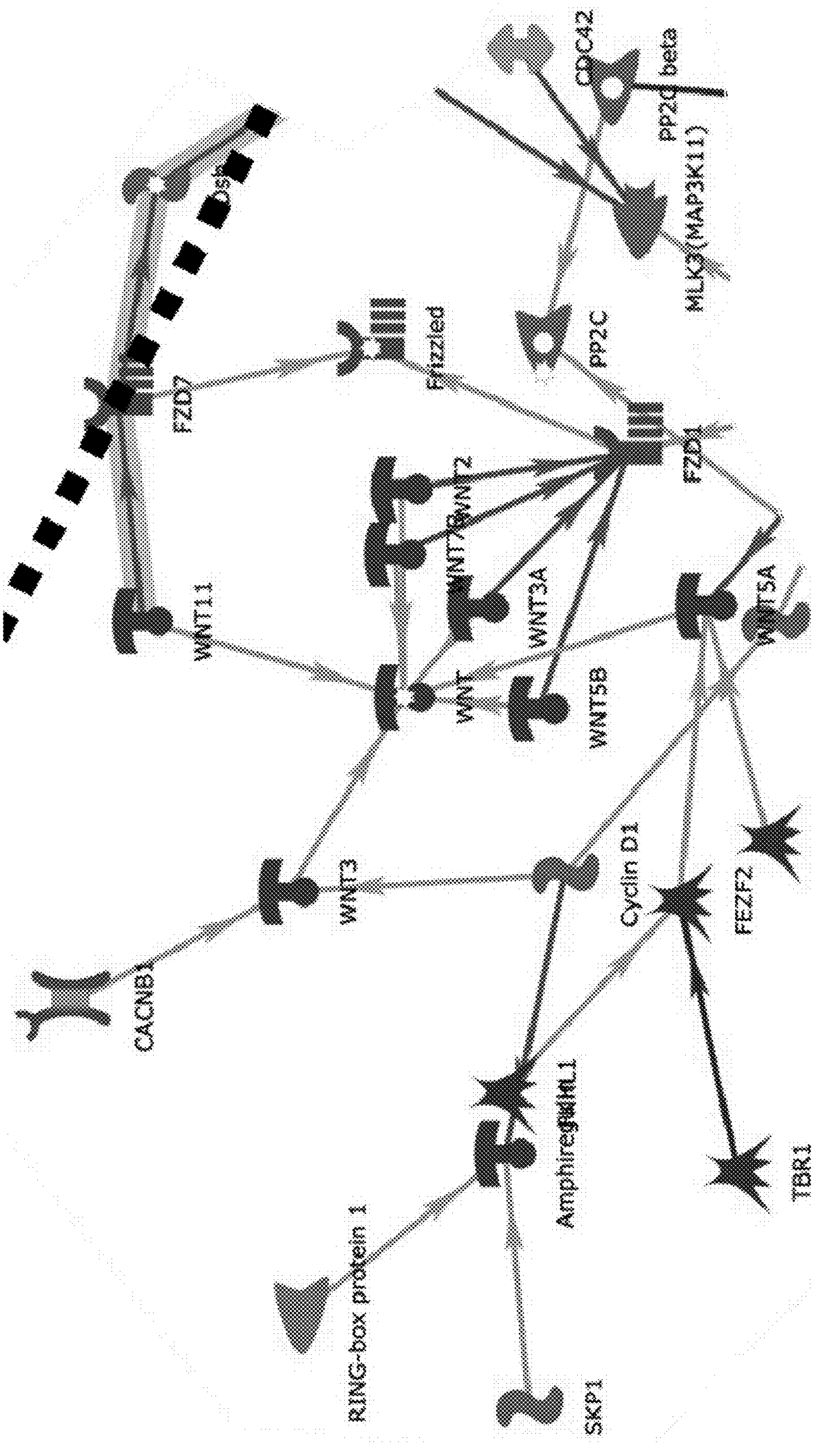
Figures 4, 12E:
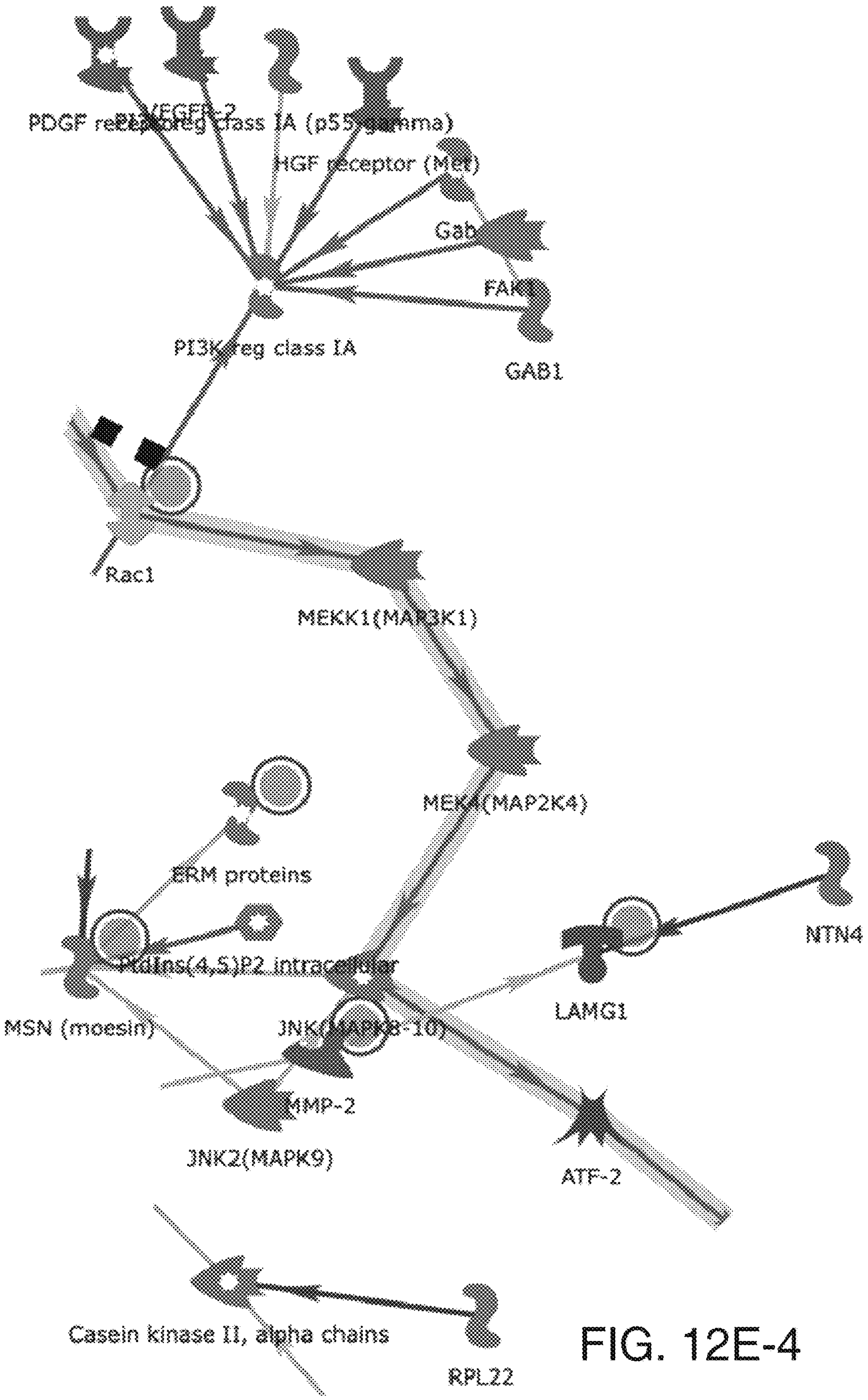
Figures 5, 12E:
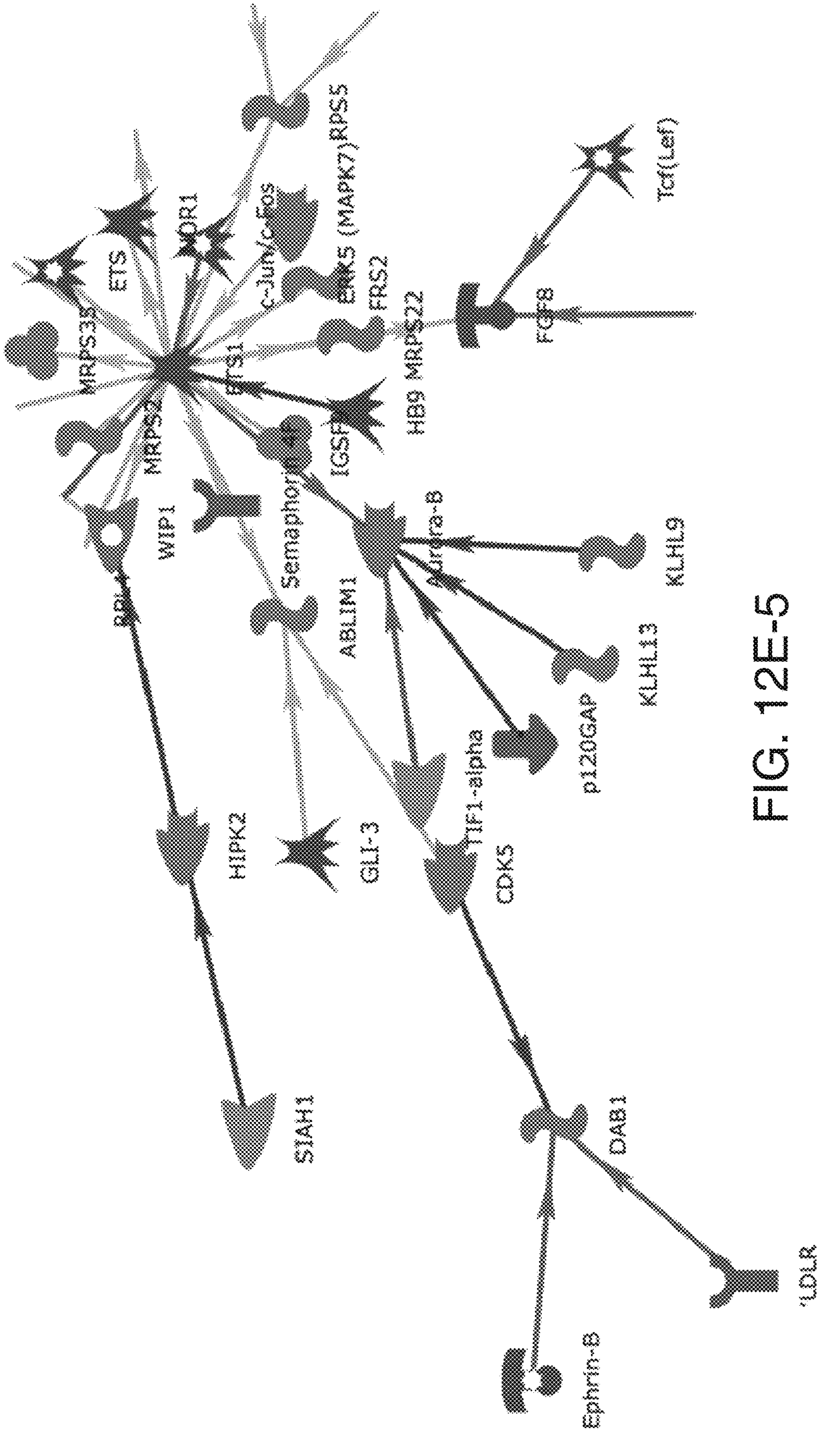
Figures 6, 12E:
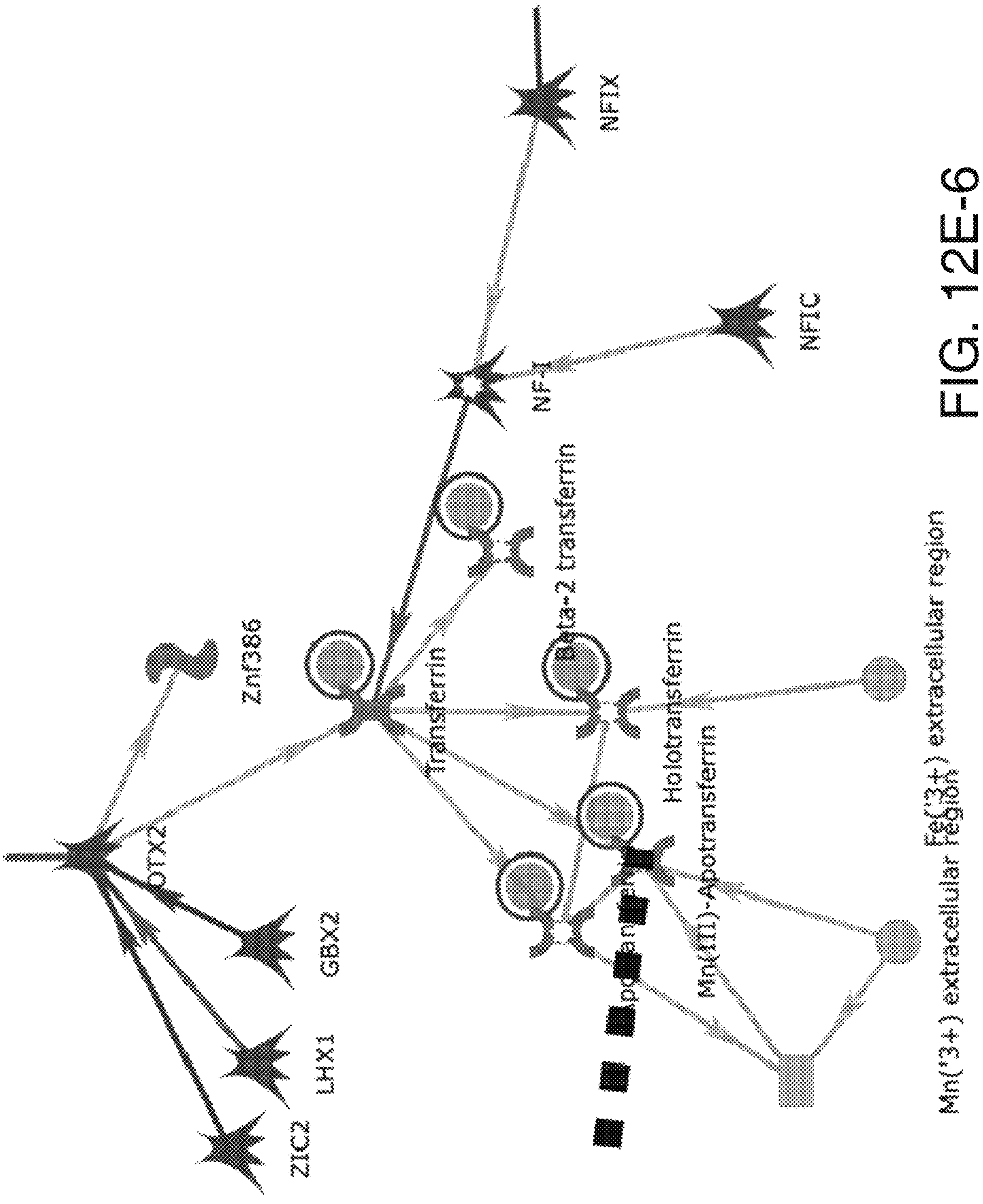
Figures 7, 12E:
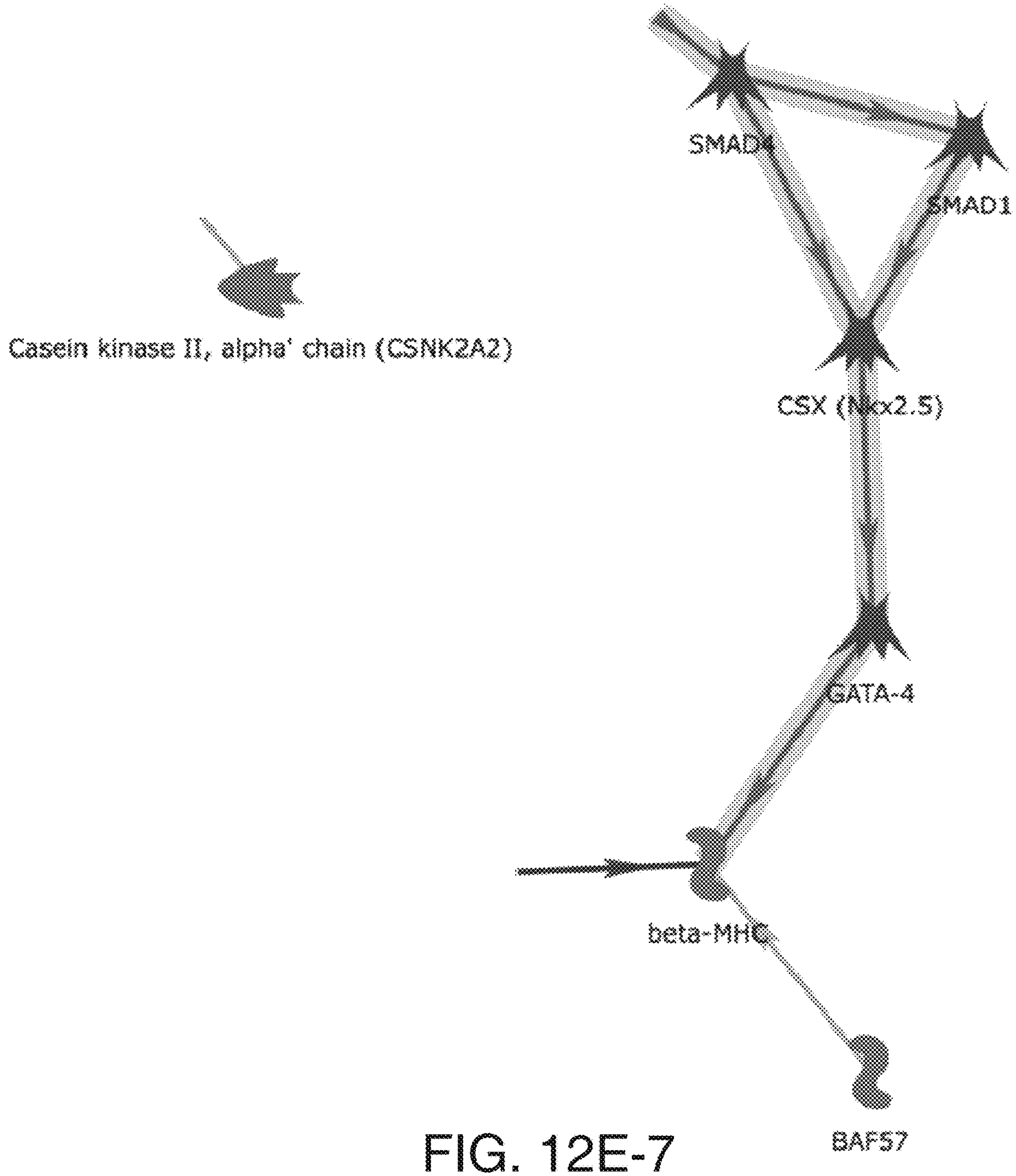
Figure 12F:
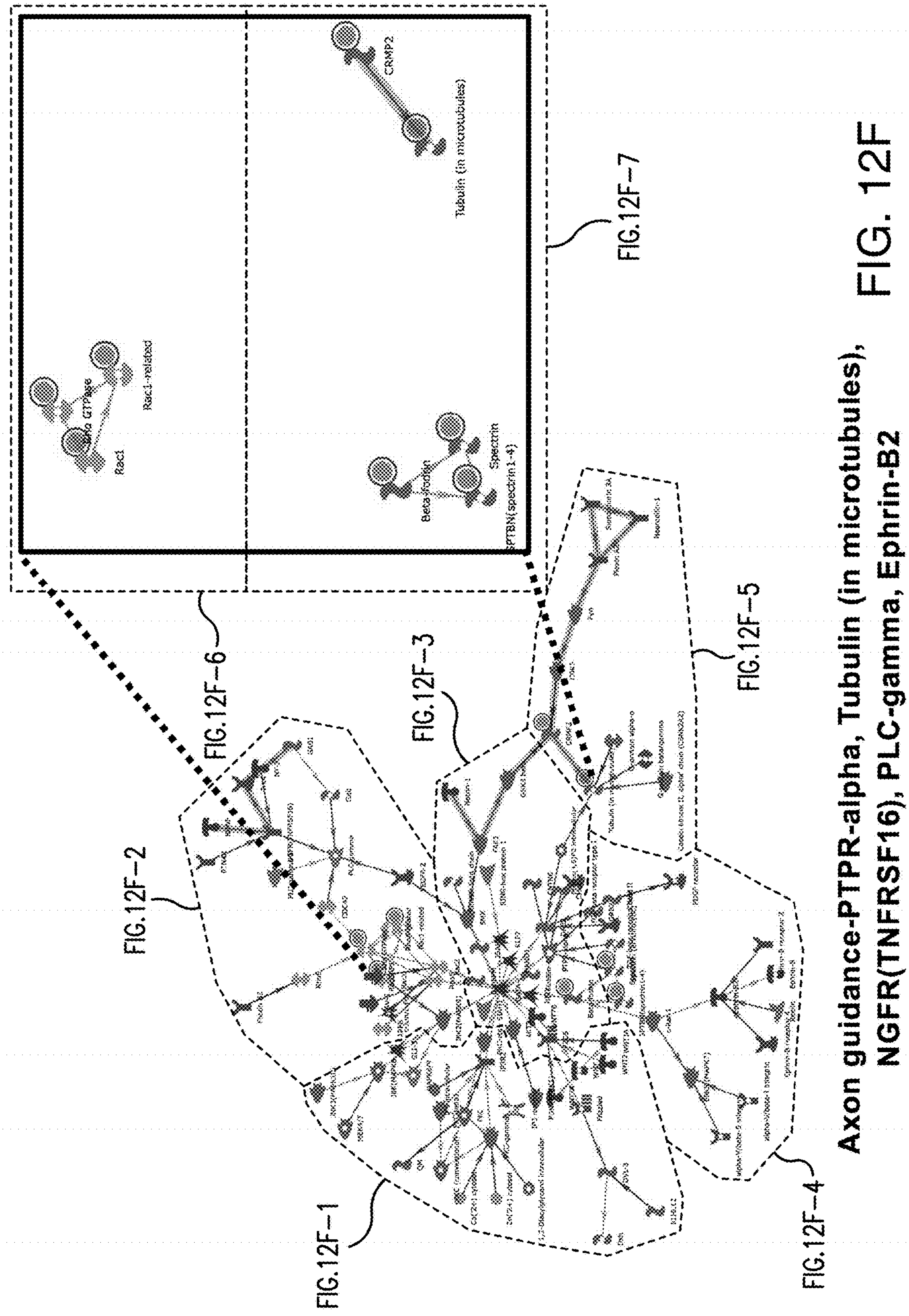
Figures 1, 12F:
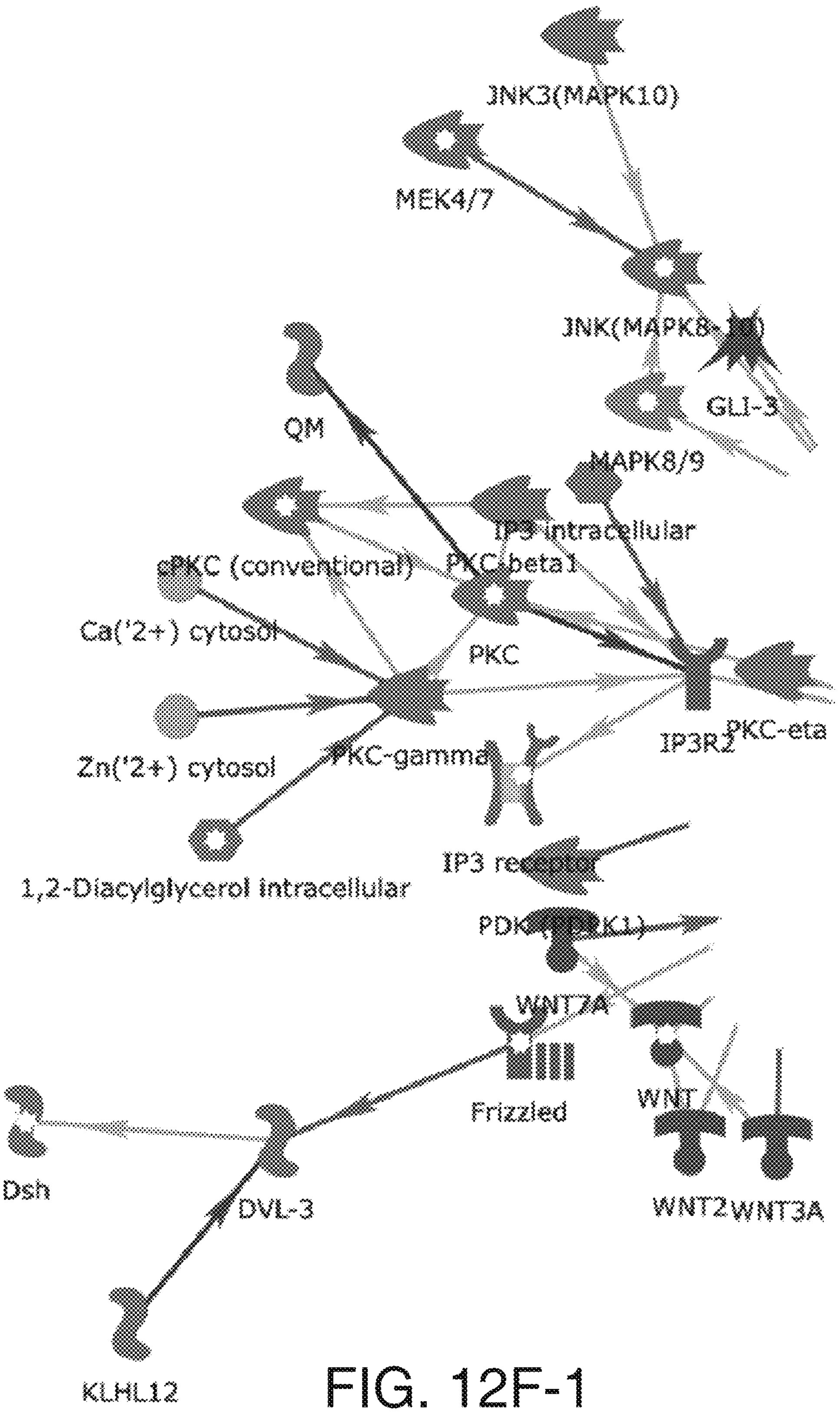
Figures 2, 12F:
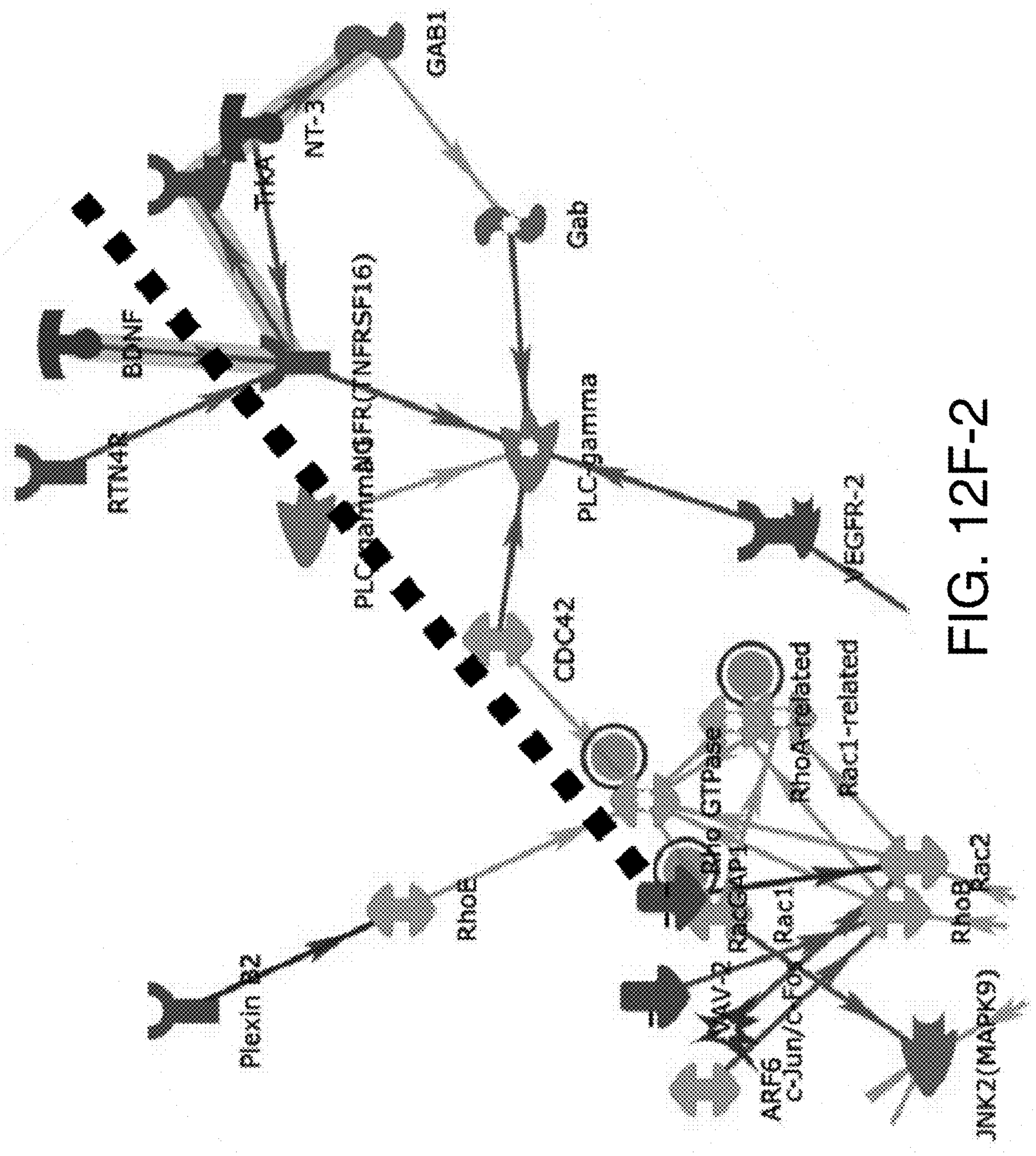
Figures 3, 12F:
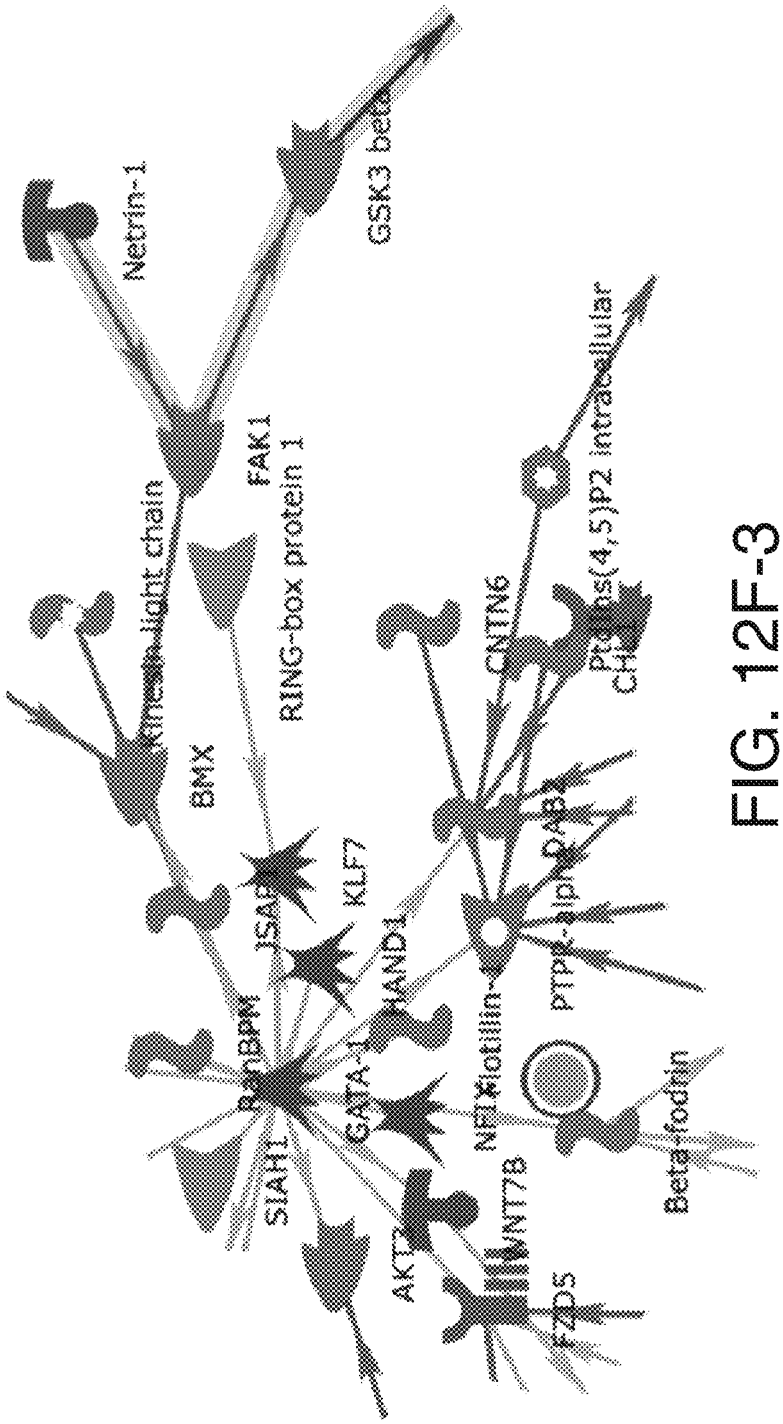
Figures 4, 12F:
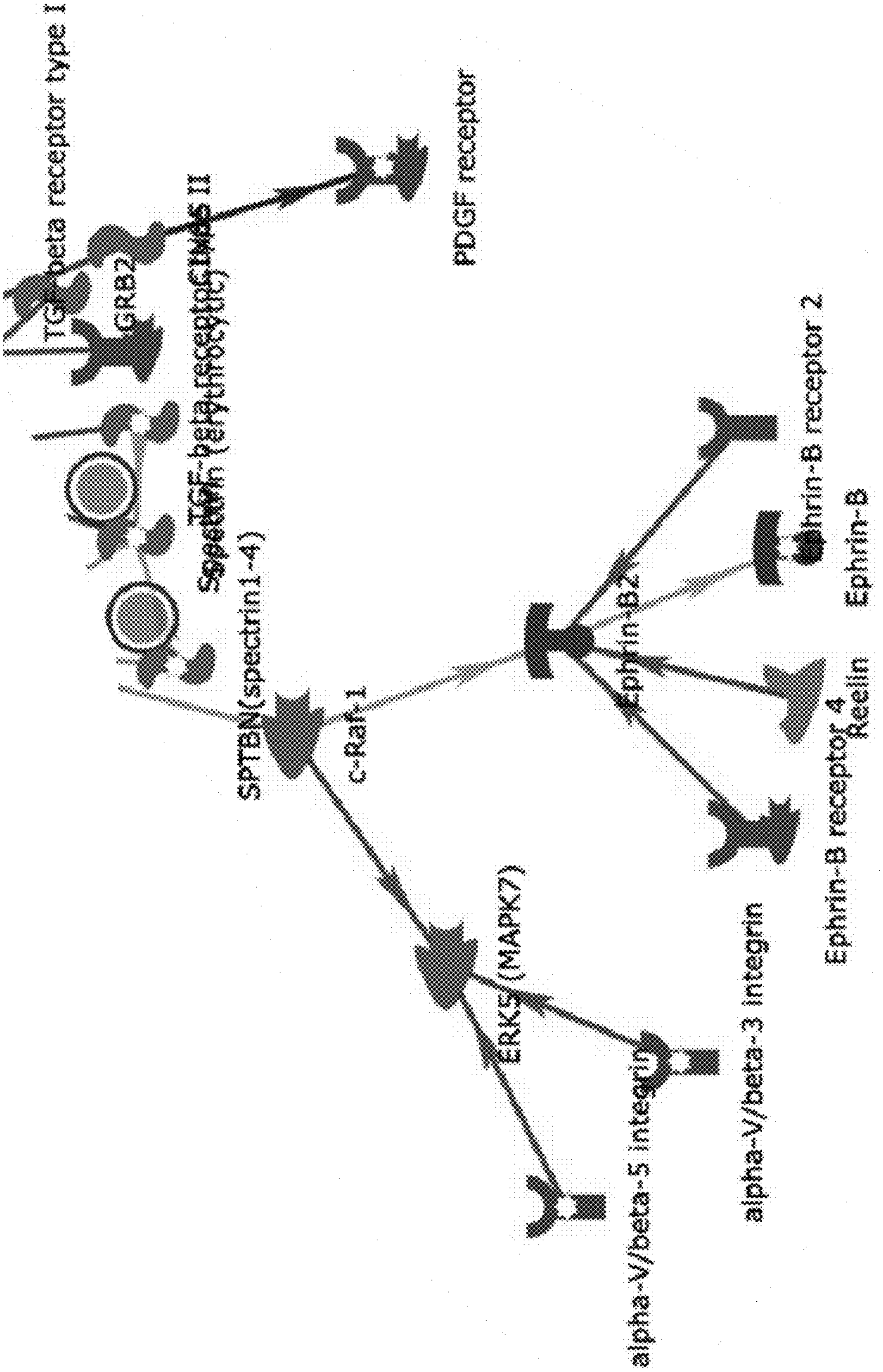
Figures 5, 12F:
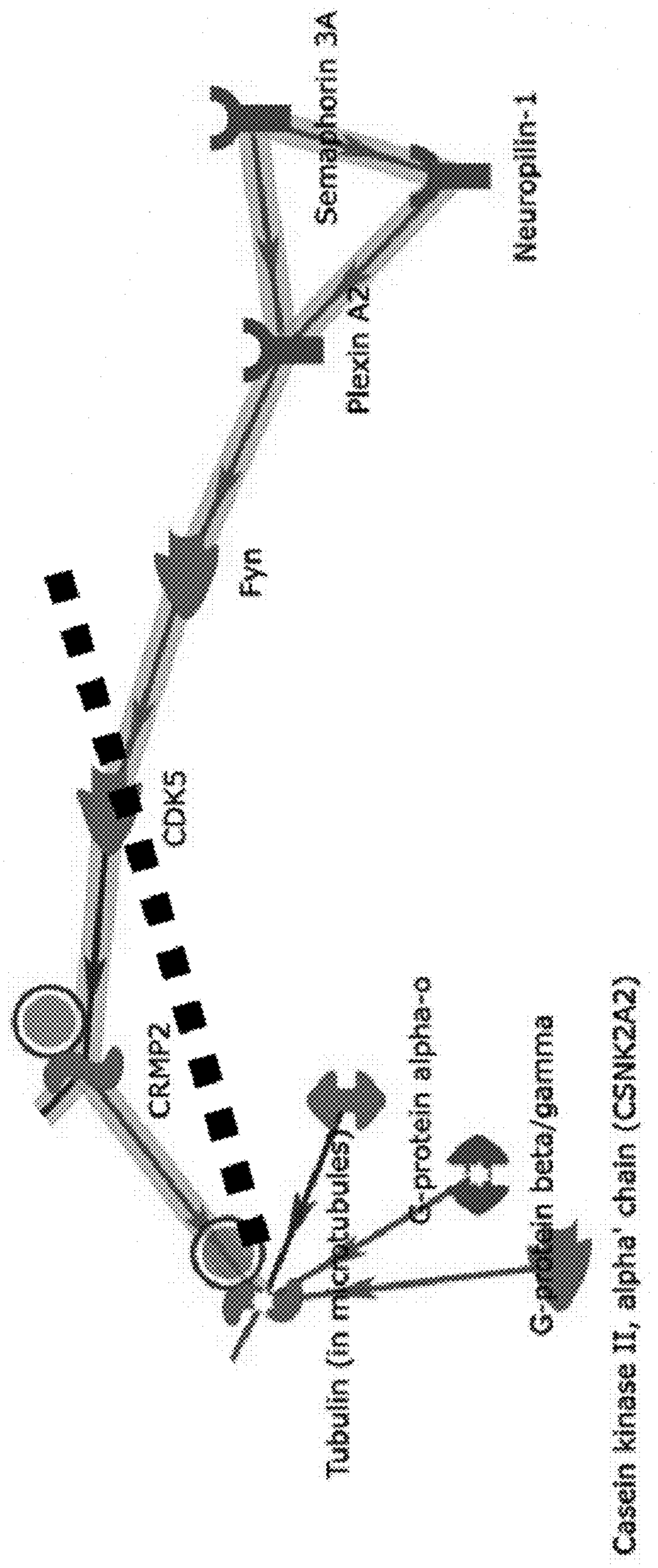
Figures 6, 12F:
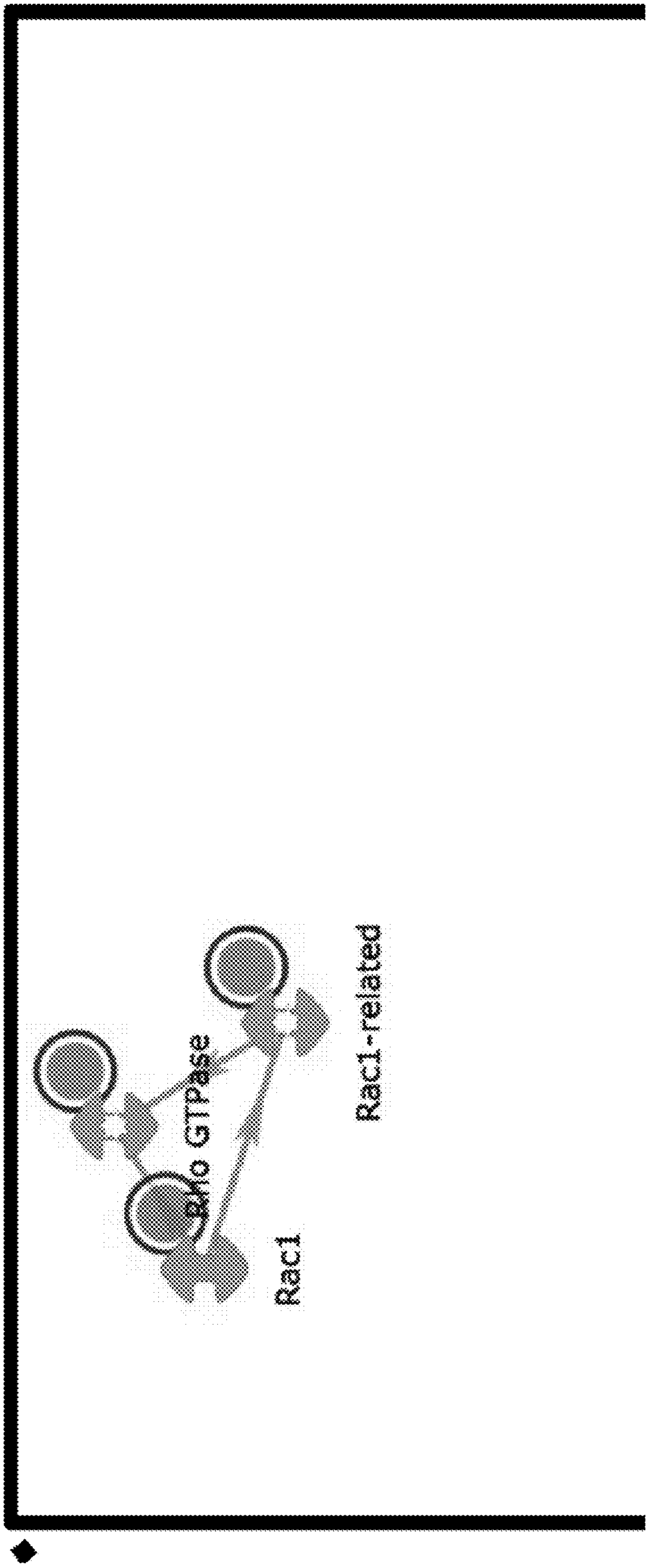
Figures 7, 12F:
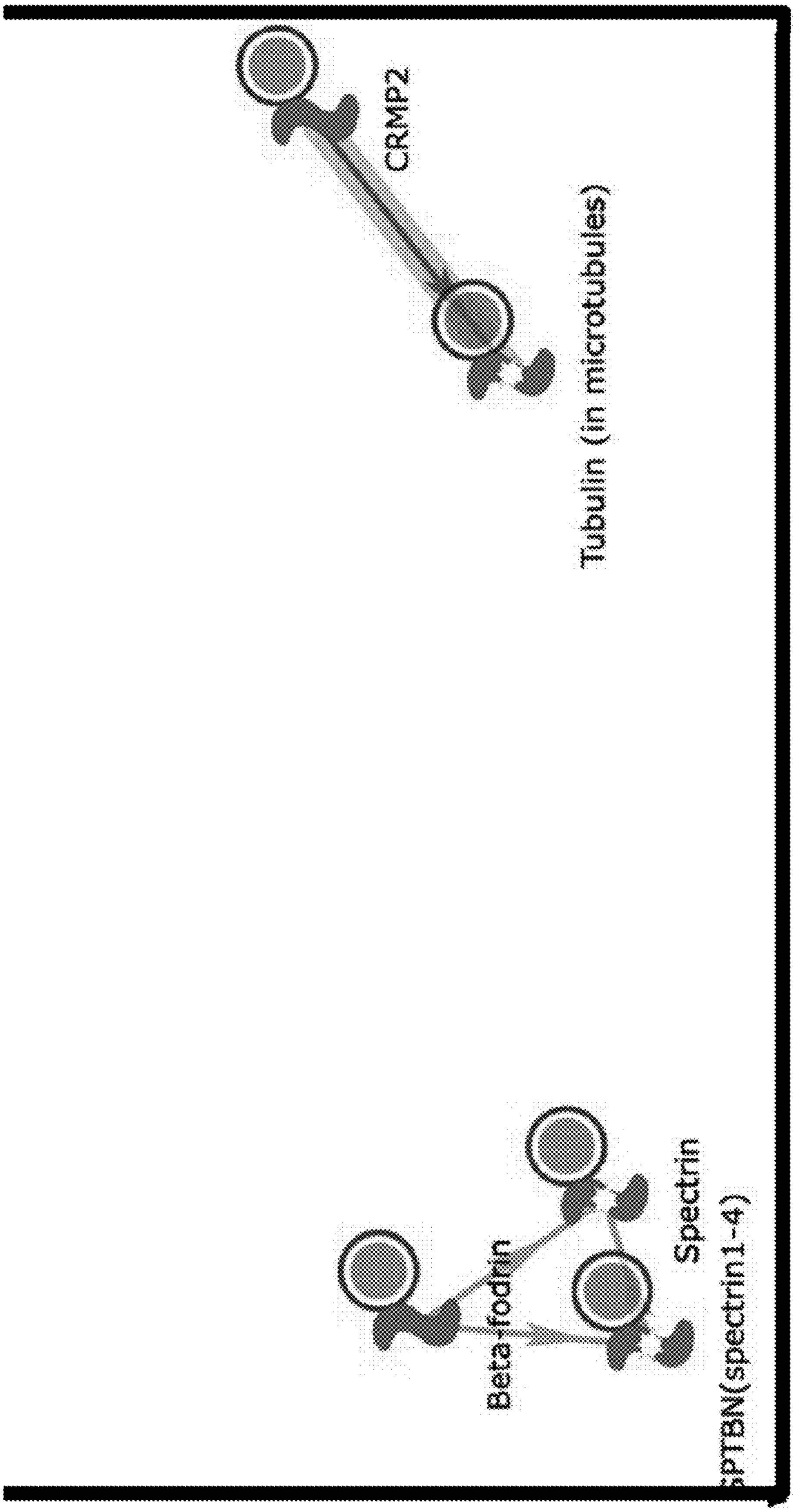

FIGS. 11A-11F provide the proteomic characterization analysis showing that the TMSC secretome contains different regenerative proteins. FIG. 11A provides gene ontology annotations showing the top 10 most significantly upregulated pathways classified in terms of Biological process (BP), Molecular Function (MF), and Cellular Component (CC) considered to be significant in TMSC-Scr and fibro-Scr. FIGS. 11B-11D provide heatmaps and hierarchical clustering analysis showing differences in secretome proteins related to response to unfolded protein response, ECM organization, and collagen catabolic process between TMSC-Scr and fibroblast-Scr. FIG. 11E provide interactome analysis showing the interaction between main proteins presented in TMSC-Scr, involved in neuroprotection (axon guidance and neurogenesis). FIG. 11F provides interactome analysis showing TMSC-Scr involved in response to hypoxia, wound healing, cell-matrix adhesion, and detoxification as analyzed by String v11 (n=2 each).

FIGS. 12A-12F provide graphs showing that the TMSC secretome involves positive regulation of axon guidance pathways. FIGS. 12A-12F provide interaction networks of different axon guidance pathways showing signaling proteins significantly ($p<0.05$, FDR<5%) uncovered in TMSC secretome. INSET pictures show active components of axon guidance pathway expressed in TMSC secretome. Spheres indicate proteins upregulated in TMSC-Scr (only pathways plotted, which include at least eight upregulated proteins).

Figure 13A:
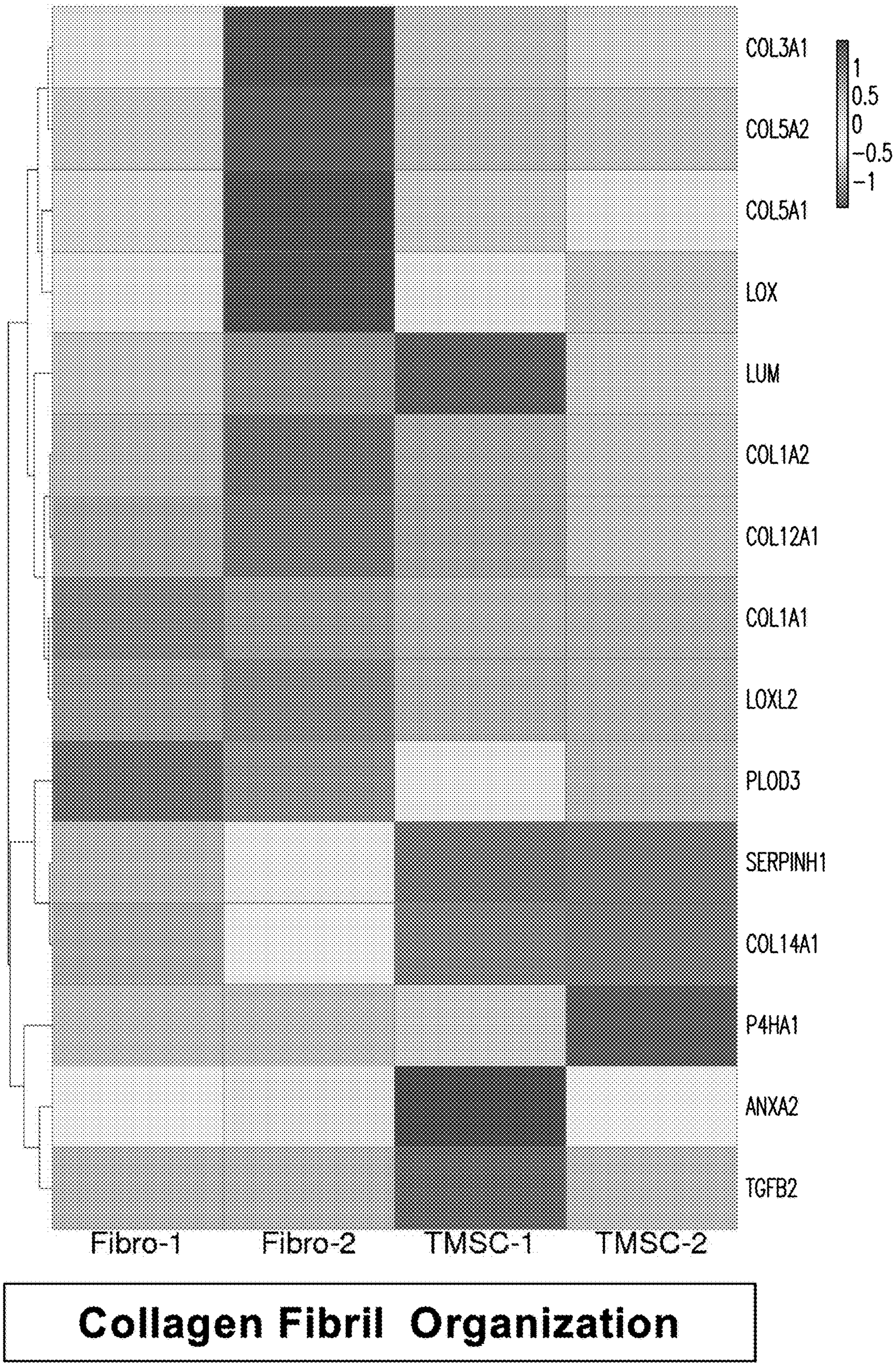
Figure 13B:
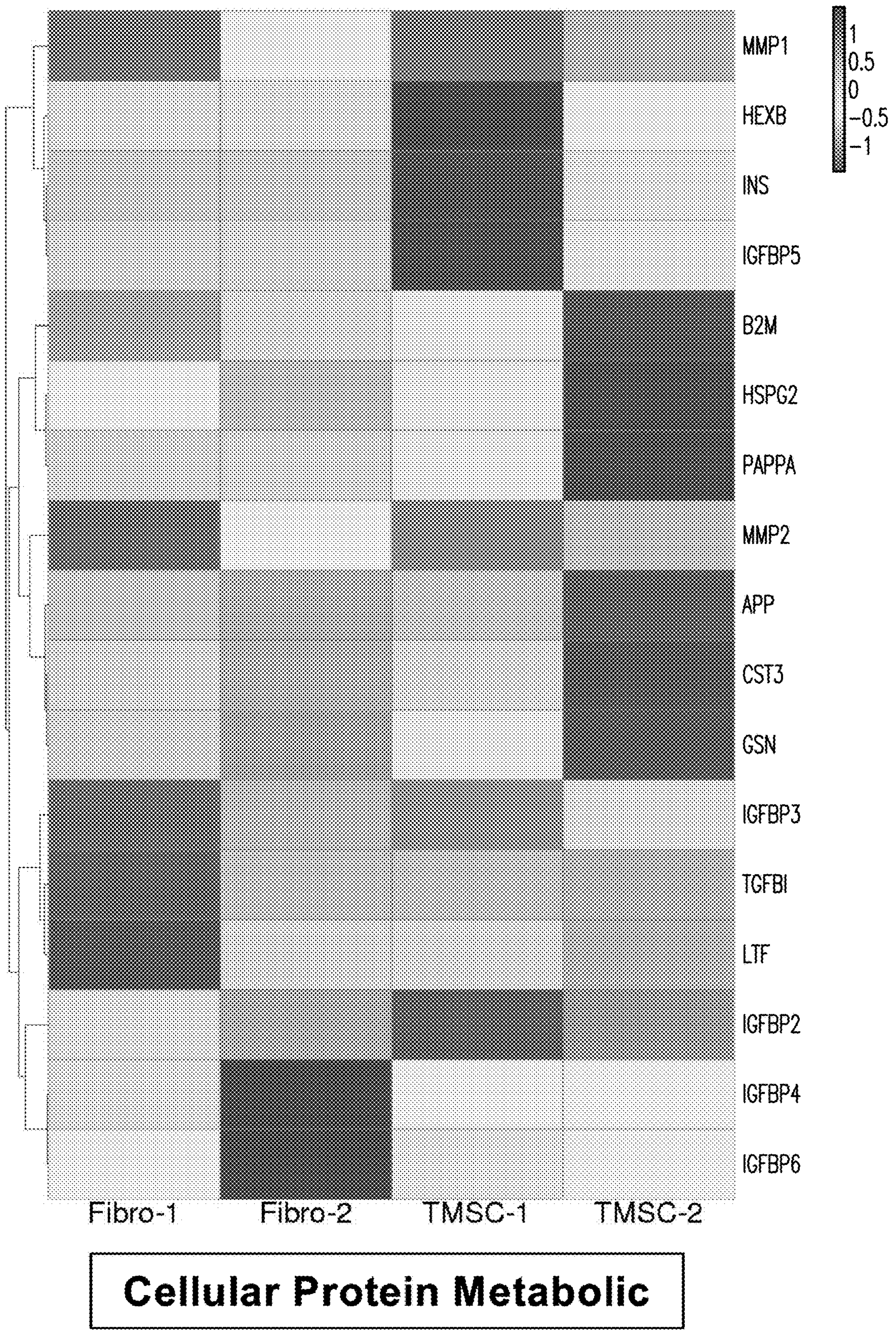
Figure 13C:
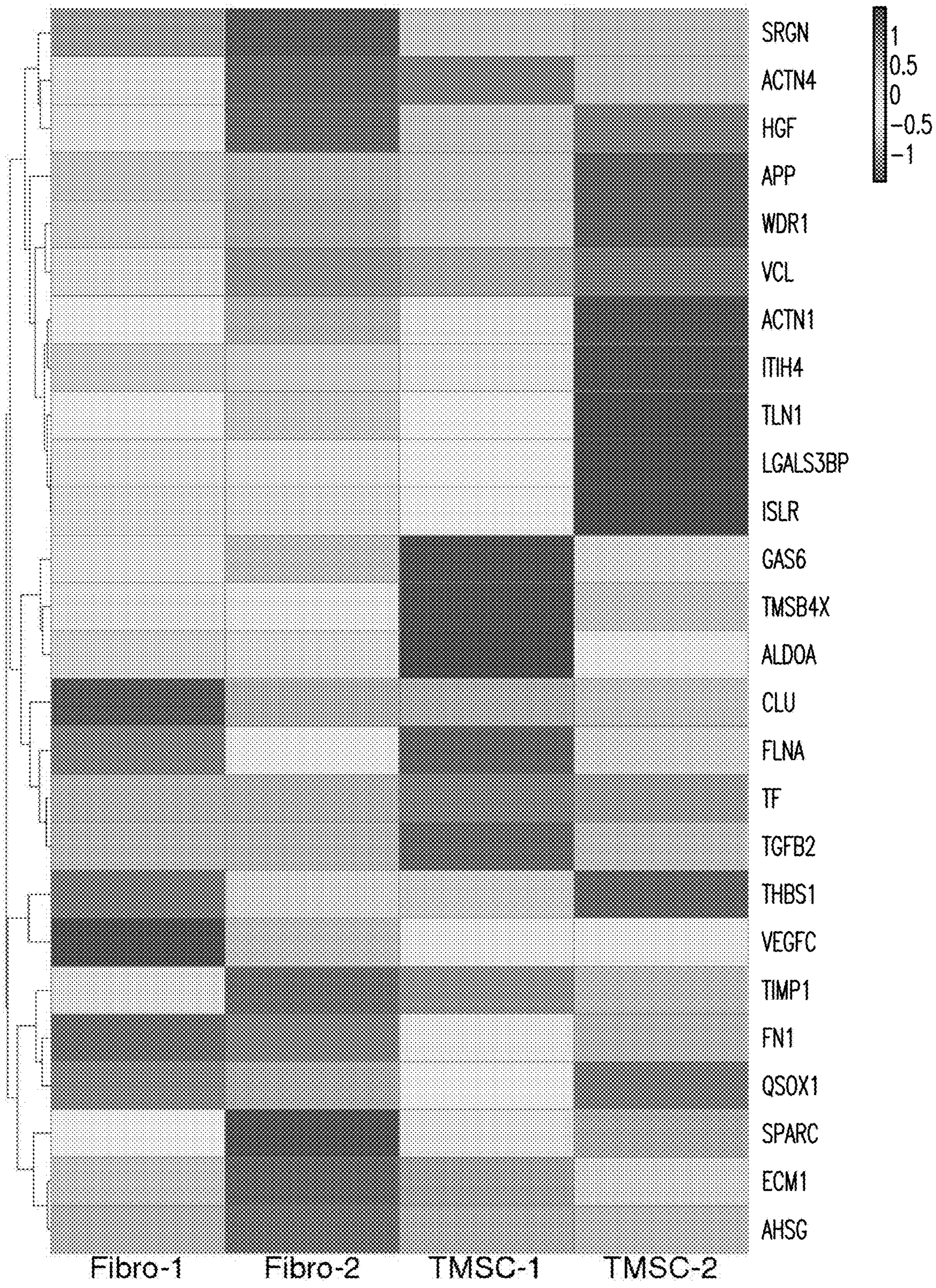
Figure 13D:
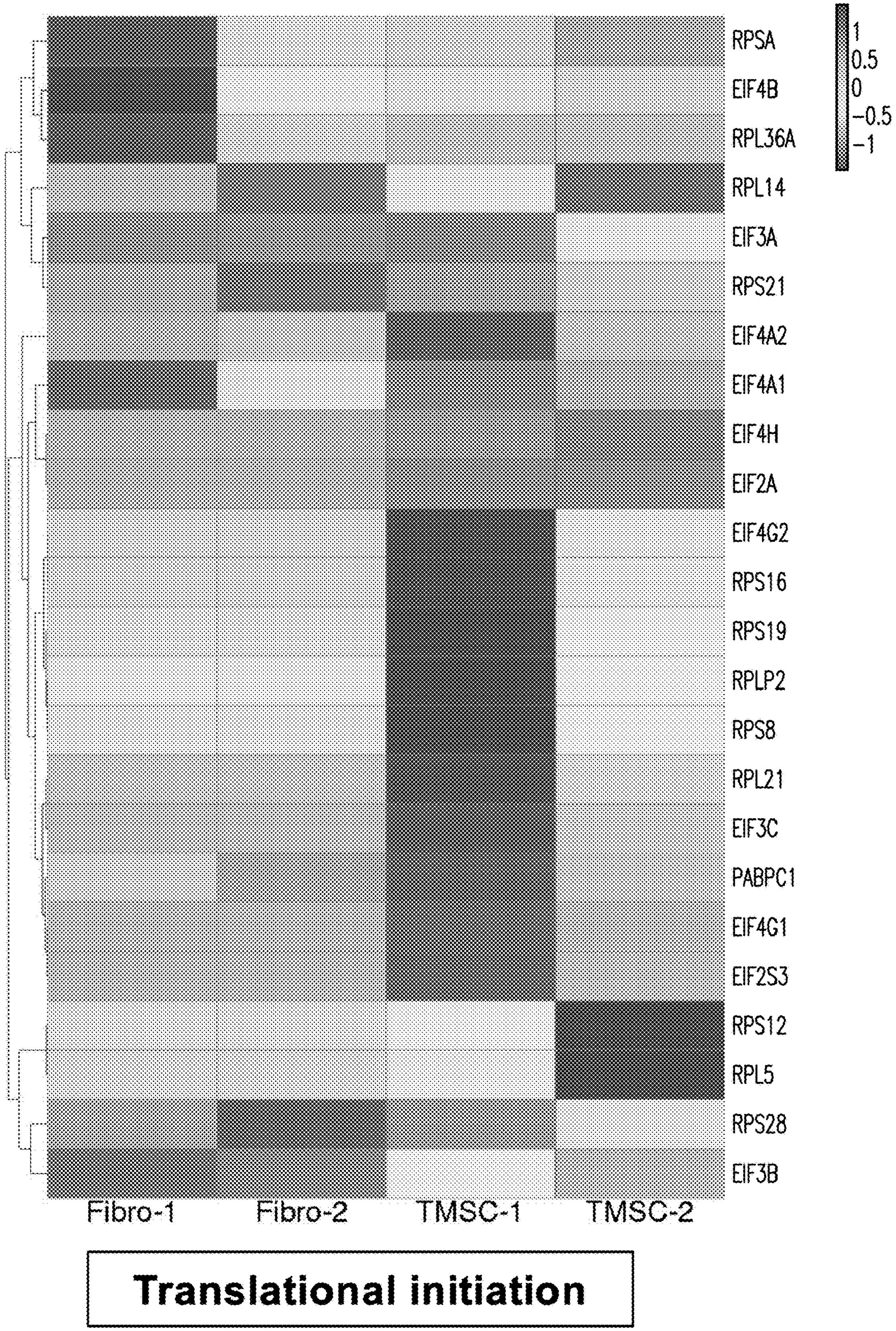
Figure 13E:
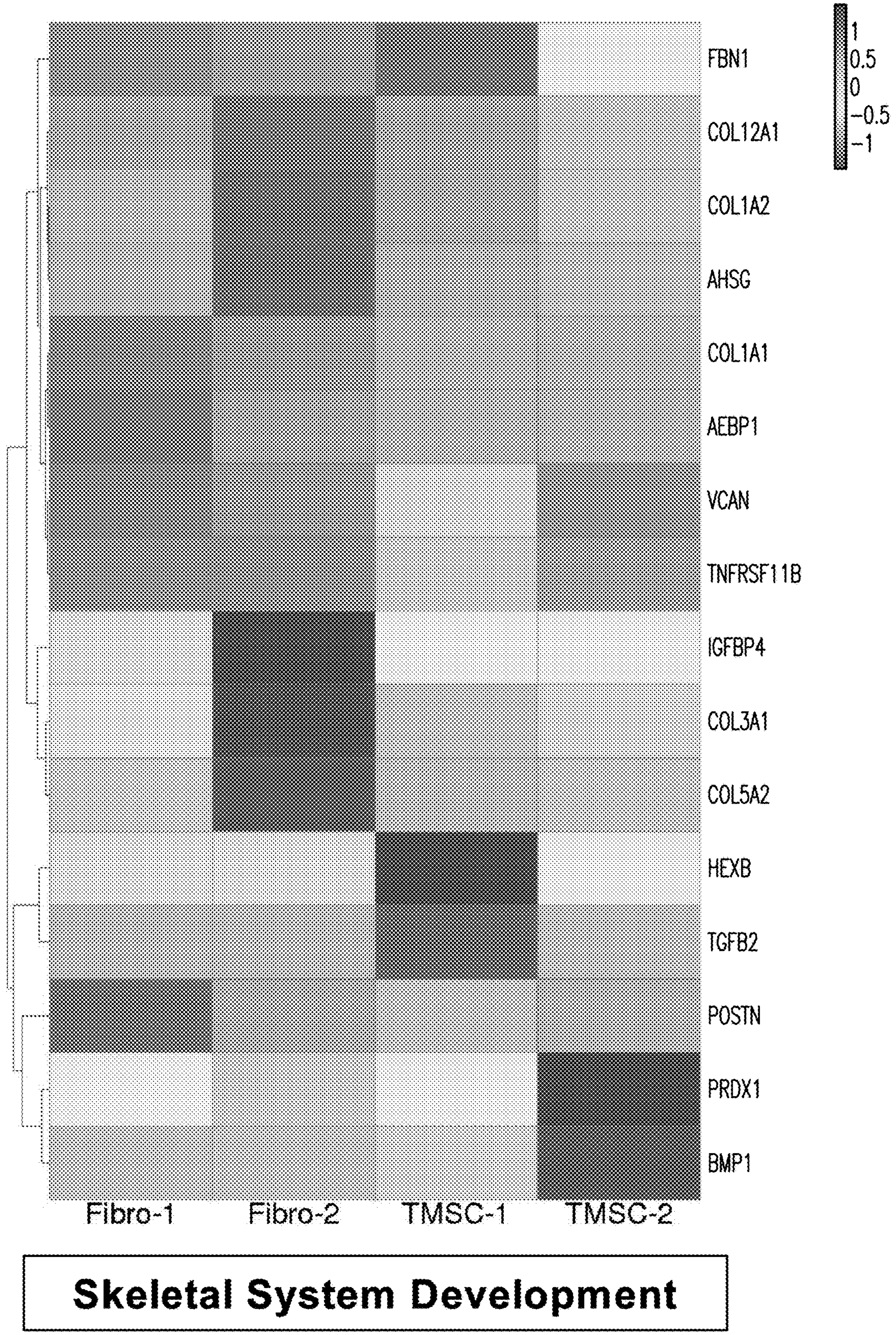
Figure 13F:
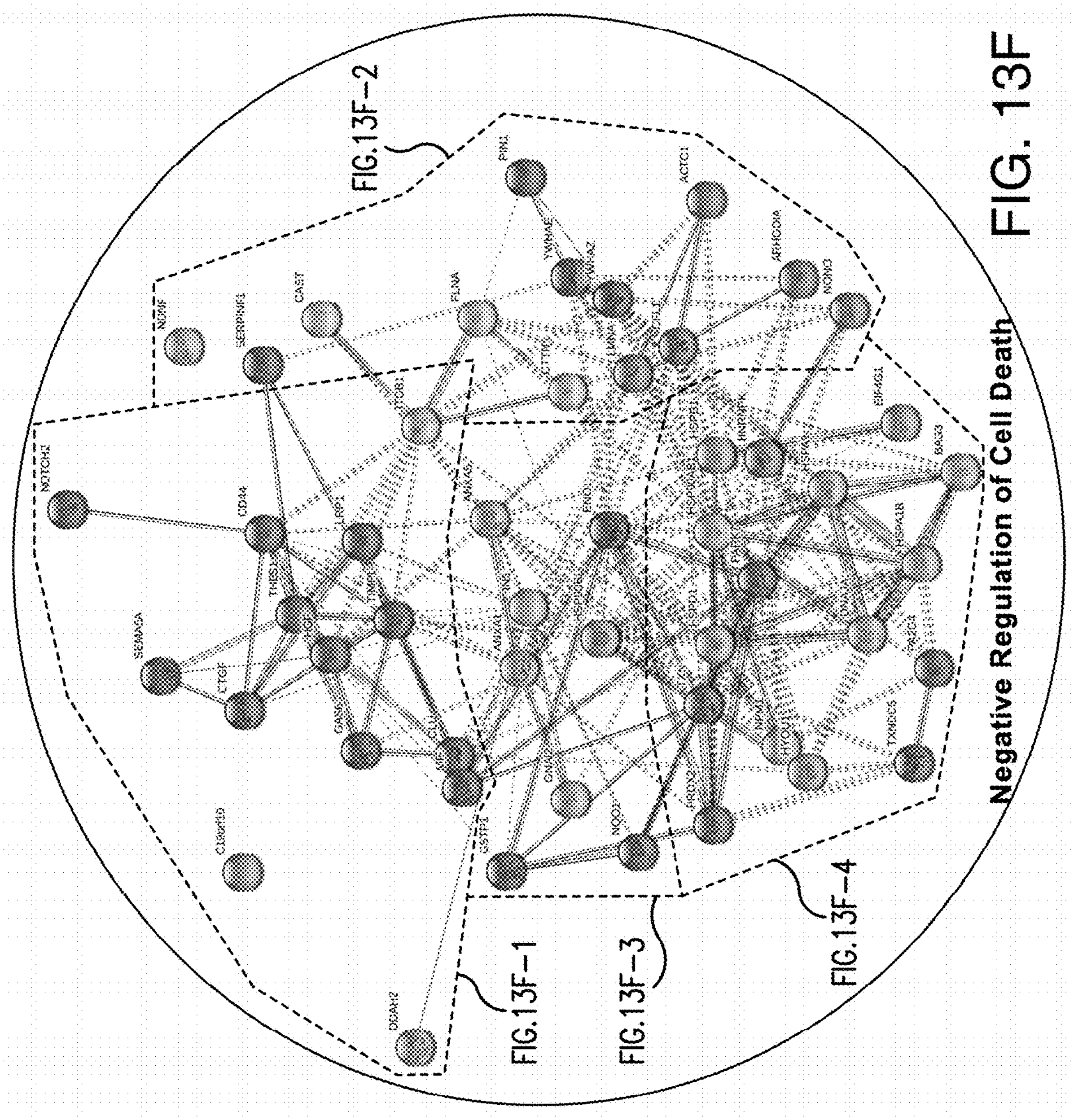
Figures 1, 13F:
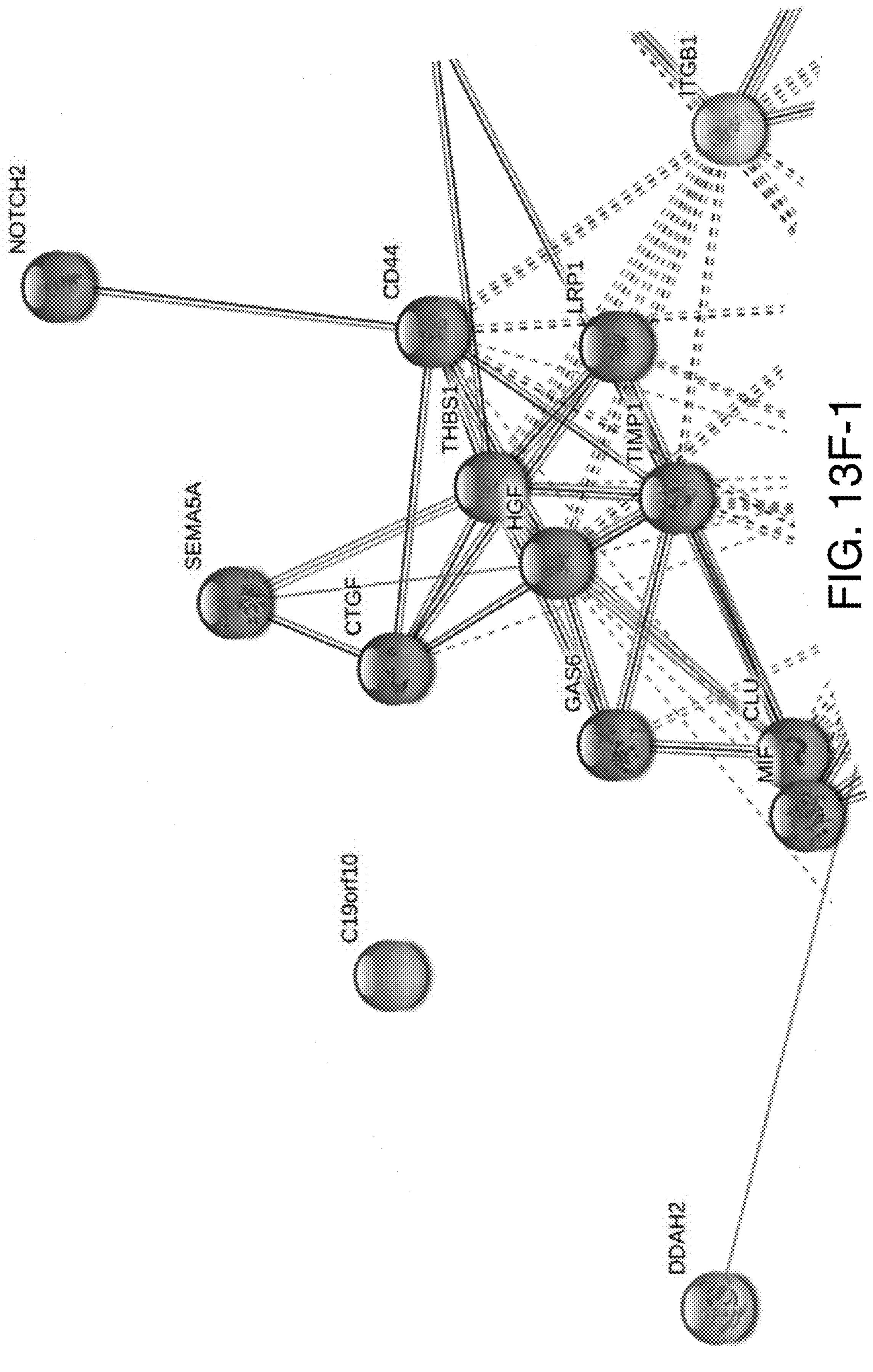
Figures 2, 13F:
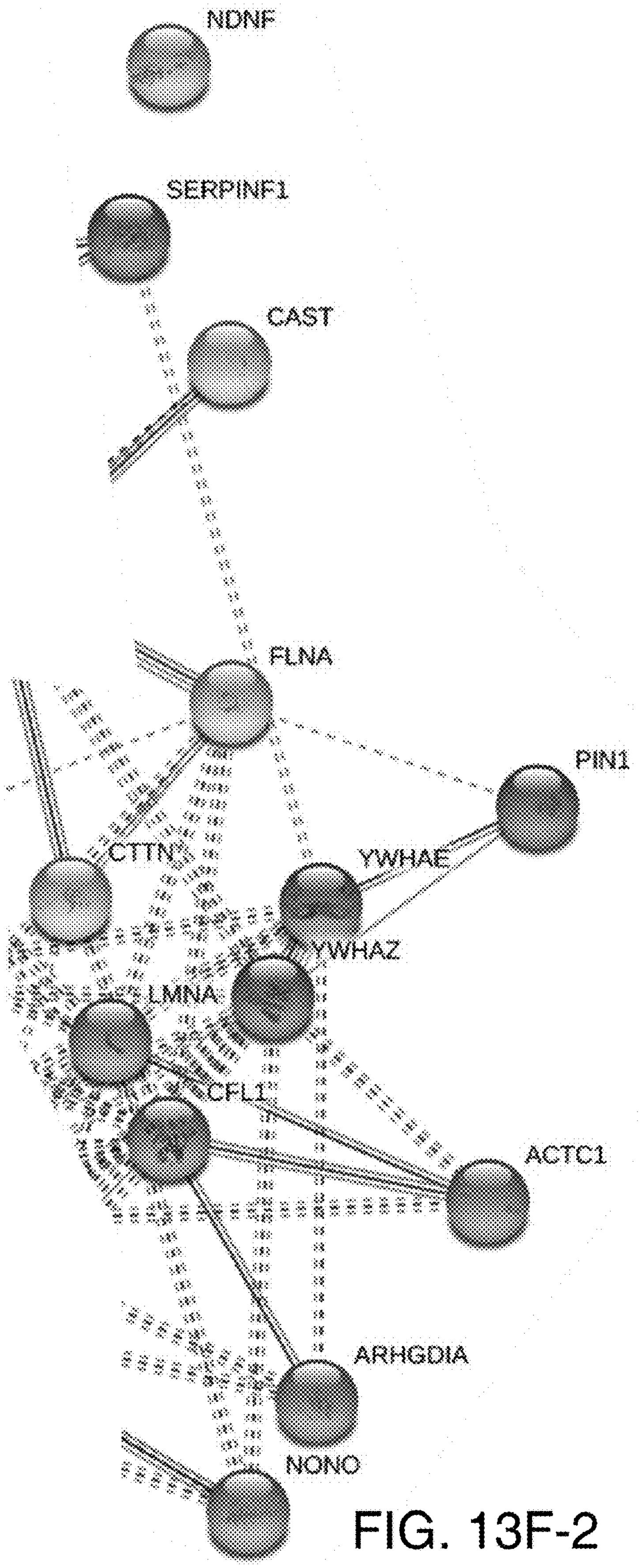
Figures 3, 13F:
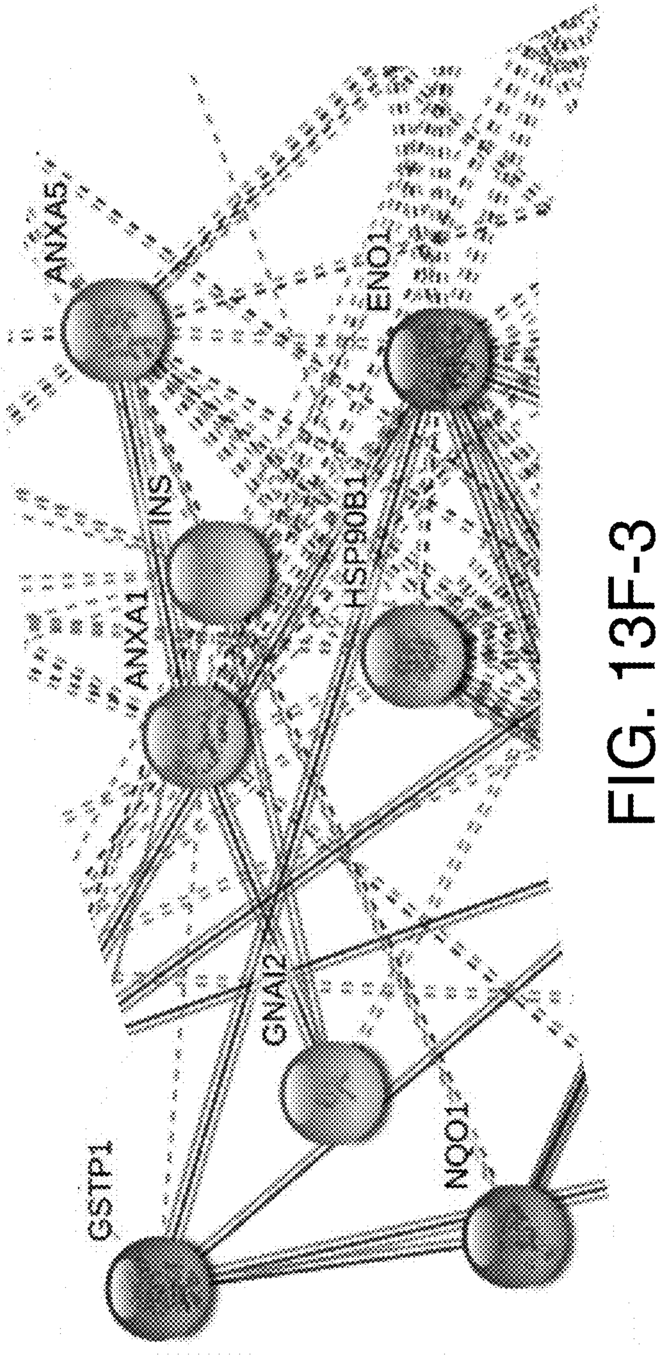
Figures 4, 13F:
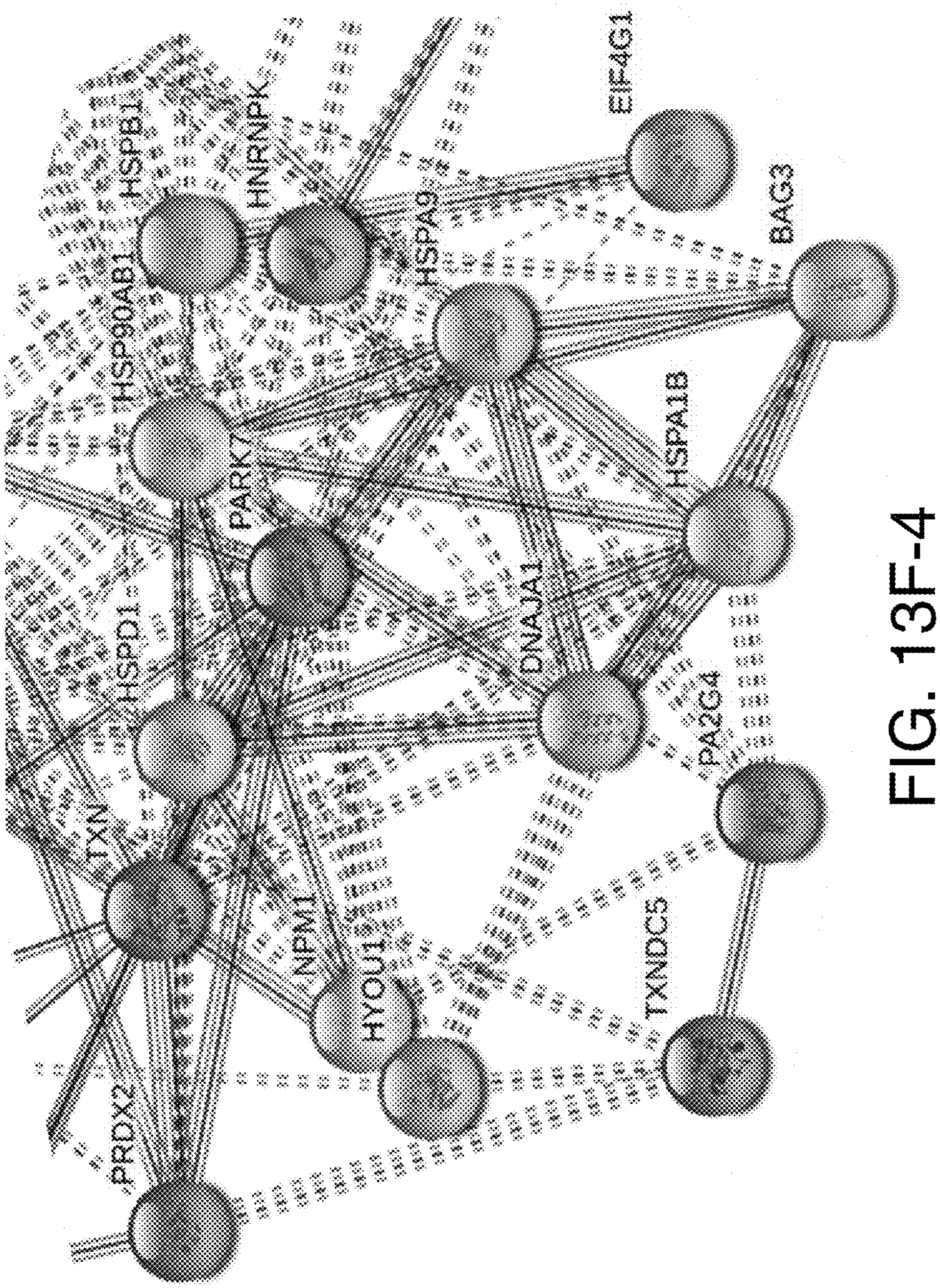
Figure 13G:
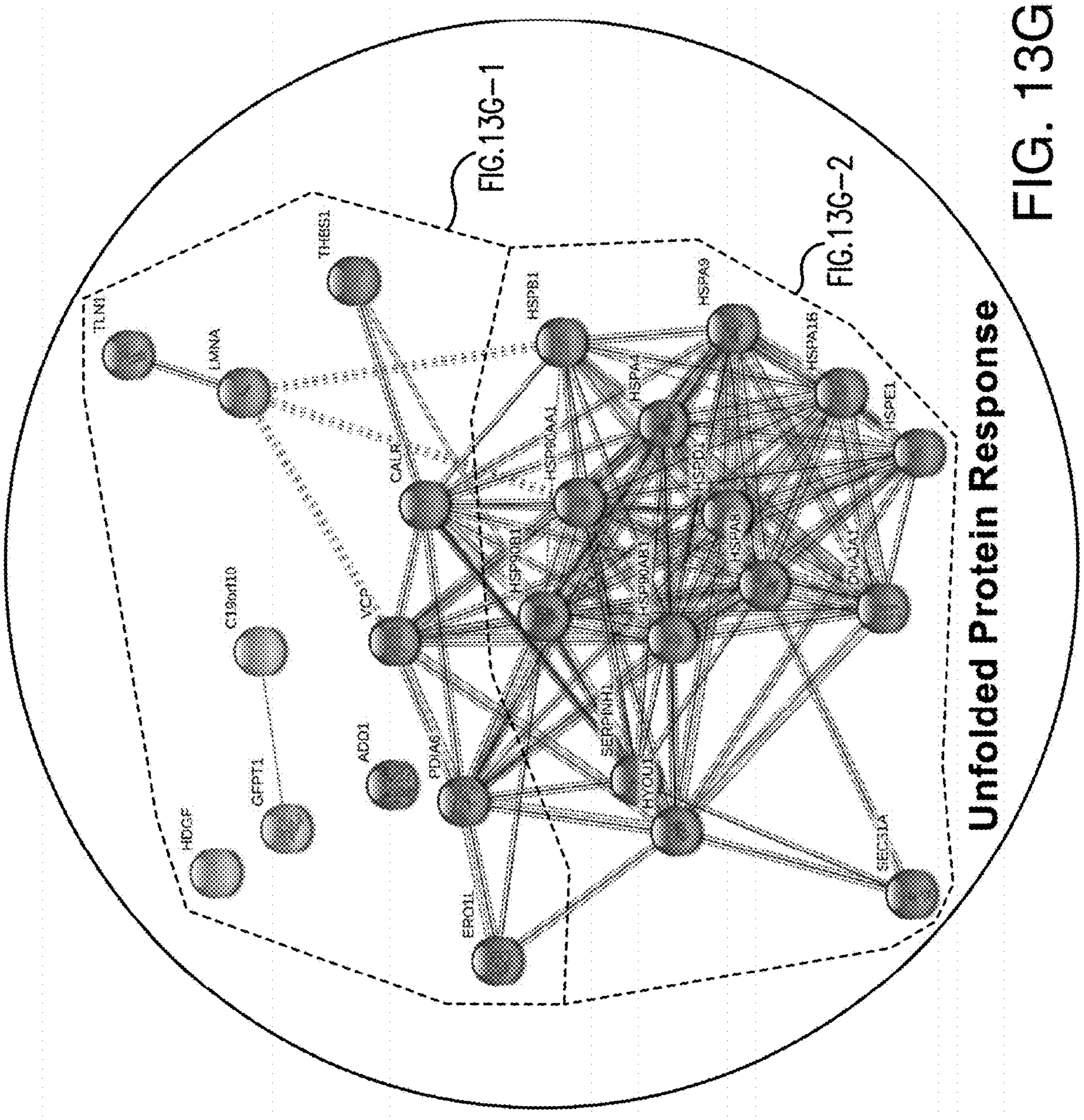
Figures 1, 13G:
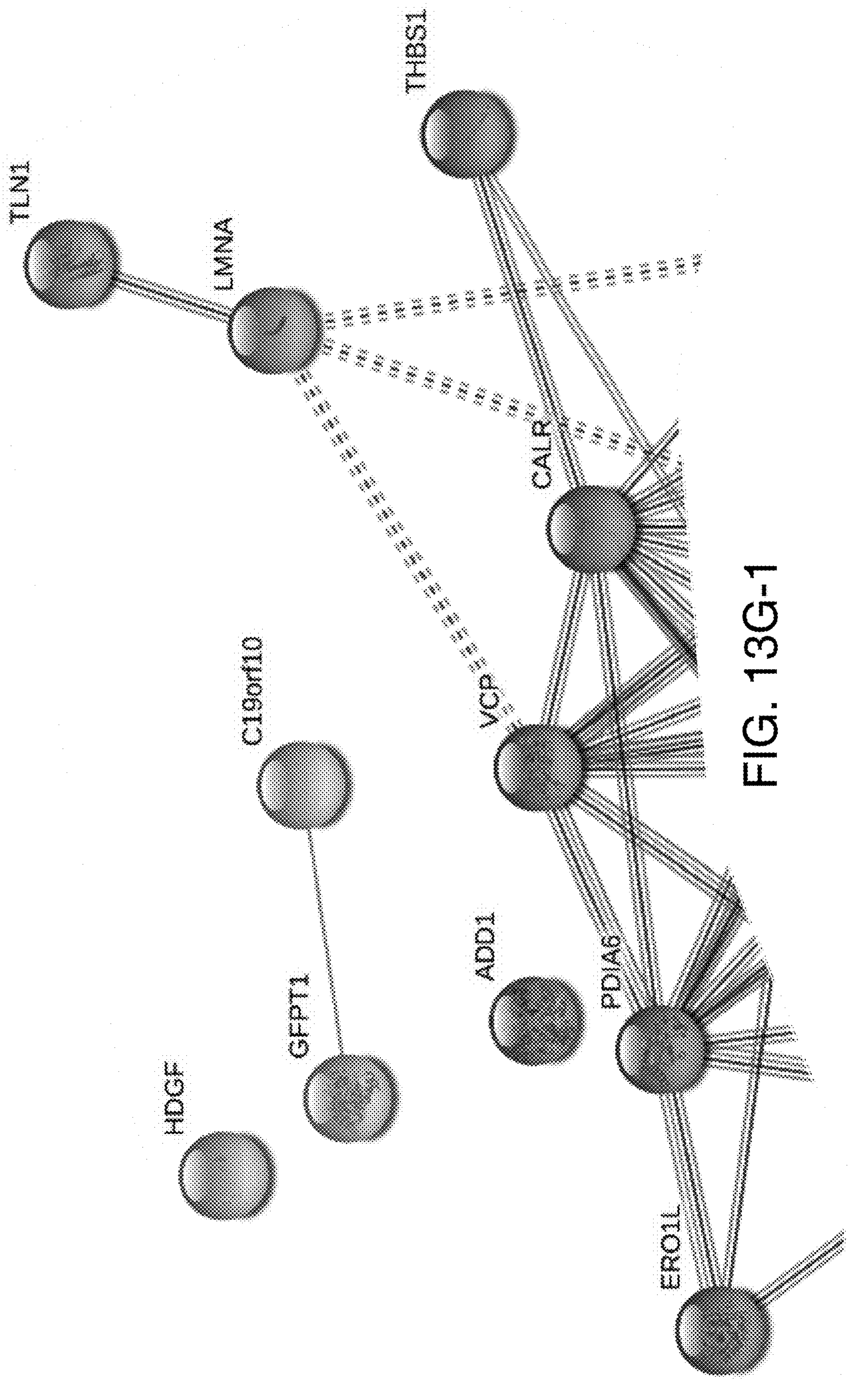
Figures 2, 13G:
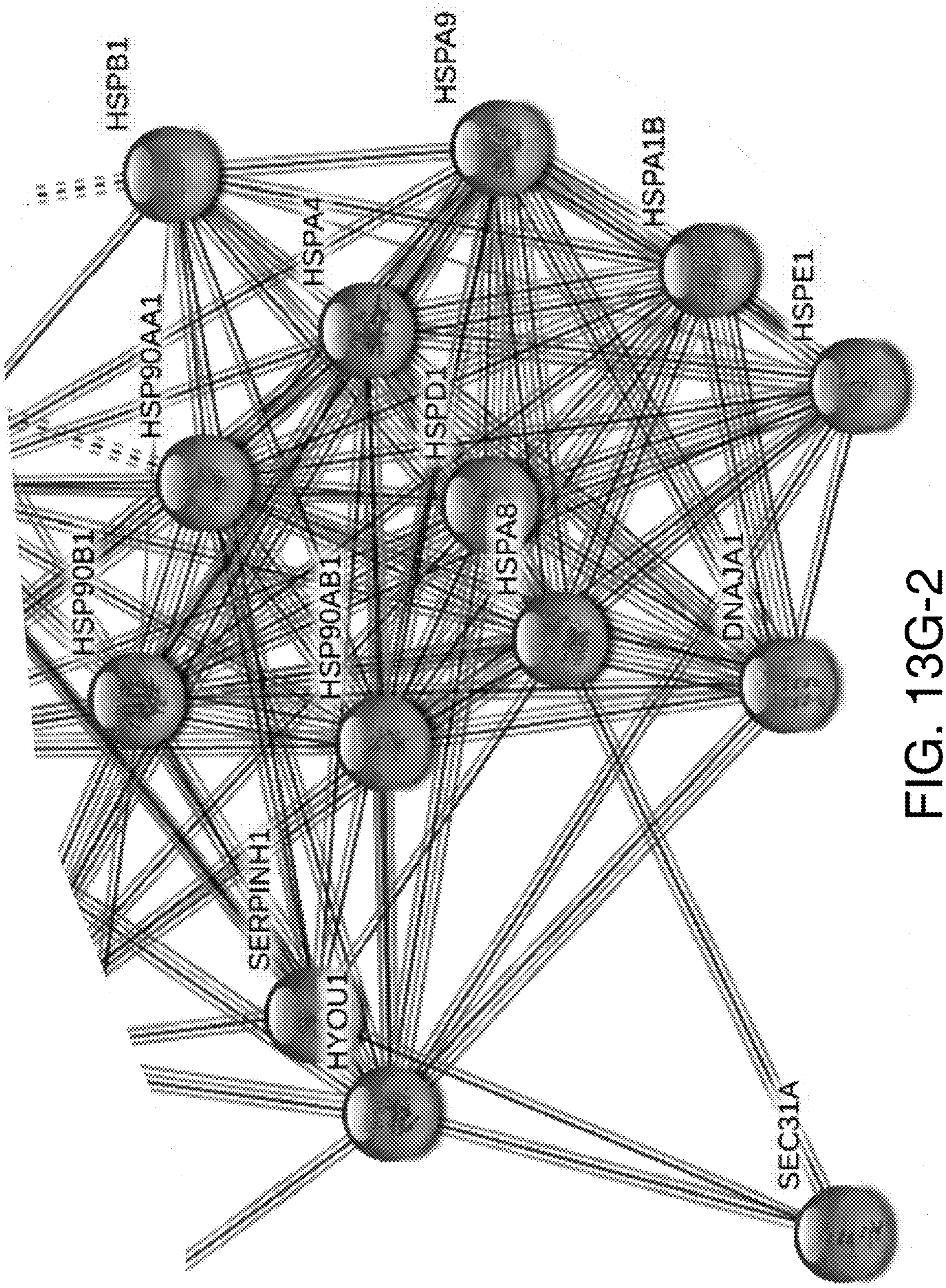

FIGS. 13A-13G provides heatmaps and graphs showing upregulation of key pathway proteins in TMSC secretome as compared to fibroblasts. FIGS. 13A-13E provide heatmaps and hierarchical clustering analysis showing differences in secretome proteins involved in different processes like collagen fibril organization, cellular protein metabolic, platelet degranulation, translation initiation, and skeletal system development between TMSC and fibroblasts. FIGS. 13F-13G provides interactome graphs showing key interactions in TMSC-Scr proteins, involved in negative regulation of cell death and response to unfolded protein (n=2, for each TMSC and fibroblast).

Figure 14:
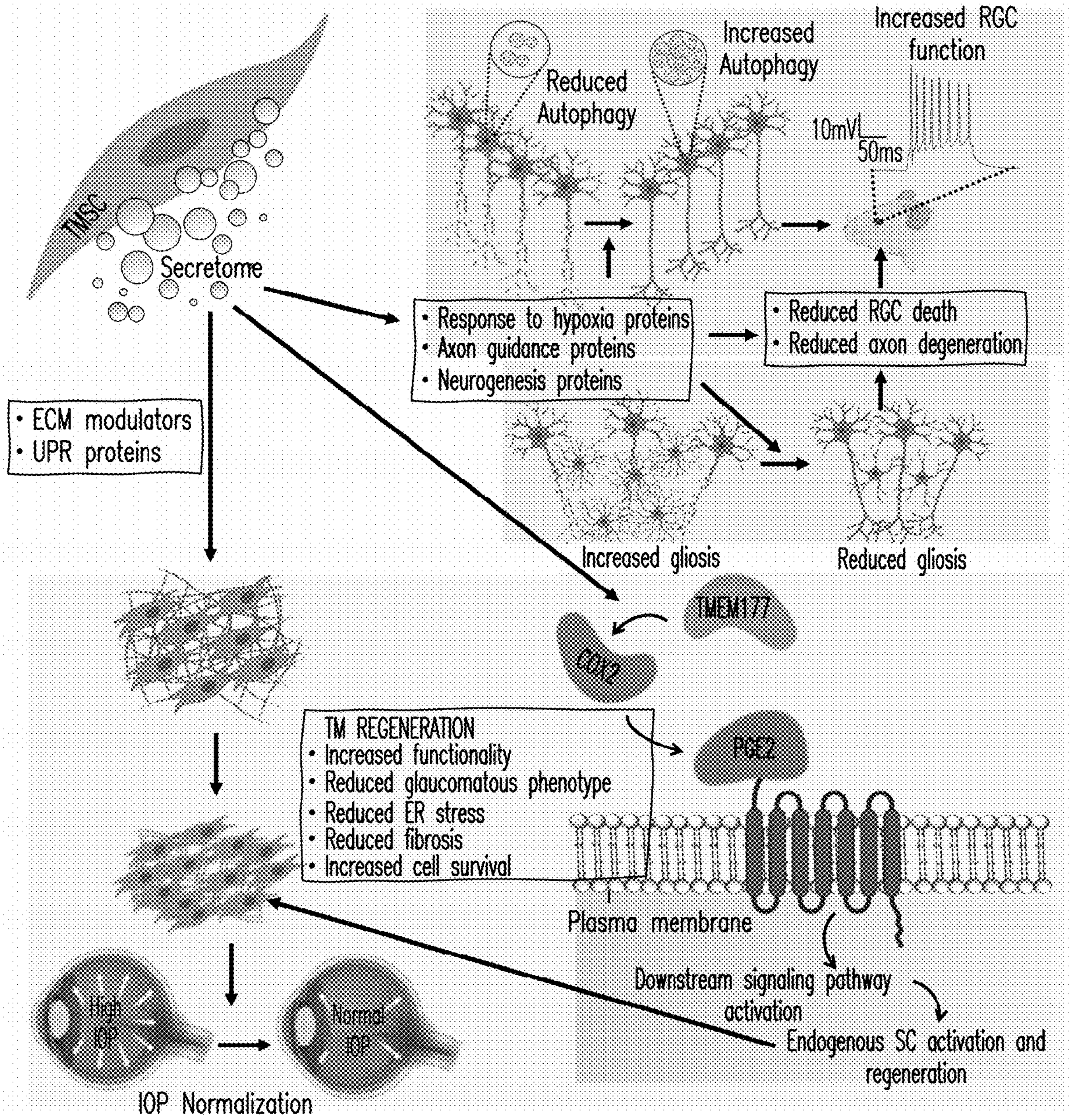

FIG. 14 provides a schematic model of the regenerative mechanisms of TMSC-Scr.

8. DETAILED DESCRIPTION

The disclosed subject matter provides compositions for treating ocular disorders. The compositions include an effective amount of a human trabecular meshwork stem cell (TMSC) secretome to reduce or treat the impairment of ocular cells. The disclosed subject matter further provides methods for ocular disorders. In certain embodiments, the disclosed compositions can be administered to the target tissue for treating ocular cell apoptosis, axon loss, vision loss, increased intraocular pressure, dysregulation of aqueous humor outflow, and/or combinations thereof.

As used herein, the following terms have the meanings ascribed to them below, unless specified otherwise. Abbreviations used herein have their conventional meaning within the chemical and biological arts.

As used in the specification and the appended claims, the singular forms "a," "an," and "the" include plural referents unless the context clearly dictates otherwise. Thus, for example, a reference to "a compound" includes mixtures of compounds.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "administering" can mean any suitable route, e.g., via topical administration, intraocular administration, or periocular administration without limitation to other routes of administration.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of" the embodiments or elements presented herein, whether explicitly set forth or not.

The term "effective amount," as used herein, refers to that amount of active agent sufficient to treat, prevent, or manage a disease. Further, a therapeutically effective amount with respect to the second targeting probe of the disclosure can mean the amount of active agent alone, or in combination with other therapies, that provides a therapeutic benefit in the treatment or management of the disease, which can include a decrease in the severity of disease symptoms, an increase in frequency and duration of disease symptom-free periods, or a prevention of impairment or disability due to the disease affliction. The term can encompass an amount that improves overall therapy, reduces or avoids unwanted effects, or enhances the therapeutic efficacy of or synergies with another therapeutic agent.

The term "secretome," as used herein, refers to an array of secretory cytokines, growth factors, small RNAs, non-coding RNAs, ECM mediators, and proteins secreted by a cell. For example, a human trabecular meshwork stem cell (TMSC) secretome can mean a set of proteins expressed by the TMSCs and secreted into the extracellular space.

A "subject" may be a human or a non-human animal, for example, but not by limitation, a non-human primate, a dog, a cat, a horse, a rodent, a cow, a goat, a rabbit, a mouse, etc.

The term "dosage" is intended to encompass a formulation expressed in terms of total amounts for a given time-frame, for example, as μg/kg/hr, μg/kg/day, mg/kg/day, or mg/kg/hr. The dosage is the amount of an ingredient administered in accordance with a particular dosage regimen. A "dose" is an amount of an agent administered to a mammal in a unit volume or mass, e.g., an absolute unit dose expressed in mg of the agent. The dose depends on the concentration of the agent in the formulation, e.g., in moles per liter (M), mass per volume (m/v), or mass per mass (m/m). The two terms are closely related, as a particular dosage results from the regimen of administration of a dose or doses of the formulation. The particular meaning in any case will be apparent from the context.

As used herein, "ocular disorder," "ophthalmic disease," "ophthalmic disorder," and the like, includes, but is not limited to, glaucoma, cataracts, leucoma, or retinal degeneration in a subject in need of such treatment comprising administering, to the subject, an effective amount of a compound as set forth above.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. Ranges disclosed herein, for example, "between about X and about Y" are, unless specified otherwise, inclusive of range limits about X and about Y as well as X and Y. With respect to sub-ranges, "nested sub-ranges" that extend from either endpoint of the range are specifically contemplated. For example, a nested sub-range of an exemplary range of 1 to 50 can include 1 to 10, 1 to 20, 1 to 30, and 1 to 40 in one direction, or 50 to 40, 50 to 30, 50 to 20, and 50 to 10 in the other direction.

The terms "treat," "treating" or "treatment," and other grammatical equivalents as used herein, include alleviating, abating, ameliorating, or preventing a disease, condition or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder.

For clarity of presentation, and not by way of limitation, the detailed description of the disclosed subject matter is divided into the following subsections:

8.1 Compositions; and 8.2 Methods of Treatment.

8.1. Compositions

The disclosed subject matter provides a composition for treating ocular disorders. In certain non-limited embodiments, the composition can include an effective amount of a secretome to treat ocular disorders. In certain embodiments, the secretome can be harvested from a human trabecular stem cell (TMSC). For example, TMSCs can be cultured as clonal culture and be used for harvesting secretome at passages 1-10. In non-limiting embodiments, the TMSCs can be used for harvesting secretomes at passages 4-7. In certain embodiments, TMSCs can be cultured with at least about 1 ml, at least about 3 ml, at least about 5 ml, at least about 10 ml, at least about 25 ml, at least about 50 ml, at least about 75 ml, or at least about 100 ml of a basal media for harvesting secretome. In non-limiting embodiments, the volume of the basal media can be from about 1 ml to about 10 ml, from about 1 ml to about 25 ml, from about 1 ml to about 50 ml, from about 1 ml to about 100 ml, from about 10 ml to about 50 ml, from about 10 ml to about 100 ml, or from about 50 ml to about 100 ml. In certain embodiments, the number of TMSCs cultured for harvesting secretome can be at least about $1\times10^5$, at least about $1\times10^6$, at least about $1\times10^7$, at least about $1\times10^8$, at least about $1\times10^9$, or at least about $1\times10^{10}$. In non-limiting embodiments, the range of TMSC population can be from about $1\times10^5$ to about $1\times10^6$, from about $1\times10^6$ to about $1\times10^7$, from about $1\times10^7$ to about $1\times10^8$, from about $1\times10^8$ to about $1\times10^9$, or from about $1\times10^9$ to about $1\times10^{10}$. In some embodiments, for secretome harvesting, TMSC cells can be cultured to the log phase and incubated with basal media without serum and growth factors at about 60% to about 70% confluence for a predetermined period. The predetermined period can be at least about 1 hour, at least about 3 hours, at least about 5 hours, at least about 10 hours, at least about 12 hours, at least about 24 hours, at least about 48 hours, or at least about 72 hours.

In non-limiting embodiments, the harvested secretome can be further concentrated. The harvested secretome can be concentrated up to about 2×, about 5×, about 10×, about 20×, about 25×, about 50×, about 75×, or about 100×. For example, the harvested secretome can be concentrated using a centrifugal filter to 25× and stored at about −80° C. until use to avoid any growth factor/protein degradation.

In certain embodiments, the disclosed secretome can be filtered to remove any cell debris. The cell-free secretome can avoid any cytotoxicity, immune responses, and/or side effects related to cell debris. In non-limiting embodiments, the disclosed secretome can include stem cell secretome for stem cell-free therapy.

In certain embodiments, the effective amount of the TMSC secretome can be at least about 1 μl of the concentrated TMSC secretome, at least about 5 μl of the concentrated TMSC secretome, at least about 10 μl of the concentrated TMSC secretome, at least about 15 μl of the concentrated TMSC secretome, at least about 20 μl of the concentrated TMSC secretome, at least about 30 μl of the concentrated TMSC secretome, at least about 50 μl of the concentrated TMSC secretome, at least about 100 μl of the concentrated TMSC secretome, at least about 250 μl of the concentrated TMSC secretome, at least about 500 μl of the concentrated TMSC secretome, or at least about 1000 μl of the concentrated TMSC secretome.

In certain embodiments, the disclosed composition can be formulated for topical administration or for injection into the eye (e.g., periocular injection) or a component of a visual apparatus (e.g., the eye itself, nerves innervating the eye, and associated musculature). Accordingly, the disclosed composition can be formulated in the form of a solution, a suspension, a gel, an emulsion, an ointment, a cream, or a controlled-release/sustain-release vehicle. In non-limiting embodiments, the disclosed composition can be formulated as an eye drop or eye ointment. It is desirable that the pharmaceutical composition is sterile or sterilizable.

In certain embodiments, the TMSC secretome can include a set of proteins that relate to axon guidance, neurogenesis, neuron death, neuron apoptosis, or combinations thereof. For example, the TMSC secretome can include proteins related to the axon guidance pathways, such as TUBB2A (Tubulin beta-2A), ACTR3, ARPC4, and Semaphorin 5A (SEMA5A). The TMSC secretome can also include proteins involved in neurogenesis (e.g., NEO1, SPTBN1, GAS6, and/or SDC2), proteins involved in negative regulation of neuron death (e.g., PARK7, HYOU1, NONO, and/or PIN1), proteins involved in the clearance of neuron apoptotic process (e.g., NQO1, HSP90AB1, G6PD, and/or UBE2V2). In some embodiments, the TMSC secretome can include proteins involved in positive regulation of neuron differentiation (e.g., CAPRIN1, CFL1, CRABP2, and CTSZ), positive regulation of neurogenesis (e.g., CRKL, CSF1, DPYSL3, and/or EIF4G1), neuron projection maintenance and development (e.g., APP, INS, MAP1A, ACTR2, ARHGDIA, CAPRIN1, and/or CFL1) and positive regulation of neuron projection development (e.g., DPYSL3, FN1, HGF, and/or ITGA3).

In certain embodiments, the disclosed TMSC secretome can include proteins related to neuroprotection and rescue RGCs from apoptosis. For example, the disclosed TMSC secretome can include a neuralized E3 ubiquitin-protein ligase 1 protein (NEURL1, formation of functional synapses), a neurofascin protein (neurite extension, axonal guidance, synaptogenesis, myelination, and neuron-glial cell interactions), and/or a neuroligin-1/3/4× protein (synapse function and synaptic signal transmission).

In certain embodiments, the disclosed composition can include an array of neuroprotective proteins, which can regulate different aspects of neurogenesis and provide neuroprotective effects on RGCs.

In certain embodiments, the disclosed composition can include an effective amount of the TMSC secretome, wherein the effective amount can be present in an amount to reduce impairment of RGCs, wherein the TMSC secretome can include proteins involved in neuroprotection, wherein the neuroprotection can be selected from the group consisting of axon guidance, neurogenesis, negative regulation of neuron death, neuron apoptosis, clearance of neuron apoptotic bodies, or combinations thereof, wherein the TMSC secretome can be a cell-free secretome, wherein the TMSC secretome can be harvested from TMSCs by incubating the TMSCs with serum-free media, wherein the TMSC secretome can be concentrated by a factor of about 25, wherein the impairment can be selected from the group consisting of cell apoptosis, axon loss, vision loss, increased intraocular pressure, dysregulation of aqueous humor outflow, and combinations thereof, wherein the ocular disorder can be glaucoma, wherein the composition can be formulated in a form, wherein the form can be selected from the group consisting of a solution, a suspension, a semi-solid gel, a gel, an emulsion, semi-liquid, an ointment, a cream, foam gel, a controlled-release/sustain-release vehicle, an eye drop, and combinations thereof, and wherein the composition is formulated in a form for injection into the subject, wherein the injection can be selected from the group consisting of a systemic injection, an intravenous injection, an intramuscular injection, and combinations thereof.

8.2. Methods of Treatment

In certain embodiments, the disclosed subject matter provides a method of treating an ocular disorder comprising administering an effective amount of a TMSC secretome to reduce impairment of RGCs in a target tissue of the subject. In non-limiting embodiments, the target tissue can be an eye or a component of the visual apparatus (e.g., the eye itself, nerves innervating the eye, and associated musculature).

In some embodiments, the disclosed composition can be administered to the target tissue by any method known in the art, including, but not limited to, topical instillation, periocular injection, intravitreal injection, systemic administration, or the insertion of a reservoir that provides sustained release of the composition. In certain embodiments, the disclosed composition can be periocularly administered. For example, a composition including about 1 ul to about 1000 ul of the concentrated TMSC secretome can be periocular injected into a target tissue. In certain embodiments, the volume of the concentrated TMSC secretome can be from about 1 μl to about 500 μl, from about 1 μl to about 400 μl, from about 1 μl to about 300 μl, from about 1 μl to about 200 μl, from about 1 μl to about 100 μl, from about 1 μl to about 50 μl, from about 1 μl to about 10 μl, or from about 1 μl to about 5 μl. In certain embodiments, the volume of the concentrated TMSC secretome can be from about 500 μl to about 1000 μl, from about 500 μl to about 900 μl, from about 500 μl to about 800 μl, from about 500 μl to about 700 μl, or from about 500 μl to about 600 μl. In certain embodiments, the volume of the concentrated TMSC secretome can be from about 100 μl to about 900 μl, from about 100 μl to about 800 μl, from about 100 μl to about 700 μl, from about 600 μl to about 500 μl, from about 100 μl to about 400 μl, from about 100 μl to about 300 μl, from about 100 μl to about 200 μl, or from about 100 μl to about 150 μl.

In one non-limiting embodiment, the disclosed composition can be administered to an affected eye topically, for example, as eye drops or as an ointment. For example, but not by way of limitation, the administration can be at least once a day, at least twice a day, at least once a week, at least twice a week, at least once a month, at least twice a month, at least six times a year, at least four times a year, at least twice a year or at least once a year, and/or up to twice a day, up to three times a day, up to once a week, up to twice a week, up to three times a month, up to six times a year, or up to four times a year. In a specific non-limiting embodiment, where the composition can be administered as eye drops, about 1 μl to about 1000 μl of the composition comprising the concentrated TMSC secretome can be administered to the affected eye at a time with the appropriate number of drops. The secretome proteins can cross the corneal barrier when they are administered in the form of eye drops.

In non-limiting embodiments, the disclosed subject matter can be used to treat the impairment of RGCs. In some embodiments, the impairment can include cell apoptosis, axon loss, vision loss, increased intraocular pressure, dysregulation of aqueous humor outflow, or combinations thereof. In particular non-limiting embodiments, the impairment can be cell apoptosis and increased intraocular pressure. The disclosed composition can also be used for any ocular disorders associated with the impairment of RGCs. Without being bound by any particular theory, it is believed that such impairment can affect and induce ocular disorders (e.g., glaucoma, cataracts, leucoma, and/or retinal degeneration).

Ocular disorders that can be treated according to the disclosed subject matter include, but are not limited to, glaucoma, cataracts, leucoma, and retinal degeneration. Retinal ganglion cell damage can be a contributor to a number of optic neuropathies (e.g., glaucoma), and it can be implicated in other diseases (e.g., multiple sclerosis). During development, RGCs can be produced in about a two-fold excess, but the insufficiency to form an efficient synaptic connection in the brain and lack of signal from neighboring retinal neurons can lead to the death of RGCs. During adulthood, pathological conditions can disrupt the synaptic connectivity or induce RGC death after optic nerve injury due to the deprivation of various factors (e.g., growth factor) or changes in electrical activity. Most optic neuropathies that involve damage to an optic nerve (e.g., traumatic optic neuropathies, ischaemic optic neuropathies, and glaucoma) can lead to RGC death by apoptosis. RGCs can be damaged in a variety of diseases that involve acute diseases (e.g., ischaemic optic neuropathy, optic neuritis, and glaucoma). For example, retinal ischemia, retinal artery, or vein occlusions can directly injure RGC cell bodies in the ganglion cell layer and can lead to vision loss. In certain embodiments, RGC viability (neuroprotection) and/or RGC function (neuroenhancement) can be enhanced by the disclosed subject matter. In non-limiting embodiments, the disclosed subject matter can be used to treat the impairment of retinal ganglion cells (RGCs). The impairment can be cell apoptosis, axon loss, vision loss, increased intraocular pressure, dysregulation of aqueous humor outflow, and/or combinations thereof. The disclosed composition can also be used for any ocular disorders associated with the impairment of RGCs. Without being bound by any particular theory, it is believed that such impairment can affect and induce ocular disorders (e.g., glaucoma, cataracts, leucoma, and/or retinal degeneration). The disclosed TMSC secretome can reduce the impairment of RGCs directly and/or indirectly.

In certain embodiments, administering the effective does of the disclosed composition can reduce the death of ocular cells and preserve cellular activities. In particular, the disclosed TMSC secretome can include proteins related to neuroprotection and rescue RGCs from apoptosis. In some embodiments, the disclosed TMSC secretome can protect RGCs from apoptosis through the neurotrophin and/or PI3-Akt signaling pathway. In certain embodiments, the disclosed TMSC secretome can prevent axon loss and vision loss. Since the RGC apoptosis leading to axon loss in the optic nerve can be the main reason for vision loss in glaucoma, the disclosed TMSC secretome can prevent/treat vision loss in genetic glaucoma by protecting RGCs from cell death. In non-limiting embodiments, the disclosed TMSC secretome can preserve RGCs' functions. Preservation of RGC functions can be important for treating primary open-angle glaucoma (POAG) and reducing IOP. In certain embodiments, administering the effective does of the disclosed composition can reduce IOP. For example, administering the disclosed composition can result in maintaining IOP at normal ranges without causing damages to the optic nerve.

In certain embodiments, the disclosed subject matter can treat ocular disorders by regenerating TM cells. In particular, the disclosed composition can preserve gene expression related to extracellular matrix (ECM) remodeling. For example, administering the disclosed composition can preserve the expression level of the CHI3L1 gene, which is a TM cell marker and involved in ECM remodeling. In non-limiting embodiments, the disclosed subject matter can also reduce mutations in genes, which can cause ocular disorders. For example, myocilin and ANGPTL7 are glaucoma associated genes, and mutations in these can be associated with glaucoma. The increased expression of Myoc and ANGPTL7 of glaucoma patients can be reduced by TMSC secretome, preventing steroid-induced glaucoma. In some embodiments, the disclosed composition can reduce the excess formation of fibrous tissues after a wound in ocular cells. For example, the disclosed subject matter can reduce fibrotic gene expression including a secreted protein acidic and cysteine-rich (SPARC) gene, fibronectin, and/or a connective tissue growth factor (CTGF) gene.

In certain embodiments, the disclosed subject matter can be used to treat ocular disorders by activating neuroprotective proteins, enzymes, or signaling pathways. For example, the expression level of TMEM177, COX2, PGE2, or combinations thereof can increase after administering the disclosed secretome of TMSC into the subject. TMEM177 can stabilize or increase the biogenesis of COX2. Increased TMEM177 after the secretome of the TMSC treatment can increase COX2 stabilization and biogenesis, leading to increased PGE2 expression that can reduce IOP. In non-limiting embodiments, the increased PGE2 can reverse glaucomatous changes and promote the self-renewal and proliferation of stem cells (e.g., ABCB5+ and OCT4+ endogenous stem cells). In non-limiting embodiments, the TMSC can be transplanted to increase the expression level of TMEM177, COX2, PGE2, or combinations thereof.

In certain embodiments, the disclosed subject matter can be used to treat gliosis. Gliosis can be caused by neurodegeneration of RGC (e.g., alteration of structure, function, and gene expression profile of glial cells). Administering the disclosed composition, including the effective amount of TMSC secretome, can reduce gliosis and further enhance regeneration in RGC. The proteins in the secretome can induce axon guidance pathway activation, neurogenesis, negative regulation of neuron death, and clearance of neuron apoptotic process leading to the enhanced RGC protection, survival, and function. In non-limiting embodiments, the TMSC secretome can increase autophagy to promote RGC survival. For example, the expression level of Beclin1 and Atg5, which controls autophagy, can be restored or increased.

In certain embodiments, the method of treating an ocular disorder can further include harvesting the TMSC secretome by incubating the TMSCs with serum-free media. For example, TMSC cells can be incubated with basal media without serum and growth factors at about 60-70% confluence for predetermined periods. The predetermined period can be at least about 1 hour, at least about 3 hours, at least about 5 hours, at least about 10 hours, at least about 12 hours, at least about 24 hours, at least about 48 hours, or at least about 72 hours.

In certain embodiments, the method of treating an ocular disorder can further include concentrating the TMSC secretome. For example, the harvested secretome can be filtered to remove any cell debris and further concentrated. The harvested secretome can be concentrated up to about 2×, about 5×, about 10×, about 20×, about 25×, about 50×, about 75×, or about 100×.

In certain embodiments, the effective amount of the TMSC secretome can be from about 0.1 mg/ml to about 1 mg/ml, from about 0.1 mg/ml to about 0.9 mg/ml, from about 0.1 mg/ml to about 0.8 mg/ml, from about 0.1 mg/ml to about 0.7 mg/ml, from about 0.1 mg/ml to about 0.6 mg/ml, from about 0.1 mg/ml to about 0.5 mg/ml, from about 0.1 mg/ml to about 0.4 mg/ml, from about 0.1 mg/ml to about 0.3 mg/ml, from about 0.1 mg/ml to about 0.2 mg/ml, from about 0.2 mg/ml to about 1 mg/ml, from about 0.2 mg/ml to about 0.9 mg/ml, from about 0.2 mg/ml to about 0.8 mg/ml, from about 0.2 mg/ml to about 0.7 mg/ml, from about 0.2 mg/ml to about 0.6 mg/ml, from about 0.2 mg/ml to about 0.5 mg/ml, from about 0.2 mg/ml to about 0.4 mg/ml, or from about 0.2 mg/ml to about 0.3 mg/ml.

In certain embodiments, the effective volume of the TMSC secretome can be from about 0.1 μl to about 1000 μl, from about 0.1 μl to about 900 μl, from about 0.1 μl to about 800 μl, from about 0.1 μl to about 700 μl, from about 0.1 μl to about 600 μl, from about 0.1 μl to about 500 μl, from about 0.1 μl to about 400 μl, from about 0.1 μl to about 300 μl, from about 0.1 μl to about 200 μl, from about 0.1 μl to about 100 μl, from about 0.1 μl to about 50 μl, from about 0.1 μl to about 10 μl, from about 0.5 μl to about 1000 μl, from about 0.5 μl to about 900 μl, from about 0.5 μl to about 800 μl, from about 0.5 μl to about 700 μl, from about 0.5 μl to about 600 μl, from about 0.5 μl to about 500 μl, from about 0. μl to about 400 μl, from about 0.5 μl to about 300 μl, from about 0.5 μl to about 200 μl, from about 0.5 μl to about 100 μl, from about 0.5 μl to about 50 μl, from about 0.5 μl to about 10 μl, from about 1 μl to about 1000 μl, from about 1 μl to about 900 μl, from about 1 μl to about 800 μl, from about 1 μl to about 700 μl, from about 1 μl to about 600 μl, from about 1 μl to about 500 μl, from about 1 μl to about 400 μl, from about 1 μl to about 300 μl, from about 1 μl to about 200 μl, from about 1 μl to about 100 μl, from about 1 μl to about 50 μl, or from about 1 μl to about 10 μl.

In certain embodiments, a treatment regimen using the disclosed composition can be combined with a regimen of treatment using other pharmaceutical agents.

In certain embodiments, the disclosed method can include harvesting the TMSC secretome by incubating the TMSCs with serum-free media, concentrating the TMSC secretome by a factor of about 25, and administering an effective amount of the TMSC secretome to reduce impairment of the RGC to a target tissue of the subject, wherein the effective amount of the TMSC secretome can be periocular administered to the target tissue, wherein the effective amount of the TMSC secretome is administered in appropriate amounts divided into multiple portions, wherein the TMSC secretome can include proteins involved in neuroprotection, wherein the neuroprotection can be selected from the group consisting of axon guidance, neurogenesis, negative regulation of neuron death, neuron apoptosis, clearance of neuron apoptotic bodies, and combinations thereof, wherein the target tissue is an eye of the subject, wherein the impairment can be selected from the group consisting of cell apoptosis, axon loss, vision loss, increased intraocular pressure, dysregulation of aqueous humor outflow, and combinations thereof, wherein the ocular disorder can be glaucoma, wherein the composition can be formulated in a form, wherein the form can be selected from the group consisting of a solution, a suspension, a semi-solid gel, a gel, an emulsion, semi-liquid, an ointment, a cream, foam gel, a controlled-release/sustain-release vehicle, and combinations thereof, wherein the effective amount of the TMSC secretome can be administered to the target tissue via an injection, wherein the injection can be selected from the group consisting of a systemic injection, an intravenous injection, an intramuscular injection, and combinations thereof, wherein the effective amount of the TMSC secretome can be present in an amount to decrease intraocular pressure of the subject by increasing an expression level of a neuroprotective factor, wherein the neuroprotective factor can be selected from the group consisting of an axon guidance factor, a neurogenesis factor, a negative regulation of neuron death factor, a clearance of neuron apoptotic bodies factor, and combinations thereof, wherein the axon guidance factor can be selected from the group consisting of Tubulin beta-2A (TUBB2A), ACTR3, ARPC4, Semaphorin 5A (SEMA5A), and combinations thereof, wherein the neurogenesis factor can be selected from the group consisting of NEO1, SPTBN1, GAS6, SDC2, and combinations thereof, wherein the negative regulation of neuron death factor can be selected from the group consisting of PARK7, HYOU1, NONO, PIN1, and combinations thereof, wherein the clearance of neuron apoptotic bodies factor can be selected from the group consisting of NQO1, HSP90AB1, G6PD, UBE2V2, and combinations thereof, wherein the effective amount of the TMSC secretome can be present in an amount to reduce gliosis by promoting regeneration of RGC, wherein the effective amount of the TMSC secretome can be present in an amount to increase autophagy in the RGC and regenerate the RGC.

9. EXAMPLES

The following examples are merely illustrative of the presently disclosed subject matter, and they should not be considered as limiting the scope of the disclosed subject matter in any way.

9.1 Example 1

Stem Cell-Free Therapy for Glaucoma and Potential Mechanisms Involved in Regeneration Experiment Design The primary objective of this research study was to evaluate the effect of human trabecular meshwork stem cell (TMSC) secretome in steroid-induced and genetic mouse models of glaucoma. Four-months old wildtype (WT) C57BL/6J mice were purchased from Jackson Laboratory as wildtype control (WT). Adult C57BL/6J mice were periocularly injected with 20 μl of dexamethasone acetate (Dex-Ac) (DE122, Spectrum Chemicals) at 10 mg/ml once a week. In the genetic POAG model, transgenic mice with myocilin Y437H mutation (Tg-MyocY437H) were obtained from North Texas Eye Research Institute and bred with C57BL/6J WT mice and genotyped to confirm the myocilin mutation. Littermates were used as controls. Primary human TMSC, TM cells, and corneal fibroblasts were derived from deidentified corneas unsuitable for corneal transplantation obtained from the Center for Organ Recovery and Education (CORE, Pittsburgh, PA) or from the corneal rims after corneal transplantation. Proper informed consent for using the donated corneas for research purposes was obtained from all the donors by the CORE. Induced pluripotent stem cells (iPSC) cell lines were used and maintained in the laboratory. Blinded methods were used for study outcomes and designs. In particular, the histological evaluations of cell immunofluorescence for different antibodies and TM and retinal ganglion cell (RGC) counts were performed by two independent researchers blindly. Axon count in the optic nerve sections was performed by an expert in a blinded fashion. qPCR experiments were performed by another researcher in a blinded manner. The sample size was estimated based on the variability of different assays and potential outliers. The sample size for Dex-Ac and Tg-MyocY437H mice cohorts was estimated by power analysis before the initiation of the experiments. The number of samples (n) used for each experiment is specified in the captions for each figure.

Primary Cell Culture and Characterization.

TMSCs were cultured in Opti-MEM (Invitrogen, Carlsbad, CA), with supplements including 5% fetal bovine serum (ThermoFisher, Pittsburgh, PA), 0.08% chondroitin sulfate, 100 μg/ml bovine pituitary extract (Life Technologies, Carlsbad, CA), 20 μg/ml ascorbic acid, 10 ng/ml epidermal growth factor (Sigma-Aldrich, St. Louis, MO), and 200 μg/ml calcium chloride (Sigma-Aldrich), 50 mg/ml gentamicin, 100 mg/ml streptomycin, and 100 IU/ml penicillin (ThermoFisher). For stem cell characterization, TM cells were cultivated in DMEM:HAM's F12 (1:1) medium with 10% FBS and confirmed by responsiveness to 100 nM Dex. TMSC were used between passages 4-7. Secretome treatment was given 1) in cell culture together with Dex (referred as "parallel TMSC-Scr") for five days (for preventive effect); 2) TM cells were treated with Dex for five days, and then secretome was supplemented in cell culture in the presence of Dex for another five days (referred as "post TMSC-Scr") (for reverse effect). Human corneal fibroblasts were collagenase digested and cultured in DMEM/F12 with 10% FBS and used between passage 4-7.

TABLE 1

Antibodies used for characterization.

| Antibody | Company | Catalog No. | Host | Application | Dilution |
|---|---|---|---|---|---|
| CHI3L1 | R&D Systems, Minneapolis, MN | AF2699 | Goat | IF | 1:200 |
| AQP1 | Santa Cruz Bioscience, Dallas, TX | sc-25287 | Rabbit | IF | 1:100 |
| Myocilin | Santa Cruz Bioscience Dallas, TX | | Rabbit | WB | 1:100 |
| Myocilin (55kDa) | Novus Biologicals, Littleton, CO | 297817 | Mouse | IF | 1:500 |
| ANGPTL7 | R&D Systems, Minneapolis, MN | MAB914 | Mouse | IF | 1:100 |
| Beclin1 (60kDa) | Cell Signaling Technologies, Danvers, MA | #3495 | Rabbit | WB | 1:1000 |
| Atg5 (55kDa) | Cell Signaling Technologies, Danvers, MA | #12994 | Rabbit | WB | 1:1000 |
| Atg7 (70kDa) | Cell Signaling Technologies, Danvers, MA | #8558 | Rabbit | WB | 1:1000 |
| Atg12 | Cell Signaling Technologies, Danvers, MA | #4180 | Rabbit | WB | 1:1000 |
| Atg16L1 | Cell Signaling Technologies, Danvers, MA | #8089 | Rabbit | WB | 1:1000 |
| COX2 (21kDa) | Santa Cruz Bioscience, Dallas, TX | sc-514489 | Mouse | IF/ WB | 1:100/ 1:500 |
| GRP78 (78kDa) | Santa Cruz Bioscience Dallas, TX | sc-376768 | Mouse | WB | 1:500 |
| TMEM177 (50kDa HC, 25kDa LC) | Invitrogen, Carlsbad, CA | A6-A1 1-9 | Mouse | IF/ WB | 1:100/ 1:500 |
| β-Actin (50kDa) | Invitrogen, Carlsbad, CA | MA5-15739 | Mouse | WB | 1:5000 |
| CD90-BV510 | BD Bioscience, San Jose, CA | 563070 | Mouse | FC | 1:100 |
| CD73-7 PE/Cy | Biolegend, San Diego, CA | 344010 | Mouse | FC | 1:100 |
| CD105-AF647 | Biolegend, San Diego, CA | 323212 | Mouse | FC | 1:100 |
| CD166-FITC | MBL, Woburn, MA | K0044-4 | Mouse | FC | 1:100 |
| NOTCH1-PE | BD PharmingenTM, San Diego, CA | 563421 | Mouse | FC | 1:100 |
| OCT4-FITC | Santa Cruz Bioscience Dallas, TX | sc-5279 | Mouse | FC | 1:100 |
| SSEA4-AF488 | eBioscience Inc., Coraopolis, PA | 53-8843-42 | Mouse | FC | 1:100 |
| CD34-FITC | Millipore, Burlington, MA | CBL5 55F | Mouse | FC | 1:100 |
| CD45-PE | BD Bioscience, San Jose, CA | 553081 | Mouse | FC | 1:100 |
| RBPMS | Invitrogen, Carlsbad, CA | PA5-31231 | Rabbit | IF | 1:100 |
| Thy1.1 | Santa Cruz Bioscience Dallas, TX | sc-53 116 | Mouse | IF | 1:100 |
| ABCB5 | Abcam, Cambridge, MA | ab140667 | Mouse | IF | 1:100 |

TABLE 1-continued

Antibodies used for characterization.

| Antibody | Company | Catalog No. | Host | Application | Dilution |
|---|---|---|---|---|---|
| CD31 | BD Bioscience, San Jose, CA | 550274 | Rat | IF | 1:100 |
| Collagen IV | Sigma Aldrich, St. Louis, MO | SAB4500385 | Rabbit | IF | 1:100 |
| Fibronectin | Abcam, Cambridge, MA | Ab23750 | Rabbit | IF | 1:100 |
| OCT4 | Millipore, Burlington, MA | MAB4401 | Mouse | IF | 1:200 |
| Ki67 | Abcam, Cambridge, MA | ab15580 | Rabbit | IF | 1:50 |
| IgG1 K Iso FITC | Bioscience Inc. San Diego, CA | 11-4714-42 | Mouse | FC | 1:100 |
| IgG2a K Isotype PE | BD PharmingenTM, San Diego, CA | 555574 | Mouse | FC | 1:100 |
| IgG1 K Iso PE/CY7 | Biolegend, San Diego, CA | 400126 | Mouse | FC | 1:100 |
| IgG1 K Iso APC | Bioscience Inc. San Diego, CA | 17-4714-42 | Mouse | FC | 1:100 |
| Anti-goat AF-555 IgG | Life Technologies, Eugene, OR | A11056 | Donkey | IF | 1:1500 |
| Anti-rabbit AF-555 IgG | Life Technologies, Eugene, OR | A32794 | Donkey | IF | 1:1500 |

Table 1 provides a listing of antibodies used in the disclosed subject matter. The acronyms provided in Table 1 are as follows: FITC is fluorescein isothiocyanate, PE is phycoerythrin, APC is allophycocyanin, HC is a heavy chain, LC is a light chain. IF is immunofluorescence. WB is western blotting. FC is flow cytometry.

RGC Induction from Human iPSCs iPSCs reprogrammed from human dermal fibroblasts using four Yamanaka factors OCT4, KLF4, SOX2, and cMyc were cultured in mTeSR Plus media (StemCell Technologies) on Matrigel (Corning)-coated plates. These cells were induced to differentiate into RGC in Neurobasal: DMEM/F12 (1:1) medium containing Glutamax, N2 and B27 supplement (Invitrogen), and 25 μM forskolin (Stemcell Technologies) for 40 days. Differentiated RGC were characterized by immunofluorescent staining with RGC markers RBPMS and Thy1.1. After 40-day induction, cells were treated with 500 μM CoCl2 (Cobalt Chloride, Sigma-Aldrich) for 48 h to induce apoptosis or in the presence of a secretome to detect the protection effect.

Flow Cytometry.

Differentiated RGC treated with different conditions were dissociated using Accutase and stained with Annexin V and 7-AAD (BD Biosciences) as per manufacturer's instructions. $2\times10^4$ cells were acquired immediately on BD FACS Aria (BD Biosciences). Cells with no staining, containing Annexin V or 7-AAD alone, were taken as controls. RGCs were handled gently during the entire procedure to prevent any mechanical damage to the cells. For stem cell characterization, TMSC were blocked in 1% bovine serum albumin (BSA) for one hour and incubated with fluorochrome-conjugated antibodies for 30-min on ice in the dark. $5'10^4$ cells were acquired per tube on BD FACS Aria (BD Biosciences). Compensations were adjusted using proper controls, and isotype controls were used to rule out spectral bleeding. Cell apoptosis was assessed by Annexin V/7-AAD staining. Data were analyzed using the FlowJo V10 software (FlowJo, Ashland, OR).

Calcein AM/Hoechst Staining.

Post secretome harvesting (~90% confluence), TMSC and corneal fibroblasts were stained for 15 minutes in the dark with the viability dyes Hoechst 33342 (1:2000) and Calcein AM (1:1000) (Invitrogen). Live cells were captured at excitation filters of the wavelength of 361 nm and 565 nm, respectively, employing TE 200-E (Nikon Eclipse).

MTT Assay.

To assess the cell viability post secretome harvesting, $5\times10^3$ TM cells were cultured per well in 96-well plates in optimum culture conditions as described above. These cells were then incubated with secretome from three different TMSCs for 48 hours. MTT reagent (Millipore, Burlington, MA) was used to assess the formation of formazan crystals at the endpoint. The optical density was measured at ELISA reader (Tecan) using 570 nm wavelength and considering 600 nm as a reference to eliminate any background noise. Cells grown in optimum culture media without secretome were taken as control.

Eye Section Processing and Staining and Cell Counting.

Whole mouse eyes were enucleated into freshly prepared 1% PFA in PBS and fixed for at least 48 h at 4° C. For plastic sectioning, eyes were embedded in glycol methacrylate A resin (JB-4, Polysciences) according to the manufacturer's instructions. Specifically, the eyes were placed in 70% ethanol and then dehydrated in increasing concentrations of ethanol to 100%. Fully dehydrated samples were infiltrated with resin monomer and its catalyst overnight. The next day, an accelerant was added, and the samples were embedded. Then 3-μm sections were made on a rotary microtome (RM2235, Leica). Slides were immediately stained for 1 minute in Mayer's hematoxylin solution (Electron Microscopy Sciences). Sections were photographed in DIC color mode using 40× oil objective (Olympus). For RGC counting, the retina was imaged at nasal and temporal sides, and three images were captured per eye. RGC counting was done in 3-4 eyes per group in both Dex-Ac and Tg-MyocY437H models using automated cell counter mode in ImageJ (NIH). Total counted RGC in a defined length of the retina were normalized to calculate cells/pm for each group.

For cryosections, fixed whole mouse eyes were embedded sagittally in OCT compound (Tissue Plus, FisherScientific) and flash-frozen in liquid nitrogen chilled isopentane. 10-μm sections through the center of the eye were made on a motorized Cryostat (CM3050 S, Leica).

Acridine Orange Staining.

This staining was used to assess autophagy. RGC were incubated with 0.1 μg/ml of acridine orange (Molecular probes) for 15 minutes. Cells were washed and maintained in PBS and photographed immediately using confocal microscopy at an excitation maximum of 502 nm and an emission maximum of 525 nm.

Immunofluorescent Staining.

Cells were cultured on glass coverslips and fixed with 4% paraformaldehyde (PFA) (Electron Microscopy Sciences). Fixed cells were permeabilized with 0.1% Triton X-100 and blocked with 1% BSA. Samples were stained with appropriate primary antibodies at 4° C. overnight. After washing with PBS, cells were then stained with corresponding secondary antibodies conjugated with fluorochromes FITC, PR, and APC. Nuclei were stained with DAPI. Samples were examined under a confocal laser scanning microscope (Olympus).

Quantitative Real-Time PCR (qPCR).

Cells were lysed with RLT buffer, and total RNAs were isolated using an RNA purification kit (RNeasy Mini Kit, Qiagen, Hilden, Germany). cDNAs were transcribed using a High-Capacity cDNA Reverse Transcription Kit (Applied Biosystems, Foster City, CA). Primers were designed using Primer3 and blasted to confirm the specificity. The primer sequences were as follows: the sequences are: MYOC (forward: AAGCCCACCTACCCCTACAC (SEQ ID NO: 1); reverse: TCCAGTGGCCTAGGCAGTAT (SEQ ID NO: 2)), ANGPTL7 (forward: GCAC-CAAGGACAAGGACAAT (SEQ ID NO: 3); reverse: GATGCCATCCAGGTGCTTAT (SEQ ID NO: 4)). RNA content was normalized by 18S rRNA (Forward: CCCTGTAATTGGAATGAGTCCAC (SEQ ID NO: 5), Reverse: GCTGGAATTACCGCGGCT (SEQ ID NO: 6)). Relative mRNA abundance was calculated as the Ct for amplification of a gene-specific cDNA minus the average Ct for 18S expressed as a power of 2 ($2^{\Delta\Delta Ct}$). Three individual gene-specific values, thus calculated, were averaged to obtain mean±SD.

Secretome Preparation.

Secretomes were harvested from both TMSC and corneal fibroblasts. $1\times10^6$ cells were cultured per T75 flask in the log phase and incubated with basal media without serum and growth factors at 60-70% confluence for 48 h. Then, the secretome was centrifuged at 3000 rpm for 5 minutes to remove any cell debris, filtered, and concentrated using 3 kDa centricon devices (Amicon) to 25× and immediately stored at −80° C. until use to avoid any growth factor/protein degradation.

Secretome Dosing and Treatment.

For cell culture, 1× secretome was mixed with basal DMEM/F12 (1:1) in dexamethasone (Dex, 100 nM/ml, Sigma Aldrich) treated TM cell or mixed with neurobasal medium (1:1) in CoCl2 treated RGC cultures. For animal experiments, 20 μl of 25× concentrated secretome was periocularly injected into each mouse eye. In the Dex-Ac model, both TMSC and fibroblast secretomes were injected at week 3, continued once a week until week-6, and animals were sacrificed at week-8. In the Tg-MyocY437H model, the secretome derived from human TMSC (TMSC-Scr) was injected at week 0 when mice were 4 months old, continued once a week until week-7, and animals were sacrificed at week-10. IOP was measured once a week.

Periocular Secretome Injection and IOP Measurement.

Two TMSC strains from two different donors at passage 4-7 were used for secretome isolation and mouse injection. Fibro-Scr was used as a control in the Dex-Ac induced model. For the Dex-Ac model, mice were divided in four groups: Dex-Ac treated mice (n=16), vehicle-injected with vehicle solution used for solubilizing Dex-Ac (n=16), TMSC-Scr group (n=16), and Fibro secretome group (n=16). For the genetic model, mice were divided into five groups: littermate group (WT, n=16), Tg-MyocY437H mice (Tg, n=16), Tg-MyocY437H mice with a periocular injection of the basal medium (Tg-Sham, n=16), and Tg mice with periocular injection of TMSC-Scr (Tg-TMSC, n=16 each). For TMSC injections, Tg-MyocY437H mice were divided into four groups as described above (n=3-4 per group) and injected with $5\times10^4$ DiO-green labeled TMSC intracamerally. In brief, mice were anesthetized with ketamine-xylazine. 20 μl of 25× concentrated secretome or basal medium was injected periocularly using a 33-gauge needle connected to a Hamilton syringe. An I-care tonometer was used to measure mouse IOP (TonoLab; Colonial Medical Supply, Windham, NH). All IOP measurements were performed between 1 PM and 3 PM. IOP measurement before injection served as a baseline, and measurements were conducted once a week for 8-10 weeks.

Pattern Electroretinography (PERG).

PERG was performed on the Celeris (Diagnosys LLC, Lowell, MA) to evaluate the RGC function. Mice (n=9-15 for each group) were dark-adapted overnight and anesthetized with intraperitoneal injections of the mixture of Ketamine and Xylazine. Mouse pupil was dilated with 0.5% Tropicamide and 2.5% Phenylephrine eye drops. A circular electrode centered on the cornea was placed in a plane perpendicular to the visual axis after applying GenTeal lubricant to avoid corneal dryness and prevent cataract formation. Pattern stimuli consisted of horizontal bars of variable spatial frequencies and contrasts that alternate at different temporal frequencies. The parameters for PERG amplitude were spatial frequency 0.155 cycles/degree, temporal frequency 2.1 reversals/sec, contrast 100%, and substantial averaging (600-1800 sweeps). The Amplitude of P1 was used to analyze the function of RGCs.

Optic Nerve Axon Count and Gliosis Quantification.

Optic nerves were removed from enucleated eyes and immediately fixed in Karnovsky's fixative containing 2% paraformaldehyde and 2.5% glutaraldehyde. Optic nerves were cut into thick sections of 350 nm using a cryotome and stained with toluidine blue. Sectioned nerves were photographed using a phase-contrast microscope (Oplympus) at 20× and 60× using oil objectives. Three images were acquired for each optic nerve, and each group included 3-4 optic nerves. Axons in the optic nerve were counted using automated analysis in Metamorph. A 400×400 pixel box was made for uniform counting that can be moved to an area that is in good focus, then segmented image with threshold segmentation. IMA was used to measure small and large axons and log out summary measurements to an excel spreadsheet. For gliosis measurement, we employed semi-automatic quantification of total glial/scar areas and degenerative axonal profiles in plastic cross-sections using threshold contrast-based segmentation in addition to shape factor and elliptical form factor. For accurate RGC axon count, the following shape measurements were taken into consideration: Perimeter—distance around the edge of the object, measuring from the midpoints of each pixel that defines its border; Shape factor—$4piA/P^2$—A value from 0-1 representing how closely the object represents a circle. A value near 0 indicates a flattened object, whereas a value of 1.0 indicates a perfect circle; Elliptical form factor—length/breadth—the ratio of an object's breadth to its length. Shape factor cut-off for gliosis quantification was set between 0.0-0.4, and elliptical for factor cut-off was set between 1.2-10000.

Immunoblotting.

Mouse limbus tissue and aqueous humor were lysed using RIPA buffer (Santa Cruz Biotechnology). Limbus tissue was sonicated to fine pieces. For secretory Myoc, aqueous humor was extracted from the eyes. Protein concentration was measured using BCA Protein Assay Kit (Pierce Biotechnology). Protein samples were loaded for each group in each well and run on 8-16% sodium dodecyl sulfate-polyacrylamide gel (ThermoFisher) for electrophoresis and then transferred to the PVDF membrane. After blocking with blocking buffer, membranes were incubated with primary antibodies overnight at 4° C. Corresponding secondary antibodies were incubated (IRDye 680LT and IRDye 800CW, LI-COR Biosciences) after three washes of 0.1% Tween 20 in Tris-buffered saline. Detection and capture of the fluorescent signal were performed using an infrared imager (Odyssey; LI-COR Biosciences). Image J was used for the quantification and analysis of protein expression with b-actin as an internal control.

Enzyme Linked Immunosorbent Assay (ELISA).

Secreted prostaglandin E2 (PGE2) was measured in aqueous humor samples using a PGE2 ELISA kit (Enzo life Sciences, ADI-901-001), and the procedure was performed according to the manufacturer's instructions. Aqueous humor was used at a dilution of 2:100 for the assay. Optical density was measured at 405 nm using 570 nm and 600 nm as normalizing wavelengths using an ELISA reader. Optical density measurements were extrapolated to measure PGE2 concentration (pg/ml) reference to standards.

Multidimensional Protein Identification Technology (MudPIT) Analysis.

TCA-precipitated proteins were urea-denatured, reduced, alkylated, and digested with endoproteinase Lys-C (Roche) followed by modified trypsin (Promega). Peptide mixtures were loaded onto 250 μm fused silica microcapillary columns packed with strong cation exchange resin (Luna, Phenomenex) and 5-μm C18 reverse-phase (Aqua, Phenomenex), and then connected to a 100 μm fused silica microcapillary column packed with 5-μm C18 reverse-phase (Aqua, Phenomenex). Loaded microcapillary columns were placed in-line with a Quaternary Agilent 1100 series HPLC pump and a LTQ orbitrap Elite mass spectrometer equipped with a nano-LC electrospray ionization source (ThermoScientific). Fully automated 10-step MudPIT runs were carried out on the electrosprayed peptides. Tandem mass (MS/MS) spectra were interpreted using ProluCID v. 1.3.3 against a database consisting of 79096 non-redundant human proteins (NCBI, 2016-06-10 release), 193 usual contaminants. To estimate false discovery rates (FDRs), the amino acid sequence of each non-redundant protein entry was randomized to generate a virtual library. This resulted in a total library of 158578 non-redundant sequences against which the spectra were matched. All cysteines were considered as fully carboxamidomethylated (+57.0215 Da statically added), while methionine oxidation was searched as a differential modification (+15.9949 Da). DTASelect v 1.9 and swallow v. 0.0.1, an in-house developed software, were used to filter ProLuCID search results at given FDRs at the spectrum, peptide, and protein levels. Here all controlled FDRs were less than 5%. All 4 data sets were contrasted against their merged data set, respectively, using Contrast v 1.9 and in house developed sandmartin v 0.0.1. Our in-house developed software, NSAF7 v 0.0.1, was used to generate spectral count-based label-free quantitation results.

GO Enrichment Analysis.

DAVID software, a free online tool (version DAVID 6.8), and GOstats (version 2.48.0) were used for the functional enrichment analysis of genes whose corresponding proteins had positively distributed normalized spectral abundance factor (dNSAF) values in both replicates of a specific cell type. Biological process (BP), cellular component (CC), and molecular function (MF) were three different categories according to which the GO terms classification was performed. The top 10 most significantly enriched GO categories for a given cell type were compared between fibroblasts and TMSC cells.

Hierarchical Clustering Analysis and Heatmap.

The hierarchical clustering analysis and heatmap plotting was performed using the R package heatmap (version 1.0.12). Comparative expression of the dNSAF protein values between TMSC and fibroblast cells was performed using heatmaps. For each row of the heatmap, the name of the gene that encodes the protein was used as the heatmap row name. Similar elements were classified in groups in a binary tree using hierarchical clustering.

Statistical Analysis.

Results were expressed as mean±standard error mean (SEM) or mean±standard deviation (SD). The statistical differences were analyzed by two-way ANOVA or one-way ANOVA, followed by Tukey posttest using PRISM. P-value less than 0.05 ($p<0.05$) was considered statistically significant.

Results and Discussion

TMSC Secretome Prevents Dexamethasone-Induced Glaucomatous Changes in TM Cells in Vitro.

TMSC was cultured from human donor eyes, and each TMSC strain was characterized from different donors by flow cytometry showing positive expression of stem cell markers CD90, CD73, CD105, CD166, SSEA4, OCT4, ABCG2, STRO-1, NOTCH-1, CD271, and negative expression of CD34 and CD45 (FIGS. 1A-1B). This demonstrates the stem cell nature of human TMSC used in the experiments. To ensure secretome was harvested from healthy cells after 48 h of starvation, the cells were stained with Annexin V and 7-Aminoactinomycin D (7-AAD) (FIG. 1C) and with Calcein AM/Hoechst 33342 (FIG. 1D), which showed >95% viable cells after secretome harvesting. The results confirmed reasonably pure secretome released by live cells with less than 5% cell death as required. Secretome from human corneal fibroblasts served as a control, and the viability of fibroblasts was also confirmed (FIG. 1C-1D). To evaluate if the TMSC secretome was cytotoxic, human TM cells were treated with TMSC-Scr for 48 h and did MTT and alamarBlue assays. The results showed no significant difference in cell viability and proliferation between cells with and without TMSC-Scr treatment (FIG. 1E-1F). Collectively, these assays demonstrate that the secretome was harvested from healthy cells and had no cytotoxicity to human TM cells, supporting its safety. Then we examined if the TMSC secretome has protective roles to human TM cells in vitro. One of the characteristics of TM cells is that they are responsive to dexamethasone (Dex) treatment with increased intracellular myocilin expression. Myocilin and angiopoietin-like 7 (ANGPTL7) are both glaucoma-associated markers. Chitinase 3 Like 1 (CHI3L1) is involved in ECM remodeling in the outflow pathway and has been used as a TM cell marker as water channel protein aquaporin 1 (AQP1). Fibronectin, an ECM component in the TM, is increased in glaucoma and is believed to contribute to TM stiffness and increased outflow resistance. Cultured TM cells were treated with 100 nM Dex for 5 days and examined that TM cells had reduced CHI3L1 and AQP1 levels and increased myocilin, ANGPTL7, and fibronectin expression as compared to no-Dex control (FIGS. 2A-2B). TMSC-Scr was added together with Dex for 5 days (Parallel TMSC-Scr, FIG. 2A) or together with Dex for another 5-day after the initial 5-day Dex-alone treatment (Post TMSC-Scr, FIG. 2B) to assess its therapeutic effect. TMSC-Scr prevented reduction and restored the levels of TM markers CHI3L1 and AQP1, and reduced myocilin, ANGPTL7, and fibronectin expression as demonstrated by immunofluorescent staining (FIGS. 2A-2G). The mRNA levels of MYOCILIN (FIG. 2H) and ANGPTL7 (FIG. 2I) were reduced by both parallel- and post-TMSC-Scr treatments. These results indicate that TMSC-Scr can prevent and reverse steroid-induced glaucomatous changes in cultured TM cells.

TMSC Secretome Reduces IOP and Prevents RGC Loss in Steroid-Induced Ocular Hypertension Mice.

To induce an ocular hypertension model, we periocularly injected 200 μg/20 μl of Dex-Ac into adult C57BL/6J mice once a week for 6 weeks and sacrificed the animals at week-8. The mouse IOP started to elevate from week-1 after Dex-Ac injection and remained elevated up to week-8 after Dex-Ac injection had been stopped for two weeks (FIGS. 3A-3B). 20 μl of 25× concentrated TMSC-Scr or fibroblast-secretome (Fibro-Scr) was injected periocularly once a week, starting at week-3 and ending at week-6. The injections of Dex-Ac and secretome from week-3 to week-6 were given at the same time but at different periocular regions (superior and inferior) to avoid reagents being intermixing before getting into target sites. One week after TMSC-Scr injection, the IOP reduced to 13.8±0.5 mmHg (week-4) as compared to mice treated with Dex-Ac alone (15.9±0.4 mmHg) and then reduced to a normal range from week-5 to -8 (10.7±0.4 mmHg), similar to that of vehicle control (12.2±0.6 mmHg). However, Fibro-Scr did not reduce the Dex-Ac elevated IOP (16.2±0.8 mmHg at week-4 and 15.4±0.5 mmHg at week-8) but remained similar to Dex-Ac treated eyes (15.9±0.9 mmHg at week-4, 15.2±0.3 mmHg at week-8). We counted the TM cells on plastic sections obtained at week-8 and found that TMSC-Scr injection increased the TM cellularity (19.1±1.7 cells/TM section) as compared to Dex-Ac mice (14.7±1.3), similar to normal control (20.7±1.5), while Fibro-Scr treatment could not increase TM cell number significantly (16.7±1.3) (FIGS. 3C-3D). A significant increase of myocilin protein level was detected in the limbal tissue (including the TM) of Dex-Ac mice by immunoblotting, which was reduced after TMSC-Scr treatment (FIG. 3E). Immunoblotting on the aqueous humor revealed a higher level of secreted myocilin in the TMSC-Scr treatment group than that in Dex-Ac mice (FIG. 3F). GRP78 is a marker of endoplasmic reticulum (ER) stress, and we observed significantly increased GRP78 expression in the limbal tissue in Dex-Ac mice as compared to control, which was reduced after TMSC-Scr treatment (FIG. 3G). Dex-Ac mice at week-8 showed significant RGC loss (28.4±5.4/mm) as compared to normal (37.6±7.6/mm) and vehicle control mice (36.9±5.6/mm) as counted on the plastic sections of the mouse eyes, which was prevented after TMSC-Scr treatment (34.5±4.7/mm) (FIGS. 3H-3I). The results indicate that TMSC-Scr promotes myocilin secretion and modulates Dex-induced ER stress of the TM cells, which contributes to the increased TM cellularity and reduced IOP. TMSC-Scr also prevents RGC loss in the steroid-induced mouse model.

TMSC Secretome Activates the COX2-PGE2 Pathway to Activate Endogenous Stem Cells.

COX2 (cyclooxygenase) is a major protein that helps the biogenesis of prostaglandin E2 (PGE2) from prostaglandin H2 (PGH2) in response to physiological demand. The presence of PGE2 in TM cells plays an important role in the maintenance of IOP in a normal range. Human TM cells secrete PGE2, which is abrogated by glucocorticoid treatment. A dramatic reduction of COX2 expression was detected in Dex-treated TM cells in vitro, which was restored after TMSC-Scr treatment (FIG. 4A). Transmembrane protein 177 (TMEM177), a mitochondrial protein, acts upstream of COX2 to increase and stabilize COX2 expression. Analysis of TMEM177 in cultured human TM cells showed a diminished expression after Dex treatment, which was restored after parallel- and post-TMSC-Scr treatments (FIG. 4B). Immunofluorescent staining and immunoblotting of mouse limbal tissue showed that COX2 levels were reduced in Dex-Ac treated tissue and increased after TMSC-Scr treatment (FIGS. 4C-4D). Immunoblotting on the mouse limbal tissue showed that TMEM177 levels had similar changes to that of COX2 (FIG. 4E). In mouse aqueous humor, PGE2 secretion was reduced after Dex-Ac treatment and was restored to normal level after TMSC-Scr treatment, but not after Fibro-Scr treatment, as detected by ELISA (FIG. 4F). PGE2 has been reported to have the ability to maintain the self-renewal of mesenchymal stem cells. Here, the ABCB5+ and OCT4+ stem cell population as well as Ki67+ proliferative cells in mouse limbus and TM tissue were diminished after Dex-Ac treatment and increased after TMSC-Scr treatment (FIGS. 4G-4H). These results indicate that the TMSC-Scr is capable of activating COX2-PGE2 signaling to sustain TMSC and TM cells for steroid-induced glaucoma.

TMSC Secretome Restores TM Cellularity and Reduces IOP in Tg-MyocY437H Mice.

To further confirm the TMSC-Scr therapeutic effects, we also investigated a genetic mouse model of glaucoma, the Tg-MyocY437H mice(18), which start to have elevated IOP at 3-4-month of age. 20 μl of 25× concentrated TMSC-Scr was periocularly injected, or 20 μl plain medium was periocularly injected as sham control into the Tg-MyocY437H mice at 4-month of age (week-0) once a week until week-7, and the mice were sacrificed at week-10 (FIG. 5A). We observed IOP reduction starting at 1-week after TMSC-Scr treatment and remaining reduced until week 10 as compared to Tg-MyocY437H mice without injection (Tg-Myoc) and with medium injection (sham), and similar to wildtype (WT) littermates (FIG. 5B). Tg-MyocY437H mice (14.8±2.5 mmHg) and sham control (15.0±1.7 mmHg) still had elevated IOP at week-10, whereas TMSC-Scr treated mice maintained the IOP at normal range (9.5±2.2 mmHg), comparable to WT control (10.3±2.2 mmHg). The TM cells on plastic sections were counted, which showed that Tg-MyocY437H mice had a reduced number of TM cells (10±1.4/TM section) as compared to WT mice (16.4±2.1/TM) at week-10 (FIGS. 6A-6B). Similar to its effects on the Dex-Ac mice, treatment with TMSC-Scr significantly increased the TM cellularity in Tg-MyocY437H mice (17.5±1.1/TM). One feature of the Tg-MyocY437H mice is that mutant Myoc cannot be secreted out but stuck in the ER of TM cells leading to ER stress. Indeed, an increased level of Myoc accumulated in the limbus tissue of the Tg-MyocY437H mice was detected, which was reduced to the level as WT control after TMSC-Scr treatment as detected by staining (FIG. 5C) and by immunoblotting (FIG. 5D). TMSC-Scr treatment also led to increased secretion of Myoc into the aqueous humor (FIG. 5E). Similar to Dex-Ac mice, GRP78 expression was significantly increased in Tg-MyocY437H mice and reduced to WT level after TMSC-Scr treatment (FIG. 5F). Using an anti-CD31 antibody to stain the Schlemm's canal and vascular endothelium to mark the TM tissue location, an increased expression of ECM marker fibronectin and collagen IV was observed in the TM in Tg-MyocY437H mice, which was reduced after TMSC-Scr treatment while the sham group showed no reduction (FIGS. 6C-6D). Similar to Dex-Ac mice, an analysis of the COX2-PGE2 signaling axis in Tg-MyocY437H mice showed increased levels of COX2 and TMEM177 by immunoblotting (FIGS. 5G-5H), PGE2 by ELISA (FIG. 5I), ABCB5+ and OCT4+ stem cells, and Ki67+ dividing cells (FIGS. 5J-5M) after TMSC-Scr treatment. These results further confirmed the therapeutic effects of the TMSC-Scr in the Tg-MyocY437H mouse model of glaucoma. Since TMSC secretome periocular injection enhanced the COX2-PGE2 signaling axis in the TM tissue of both Dex-Ac and Tg-MyocY437H mice, we investigated whether COX2 is upregulated in the TM tissue after TMSC intracameral injection and homing to the TM tissue. $5\times10^4$ DiO labeled TMSC was intracamerally injected per eye in Tg-MyocY437H mice, and at 2-month after injection, COX2 expression was significantly increased in the TM as well as ciliary body (FIGS. 7A-7C). TMSC homed into the TM region and expressed COX2 (FIG. 7D). Similarly, TMEM177 expression was also increased in the TM and ciliary body (FIGS. 7E-7F) as well as the transplanted TMSC after TMSC injection (FIG. 7G).

TMSC Secretome Prevents RGC Death In Vitro and In Vivo.

Preserving and restoring the RGC and their function is the ultimate goal of glaucoma treatment. Pattern electroretinography (PERG) is an optimal approach to evaluate RGC function. PERG shows that TMSC-Scr treatment preserved the RGC function of Tg-MyocY437H mice as indicated by increased amplitude of P1 wave (7.74±1.75 μV), similar to that of WT (7.76±1.14 μV), while the sham treatment could not recover P1 amplitude (4.05±1.95 μV), similar to that of untreated Tg-MyocY437H (5.86±2.24 μV) (FIG. 8A-8B). RGC numbers counted from retinal plastic sections showed an average of about 36% loss of the RGC of Tg-MyocY437H mice (24.3±7.8 cells/mm) as compared to WT (37.8±9.3 cells/mm). This loss was rescued by TMSC-Scr treatment (37.3±9.4 cells/mm) while no protective effect was observed in the sham group (28.5±9.2 cells/mm) (FIGS. 8C-8D). Consistently, the optic nerves of Tg-MyocY437H mice had reduced axon number (146.0±42.5 axons/400 $\mu m^2$) as compared to WT control (184.0±45.0 axons/400 $\mu m^2$). The axon reduction was rescued in mice receiving TMSC-Scr treatment (164.7±32.2 axons/400 $\mu m^2$), but sham injection did not show any effect (128.1±37.5 axons/400 μm2) (FIGS. 8E-8F). Gliosis in the optic nerve (FIG. 8E, long streaks), hypertrophy, or proliferation of glial cells in response to neural damage, was correlated to the axonal degeneration in the optic nerve (FIG. 8F). The gliotic area was increased in Tg-MyocY437H mice and reduced in TMSC-Scr treated mice (FIGS. 8E and 8G). These results indicate that TMSC-Scr has therapeutic effects on preventing and rescuing RGC from degeneration in a genetic glaucoma model.

To explore the potential of RGC regeneration in a more controlled system, human iPSCs were differentiated to RGC, which expressed RGC markers RNA-binding protein with multiple splicing (RBPMS) and Thy1.1 with extensive elongated axons (FIG. 9A). CoCl2 is known to induce RGC apoptosis via induction of hypoxia. After iPSC-RGC cells were treated with 500 μM CoCl2 for 48 h, significant apoptotic cells were detected by Annexin V and 7-AAD staining examined by flow cytometry (FIG. 9B). TMSC-Scr treatment effectively prevented CoCl2-induced apoptosis, and TMSC-Scr alone (0+TMSC-Scr) did not show cell toxicity (FIG. 9B). Autophagosomes become acidic when fused with lysosomes, which results in the loss of green fluorescence in acridine orange, leaving only red fluorescence, so acridine orange has been used to detect cell autophagy. Acidic vesicular organelles in autophagic cells show bright red fluorescence with higher red indicating higher autophagy, while cell cytoplasm and nucleus show green fluorescence. The red fluorescence, an indicator of autophagolysosome formation, was significantly reduced after CoCl2 treatment and increased to normal after TMSC-Scr treatment, associated with increased cell survival (FIG. 9C). The involvement of autophagy was further confirmed by immunoblotting of autophagy proteins Beclin1 and Atg5, which were reduced after CoCl2 treatment and increased after TMSC-Scr treatment (FIG. 9D). TMSC-Scr had no effect on the levels of Atg7, Atg12, and Atg16L1, which were reduced after CoCl2 treatment (FIG. 9D). The results indicate that TMSC-Scr can protect RGC from apoptosis by modulating autophagy.

TMSC Secretome Contains Cytoprotective and Neuroprotective Proteins Revealed by Proteomic Analysis.

The label-free proteomic identification and quantification of secretome proteins from two strains of human TMSC from different donors were performed and compared with the secretomes from two fibroblast strains. Total proteins expressed in secretomes of both TMSC strains and fibroblast strains were identified, and significant gene ontology (GO) terms uncovered in the proteomes of both TMSC and fibroblast secretomes were identified. Total GO terms discovered in the secretomes of TMSC and fibroblasts were also identified. 841 and 1196 total number of proteins were identified from the TMSC1 and TMSC2 secretomes, and 415 and 291 proteins in the secretomes of fibroblast1 and fibroblast2. Out of these, 549 proteins were commonly secreted by both TMSC strains, while 212 proteins were in both fibroblast strains with positive distributed normalized spectral abundance factor (dNSAF) average values. 165 proteins were expressed in both TMSC and fibroblast secretomes, and both cell types showed different expressions for these proteins (FIGS. 10A-10B). As observed by pathway enrichment and comparative analysis, TMSC-Scr showed upregulation of important proteins related to unfolded protein response (UPR), ECM organization proteins, and collagen catabolic process proteins (FIGS. 11A-11D). TMSC-Scr also showed upregulation of proteins related to protein folding, cell-cell adhesion, and mRNA protein stability (FIGS. 10C-10F). TMSC-Scr displayed an array of neuroprotective proteins which regulate different aspects of neurogenesis and can account for the neuroprotective effect of TMSC-Scr on RGC. Out of the 549 proteins present in the secretomes of both TMSC strains, 74 proteins related to the axon guidance pathway and 78 proteins involved in neurogenesis were found to be unique to the TMSC-Scr (FIG. 11E). Table 2 highlights important proteins in TMSC-Scr with their functions involved in direct regulation of neural differentiation, regeneration, and protection in contrast to Fibro-Scr.

TABLE 2

List of proteins directly involved in neural differentiation, regeneration, and protection uncovered in secretome from both TMSC and fibroblasts.

| Sr. No. | Accession No. | Name | TMSC | Fibro | Function |
|---|---|---|---|---|---|
| 1 | NP_001611.1 | AHNAK | + | − | Neuroblast differentiation-associated protein. It is involved in neuronal cell differentiation |
| 2 | NP_000843.1 | GSTP1 | + | + | Soluble glutathione S-transferases. It prevents neurodegeneration by inhibiting CDK5 activity |
| 3 | NP_002366.2 | MAP4 | + | + | Promotes microtubule assembly. |
| 4 | NP_002282.2 | LAMB1 | + | + | It plays a major role in cerebral cortical development by maintaining the integrity of basement membrane/glia limitans which acts as a radial glial cells endfeet anchor and also provide a physical barrier to migrating neurons. |

TABLE 2-continued

List of proteins directly involved in neural differentiation, regeneration, and protection uncovered in secretome from both TMSC and fibroblasts.

| Sr. No. | Accession No. | Name | TMSC | Fibro | Function |
|---|---|---|---|---|---|
| 5 | NP_ 001104026.1 | FLNA | + | + | It facilitates ventricular zone to cortical plate neuroblast migration. |
| 6 | NP_005498.1 | CFL1 | + | + | It is involved in the migration of neural crest cells and morphogenesis of neural tubes. |
| 7 | NP_001419.1 | ENO1 | + | − | It is involved in neuroprotection by stimulating the production of immunoglobulin in neurons. |
| 8 | NP_ 001157789.1 | FLNB | + | + | It facilitates ventricular zone to cortical plate neuroblast migration. |
| 9 | NP_002606.3 | SERPINF1 | + | + | It induces extensive neuronal differentiation. |
| 10 | NP_006608.1 | NES | + | + | It is important for the development of the eye and brain and promotes renewal, proliferation, and survival of neural progenitor cells. |
| 11 | NP_859048.1 | PRDX1 | + | − | It is involved in the differentiation of postmitotic motor neurons. |
| 12 | NP_001531.1 | HSPB1 | + | − | it is involved in the axonal transport of neurofilament proteins. |
| 13 | NP_000921.1 | PLAT | + | − | It plays an important role in neuronal migration. |
| 14 | NP_002323.2 | LRP1 | + | + | It promotes neurotransmission by modulating calcium signaling in neurons. |
| 15 | NP_055070.1 | CNPY2 | + | − | It induces neurite outgrowth. |
| 16 | NP_ 001184222.1 | DPYSL2 (CRMP2) | + | − | It regulates neuronal polarity, migration, growth cone collapse, axon growth and guidance, and development. It is mandatory for class 3 semaphorins signaling and cytoskeleton remodeling. |
| 17 | NP_ 001184223.1 | DPYSL3 (CRMP3) | + | + | It regulates neuronal polarity, migration, growth cone collapse, axon growth and guidance, and development. It is mandatory for class 3 semaphorins signaling and |

TABLE 2-continued

List of proteins directly involved in neural differentiation, regeneration, and protection uncovered in secretome from both TMSC and fibroblasts.

| Sr. No. | Accession No. | Name | TMSC | Fibro | Function |
|---|---|---|---|---|---|
| | | | | | cytoskeleton remodeling. |
| 18 | NP_ 001014436.1 | DBNL | + | − | It is involved in the formation of neuron synapses, neurites, and neurons. |
| 19 | NP_647539.1 | YWHAB (14-3-3 proteinbeta/ alpha) | + | − | It prevents neuronal apoptosis by preventing the nuclear translocation of p-SRPK2 and ultimately inhibiting the expression of cyclin D1. |
| 20 | NP_000081.1 | COL3A1 | + | + | It plays an important role in cortical development and inhibition of neuronal migration. |
| 21 | NP_005900.2 | MAP1B | + | + | It facilitates neurite extension. |
| 22 | NP_940978.2 | AGRN | + | − | It regulates neurite outgrowth. |
| 23 | NP_065393.1 | RTN4 (Nogo-A) | + | + | It is involved in the negative regulation of axon-axon growth and adhesion and also promotes extension, branching, and fasciculation of the neurite in the nervous system during development. It also maintains neuronal migration, stabilizes neuron wiring, and restricts neuron plasticity in the adult central nervous system. |
| 24 | NP_006448.4 | PDLIM5 | + | − | It promotes morphogenesis of the dendritic spine in neurons. It also inhibits excitatory synapses by preventing postsynaptic growth. |
| 25 | NP_078850.3 | NDNF | + | + | It is involved in neurite outgrowth, neuronal survival, growth, and migration. |
| 26 | NP_ 001034438.1 | EFEMP1 | + | + | It promotes the supporting activity of glial cells to increase neurite outgrowth. It also controls the differentiation and migration of glial cells. |
| 27 | NP_001739.2 | CAPN2 | + | − | It promotes the formation of translation products of CPEB3 upon neuronal stimulation by cleaving CPEB3 and abolishing translational repression. |
| 28 | NP_004386.2 | DBN1 | + | + | It maintains neuronal extension, dendrite plasticity, and migration. It also promotes actin polymerization at immunological synapses. |
| 29 | NP_ 001166094.1 | NEO1 | + | − | It promotes neural tube formation. It also interacts with Netrin to form a chemoattractive cue axon guidance and cell-cell adhesion. |
| 30 | NP_ 001180499.1 | CSRP1 | + | − | It is involved in neuronal development. |
| 31 | NP_002841.3 | PTPRS | + | − | It is important for the normal development of the brain. It stimulates neurite outgrowth in response to the heparan sulfate proteoglycan GPC2 while inhibits axonal outgrowth and formation of neurites in response to chondroitin sulfate proteoglycans. |
| 32 | NP_000811.1 | GAS6 | + | − | It promotes migration and survival of neurons. |
| 33 | NP_006591.1 | NUDC | + | − | It is involved in the migration of neurons and neurogenesis. |
| 34 | NP_005889.3 | CAPRIN1 (RNG105) | + | − | It is involved in the translation required for neuronal synaptic plasticity. |
| 35 | NP_ 001123575.1 | COL13A1 | + | − | It promotes acetylcholine receptor clustering at neuromuscular junctions and promotes cell-cell and cell-matrix adhesion. |
| 36 | NP_981946.1 | STMN1 | + | + | It increases microtubule disassembly. During neurogenesis, it is also involved in axon formation. |
| 37 | NP_037481.1 | NENF | + | − | It is a neurotrophic factor promoting the survival of neurons. During embryonic development, it inhibits differentiation of astrocytes and increases cell proliferation and neurogenesis of |

TABLE 2-continued

List of proteins directly involved in neural differentiation, regeneration, and protection uncovered in secretome from both TMSC and fibroblasts.

| Sr. No. | Accession No. | Name | TMSC | Fibro | Function |
|---|---|---|---|---|---|
| | | | | | neural progenitor. It also plays an important role in energy balance. |
| 38 | NP_001719.2 | BSG | + | − | It promotes the formation of a neural network. In cell culture, it increases astrocyte process outgrowth. |
| 39 | NP_ 001243048.1 | NAA10 | + | − | It is involved in the growth and development of neurons. |
| 40 | NP_004589.1 | SPOCK1 (Testican-1) | + | + | It is involved in various neuronal mechanisms in the central nervous system. |
| 41 | NP_003245.1 | TIMP1 | + | − | It provides neuroprotection against Aβ insult by activating the Akt pathway. |
| 42 | NP_000347.2 | TCOF1 | − | + | Required for neural crest specification. |

STRING analysis of TMSC-Scr showed interaction patterns between proteins involved in response to hypoxia, wound healing, cell-matrix adhesion, and detoxification (FIG. 11F). A confirmatory analysis of axon guidance pathways by MetaCore modeling showed positively regulated pathways in TMSC-Scr but not in Fibro-Scr (FIGS. 12A-12F). TMSC-Scr also showed variable expression of proteins related to collagen fibril organization, cellular protein metabolism, platelet degranulation, translation initiation, and skeletal system development (FIGS. 13A-13E). Apart from these, an interaction was observed between TMSC-Scr proteins involved in negative regulation of cell death and unfolded protein response (FIGS. 13F-13G). Functional analysis identified 15 proteins in TMSC-Scr which were involved in promoting cell proliferation and maintenance of stemness in progenitor cells (e.g., NUDC, NAP1L1, NENF, and MYDGF), while only 6 of these proteins could be identified in Fibro-Scr (Table 3).

TABLE 3

List of the proteins directly involved in promoting cell proliferation and maintenance of sternness in progenitor cells, identified in secretome of TMSC and fibroblasts.

| Sr. No | Accession No. | Name | TMSC | Fibro | Function |
|---|---|---|---|---|---|
| 1 | NP_009016.1 | FSTL1 | + | + | Modulates cell proliferation and helps in the maintenance of stemness. |
| 2 | NP_00 1054.1 | TF | + | − | Stimulates cell proliferation. |
| 3 | NP_004416.2 | ECM1 | + | + | Increases cell proliferation and maintains stemness by stabilizing β-catenin. |
| 4 | NP_006608.1 | NES | + | + | Required for mitogen-stimulated proliferation and involved in self-renewal of neural progenitor cells. |
| 5 | NP_002511.1 | NPM 1 | + | + | Promotes proliferation by regulating ribosome biogenesis. |
| 6 | NP_733821.1 | LMNA | + | + | Supports cell proliferation, knockdown induces cell senescence. |
| 7 | NP_7573 51.1 | CSF1 | + | + | Induces proliferation in progenitor cells. |
| 8 | NP_06 1980.1 | MYDGF or C19orf10 | + | − | Secreted by Bone marrow-cells to promote cardiac tissue repair and promotes cardiomyocyte proliferation and heart regeneration in neonate's hearts. Stimulates endothelial cell proliferation through a MAPK1/3-, STAT3-pathway. Increase cardiomyocyte proliferation through PI3K/AKT-signaling pathway. |
| 9 | NP_002473 .2 | NASP | + | − | Required for cell proliferation. |
| 10 | NP_006591.1 | NUDC | + | − | Highly expressed in human bone marrow, myeloid and erythroid progenitors induces cell proliferation. |
| 11 | NP_ 001294853.1 | NAP1L1 | + | − | Regulates embryonic neural progenitor cell proliferation. |
| 12 | NP _0058 89.3 | CAPRIN1 | + | − | Increases cellular proliferation. |
| 13 | NP_0777 19.2 | NOTCH2 | + | − | Mediates cell growth and prevents apoptosis. |
| 14 | NP_006182.2 | PA2G4 | + | − | Maintains cell growth and promotes proliferation. |
| 15 | NP_03 7481.1 | NENF | + | − | Increases cell proliferation and promotes hippocampal neurogenesis. |

These results show that the TMSC-Scr is rich in the factors important for neuronal development and protection as well as cell survival, which can explain its protective effect on RGC and TM cells. A detailed summary of the therapeutic effect induced by TMSC-Scr on various aspects of glaucoma involving different pathways is shown in FIG. 14.

Discussion

The therapeutic potential of the secretome from human TMSC was explored, and potential mechanisms were discovered. TMSC-Scr was able to prevent as well as reverse Dex-induced TM cell changes in culture. By minimal invasive periocular injection, TMSC-Scr reduced the IOP, increased the TM cellularity, remodeled the ECM of the TM, activated the endogenous stem cells, promoted cell proliferation, and prevented and reversed RGC loss as well as preserved the RGC function in both steroid-induced and genetic myocilin mutant mouse models. The rejuvenating and therapeutic effects of TMSC-Scr on glaucoma are associated with the activation of COX2-PGE2 signaling as well as their neuroprotective proteins. Our novel discovery indicates the feasibility of stem cell-free therapies for glaucoma in preserving both the TM function and RGC function. Steroid-induced ocular hypertension is a common side-effect among patients using steroid therapy. Myocilin mutations have been reported to be the most common form of genetic glaucoma. The results show that Dex treatment leads to increased fibrotic ECM proteins, such as fibronectin as well as myocilin in the TM, resulting in protein misfolding, ER stress, and IOP elevation. A transgenic mouse model with myocilin Y437H mutation is characterized by increased IOP, persistent TM ER stress, and RGC loss and axonal degeneration, which resembles POAG in patients. All these characteristics of the Tg-MyocY437H mice were identified through the disclosed experiments. These two mouse models represent typical steroid-induced and genetic glaucoma. TM cell loss is associated with elevated IOP in glaucoma, and reducing IOP is the only effective treatment so far. TMSC-Scr treatment led to reduced IOP in both mouse models of glaucoma, which started as early as the following week of secretome periocular injection and effectively maintained at normal range two to three weeks after secretome withdrawal when experiments terminated.

CHI3L1 and AQP1 are involved in the TM cell function of remodeling ECM, maintaining TM homeostasis, and modulate aqueous outflow. After Dex-Ac treatment, TM cells lose these proteins and become stiffer. Increased CHI3L1 and AQP1 and reduced glaucoma-associated genes MYOCILIN and ANGPTL7 after TMSC-Scr treatment in Dex-treated TM cells reflect the rejuvenating ability of TMSC-Scr on TM cells. Postoperative fibrosis is a major complication in glaucoma, and fibronectin is the main fibrotic protein. TMSC-Scr treatment in Dex-treated cells shows TMSC-Scr mediated fibrosis reduction. Additionally, secretome treatment increased the number of TM cells reflecting its ability to regenerate TM tissue in vivo. Collagen forms a major connective tissue protein in ECM, and its degradation by matrix metalloproteinases (MMPs) is crucial for remodeling and repairing of tissue. TMSC-Scr treatment dramatically downregulated the fibrotic ECM components fibronectin and collagen IV, which can help TM cell survival. The TMSC-Scr proteins involved in ECM organization and collagen catabolic process can lead to enhanced ECM turnover and lower IOP. ER stress of the TM cells is involved in both glaucoma models. To counteract protein misfolding, cells activate the UPR pathway. ER chaperones GRP78 and CHOP are activated by UPR, resulting in the restoration of ER homeostasis by proteasome-mediated induction of ER-associated degradation. Here, the presence of UPR in TMSC-Scr can further induce the cellular responsiveness of TM cells to reduce ER stress.

Prostaglandin analogs are commonly used for glaucoma treatment to reduce IOP. COX2, a rate-limiting enzyme, is known to convert arachidonic acid to PGH2, which is isomerized to PGE2 by PGE2 synthase. COX2 modulates PGE2 synthesis in response to growth factors, inflammatory cytokines, and other physiological demands. Under normal conditions, COX2 is restricted mostly in the kidney. COX2 expression can be increased substantially in other tissues in response to proinflammatory cytokines or sheer stress. COX2 expression is completely lost in the non-pigmented secretory epithelium of the ciliary body and aqueous humor of end-stage POAG human eyes. Glucocorticoids are well known for inhibiting COX2 activity. Human TM cells can secrete PGE2, which was inhibited significantly after a moderate Dex treatment. Mitochondrial TMEM177 has also been reported to associate with COX2 to stabilize/increase the biogenesis of COX2. Hence, increased TMEM177 after TMSC-Scr treatment can be responsible for increased COX2 stabilization and biogenesis, which further indicates its therapeutic potential for glaucoma. Further evaluation of increased TMEM177/COX2 expression in Tg-MyocY437H mice after TMSC transplantation confirmed that both stem cell-based and cell-free therapy involves upregulation of COX2 to impart a therapeutic benefit.

Mobilization and maintenance of endogenous stem cells are very crucial for inducing tissue regeneration. Endogenous stem cell regeneration involves a complex interplay of cues in terms of growth factors, modulation in stem cell niche, and chemokines inducing differentiation, proliferation, and migration of these cells. Glaucoma and ER stress can decrease endogenous stem cells and increase apoptosis. PGE2 has been reported to increase the self-renewal and proliferation of stem cells. Increased PGE2 secretion in the aqueous humor of both mouse models after TMSC-Scr treatment can be crucial for maintaining the ABCB5+ and OCT4+ endogenous stem cells and reversing glaucomatous changes. The stem cell proliferation and renewal are further enhanced by TMSC-Scr by the presence of crucial proteins involved in promoting cell proliferation and stemness in progenitor cells. Hypoxia can lead to RGC death by inducing a number of degenerative changes. The increased secretion of response to hypoxia proteins in TMSC-Scr can be responsible for RGC survival/rescue in hypoxic conditions. The optic nerve is a tract of the central nervous system and is comprised of axons of RGC with various glial cells like oligodendrocytes, astrocytes, microglia as support cells. Neurodegeneration of RGC results in alteration of structure, function, and gene expression profile of glial cells, termed as gliosis. Gliosis is associated with neurodegeneration in chronic and age-related models of glaucoma. Reduced gliosis after TMSC-Scr treatment can further enhance regeneration in RGC. The proteins uncovered in TMSC-Scr involving proteins related to axon guidance pathway, neurogenesis, negative regulation of neuron death, and clearance of neuron apoptotic process can directly enhance RGC protection, survival, and function by activation of some intrinsic developmental pathways, which can result in RGC regeneration, which will be interesting for future investigations. Furthermore, therapeutic effects of TMSC-Scr given through the periocular route emphasize that secretome proteins can cross the corneal barrier and can be a good approach for the development of glaucoma eye drops. Autophagy has been reported to promote RGC survival following optic nerve axotomy. TMSC-Scr was able to restore the levels of Beclin1 and Atg5 indicating that TMSC-Scr induced increased autophagy is mediated by these proteins.

Stem cell secretome therapy, with low risk, minimal invasive administration, and effectiveness, is an attractive treatment strategy for glaucoma, which can be soon for clinical trials after confirmation in animals more relevant to humans like non-human primates. The key secretome proteins that have been identified in the current experiments can potentially lead to the designing of small molecule-based therapeutics for glaucoma in the future.

10. REFERENCES

1. A. W. Scott, N. M. Bressler, S. Folkes, J. S. Wittenborn, J. Jorkasky, Public Attitudes About Eye and Vision Health. JAMA Ophthalmol 134, 1111-1118 (2016).
2. Y. C. Tham et al., Global prevalence of glaucoma and projections of glaucoma burden through 2040: a systematic review and meta-analysis. Ophthalmology 121, 2081-2090 (2014).
3. D. L. Epstein, Framing glaucoma questions: what are the opportunities for glaucoma treatment? A personal perspective. Invest Ophthalmol Vis Sci 53, 2462-2463 (2012).
4. J. Alvarado, C. Murphy, J. Polansky, R. Juster, Age-related changes in trabecular meshwork cellularity. Invest Ophthalmol Vis Sci 21, 714-727 (1981).
5. L. Guo et al., Retinal ganglion cell apoptosis in glaucoma is related to intraocular pressure and IOP-induced effects on extracellular matrix. Invest Ophthalmol Vis Sci 46, 175-182 (2005).
6. H. Chen et al., Commensal microflora-induced T cell responses mediate progressive neurodegeneration in glaucoma. Nat Commun 9, 3209 (2018).
7. Y. Du, H. Yun, E. Yang, J. S. Schuman, Stem cells from trabecular meshwork home to TM tissue in vivo. Invest Ophthalmol Vis Sci 54, 1450-1459 (2013).
8. H. Yun et al., Human stem cells home to and repair laser-damaged trabecular meshwork in a mouse model. Commun Biol 1, 216 (2018).
9. R. Manuguerra-Gagne et al., Transplantation of mesenchymal stem cells promotes tissue regeneration in a glaucoma model through laser-induced paracrine factor secretion and progenitor cell recruitment. Stem Cells 31, 1136-1148 (2013).
10. C. Roubeix et al., Intraocular pressure reduction and neuroprotection conferred by bone marrow-derived mesenchymal stem cells in an animal model of glaucoma. Stem Cell Res Ther 6, 177 (2015).
11. Y. Zhou et al., Adipose-derived stem cells integrate into trabecular meshwork with glaucoma treatment potential. FASEB J 34, 7160-7177 (2020).
12. W. Zhu et al., Transplantation of iPSC-derived TM cells rescues glaucoma phenotypes in vivo. Proc Natl Acad Sci USA 113, E3492-3500 (2016).
13. L. Gao et al., Exosomes secreted by hiPSC-derived cardiac cells improve recovery from myocardial infarction in swine. Sci Transl Med 12, (2020).
14. X. Xia et al., Mesenchymal stem cells promote healing of nonsteroidal anti-inflammatory drug-related peptic ulcer through paracrine actions in pigs. Sci Transl Med 11, (2019).
15. A. Kumar, Y. Xu, E. Yang, Y. Du, Stemness and Regenerative Potential of Corneal Stromal Stem Cells and Their Secretome After Long-Term Storage: Implications for Ocular Regeneration. Invest Ophthalmol Vis Sci 59, 3728-3738 (2018).
16. O. P. B. Wiklander, M. A. Brennan, J. Lotvall, X. O. Breakefield, S. El Andaloussi, Advances in therapeutic applications of extracellular vesicles. Sci Transl Med 11, (2019).
17. G. C. Patel et al., Dexamethasone-Induced Ocular Hypertension in Mice: Effects of Myocilin and Route of Administration. Am J Pathol 187, 713-723 (2017).
18. G. S. Zode et al., Reduction of ER stress via a chemical chaperone prevents disease phenotypes in a mouse model of primary open angle glaucoma. J Clin Invest 121, 3542-3553 (2011).
19. Y. Du et al., Multipotent stem cells from trabecular meshwork become phagocytic TM cells. Invest Ophthalmol Vis Sci 53, 1566-1575 (2012).
20. A. Kumar, Y. Xu, Y. Du, Stem Cells from Human Trabecular Meshwork Hold the Potential to Develop into Ocular and Non-Ocular Lineages After Long-Term Storage. Stem Cells Dev 29, 49-61 (2020).
21. K. W. Witwer et al., Standardization of sample collection, isolation and analysis methods in extracellular vesicle research. J Extracell Vesicles 2, (2013).
22. Y. Du et al., Stem cell therapy restores transparency to defective murine corneas. Stem Cells 27, 1635-1642 (2009).
23. K. E. Keller et al., Consensus recommendations for trabecular meshwork cell isolation, characterization and culture. Exp Eye Res 171, 164-173 (2018).
24. S. Xiong et al., alpha5beta1 Integrin Promotes Anchoring and Integration of Transplanted Stem Cells to the Trabecular Meshwork in the Eye for Regeneration. Stem Cells Dev, (2020).
25. E. R. Tamm, Myocilin and glaucoma: facts and ideas. Prog Retin Eye Res 21, 395-428 (2002).
26. N. Comes, L. K. Buie, T. Borras, Evidence for a role of angiopoietin-like 7 (ANGPTL7) in extracellular matrix formation of the human trabecular meshwork: implications for glaucoma. Genes Cells 16, 243-259 (2011).
27. W. D. Stamer, R. E. Seftor, R. W. Snyder, J. W. Regan, Cultured human trabecular meshwork cells express aquaporin-1 water channels. Curr Eye Res 14, 1095-1100 (1995).
28. J. A. Faralli, M. S. Filla, D. M. Peters, Role of Fibronectin in Primary Open Angle Glaucoma. Cells 8, (2019).
29. Y. Wang et al., Endoplasmic Reticulum Stress Response of Trabecular Meshwork Stem Cells and Trabecular Meshwork Cells and Protective Effects of Activated PERK Pathway. Invest Ophthalmol Vis Sci 60, 265-273 (2019).
30. G. S. Zode et al., Ocular-specific ER stress reduction rescues glaucoma in murine glucocorticoid-induced glaucoma. J Clin Invest 124, 1956-1965 (2014).
31. G. Eibl et al., PGE(2) is generated by specific COX-2 activity and increases VEGF production in COX-2-expressing human pancreatic cancer cells. Biochem Biophys Res Commun 306, 887-897 (2003).
32. A. Kaplan-Messas, N. Naveh, I. Avni, J. Marshall, Ocular hypotensive effects of cholinergic and adrenergic drugs may be influenced by prostaglandins E2 in the human and rabbit eye. Eur J Ophthalmol 13, 18-23 (2003).
33. R. N. Weinreb, M. D. Mitchell, J. R. Polansky, Prostaglandin production by human trabecular cells: in vitro inhibition by dexamethasone. Invest Ophthalmol Vis Sci 24, 1541-1545 (1983).
34. I. Lorenzi et al., The mitochondrial TMEM177 associates with COX20 during COX2 biogenesis. Biochim Biophys Acta Mol Cell Res 1865, 323-333 (2018).
35. B. C. Lee et al., PGE2 maintains self-renewal of human adult stem cells via EP2-mediated autocrine signaling and its production is regulated by cell-to-cell contact. Sci Rep 6, 26298 (2016).

36. V. Porciatti, Electrophysiological assessment of retinal ganglion cell function. Exp Eye Res 141, 164-170 (2015).
37. A. R. Rodriguez, L. P. de Sevilla Muller, N. C. Brecha, The RNA binding protein RBPMS is a selective marker of ganglion cells in the mammalian retina. J Comp Neurol 522, 1411-1443 (2014).
38. A. M. Siddiqui, T. F. Sabljic, P. D. Koeberle, A. K. Ball, Downregulation of BM88 after optic nerve injury. Invest Ophthalmol Vis Sci 55, 1919-1929 (2014).
39. P. Fu, Q. Wu, J. Hu, T. Li, F. Gao, Baclofen Protects Primary Rat Retinal Ganglion Cells from Chemical Hypoxia-Induced Apoptosis Through the Akt and PERK Pathways. Front Cell Neurosci 10, 255 (2016).
40. N. Mohan, N. L. Banik, S. K. Ray, Combination of N-(4-hydroxyphenyl) retinamide and apigenin suppressed starvation-induced autophagy and promoted apoptosis in malignant neuroblastoma cells. Neurosci Lett 502, 24-29 (2011).
41. G. Li et al., In vivo measurement of trabecular meshwork stiffness in a corticosteroid-induced ocular hypertensive mouse model. Proc Natl Acad Sci USA 116, 1714-1722 (2019).
42. T. Stahnke et al., Different fibroblast subpopulations of the eye: a therapeutic target to prevent postoperative fibrosis in glaucoma therapy. Exp Eye Res 100, 88-97 (2012).
43. A. Jablonska-Trypuc, M. Matejczyk, S. Rosochacki, Matrix metalloproteinases (MMPs), the main extracellular matrix (ECM) enzymes in collagen degradation, as a target for anticancer drugs. J Enzyme Inhib Med Chem 31, 177-183 (2016).
44. S. Oyadomari, M. Mori, Roles of CHOP/GADD153 in endoplasmic reticulum stress. Cell Death Differ 11, 381-389 (2004).
45. L. J. Crofford, COX-1 and COX-2 tissue expression: implications and predictions. J Rheumatol Suppl 49, 15-19 (1997).
46. H. Sano et al., In vivo cyclooxygenase expression in synovial tissues of patients with rheumatoid arthritis and osteoarthritis and rats with adjuvant and streptococcal cell wall arthritis. J Clin Invest 89, 97-108 (1992).
47. C. Maihofner et al., Expression of cyclooxygenase-1 and -2 in normal and glaucomatous human eyes. Invest Ophthalmol Vis Sci 42, 2616-2624 (2001).
48. E. Garbe, J. LeLorier, J. F. Boivin, S. Suissa, Risk of ocular hypertension or open-angle glaucoma in elderly patients on oral glucocorticoids. Lancet 350, 979-982 (1997).
49. F. D. Miller, D. R. Kaplan, Mobilizing endogenous stem cells for repair and regeneration: are we there yet? Cell Stem Cell 10, 650-652 (2012).
50. A. Bosco et al., Neurodegeneration severity can be predicted from early microglia alterations monitored in vivo in a mouse model of chronic glaucoma. Dis Model Mech 8, 443-455 (2015).
51. B. Laha, B. K. Stafford, A. D. Huberman, Regenerating optic pathways from the eye to the brain. Science 356, 1031-1034 (2017).
52. N. Rodriguez-Muela, F. Germain, G. Marino, P. S. Fitze, P. Boya, Autophagy promotes survival of retinal ganglion cells after optic nerve axotomy in mice. Cell Death Differ 19, 162-169 (2012).

All patents, patent applications, publications, product descriptions, and protocols cited in this specification are hereby incorporated by reference in their entireties. In case of a conflict in terminology, the present disclosure controls.

While it will become apparent that the subject matter herein described is well calculated to achieve the benefits and advantages set forth above, the presently disclosed subject matter is not to be limited in scope by the specific embodiments described herein. It will be appreciated that the disclosed subject matter is susceptible to modification, variation, and change without departing from the spirit thereof. Those skilled in the art will recognize or be able to ascertain using no more than routine experimentation, many equivalents to the specific embodiments described herein. Such equivalents are intended to be encompassed by the following claims.

The invention claimed is:

1. A composition consisting essentially of:

(a) a serum-free media in an amount of from about 1 mL to about 100 mL and (b) a therapeutically effective amount of a clonal culture human trabecular meshwork stem cell (TMSC) secretome, wherein the clonal culture TMSC secretome consists essentially of filtered proteins, wherein the filtered proteins have a molecular weight ranging from about 3 kDa to about 90 kDa, wherein the filtered proteins are formulated to a concentration from about 20× to about 50× relative to the concentration of the TMSC secretome prior to filtering, and wherein the therapeutically effective amount of the clonal culture TMSC secretome is at least 10 μL to reduce impairment of a retinal ganglion cell (RGC), wherein the clonal culture TMSC secretome consists essentially of filtered proteins involved in neuroprotection selected from the group consisting of TUBB2A (Tubulin beta-2A), ACTR3 (actin related protein 3), ARPC4 (Actin Related Protein 2/3 Complex Subunit 4), SEMA5A (Semaphorin 5A), NEO1 (Neogenin 1), SPTBN1 (spectrin beta, non-erythrocytic 1), GAS6 (growth arrest specific 6), SDC2 (syndecan 2), NQO1 (NAD(P)H quinone dehydrogenase 1), HSP90AB1 (heat shock protein 90 alpha family class B member 1), G6PD (glucose-6-phosphate dehydrogenase), UBE2V2 (ubiquitin conjugating enzyme E2 V2), and combinations thereof, and wherein the composition is formulated in a form selected from the group consisting of an emulsion, a foam gel, a controlled-release solution, a sustained-release solution, and combinations thereof.

2. The composition of claim 1, wherein the clonal culture TMSC secretome:

(a) is a cell-free secretome; and/or (b) is harvested from clonal culture TMSCs by incubating the clonal culture TMSCs with the serum-free media.

3. The composition of claim 1, wherein the impairment is selected from the group consisting of cell apoptosis, axon loss, vision loss, increased intraocular pressure, dysregulation of aqueous humor outflow, and combinations thereof.

4. The composition of claim 3, wherein the increased intraocular pressure is an ocular disorder and wherein the ocular disorder is glaucoma.

5. The composition of claim 1, wherein the composition is formulated in a form:

(a) as an eye drop; or (b) for injection.

6. The composition of claim 5, wherein the injection is selected from the group consisting of a periocular injection, a systemic injection, an intravenous injection, an intramuscular injection, and combinations thereof.

* * * * *